(12) United States Patent
Egebjerg et al.

(10) Patent No.: US 12,404,325 B2
(45) Date of Patent: Sep. 2, 2025

(54) ANTI IL-6 DOMAIN ANTIBODIES WITH FATTY ACID SUBSTITUENTS

(71) Applicant: Novo Nordisk A/S, Bagsvaerd (DK)

(72) Inventors: Thomas Egebjerg, Ganloese (DK); Jais Rose Bjelke, Smoerum (DK); Che Yang, Frederiksberg (DK); Steffen Reedtz-Runge, Birkeroed (DK); Katharina Luise Maria Kopp, Broenchoej (DK); Emma Balantic-Nielsen, Ballerup (DK); Philip Jonas Sassene, Copenhagen V (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 18/830,877

(22) Filed: Sep. 11, 2024

(65) Prior Publication Data
US 2025/0101094 A1 Mar. 27, 2025

(30) Foreign Application Priority Data
Sep. 11, 2023 (EP) .................... 23196627

(51) Int. Cl.
| | | |
|---|---|---|
| C07K 16/24 | (2006.01) | |
| A61K 9/00 | (2006.01) | |
| A61K 9/20 | (2006.01) | |
| A61K 31/455 | (2006.01) | |
| A61K 31/609 | (2006.01) | |
| A61K 39/395 | (2006.01) | |
| A61P 9/10 | (2006.01) | |
| A61P 29/00 | (2006.01) | |
| A61K 39/00 | (2006.01) | |
| C07K 14/54 | (2006.01) | |

(52) U.S. Cl.
CPC .......... *C07K 16/248* (2013.01); *A61K 9/0053* (2013.01); *A61K 9/2013* (2013.01); *A61K 31/455* (2013.01); *A61K 31/609* (2013.01); *A61K 39/3955* (2013.01); *A61P 9/10* (2018.01); *A61K 2039/505* (2013.01); *C07K 14/5412* (2013.01); *C07K 2317/565* (2013.01); *C07K 2317/569* (2013.01); *C07K 2317/92* (2013.01); *C07K 2317/94* (2013.01)

(58) Field of Classification Search
CPC .............. C07K 14/5412; C07K 16/248; A61K 39/3955; A61P 9/10
See application file for complete search history.

(56) References Cited

FOREIGN PATENT DOCUMENTS

| | | | |
|---|---|---|---|
| EP | 0171142 | B1 | 7/1992 |
| EP | 0967284 | A1 | 12/1999 |
| EP | 1085089 | A2 | 3/2001 |
| GB | 2357768 | A | 7/2001 |
| WO | 9849185 | A1 | 11/1998 |
| WO | 0055318 | A2 | 9/2000 |
| WO | 0078972 | A2 | 12/2000 |
| WO | 2004037999 | A2 | 5/2004 |
| WO | 2007104529 | A2 | 9/2007 |
| WO | 2008065378 | A2 | 6/2008 |
| WO | 2008071685 | A1 | 6/2008 |
| WO | 2010030182 | A2 | 3/2010 |
| WO | 2011051327 | A2 | 5/2011 |
| WO | 2016102562 | A1 | 6/2016 |
| WO | 2019016300 | A1 | 1/2019 |
| WO | 2019215063 | A1 | 11/2019 |
| WO | 21231676 | A1 | 11/2021 |
| WO | 22029231 | A1 | 2/2022 |
| WO | 2022096636 | A1 | 5/2022 |
| WO | 2022129572 | A1 | 6/2022 |
| WO | 23031455 | A1 | 3/2023 |
| WO | 23139187 | A1 | 7/2023 |

OTHER PUBLICATIONS

Carty et al., "Association of genetic variation in serum amyloid-A with cardiovascular disease and interactions with IL-6, IL1RN, IL1beta and TNF genes in the Cardiovascular Health Study", J Atheroscler Thromb., Sep. 2009, vol. 16, No. 4, pp. 419-430.
Dich et al., "Metabolism and Distribution of I-labelled Albumin in the Pig", Can J Comp Med Vet Sci., Nov. 1963, vol. 27, No. 11, pp. 269-273.
Drake et al., "Characterizing high-affinity antigen/antibody complexes by kinetic- and equilibrium-based methods", Analytical Biochemistry, May 2004, vol. 328, pp. 35-43.
Durocher et al. "High-Level and High-throughput recombinant protein production by transient transfection of suspension-growing human 293-EBNA1 cells" Nucleic Acids Research, Jan. 2002, vol. 30, No. 2, e9- pp. 1-9.
Fraley et al., "The Gyrolab™ immunoassay system: a platform for automated bioanalysis and rapid sample turnaround", Bioanalysis, Jul. 2013, vol. 5, pp. 1765-1774.
Gasteiger et al. "Protein Identification and Analysis Tools on the ExPASy Server", Proteomics Protocols Handbook, 2005, pp. 571-607.
Hagihara et al., "IL-6 plays a critical role in the synergistic induction of human serum amyloid A (SAA) gene when stimulated with proinflammatory cytokines as analyzed with an SAA isoform real-time quantitative RT-PCR assay system", Biochem Biophys Res Commun., Feb. 2004, vol. 314, No. 2, pp. 363-369.
Jia et al., "A novel method of Multiplexed Competitive Antibody Binning for the characterization of monoclonal antibodies", Journal of Immunological Methods, May 2004, vol. 288, pp. 91-98.
Martin, "Antibodies", Institute of Structural and Molecular Biology, 6 pages, retrieved on Sep. 9, 2024 from: http://www.bioinf.org.uk/abs/.
Martin, "Chapter 3—Protein Sequence and Structure Analysis of Antibody Variable Domains", Antibody Engineering, 2010, vol. 2, pp. 33-51.

(Continued)

*Primary Examiner* — Zachary C Howard
(74) *Attorney, Agent, or Firm* — Elizabeth A. Dingess-Hammond

(57) ABSTRACT

The present invention relates to compounds (e.g. ISVDs, polypeptides, polypeptide derivatives) capable of binding to Interleukin-6 (IL-6) and their use in the treatment of inflammatory diseases such as, e.g. cardiovascular disease (CVD).

15 Claims, 12 Drawing Sheets

Specification includes a Sequence Listing.

(56) References Cited

OTHER PUBLICATIONS

Miller et al., "Epitope binning of murine monoclonal antibodies by a multiplexed pairing assay", Journal of Immunological Methods, Feb. 2011, vol. 365, pp. 118-125.

Needleman et al., "A general method applicable to the search for similarities in the amino acid sequence of two proteins", Journal of Molecular Biology, Mar. 1970, vol. 48, No. 3, pp. 443-453.

Ober et al., "Differences in promiscuity for antibody-FcRn interactions across species: implications for therapeutic antibodies", Intern. Immunology, Dec. 2001, vol. 13, pp. 1551-1559.

Petersson et al., "Orally delivered single-domain antibodies against gastrointestinal pathogens", Trends Biotechnol., Feb. 2023, vol. 41, No. 7, pp. 875-886.

Rezaie et al., "Expression and Purification of a Soluble Tissue Factor Fusion Protein with an Epitope for an Unusual Calcium-Dependent Antibody," Protein Expression and Purification, Dec. 1992, vol. 3, pp. 453-460.

Stearns et al., "The interaction of a Ca2+-dependent monoclonal antibody with the protein C activation peptide region. Evidence for obligatory Ca2+ binding to both antigen and antibody," JBC, Jan. 1988, vol. 263, pp. 826-832.

Thompson et al., "A brief elevation of serum amyloid A is sufficient to increase atherosclerosis", J Lipid Res., Nov. 2014, vol. 56, No. 2, pp. 286-293.

Verduyn et al., "Effect of benzoic acid on metabolic fluxes in yeasts: a continuous-culture study on the regulation of respiration and alcoholic fermentation", Yeast, Jul. 1992, vol. 8, pp. 501-517.

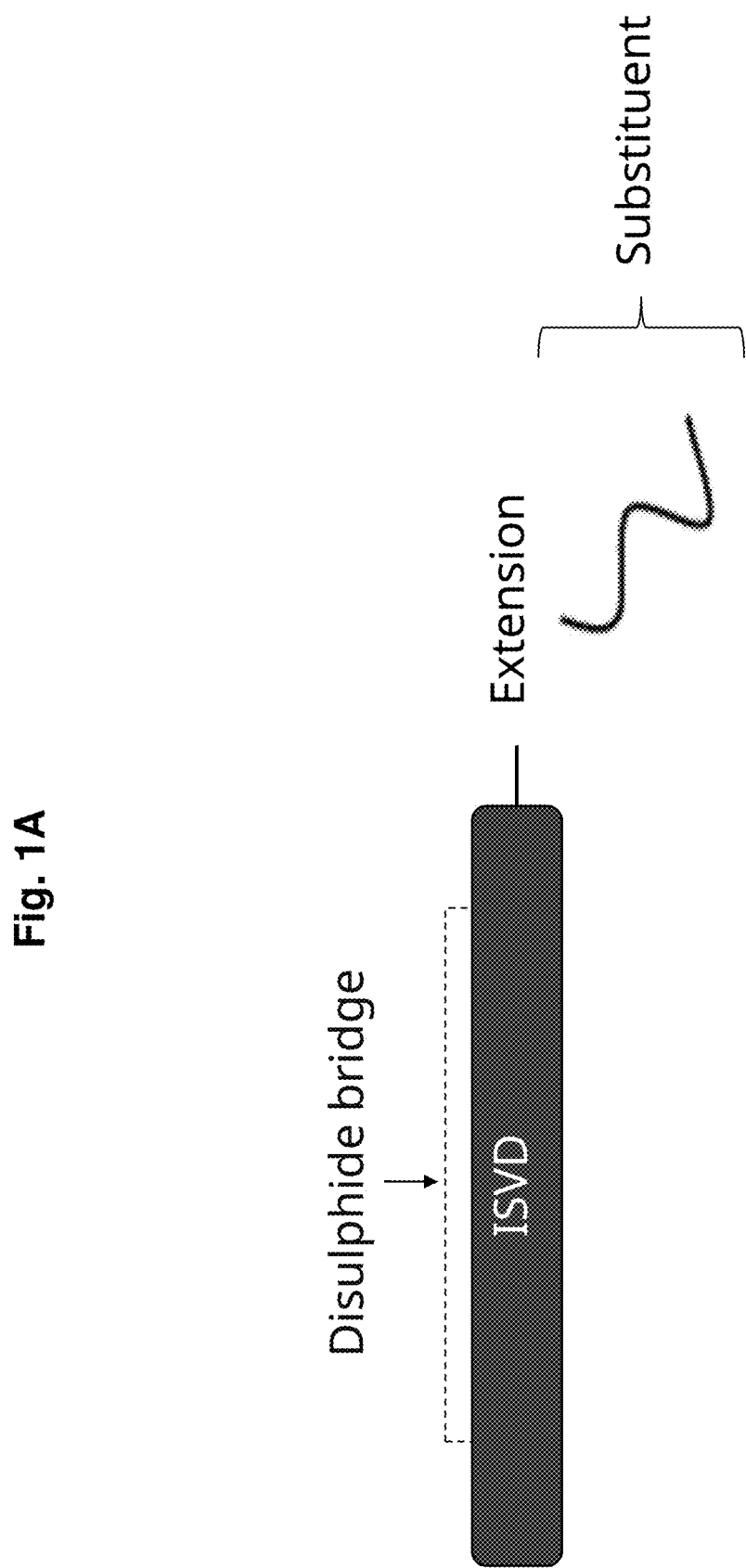

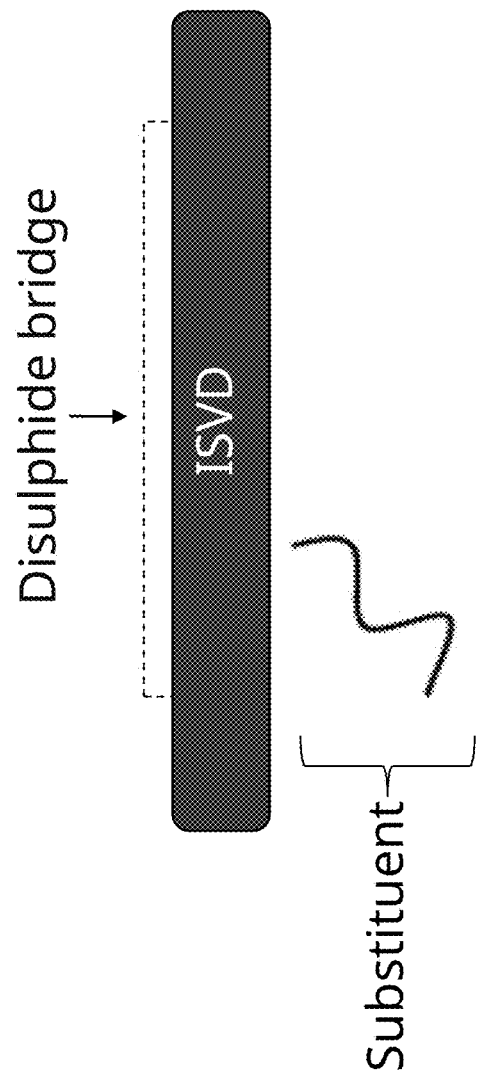

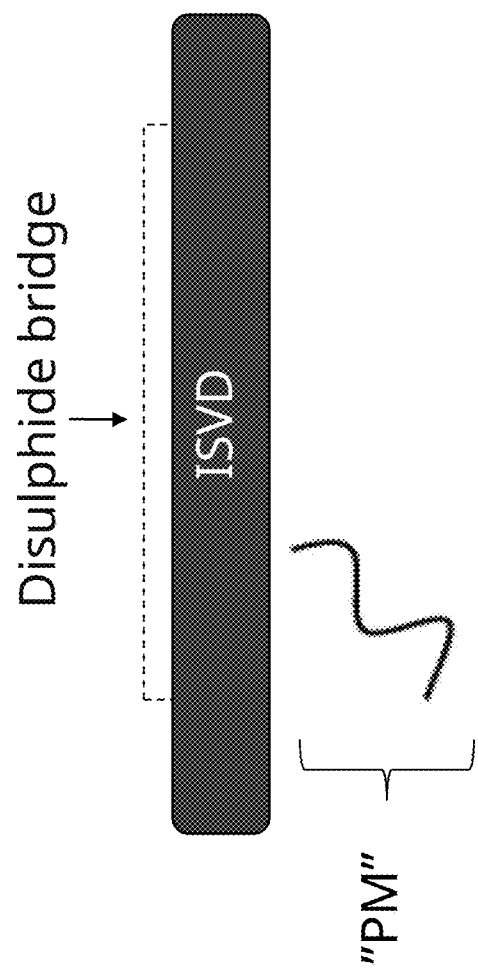

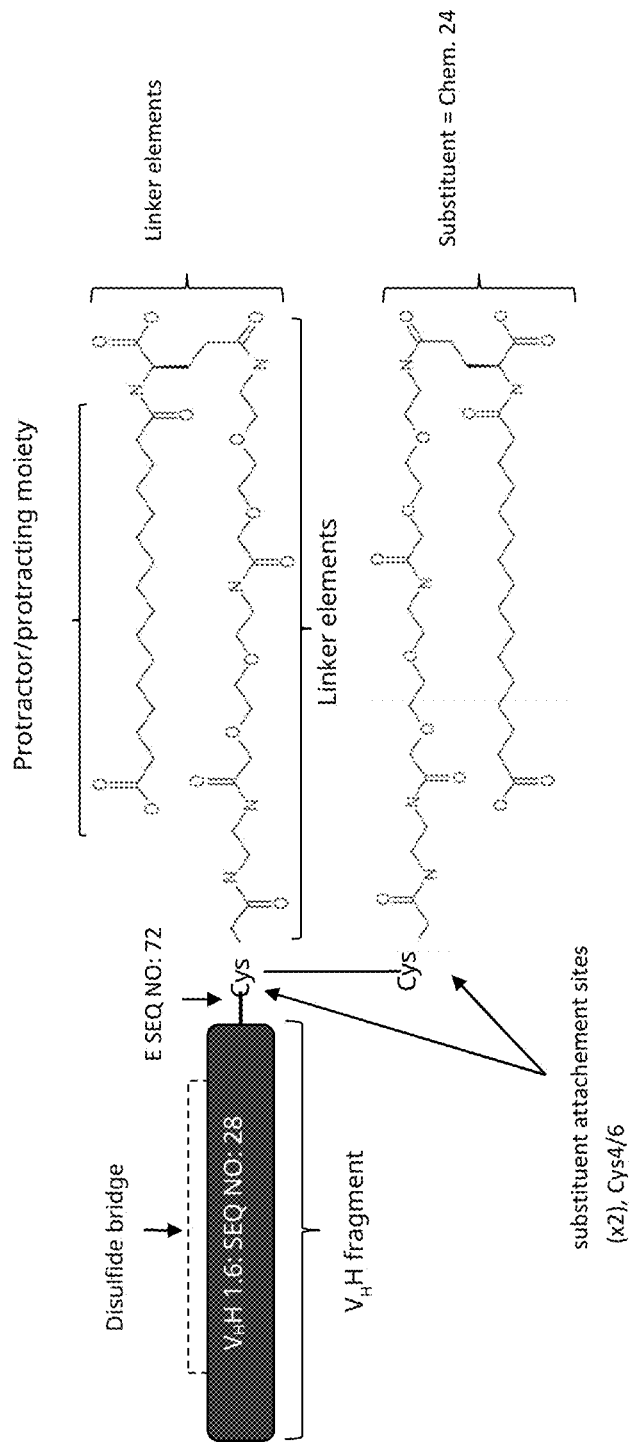

ANTI IL-6 DOMAIN ANTIBODIES WITH FATTY ACID SUBSTITUENTS

TECHNICAL FIELD

The invention relates to compounds capable of binding to Interleukin-6 (IL-6) and their use in the treatment of inflammatory diseases such as, e.g. cardiovascular disease (CVD).

CROSS-REFERENCE TO RELATED APPLICATIONS

This application claims priority to European Patent Application 23196627.6, filed Sep. 11, 2023; the content of which is incorporated herein by reference.

INCORPORATION-BY-REFERENCE OF THE SEQUENCE LISTING

The instant application contains a Sequence Listing which has been submitted in XML format via the USPTO electronic filing system and is hereby incorporated by reference in its entirety. Said XML file, created on Sep. 10, 2024, is named "230041US01_Sequence listing_ST26", and is 169 kilobytes in size.

BACKGROUND

CVD is a major global health burden and one of the leading causes of death worldwide. Despite advances in medical treatments and preventative measures, the prevalence of CVD continues to rise globally, placing a significant strain on healthcare systems and economies. Therefore, there is an urgent need to develop new and innovative therapeutics that can prevent and treat CVD more effectively. The development of new therapeutics may prolong the lives of millions of people and help alleviate the social and economic impact of cardiovascular disease.

Over the past 40 years, the most successful pharmacologic approach to cardiovascular disease prevention has been aggressive lowering of low-density lipoprotein (LDL). Lowering of LDL can be achieved through lifestyle modifications, such as regular exercise and following a diet which is rich in fruits, vegetables, whole grains, lean protein, and low in saturated and trans fats, cholesterol and sodium, and/or medication. Typical LDL lowering medication includes statins, Proprotein Convertase Subtilisin/kexin type 9 (PCSK9) inhibition, bile acid sequestrants, etc.

IL-6 is a multifunctional cytokine that plays a crucial role in mediating various immune responses and inflammatory processes (e.g. upregulation of acute phase proteins or T cell differentiation) through its transient upregulation in response to infection or tissue damage. Dysregulation of IL-6 signaling has been implicated in the pathogenesis of several diseases, including autoimmune disorders, cancer, and chronic inflammatory conditions. IL-6 has also been associated with CVD through its role in inflammation, a process that plays a key role in the development and progression of CVD. IL-6 can promote the production of other pro-inflammatory cytokines, such as tumor necrosis factor (TNF)-α and interleukin-1 β (IL-1β), which can contribute to endothelial dysfunction, plaque formation, and atherosclerosis, all of which are hallmarks of CVD.

Targeting IL-6 has been explored as a potential therapeutic strategy in various diseases, including rheumatoid arthritis, multiple myeloma, Castleman's disease, and COVID-19. One approach is to block the IL-6 receptor, which is responsible for the downstream effects of IL-6 signaling. This can be achieved using monoclonal antibodies, such as tocilizumab and sarilumab, which have been approved for use in rheumatoid arthritis. Another approach is to inhibit IL-6 production or activity through small molecule inhibitors. While antibodies have shown therapeutic efficacy, they also have limitations, including high production costs, immunogenicity, and the requirement for parenteral administration. Small molecule inhibitors targeting IL-6 signaling components suffer from off-target effects and limited selectivity.

There remains therefore a need for novel compounds targeting the IL-6 pathway that can overcome one or more limitations associated with existing therapeutic approaches and allow for an efficient treatment of inflammatory and/or cardiovascular disease.

SUMMARY

The present disclosure relates to anti-IL-6 compounds that are highly potent. As reported herein, the inventors succeeded in generating several IL-6-antigen-binding molecules having suitable qualities for development as therapeutic products, in particular oral therapeutics.

The inventors have designed anti-IL-6 compounds with robust biochemical and biophysical properties suitable for clinical scale manufacturing (including expression, purification, and formulation). In addition, the compounds disclosed herein can be and have been humanised, thereby minimising the risk of immunogenicity in human in vivo therapy.

Aspects of the disclosure are set out below and/or in the appended claims, and further embodiments and preferred features of the disclosure are described below.

The present invention aims to provide compounds (such as e.g., immunoglobulin single variable domain (ISVD), polypeptides, polypeptide derivatives) against inflammatory diseases such as, e.g., CVD, with improved prophylactic, therapeutic and/or pharmacological properties, preferably in addition to other advantageous properties (such as, e.g., improved ease of preparation, good stability, improved bioavailability, improved potency, improved specificity, improved half-life and/or reduced costs of goods) compared to the prior art. In particular, the present invention aims to provide ISVDs, polypeptides comprising the same, and derivatives of such polypeptides, capable of binding IL-6.

From different screening campaigns ISVDs, such as, e.g. $V_HH$, were isolated and further engineered with diverse and favourable features, including increased bioavailability, stability, affinity, and/or inhibitory activity.

In particular, the inventors were able to develop anti-IL-6 compounds that are suitable for oral administration. Developing anti-IL-6 compounds suitable for oral administration is no easy feat, requiring the development of compounds that strike improvements of bioavailability, potency, half-life, and/or isoelectric point (pI), among other features, or a suitable balance in the improvement of desirable features. In particular, the inventors were able to develop anti-IL-6 compounds that are suitable for oral administration due to improved bioavailability, potency, half-life, and/or isoelectric point (pI). The polypeptide derivatives as described herein are highly potent, provide a sufficiently long half-life, and sufficient bioavailability to allow for effective peroral administration. In a first aspect, the present disclosure relates to an ISVD capable of binding to IL-6. Preferably, the ISVDs of the disclosure are isolated ISVD. The ISVDs of the present disclosure may thus comprise a binding site for IL-6. An example of an ISVD is a $V_HH$. The ISVD of the present disclosure may comprise framework region(s), e.g., FR1, FR2, FR3, FR4, and said framework region(s) may be interrupted by a complementarity-determining region (CDR), e.g., CDR1, CDR2, CDR3.

In a second aspect, the present disclosure relates to polypeptide(s) comprising an ISVD according to the first aspect of the disclosure and further comprising an extension, such as a C-terminal extension. The C-terminal extension may be 1 to 20 amino acids in length, such as 1 to 6 amino acids in length. The C-terminal extension may comprise one or more cysteine(s) and/or one or more lysine(s). The C-terminal extension may be suitable for further derivatisation. A polypeptide according to the second aspect of the disclosure may therefore be described as comprising an ISVD according to the first aspect of the disclosure which is fused at its C-terminal to an extension.

In a third aspect, the present disclosure relates to polypeptide derivative(s) comprising the ISVD according to the first aspect of the disclosure or a polypeptide according to the second aspect of the disclosure, and further comprising one or more substituent. The polypeptide derivative(s) may comprise two substituents. The substituent(s) may be conjugated to a suitable amino acid moiety, such as to the functional group of a lysine or a cysteine. The substituent(s) may be attached to the C-terminal extension. The polypeptide derivative(s) may have a prolonged half-life in vivo compared to the corresponding polypeptide or ISVD.

In a fourth aspect, the disclosure relates to an antibody or antibody fragment or an antibody derivative or a polypeptide derivative, wherein the antibody or the antibody fragment or the antibody derivative or polypeptide derivative is capable of binding IL-6 at an epitope comprising at least the amino acid residues 26, 30, 33, 34, 73, 74, 75, 78, 171, 175, 178, 179, 182, and 183 of mature human IL-6, as set forth in SEQ ID NO: 89.

In fifth aspect, the disclosure relates to a nucleic acid molecule, preferably in isolated form, encoding an ISVD according to first aspect of the disclosure or a polypeptide according the second aspect of the disclosure.

In sixth aspect, the disclosure relates to an expression vector comprising a nucleic acid molecule according to the fifth aspect of the disclosure.

In seventh aspect, the invention relates to a host cell carrying an expression vector according to the sixth aspect of the disclosure.

In an eighth aspect, the invention relates to a method of manufacturing an ISVD according to first aspect of the disclosure or a polypeptide according the second aspect of the disclosure or a polypeptide derivative according to the third aspect of the disclosure, comprising the steps of
  a. Culturing a host cell according to the seventh aspect of the disclosure under conditions that allow expression of an ISVD according to the first aspect of the disclosure or a polypeptide according to the second aspect of the disclosure;
  b. Recovering the ISVD or the polypeptide obtainable in step a; and/or optionally
  c. Attaching one or more substituent(s) capable of extending the half-life of the polypeptide, optionally wherein each substituent is Chem. 24; and/or optionally
  d. purifying the so-obtained ISVD or polypeptide or polypeptide derivative.

In a ninth aspect, the disclosure relates to a pharmaceutical composition comprising an ISVD according to the first aspect of the invention or a polypeptide according to the second aspect of the disclosure or a polypeptide derivative according to the third aspect of the disclosure.

In a tenth aspect, the disclosure relates to an ISVD according to the first aspect of the disclosure or a polypeptide according to the second aspect of the disclosure or a polypeptide derivative according to the third aspect of the disclosure or a pharmaceutical composition according to the ninth aspect of the disclosure for use in medicine. In some embodiments, disclosure relates to an ISVD according to the first aspect of the disclosure or a polypeptide according to the second aspect of the disclosure or a polypeptide derivative according to the third aspect of the disclosure or a pharmaceutical composition according to the ninth aspect of the disclosure for use in the treatment of inflammatory disease. In some embodiments, disclosure relates to an ISVD according to the first aspect of the disclosure or a polypeptide according to the second aspect of the disclosure or a polypeptide derivative according to the third aspect of the disclosure or a pharmaceutical composition according to the ninth aspect of the disclosure for use in the treatment of cardiovascular disease.

In a further aspect the invention relates to the individual component (intermediate) ISVDs that are part of an ISVD polypeptide derivative or $V_HH$ polypeptide derivative according to the first aspect, such as a particular anti-IL-6 $V_HH$ fragment or a particular anti-IL-6 $V_HH$ fragment thereof.

The polypeptide derivatives as described herein are highly potent, provide a sufficiently long half-life, and/or sufficient bioavailability to allow for effective subcutaneous administration as well as peroral administration.

Other aspects, advantages, applications and uses of the polypeptides and compositions will become clear from the further disclosure herein. Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

BRIEF DESCRIPTION OF DRAWINGS

FIGS. 1A-C show non-limiting examples of anti-IL-6 polypeptide derivatives comprising a substituent. In the embodiments shown in FIGS. 1A and 1B, there is further provided an extension at the C-terminus or N-terminus, respectively, of the ISVD. The dashed line indicates a disulphide bridge.

FIGS. 1D-F show non-limiting examples of anti-IL-6 polypeptide derivatives wherein the substituent is a protraction moiety. "E"—extension; "PM"—protraction moiety. The dashed line indicates a disulphide bridge.

FIG. 3A shows a detailed figurative description of compound 9, which represents a non-limiting example of anti-IL-6 polypeptide derivatives. The dashed line indicates a disulphide bond. Hydrogen atoms have been omitted for clarity.

DESCRIPTION

Figure 1B:
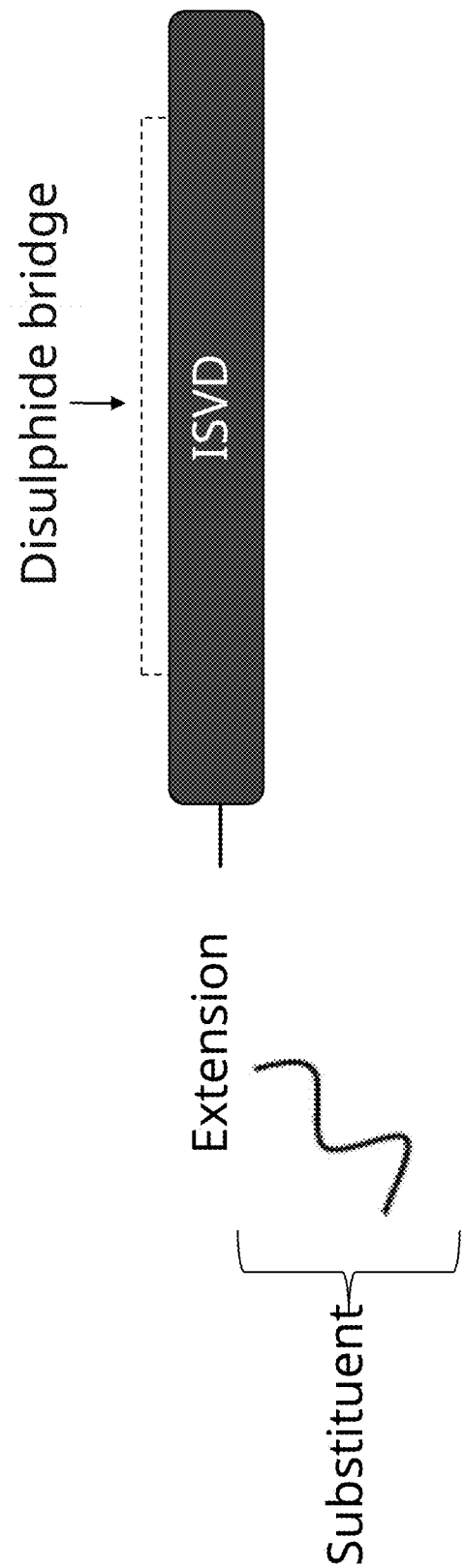

There remains a need for safe and efficacious medicaments for inflammatory disease, such as, e.g., cardiovascular disease. An object of the present disclosure is to provide compounds that combine the advantageous properties of antibody drugs and small molecules drugs. For instance, antibody drugs are typically capable of targeting a broader range of antigens and receptors that are inaccessible or difficult to reach by peptides or small molecules, and often result in higher efficacy and specificity. Small molecules on the other hand can be administered orally, which is a more convenient administration route for patients.

It is therefore an object of the present disclosure to provide highly potent compounds capable of binding IL-6 that have sufficient bioavailability to allow for peroral administration, and provide a sufficiently long half-life to allow for once daily and optionally once weekly dosing. Also, and alternatively, the compounds disclosed herein are suitable for subcutaneous injection.

Disclosed herein are compounds capable of binding to IL-6. Compounds disclosed herein have high in vitro potency. For instance, in vitro potencies of compounds disclosed herein may be between 1-50 pM, such as between 5-35 pM, such as between 10-20 pM, optionally measured as disclosed in the example section such as EXAMPLE 8: REPORTER GENE ASSAY AND SPR EXPERIMENTS. One example of a method to measure potency is a reporter gene assay utilizing a recombinant cell line expressing IL-6 and gp130 receptors, in which activation of said receptors by IL-6 results in Signal transducer and activator of transcription-3 (STAT-3) phosphorylation and subsequent transcription of an introduced luciferase reporter gene with a STAT-3 response element that can be followed using an appropriate luciferase substrate e.g. bioluminescence measurement of the conversion of oxyluciferin. In vitro potency can be measured as disclosed in EXAMPLE 8: REPORTER GENE ASSAY AND SPR EXPERIMENTS and as found in Report Gene Assay (RGA) section of the Materials and Methods of the Examples.

Also, or alternatively, compounds disclosed herein show prolonged half-life (reducing the required frequency of administration). Conveniently, compounds having a protracting moiety have considerably prolonged half-life as compared to the same compound without a protracting moiety. For instance, a $V_HH$ polypeptide derivative has a longer half-life than the corresponding $V_HH$ on itself. The prolonged half-life is achieved via introduction of substituents having protractor motifs/protraction moieties, e.g., fatty acid conjugations, Fc domain, FcRn-binder peptide, Fc-binder peptide, and albumin-binder peptide. The prolonged in vivo half-life of compounds having a substituent (e.g. polypeptide derivatives or protracted compounds) is demonstrated in animal models such as rat, dog and pig. Non-protracted compounds, such as e.g., ISVDs or polypeptides show very rapid clearance in dog and pig.

Also, or alternatively, compounds disclosed herein have been engineered to enable peroral administration in addition to also being suitable for e.g., parenteral administration.

Conveniently, compounds disclosed herein may have an isoelectric point between 3 and 7, such as between 3.5 and 6, such as between 4 and 5 (including the endpoints of the range).

Definitions

Unless indicated or defined otherwise, all terms used have the usual meaning in the art, which will be clear to the skilled person.

Unless indicated otherwise, all methods, steps, techniques, and manipulations that are not specifically described in detail can be performed and have been performed in a manner known per se, as will be clear to the skilled person.

Greek letters may be represented by their symbol or the corresponding written name, for example: α=alpha; β=beta; ε=epsilon; γ=gamma; ω=omega; etc. Also, the Greek letter of μ may be represented by "u", e.g., in μl=ul, or in μM=uM.

An asterisk (*) or a

in a chemical formula/structure may be used to designate a point of attachment.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein. Unless otherwise indicated, the term "at least" preceding a series of elements is to be understood to refer to every element in the series.

Those skilled in the art will recognise or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term.

The term "comprise", and variations thereof such as "comprises" and "comprising", will be understood to imply the inclusion of a stated integer or element or step or group of integer or element or step, but not the exclusion of any other integer or element or step or group of integer or element or step. When used herein the term "comprise" can be substituted with the terms "contain" or "include" or sometimes "have".

The term "about" is used herein to mean approximately, roughly, or around. When the term "about" is used in conjunction with a numerical range, it modifies that range by extending the boundaries above and below the numerical values set forth. In general, the term "about" can modify a numerical value above and below the stated value by 20 percent, up or down (higher or lower), preferably 15 percent, up or down (higher or lower), more preferably within 10 percent, up or down (higher or lower), and most preferably by 5 percent, up or down (higher or lower).

The term "affinity" denotes the strength or stability of a molecular interaction. The affinity is commonly given by the $K_D$ or dissociation constant, which has units of mol/litre (or M). The affinity can also be expressed as an association constant, $K_A$, which equals $1/K$, and has units of (mol/litre)$^{-1}$ (or M$^{-1}$). Herein, the stability of the interaction between two molecules will mainly be expressed in terms of the $K_D$ value of their interaction; it being clear to the skilled person that in view of the relation $K_A=1/K_D$ specifying the strength of molecular interaction by its $K_D$ value can also be used to calculate the corresponding $K_A$ value. The $K_D$ value characterizes the strength of a molecular interaction also in a thermodynamic sense as it is related to the change of free energy ($\Delta G$) of binding by the well-known relation $\Delta G=RT \ln(K_D)$ (equivalently $\Delta G=-RT \ln(K_A)$), where R equals the gas constant, T equals the absolute temperature and ln denotes the natural logarithm. The $K_D$ for biological interactions which are considered meaningful (e.g. specific) are typically in the range of $10^{-12}$ M (0.001 nM) to $10^{-5}$ (10000 nM). The stronger an interaction is, the lower is its $K_D$. The $K_D$ can also be expressed as the ratio of the dissociation rate constant of a complex, denoted $k_{off}$, to the rate of its association, denoted $k_{on}$ (so that $K_D=k_{off}/k_{on}$ and $K_A=k_{on}/k_{off}$). The off-rate $k_{off}$ has units s$^{-1}$ (where s is the SI unit notation of second). The on-rate $k_{on}$ has units M$^{-1}$s$^{-1}$. The on-rate may vary between $10^2$ M$^{-1}$s$^{-1}$ to about $10^8$ M$^{-1}$s$^{-1}$, approaching the diffusion-limited association rate constant for bimolecular interactions.

Specific binding of an antigen-binding polypeptide, such as an ISVD, to an antigen or antigenic determinant can be determined in any suitable manner known per se, including, for example, saturation binding assays and/or competitive binding assays, such as radio-immunoassays (RIA), enzyme immunoassays (EIA) and sandwich competition assays, and the different variants thereof known per se in the art; as well as the other techniques mentioned herein.

The affinity of a molecular interaction between two molecules can be measured via different techniques known per se, such as the well-known surface plasmon resonance (SPR) biosensor technique (see, for example, Ober et al. 2001, Intern. Immunology 13:1551-1559) where one molecule is immobilised on the biosensor chip and the other molecule is passed over the immobilised molecule under flow conditions, yielding $k_{on}$, $k_{off}$ measurements and hence $K_D$ (or $K_A$) values. This can for example be performed using the well-known BIACORE™ instruments (Cytiva). Kinetic Exclusion Assay (KINEXA®) (Drake et al. 2004, Analytical Biochemistry 328:35-43) measures binding events in solution without labelling of the binding partners and is based upon kinetically excluding the dissociation of a complex. In-solution affinity analysis can also be performed using the GYROLAB® immunoassay system, which provides a platform for automated bioanalysis and rapid sample turnaround (Fraley et al. 2013, Bioanalysis 5:1765-74). It will also be clear to the skilled person that the measured $K_D$ may correspond to the apparent $K_D$, the measuring process somehow influences the intrinsic binding affinity of the implied molecules for example by artifacts related to the coating on the biosensor of one molecule. Also, an apparent $K_D$ may be measured if one molecule contains more than one recognition site for the other molecule. In such situation the measured affinity may be affected by the avidity of the interaction by the two molecules. In particular, the accurate measurement of $K_D$ may be quite labour-intensive and as consequence, often apparent $K_D$ values are determined to assess the binding strength of two molecules. It should be noted that as long as all measurements are made in a consistent way (e.g., keeping the assay conditions unchanged) apparent $K_D$ measurements can be used as an approximation of the true $K_D$ and hence in the present document $K_D$ and apparent $K_D$, should be treated with equal importance or relevance.

Amino acids are molecules containing an amine group and a carboxylic acid group, and, optionally, one or more additional groups, often referred to as a side chain. The term "amino acid" includes canonical amino acids (which are genetically encoded), and unnatural amino acids. Non-limiting examples of unnatural amino acids are Aib (α-aminoisobutyric acid), deamino histidine (alternative name 3-(imidazol-4-yl) propanoic acid, abbreviated Imp (imidazopropionyl) and the d-isomers of the canonical amino acids. All amino acid residues within the polypeptide for which the optical isomer is not stated is herein to be understood to mean the l-isomer, unless otherwise specified. Amino acid residues will be indicated according to the standard three-letter or one-letter amino acid code.

The term "amino acid difference" as used herein means a substitution or deletion of an amino acid.

The term "antibody" herein refers to a protein, comprising or derived from an immunoglobulin sequence, which is capable of binding to an antigen or a portion thereof. An "antibody" includes—but is not limited to—full-length antibodies comprising at least four polypeptide chains: two heavy chains (HC) and two light chains (LC) that are connected by disulphide bonds as well as antibodies comprising at least three polypeptide chains: two heavy chains (HC) and one light chain (LC) that are connected by disulphide bonds as well as recombinant or modified antibodies (e.g., chimeric antibodies, humanized antibodies, human antibodies, etc.). One class of immunoglobulins is the IgGs. In humans, the IgG class may be divided into four sub-classes IgG1, IgG2, IgG3 and IgG4, based on the sequence of their heavy chain constant regions. The light chains can be divided into two types, kappa and lambda chains, based on differences in their sequence composition. IgG molecules are composed of two heavy chains, interlinked by two or more disulphide bonds, and two light chains, each attached to a heavy chain by a disulphide bond. For the avoidance of doubt, the term "antibody" also encompasses single-domain antibodies (sdAb).

The term "antigen binding site" is used interchangeably with "antigen binding domain" and shall be taken to mean a region of an antibody that is capable of specifically binding to an antigen. The antigen binding domain need not be in the context of an entire antibody, e.g., it can be in isolation (e.g., a domain antibody) or in another form, e.g., as described herein, such as, e.g., a polypeptide comprising an ISVD. For instance, "conventional" immunoglobulins (e.g. monoclonal antibodies) or fragments (such as Fab, Fab', F(ab')$_2$, scFV, di-scFv) comprise two immunoglobulin domains, in particular two variable domains, interacting to form an antigen binding site. Typically, in conventional immunoglobulins, a heavy chain variable domain (V$_H$) and a light chain variable domain (V$_L$) interact to form an antigen binding site. In this case, the complementarity determining regions (CDRs) of both V$_H$ and V$_L$ will contribute to the antigen binding site, i.e. a total of 6 CDRs will be involved in the antigen binding site formation. Immunoglobulin single variable domains (ISVDs) are capable of specifically binding to an epitope of the antigen without pairing with an additional immunoglobulin variable domain. The binding site of an immunoglobulin single variable domain is formed by a single V$_H$, a single V$_H$H or single V$_L$ domain. As such, the single variable domain may be a light chain variable domain sequence (e.g., a V$_L$-sequence) or a suitable fragment thereof; or a heavy chain variable domain sequence (e.g., a V$_H$-sequence or VAH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

An immunoglobulin single variable domain (ISVD), an antibody, a polypeptide, or generally an antigen binding protein or an antigen binding polypeptide or a fragment thereof that can "bind to" or that can "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein. For instance, in the context of targeting Interleukin-6 (IL-6), one may refer to a construct binding IL-6 as "anti"-IL-6.

The term "conservative substitution" as used herein refers to the case where an amino acid may be substituted by an amino acid with similar biochemical properties, for example, a basic amino acid may be substituted to another basic amino acid (e.g. lysine to arginine), an acidic amino acid may be substituted to another acidic amino acid (e.g. glutamate to aspartate), a neutral amino acid may be substituted to another neutral amino acid (e.g. threonine to serine), a charged amino acid may be substituted to another charged amino acid (e.g. glutamate to aspartate), a hydrophilic amino acid may be substituted to another hydrophilic amino acid (e.g. asparagine to glutamine), a hydrophobic amino acid may be substituted to another hydrophobic amino acid (e.g. alanine to valine), a polar amino acid may be substituted to another polar amino acid (e.g. serine to threonine), an aromatic amino acid may be substituted to another aromatic amino acid (e.g. phenylalanine to tryptophan) and an aliphatic amino acid may be substituted to another aliphatic amino acid (e.g. leucine to isoleucine).

The terms "(cross)-block", "(cross)-blocked", "(cross)-blocking", "competitive binding", "(cross)-compete", "(cross)-competing" and "(cross)-competition" are used interchangeably herein to mean the ability of an immunoglobulin, antibody, ISVD, polypeptide or other binding agent to interfere with the binding of other immunoglobulins, antibodies, ISVDs, polypeptides or binding agents to a given target. The extent to which an immunoglobulin, antibody, ISVD, polypeptide or other binding agent is able to interfere with the binding of another to the target, and therefore whether it may be said to cross-block according to the invention, may be determined using competition binding assays, which are common in the art, such as for instance by screening purified ISVDs against ISVDs displayed on phage in a competition ELISA. Methods for determining whether an immunoglobulin, antibody, immunoglobulin single variable domain, polypeptide or other binding agent directed against a target (cross)-blocks, is capable of (cross)-blocking, competitively binds or is (cross)-competitive as defined herein are described e.g., in Xiao-Chi Jia et al. (Journal of Immunological Methods 288; 91-98, 2004), Miller et al. (Journal of Immunological Methods 365; 118-125, 2011) and/or the methods described herein.

The term "derivative" as used herein refers to a chemically modified polypeptide having a substituent covalently linked to an amino acid of the polypeptide. Typically, a polypeptide derivative refers to a polypeptide comprising an ISVD wherein said polypeptide carries a substituent. For instance, the substituent may be covalently attached to the thiol group of a cysteine. The resultant construct (ie. the polypeptide carrying a substituent) may be referred to as a polypeptide derivative.

The term "EC$_{50}$" as used herein relates to the concentration required to induce 50% of the maximum effect, i.e. typically pharmacological or therapeutic effect. The term "ED$_{50}$" as used herein relates to the dose for 50% to induce the pharmacological or therapeutic effect. Typically, EC$_{50}$/ED$_{50}$ measurements are conducted in pharmacology in vivo models, whereas IC$_{50}$ measurements can be conducted both in vitro and in vivo.

The term "epitope" as used herein refers a specific binding site on an antigen or on an antigenic structure for which e.g., an ISVD, or a polypeptide comprising an ISVD, or a polypeptide derivative comprising an ISVD, has specificity and affinity. Epitopes usually consist of surface elements of molecules, such as amino acids or sugar side chains, and usually have specific three-dimensional structural characteristics, as well as specific charge characteristics. Conformational and non-conformational epitopes are distinguished in that the binding to the former but not the latter is lost in the presence of denaturing agents capable of disrupting the structure of the protein. An epitope can be a linear epitope, a conformational epitope, or a hybrid epitope. The term "epitope" may be used in reference to a structural epitope. A structural epitope, according to some embodiments, may be used to describe the region of an antigen which is covered by an antibody (e.g., an antibody's footprint when bound to the antigen). In some embodiments, a structural epitope may describe the amino acid residues of the antigen that are within a specified proximity (e.g., within a specified number of Angstroms) of an amino acid residue of the antibody. The term "epitope" may also be used in reference to a functional epitope. A functional epitope, according to some embodiments, may be used to describe amino acid residues of the antigen that interact with amino acid residues of the antibody in a manner contributing to the binding energy between the antigen and the antibody. An epitope can be determined according to different experimental techniques, also called "epitope mapping techniques." It is understood that the determination of an epitope may vary based on the different epitope mapping techniques used and may also vary with the different experimental conditions used, e.g., due to the conformational changes or cleavages of the antigen induced by specific experimental conditions.

The term "excipient" as used herein refers to an inert substance added to a pharmaceutical composition to further facilitate administration of an active ingredient. Non-limiting examples of excipients include calcium carbonate, calcium phosphate, various sugars and types of starch, L-arginine, nicotinamide, SNAC, magnesium stearate, sodium stearyl fumarate cellulose derivatives, gelatine, vegetable oils and polyethylene glycols.

The term "extension" (E) as used herein refers to a peptide or polypeptide suitable for being attached to an ISVD. The extension can be of a few amino acids, 1 to 10 amino acids, it can be longer, 10 to 30 amino acids, or it can be very long, more than 30 amino acids. An extension is preferably present in the C-terminal end (C-terminal extension) of an ISVD, ISVD polypeptide, ISVD polypeptide derivative, $V_HH$, $V_HH$ polypeptide or $V_HH$ polypeptide derivative. The extension is preferably recombinantly fused to the ISVD. In other embodiments, the extension is recombinantly expressed with the ISVD. In other embodiments the extension is conjugated to the ISVD by any suitable means, such as by chemical conjugation. In other embodiments, the extension may be linked to the ISVD via other means, such as click-chemistry. In some embodiments, the extension is linked to the ISVD as a C-terminal extension thereof or a N-terminal extension thereof. It is understood that the resultant construct of an ISVD which is provided with an extension, such as a C-terminal extension for instance, may be referred to broadly as a polypeptide or, more specifically, a polypeptide comprising an ISVD. In some embodiments, the extension is provided as a structure linked to any residue between the C-terminal and N-terminal of the ISVD, such as for example by acylation. In certain embodiments, a purpose of the extension is to be a site of attachment for one or more substituents (which may further comprise or be protracting moiety(ies)), e.g., via one or more cysteine(s). A non-limiting example of an extension is GQACPC (SEQ ID NO: 72). For instance, in a non-limitative embodiment, an ISVD is provided with a C-terminal extension of amino acid residues GQACPC (SEQ ID NO: 72), such as to form a polypeptide comprising the ISVD, wherein the cysteines at position 4 and 6 in accordance with the positioning of SEQ ID No. 72 may each individually be sites of attachments for substituents.

The term "fatty acid" refers to an optionally substituted carboxylic acid with an aliphatic, wherein the aliphatic chain is saturated or unsaturated. Non limiting examples of fatty acids are C12-C24 carboxylic acid.

"Framework" or "FR" regions are those variable domain regions other than the hypervariable region residues. Thus, compounds disclosed herein comprise from N- to C-terminus the domains FR1, CDR1, FR2, CDR2, FR3, CDR3, and FR4.

The term "free cysteine" as used herein refers to a cysteine residue in a polypeptide chain that is available for reaction, e.g., chemical conjugation and, thus, not part of a natural or an engineered internal disulphide bridge. In essence, free cysteines can be used for conjugation, albeit free cysteine residues, including recombinantly introduced free cysteines, are often blocked with small thiols, such as cysteine, homocysteine, or glutathione, during recombinant expression of polypeptides in host cells. This is also observed in the recombinant production of ISVD polypeptides wherein one or more free cysteine(s) has/have been introduced. Thus, a reduction reaction using a proper reducing agent, such as a disulphide reducing agent may be used. A non-limiting example of a reducing agent is bis(p-sulfonatophenyl)phenylphosphine dihydrate or tris(2-carboxyethyl)phosphine hydrochloride, which can be used to liberate and prepare the free cysteine for conjugation to a moiety of interest, such as—but not limited to—a substituent (which may comprise or be a protraction moiety).

The half maximal inhibitory concentration ($IC_{50}$) can be a measure of the efficacy of a compound in inhibiting a biological or biochemical function, e.g., a pharmacological effect. This quantitative measure indicates how much of the ISVD (e.g., a $V_HH$ polypeptide) is needed to inhibit a given biological process (or component of a process, e.g., an enzyme, cell receptor, chemotaxis, anaplasia, metastasis, invasiveness, etc.) by half. In other words, it is the half maximal (50%) inhibitory concentration (IC) of a substance (50% IC, or $IC_{50}$). $IC_{50}$ values can be calculated for a given antagonist such as the polypeptide or ISVD (e.g., a Nanobody™) of the invention by determining the concentration needed to inhibit half of the maximum biological response of the agonist. The $IC_{50}$ of a drug can be determined by constructing a dose-response curve and examining the effect of different concentrations of antagonist such as the ISVD (e.g., a $V_HH$ polypeptide) of the invention on reversing agonist activity.

The "HPC4-tag" refers to a 12 amino acid sequence derived from protein C (SEQ ID NO: 87), which is a vitamin K-dependent plasma zymogen. Protein C is activated by proteolytic cleavage of the thrombin-thrombomodulin complex to form an anticoagulant enzyme. This peptide can be expressed and detected with the protein of interest as an amino-terminal or carboxy-terminal fusion.

The term "host cell" as used herein covers any kind of cellular system which can be engineered to generate the ISVDs disclosed herein. Host cells include—but is not limited to—cultured cells, e.g., mammalian cultured cells, such as CHO cells, HEK293T cells, HEK EXPI cells, BHK cells, NS0 cells, SP2/0 cells, YO myeloma cells, P3X63 mouse myeloma cells, PER cells, PER.C6 cells or hybridoma cells, yeast cells, fungal cells, and insect cells.

The term "hydrotrope" as used herein refers to a compound capable of increasing the solubility of poorly soluble drugs in the solid form. Hydrotropes can be added during the manufacturing process to improve the bioavailability of the drug once it is administered. These substances work by enhancing the solubility of the drug in the stomach fluid, which facilitates its absorption across the intestinal walls. Non limiting examples of hydrotropes include urea, nicotinamide, and pyridoxine hydrochloride.

The term "hypervariable region" as used herein refers to the amino acid residues of an antibody which are responsible for antigen-binding. The hypervariable region comprises the "complementarity determining regions" also known as "CDRs".

The term "identity" as known in the art, refers to a relationship between the sequences of two or more polypeptides, as determined by comparing the sequences. In the art, "identity" also means the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods.

"IL-6" is interleukin 6. IL-6 may also be referred to herein as "the antigen". The full-length amino acid sequence of hIL-6 is SEQ ID NO: 88. This sequence is cleaved in vivo to remove an N-terminal leader peptide, to produce mature IL-6. Mature hIL-6 has amino sequence SEQ ID NO: 89. The mature sequence represents the in vivo circulating IL-6, which is the target antigen for therapeutic and in vivo diagnostic applications as described herein. Accordingly, unless the context requires otherwise, IL-6 referred to herein is mature hIL-6. IL-6 may be fused to a moiety for detection and/or purification and/or immobilisation, such as e.g., a His-tag or HPC4-tag, e.g., for use in assays as described herein.

The term "immunoglobulin single variable domain (ISVD)", which is interchangeably used with "single variable domain" or "single-domain antibody", refers to an immunoglobulin molecule wherein the antigen binding site is present on, and formed by, a single immunoglobulin domain. An immunoglobulin single variable domain (ISVD) can for example comprise or consist of a heavy chain ISVD, such as a $V_H$, $V_HH$, including a camelid $V_HH$ or humanised $V_HH$. Preferably, it is a $V_HH$, including a camelid $V_HH$ or humanized $V_HH$. Heavy chain ISVDs can be derived from a conventional four-chain antibody or from a heavy chain antibody. The term "ISVD", includes—but is not limited to—variable domains of camelid heavy chain antibodies ($V_HHs$), domain antibodies (dABs), and ISVDs derived from shark (IgNAR domains). Like a conventional antibody, an ISVD is capable of binding selectively to a specific antigen. Typically, ISVDs have a molecular weight of only 12-18 kDa, which makes them much smaller than conventional antibodies. For comparison, conventional antibodies typically have a molecular weight of about 120-160 kDa. Generally, an ISVD has an amino acid sequence comprising four framework regions (FR1, FR2, FR3, FR4) and three complementarity determining regions (CDR1, CDR2, CDR3), preferably according to the following formula (Formula I): FR1-CDR1-FR2-CDR2-FR3-CDR3-FR4 (Kabat definition).

The acronym "$V_HH$", as used herein, stands for Variable Heavy domain of Heavy chain.

Regarding the CDRs, as is well-known in the art, there are multiple conventions to define and describe the CDRs of a $V_H$ or $V_HH$ fragment, such as the Kabat definition (which is based on sequence variability and is the most commonly used) and the Chothia definition (which is based on the location of the structural loop regions). Reference is for example made to the website www.bioinf.org.uk/abs/.

Herein, CDR sequences of ISVDs such as $V_HH$ are determined using the Kabat definition (Kontermann and Dübel, 2010, Eds., Antibody Engineering, vol 2, Springer Verlag Heidelberg Berlin, Martin, Chapter 3, pp. 33-51). According to this method, the CDRs of the variable domain is defined as position 31-35 (CDR1), position 50-65 (CDR2) and position 95-102 (CDR3). It is however recognised that the boundaries of the CDR and FR regions can vary from those specified. However, when referring to specific amino acid residue positions in the compounds described herein including CDRs and FRs consecutive numbering is used unless otherwise stated.

The term "isoelectric point" or "pI" as used herein refers to the pH value where the overall net charge of a protein—such as an antibody—is zero. In proteins there may be many charged groups, and at the isoelectric point the sum of all these charges is zero. At a pH above the isoelectric point the overall net charge of the protein will be negative, whereas at pH values below the isoelectric point the overall net charge of the protein will be positive. The pI may be either a theoretical or an experimentally determined isoelectric point. The skilled person is aware of methods to determine the isoelectric point of a protein. Most commonly, the isoelectric point of a protein is computed based on the amino acid sequence of the protein. Numerous (online) tools allowing the determination of the isoelectric point of a protein are available, such as "ExPASy Compute pI/Mw"; see Protein Identification and Analysis Tools on the ExPASy Server; Gasteiger E., Hoogland C., Gattiker A., Duvaud S., Wilkins M. R., Appel R. D., Bairoch A.; (In) John M. Walker (ed): The Proteomics Protocols Handbook, Humana Press (2005), pp. 571-607. Preferably, the algorithm of Skoog & Wichman, 1986. pKa of amino acid residues is used for calculating pI. The pI can also be determined experimentally and charge variants can, for example, be separated using charged based-separation techniques such as isoelectric focusing (IEF) gel electrophoresis, capillary isoelectric focusing (cIEF) gel electrophoresis.

The term "isolated", as used herein, refers to material that is removed from its original or native environment (e.g., the natural environment if it is naturally occurring). For instance, a naturally occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such a vector or composition is not part of the environment in which it is found in nature. A nucleic acid or amino acid sequence is considered to be "(in) (essentially) isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid sequence is considered "(essentially) isolated" when it has been purified at least 2-fold, in particular at least 10-fold, more in particular at least 100-fold, and up to 1000-fold or more. A nucleic acid or amino acid that is "in (essentially) isolated form" is preferably essentially homogeneous, as determined using a suitable technique, such as a suitable chromatographical technique, such as polyacrylamide-gel electrophoresis.

The term "lipophilic moiety" as used herein refers to a moiety that comprises an aliphatic hydrocarbon moiety with a total of more than 6 and less than 30 carbon atoms, preferably more than 8 and less than 20 carbon atoms.

The term "oral bioavailability" or "peroral bioavailability" as used herein refers to the amount of administered drug in systemic circulation after peroral administration (estimated as the area under the plasma concentration versus time curve) relative to the amount of administered drug in systemic circulation after intravenous administration of said drug.

The part of an antigen-binding molecule (such as an immunoglobulin, a conventional antibody, an immunoglobulin single variable domain (ISVD), a polypeptide of the invention and/or a polypeptide derivative of the invention) that recognizes the epitope is called a "paratope".

The term "plasma half-life" as used herein refers to the time required for half the quantity of a substance administered to a patient to be metabolized or eliminated from the serum or plasma of the patient by normal biological processes.

The term "protraction/protracting moiety", "protraction moiety" or "protracting moiety" as used herein refers to a moiety having half-life extending properties and may interchangeably used with the term "protractor" (P). The term "protraction" thus refers to half-life extension and a protractor or protraction moiety thus serves the purpose of the extending the half-life of the ISVD and/or ISVD polypeptides disclosed herein. The protraction or protraction moiety is optionally attached to the ISVD or polypeptide via a "linker" ($L_p$). Such linker ($L_p$) may be composed of one or various "linker elements". In an embodiment where the linker ($L_p$) consists of a single linker element, the linker ($L_p$) and linker element may be referred to synonymously. In an embodiment where the linker ($L_p$) is composed of various linker elements in series, or at least partially in series, the "linker elements" are thus comprised within the linker ($L_p$). Each protractor or protraction moiety preferably attaches to a surface exposed lysine or a cysteine residue in the polypeptide backbone of the compound. The attachment point is generally referred to as R1 (and in case of attachment of more than one protraction moiety R2, R3 and so forth wherein $R^1 \neq R2 \neq R3$ and so forth). In this regard, the protractor/protraction moiety (P) and linker ($L_p$) may be provided in series such as to form P-$L_p$ or $L_p$-P, or more explicitly P-$L_p$-Rn or Rn-$L_p$-P (where n is an integer in accordance with the previously stated attachment point reference of R1, R2, R3, etc.) The skilled person will be able to identify other surface exposed residue(s) suitable for attachment. In some embodiments, where there is provided a protractor/protraction moiety (P) and linker ($L_p$), which is to be attached to an amino acid of a polypeptide (such as an ISVD, $V_HH$, ISVD polypeptide, $V_HH$ polypeptide, etc.), each one of the protractor/protraction moiety (P) and a linker ($L_p$) individually may be referred to as "substituent elements", whereas the resultant of the protractor/protraction moiety (P) and linker ($L_p$) may be referred to as a "substituent". Written otherwise, and for the avoidance of doubt, a substituent having half-life extending properties may be referred to as comprising a protracting moiety. It is understood that, in certain non-limiting embodiments, the term protractor or protraction moiety may be interchangeably used with "substituent". This may be the case, for instance, in embodiments wherein the protractor/protraction moiety (P) is attached to the amino acid of the polypeptide without a linker ($L_p$), such that the substituent constitutes of the protractor/protraction moiety.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings. Some other techniques, computer algorithms and settings for determining the degree of sequence identity are for example described in WO 04/037999, EP 0967284, EP 1085089, WO 00/55318, WO 00/78972, WO 98/49185 and GB 2357768. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence. For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein. Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence. In the present invention similarity and identity were determined using Needleman (Needleman et al. J. Mol. Biol. 1970; 48:443-453) from EMBOSS-6.6.0 using the parameters 10 and 0.5 for gaps opening and extensions, respectively (gapopen=10, gapextend=0.5).

The term "substituent", as used herein, refers to a moiety that is covalently attached to an amino acid of a polypeptide (e.g., an ISVD, a $V_HH$, a ISVD polypeptide, a $V_HH$ polypeptide). If a substituent is attached to a polypeptide, the polypeptide is said to be "substituted". When a substituent is covalently attached to a polypeptide or to an amino acid residue, said polypeptide or amino acid is said to "carry" a substituent. The substituent may comprise a series of individually defined moieties; these moieties may be referred to as "substituent elements". Non-limiting examples of "substituent elements" are a "protractor" (or "protraction moiety") and a "linker".

In some embodiments, the substituent may be capable of forming non-covalent binding interactions with albumin, thereby promoting the circulation of the compound in the blood stream, and thus having the effect of protracting the time of which the compound is present in the blood stream, since the aggregate of the substituent-carrying compound and albumin is only slowly disintegrated to release the free form of the compound; thus, the substituent, as a whole, may also be referred to as an "albumin-binding moiety", and the substituent may be said to have a "protracting effect". The substituent may comprise a portion which is particularly relevant for the albumin binding and thereby the protraction, which portion may be referred to as a "protractor" or a "protracting moiety". The term "protractor" and "protracting moiety" are used interchangeably herein. The "protractor" may be a lipophilic moiety (e.g., a fatty acid). The "protractor" may be a fatty acid (e.g. a C12-C22 carboxylic acid). A non-limiting example of a "protractor" is shown in Table 7. Non-limiting examples of substituents are shown in Table 9. Other examples of suitable substituents are described in e.g. WO23139187A1, WO19016300A1, WO16102562, WO21231676A1, WO22029231, WO23031455A1.

Unless otherwise stated, "binding IL-6" refers to binding mature hIL-6 (SEQ ID NO: 89).

The term "variant" as used herein refers to an ISVD or polypeptide that differs from a parent ISVD or polypeptide by one or more amino acid deletion(s), substitution(s), or addition(s), yet retains one or more specific functions or biological activities of the parent ISVD or polypeptide.
Immunoglobulin Single Variable Domain (ISVD)

In a first aspect, the disclosure relates to an ISVD capable of binding to IL-6. The ISVD as disclosed herein can be an isolated ISVD. Preferably the ISVD is a $V_HH$, such as, e.g., a humanised $V_HH$.

In some embodiments, the ISVD is capable of binding specifically to an epitope of IL-6, wherein the epitope comprises residues 26, 30, 33, 34, 73, 74, 75, 78, 171, 172, 175, 176, 178, 179, 182, and 183, as set forth in SEQ ID NO: 89.

A non-limiting example of the structure of an ISVD according to the first aspect of the disclosure can be considered as comprising four framework regions (FRs), e.g., FR1, FR2, FR3, and FR4, and said framework regions being interrupted by three CDRs, e.g., CDR1, CDR2, and CDR3 (Kabat definition). In such an immunoglobulin sequence, the framework sequences may be any suitable framework sequences, and examples of suitable framework sequences will be clear to the skilled person, for example based on standard textbooks and further disclosure mentioned herein.

In some embodiments, the ISVD comprises:
CDR1: EYAVG (SEQ ID NO: 3), or an amino acid sequence with 1 or 2 amino acid difference(s) with SEQ ID NO: 3;
CDR2: DIGEQAENTWYAESVLG (SEQ ID NO: 7), or an amino sequence with 1, 2, 3, or 4 amino acid difference(s) with SEQ ID NO: 7;
CDR3: DKYGVGGNAQGYYDS (SEQ ID NO: 17), or an amino acid sequence with 1 or 2 amino acid difference(s) with SEQ ID NO: 17. (Kabat definition)

In some embodiments, the ISVD comprises a CDR1 selected from the list consisting of SEQ ID NO: 3, SEQ ID NO: 4, SEQ ID NO: 5, or SEQ ID NO: 6; a CDR2 selected from the list consisting of SEQ ID NO: 7, SEQ ID NO: 8, SEQ ID NO: 9, SEQ ID NO: 12, SEQ ID NO: 13, SEQ ID NO: 14, SEQ ID NO: 15, and SEQ ID NO: 16; and a CDR3 selected from the list consisting of SEQ ID NO: 17, SEQ ID NO: 18, SEQ ID NO: 19, and SEQ ID NO: 20. (Kabat definition).

In some embodiments, the ISVD comprises a CDR1 of SEQ ID NO: 3; a CDR2 selected from the list consisting of SEQ ID NO: 7, SEQ ID NO: 8, and SEQ ID NO: 12; and a CDR3 selected from the list consisting of SEQ ID NO: 17, SEQ ID NO: 18, and SEQ ID NO: 19. (Kabat definition)

In some embodiments, the ISVD comprises

CDR1:
NYWMY; (SEQ ID NO: 6)

CDR2:
GINTGGSTPDYADSVKG; and/or (SEQ ID NO: 16)

CDR3:
DTPRVFRLDHYSP (Kabat definition). (SEQ ID NO: 20)

In preferred embodiments, the ISVD comprises CDR1: EYAVG (SEQ ID NO: 3); CDR2: DIGEQAENTWYAESVLG (SEQ ID NO: 7); and/or CDR3: DKYGVGGNAQGYYDS (SEQ ID NO: 17) (Kabat definition).

In some embodiments, the ISVD comprises a CDR1 selected from Table 1, a CDR2 selected from Table 2, and a CDR3 selected from Table 3.

TABLE 1

Non-limiting examples of CDR1 (Kabat definition).

| CDR | Amino acid sequence | SEQ ID # |
|---|---|---|
| CDR1.1 | EYAVG | SEQ ID NO: 3 |
| CDR1.2 | SYAVG | SEQ ID NO: 4 |
| CDR1.3 | EYAMA | SEQ ID NO: 5 |
| CDR1.4 | NYWMY | SEQ ID NO: 6 |

TABLE 2

Non limiting examples of CDR2 (Kabat definition).

| CDR | Amino acid sequence | SEQ ID # |
|---|---|---|
| CDR2.1 | DIGEQAENTWYAESVLG | SEQ ID NO: 7 |
| CDR2.2 | DIGENAENTWYAESVLG | SEQ ID NO: 8 |
| CDR2.3 | DIGENAENTWYAHSVLG | SEQ ID NO: 9 |
| CDR2.7 | DIGEQAENTWYAHSVLG | SEQ ID NO: 12 |
| CDR2.8 | DIGENADNTWYAHSVLG | SEQ ID NO: 13 |
| CDR2.9 | DIGESGGTWYADSVKG | SEQ ID NO: 14 |
| CDR2.10 | DIGENADNTWYAHSVKG | SEQ ID NO: 15 |
| CDR2.11 | GINTGGSTPDYADSVKG | SEQ ID NO: 16 |

TABLE 3

Non limiting examples CDR3 (Kabat definition).

| CDR | Amino acid sequence | SEQ ID # |
|---|---|---|
| CDR3.1 | DKYGVGGNAQGYYDS | SEQ ID NO: 17 |
| CDR3.2 | DSYGVGGGAQGYYDS | SEQ ID NO: 18 |
| CDR3.3 | DSYGVGGGAERYYDS | SEQ ID NO: 19 |
| CDR3.4 | DTPRVFRLDHYSP | SEQ ID NO: 20 |

In some embodiments, the ISVD comprises an amino acid sequence according to Formula II (SEQ ID No. 21): $X_1X_2$QLVESGGG$X_{11}$VQPGGSL$X_{19}$LSCTTSGR$X_{28}$F$X_{30}$$X_{31}$YAVGWFRQ$X_{40}$PG$X_{43}$EREFVA$X_{50}$IGE $X_{54}$A$X_{56}$NTWYA$X_{62}$SV$X_{65}$GRFTISRD$X_{74}$AKNTVYL$X_{82}$M$X_{84}$$X_{85}$LKPEDTAVYYCAAD$X_{100}$YGVGG$X_{106}$AQGYYDSWGQGTQVTVSS (SEQ ID NO: 21), wherein
$X_1$ is Q or E;
$X_2$ is L or V;
$X_{11}$ is L or W
$X_{19}$ is K or Q;
$X_{28}$ is R, T, E, H, or K;
$X_{30}$ is S, Q, or D;
$X_{31}$ is S or E;
$X_{40}$ is A or G;
$X_{43}$ is K or Q;
$X_{50}$ is D or E;
$X_{54}$ is Q, N, T, or E;
$X_{56}$ is E or D;
$X_{62}$ is H or E;
$X_{65}$ is K or L;

$X_{74}$ is E, N or D;
$X_{82}$ is E or Q;
$X_{84}$ is D or N;
$X_{85}$ is G or S;
$X_{100}$ is K or S; and
$X_{106}$ is N or G. (consecutive numbering)

In preferred embodiments, the ISVD comprises an amino acid sequence according to Formula III (SEQ ID No. 22):
EVOLVESGGGX$_{11}$VQPGGSLX$_{19}$LSCTTSGRX$_{28}$FX$_{30}$
EYAVGWFRQX$_{40}$PGX$_{43}$EREFVADIGEX$_{54}$A
ENTWYAX$_{62}$SVLGRFTISRDX$_{74}$AKNTVYLX$_{82}$MX$_{84}$
X$_{85}$LKPEDTAVYYCAADKYGVGGNAQGYYD
SWGQGTQVTVSS (SEQ ID NO: 22), wherein
$X_{11}$ is L or W, preferably L;
$X_{19}$ is K or Q;
$X_{28}$ is R or K;
$X_{30}$ is S or D;
$X_{40}$ is A or G;
$X_{43}$ is K or Q;
$X_{54}$ is Q or N;
$X_{62}$ is H or E;
$X_{74}$ is E or D;
$X_{82}$ is E or Q;
$X_{84}$ is D or N, preferably D; and
$X_{85}$ is G or S. (consecutive numbering).

Conveniently, an ISVD having glutamic acid in amino acid position 1 and/or alanine or glycine in amino acid position 40 and/or histidine or glutamic acid in amino acid position 62 and/or glutamic acid in amino acid position 82 and/or aspartic acid in amino acid position 84 may lead to de-immunisation. An ISVD according to the disclosure having glutamic acid in amino acid position 1 and/or leucine in amino acid position 11 and/or aspartic acid in amino acid position 84 may have improved chemical stability. The pI of an ISVD according to the disclosure may conveniently be lowered by having glutamic acid in amino acid position 1 and/or glutamine in amino acid position 19 and/or aspartic acid in amino acid position 30 and/or glutamine in amino acid position 43 and/or glutamic acid in amino acid position 62 and/or aspartic acid in amino acid position 74 and/or glutamine or glutamic acid in amino acid position 82 and/or aspartic acid in amino acid position 84. The binding affinity of an ISVD according to the disclosure may be improved by having a lysine or arginine in amino acid position 28 and/or aspartic acid or serine in amino acid position 30 and/or glutamic acid in amino acid position 31 and/or a asparagine or glutamine in amino acid position 54 and/or aspartic acid or glutamic acid in amino acid position 54 and/or a lysine or leucine in amino acid position 65 and/or aspartic acid or glutamic acid in amino acid position 74 and/or glycine or serine in amino acids position 85 and/or lysine in amino acid position 100 and/or asparagine in amino acid position 106.

In some embodiments, the ISVD comprises or consist of SEQ ID NO: 23, SEQ ID NO: 24, SEQ ID NO: 25, SEQ ID NO: 26, SEQ ID NO: 27, SEQ ID NO: 28, SEQ ID NO: 29, or SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 103.

In some embodiments, the ISVD comprises or consist of SEQ ID NO: 38. In some embodiments, the ISVD comprises or consists of a sequence having at least 90, 91, 92, 93, 94, 95, 96, 97, 98, or 99% sequence identity with SEQ ID NO: 38.

In preferred embodiments, the ISVD comprises or consists of SEQ ID NO: 23, SEQ ID NO: 24, SEQ ID NO: 25, SEQ ID NO: 26, SEQ ID NO: 27, SEQ ID NO: 28, or SEQ ID NO: 29.

In further preferred embodiments, the ISVD comprises or consists of EVOLVESGGGLVQPGGSLKLSCTTSGRRF-SEYAVGWFRQAPGKEREFVADIGEQAENTWYAE SVLGRFTISRDDAKNTVYLEMDGLKPEDTAVYY-CAADKYGVGGNAQGYYDSWGQGTQVTVSS (SEQ ID NO: 28). In some embodiments, the ISVD comprises an amino acid sequence as set out in SEQ ID NO: 28.

In some embodiments, the ISVD comprises or consists of a sequence having at least 90, 91, 92, 93, 94, 95, 96, 97, 98, or 99% sequence identity with SEQ ID NO: 28. In some embodiments, the ISVD comprises an amino acid sequence as set out in SEQ ID NO: 28. In some embodiments, the ISVD consists of an amino acid sequence as set out in SEQ ID NO: 28.

In some embodiments, the ISVD is selected from Table 4. In some embodiments, the ISVD comprises or consists of any one of the sequences shown in Table 4.

In some embodiments, the ISVD comprises a tryptophan in position 58 or 59 capable of forming cation-pi interaction with Arg179 and hydrophobic interaction with Phe78 of mature hIL-6 (SEQ ID NO: 89).

In some embodiments, the ISVD is capable of binding IL-6 via a paratope comprising amino acid residue 50, 53, 54, 57, 58, 59, 101, 102, 103, 104, and 105, as set forth in SEQ ID NO: 89. In particularly preferred embodiments, the ISVD is capable of binding IL-6 via a paratope comprising amino acid residues 50, 53, 54, 57, 58, 59, 60, 65, 99, 101, 102, 103, 104, 105, 106, and 110, as set forth in SEQ ID NO: 28.

TABLE 4

Exemplary amino acid sequences of ISVDs. The estimated CDR regions are bold and underlined.

| V$_H$H ID<br>V$_H$H (CDR1, 2, 3) | Amino acid sequence (estimated CDR regions bold and underlined) | SEQ ID Nos<br>V$_H$H (CRD1, 2, 3)<br>(Kabat definition) |
|---|---|---|
| VHH_1.1<br>(CDR1.1,<br>CDR2.7, CDR3.1) | EVQLVESGGGWVQPGGSLQLSCTTSGRRFS<br>EYAVGWFRQAPGQEREFVADIGEQAENTWY<br>AHSVLGRFTISRDEAKNTVYLQMDSLKPEDTA<br>VYYCAADKYGVGGNAQGYYDSWGQGTQVTV<br>SS | 23 (3, 12, 17) |
| VHH_1.2<br>(CDR1.1,<br>CDR2.1, CDR3.1) | EVQLVESGGGLVQPGGSLKLSCTTSGRRFSE<br>YAVGWFRQGPGKEREFVADIGEQAENTWYA<br>ESVLGRFTISRDDAKNTVYLQMDSLKPEDTAV<br>YYCAADKYGVGGNAQGYYDSWGQGTQVTVS<br>S | 24 (3, 7, 17) |

TABLE 4-continued

Exemplary amino acid sequences of ISVDs. The estimated CDR regions are bold and underlined.

| V$_H$H ID<br>V$_H$H (CDR1, 2, 3) | Amino acid sequence (estimated CDR regions bold and underlined) | SEQ ID Nos<br>V$_H$H (CRD1, 2, 3)<br>(Kabat definition) |
|---|---|---|
| VHH_1.3<br>(CDR1.1,<br>CDR2.7, CDR3.1) | EVQLVESGGGLVQPGGSLQLSCTTSGRRFSE<br>YAVGWFRQGPGKEREFVADIGEQAENTWYA<br>HSVLGRFTISRDDAKNTVYLQMDSLKPEDTAV<br>YYCAADKYGVGGNAQGYYDSWGQGTQVTVS<br>S | 25 (3, 12, 17) |
| VHH_1.4<br>(CDR1.1,<br>CDR2.3, CDR3.1) | EVQLVESGGGLVQPGGSLQLSCTTSGRKFDE<br>YAVGWFRQAPGKEREFVADIGENAENTWYA<br>HSVLGRFTISRDDAKNTVYLQMDSLKPEDTAV<br>YYCAADKYGVGGNAQGYYDSWGQGTQVTVS<br>S | 26 (3, 9, 17) |
| VHH_1.5<br>(CDR1.1,<br>CDR2.2, CDR3.1) | EVQLVESGGGLVQPGGSLQLSCTTSGRKFDE<br>YAVGWFRQGPGKEREFVADIGENAENTWYA<br>ESVLGRFTISRDDAKNTVYLQMDSLKPEDTAV<br>YYCAADKYGVGGNAQGYYDSWGQGTQVTVS<br>S | 27 (3, 8, 17) |
| VHH_1.6<br>(CDR1.1,<br>CDR2.1, CDR3.1) | EVQLVESGGGLVQPGGSLKLSCTTSGRRFSE<br>YAVGWFRQAPGKEREFVADIGEQAENTWYA<br>ESVLGRFTISRDDAKNTVYLEMDGLKPEDTAV<br>YYCAADKYGVGGNAQGYYDSWGQGTQVTVS<br>S | 28 (3, 7, 17) |
| VHH_1.7<br>(CDR1.1,<br>CDR2.2, CDR3.1) | EVQLVESGGGLVQPGGSLQLSCTTSGRKFDE<br>YAVGWFRQGPGQEREFVADIGENAENTWYA<br>ESVLGRFTISRDDAKNTVYLEMDGLKPEDTAV<br>YYCAADKYGVGGNAQGYYDSWGQGTQVTVS<br>S | 29 (3, 8, 17) |
| VHH_1.8<br>(CDR1.3,<br>CDR2.9, CDR3.3) | EVQLVESGGGLVQAGGSLRLSCTASGGTFSE<br>YAMAWFRQAPGKEREFVTDIGESGGTWYAD<br>SVKGRFTISRDNAKNTVYLQMNSLRPEDTAVY<br>YCAADSYGVGGGAERYYDSWGQGTQVTVSS | 30 (5, 14, 19) |
| VHH_1.9<br>(CDR1.2,<br>CDR2.10,<br>CDR3.2) | EVQLVESGGGLVQPGGSLRLSCTTSGRTFSS<br>YAVGWFRQAPGKEREFVADIGENADNTWYA<br>HSVKGRFTISRDNAKNTVYLQMNSLKPEDTAV<br>YYCAADSYGVGGGAQGYYDSWGQGTQVTVS<br>S | 31 (4, 15, 18) |
| VHH_1.10<br>(CDR1.3,<br>CDR2.9, CDR3.3) | QVQLVESGGGLVQAGGSLRLSCTASGGTFGE<br>YAMAWFRQAPGKEREFVTDIGESGGTWYAD<br>SVKGRFTISRDNAKNTVYLQMNSLRPEDTAVY<br>YCAADSYGVGGGAERYYDSWGQGTQVTVSS | 32 (5, 14, 19) |
| VHH_1.11<br>(CDR1.2,<br>CDR2.10,<br>CDR3.2) | QLQLVESGGGWVQPGGSLKLSCTTSGRTFSS<br>YAVGWFRQAPGKEREFVADIGENADNTWYA<br>HSVKGRFTISRDNAKNTVYLQMNSLKPEDTAV<br>YYCAADSYGVGGGAQGYYDSWGQGTQVTVS<br>S | 33 (4, 15, 18) |
| VHH_1.12<br>(CDR1.2,<br>CDR2.10,<br>CDR3.2) | QLQLVESGGGWVQPGGSLQLSCTTSGRTFSS<br>YAVGWFRQAPGQEREFVADIGENADNTWYA<br>HSVKGRFTISRDNAKNTVYLQMDSLKPEDTAV<br>YYCAADSYGVGGGAQGYYDSWGQGTQVTVS<br>S | 34 (4, 15, 18) |
| VHH_1.13<br>(CDR1.3,<br>CDR2.9, CDR3.3) | EVQLVESGGGLVQAGGSLQLSCTASGGTFSE<br>YAMAWFRQAPGQEREFVTDIGESGGTWYAD<br>SVKGRFTISRDNAKNTVYLQMDSLRPEDTAVY<br>YCAADSYGVGGGAERYYDSWGQGTQVTVSS | 35 (5, 14, 19) |
| VHH_1.14<br>(CDR1.1,<br>CDR2.7, CDR3.1) | QLQLVESGGGWVQPGGSLQLSCTTSGRRFS<br>EYAVGWFRQAPGQEREFVADIGEQAENTWY<br>AHSVLGRFTISRDEAKNTVYLQMDSLKPEDTA<br>VYYCAADKYGVGGNAQGYYDSWGQGTQVTV<br>SS | 36 (3, 12, 17) |

TABLE 4-continued

Exemplary amino acid sequences of ISVDs. The estimated CDR regions are bold and underlined.

| $V_HH$ ID<br>$V_HH$ (CDR1, 2, 3) | Amino acid sequence (estimated CDR regions bold and underlined) | SEQ ID Nos<br>$V_HH$ (CRD1, 2, 3)<br>(Kabat definition) |
|---|---|---|
| VHH_1.15<br>(CDR1.1,<br>CDR2.7, CDR3.1) | QLQLVESGGGWVQPGGSLKLSCTTSGRRFSE<br>YAVGWFRQAPGKEREFVADIGEQAENTWYA<br>HSVLGRFTISRDEAKNTVYLQMNSLKPEDTAV<br>YYCAADKYGVGGNAQGYYDSWGQGTQVTVS<br>S | 37 (3, 12, 17) |
| VHH_1.16<br>(CDR1.4,<br>CDR2.11,<br>CDR3.4) | EVQLVESGGGLVQPGGSLRLSCAASGFTFSN<br>YWMYWVRQAPGKGLEWVSGINTGGSTPDYA<br>DSVKGRFAISRDNAKNTLYLQMNSLRPEDTAV<br>YYCAADTPRVFRLDHYSPLGQGTQVTVSS | 38 (6, 16, 20) |
| VHH_1.17<br>(CDR1.4,<br>CDR2.11,<br>CDR3.4) | EVQLVESGGGLVQPGGSLQLSCAASGFTFSN<br>YWMYWVRQAPGQGLEWVSGINTGGSTPDYA<br>DSVKGRFAISRDNAKNTLYLQMDSLRPEDTAV<br>YYCAADTPRVFRLDHYSPLGQGTQVTVSS | 103 (6, 16, 20) |

Polypeptide

In a second aspect, the disclosure relates to a polypeptide comprising an ISVD according to the first aspect of the invention and an extension, optionally wherein the extension is a C-terminal extension.

In some embodiments, the extension is 1 to 20 amino acids in length. In some embodiments, the extension is 1 to 15 amino acids in length, such as 1 to 10 amino acids in length. In preferred embodiments, the extension is 1 to 6 amino acids in length.

In some embodiments, the extension is between 4 to 6 amino acids in length. In some embodiments, the extension is 4 amino acids in length. In some embodiments, the extension is 5 amino acids in length. In some embodiments, the extension is 6 amino acids in length.

One of skill in the art understands that an extension may be linked to the ISVD according to the first aspect of the invention as a C-terminal extension thereof, a N-terminal extension thereof or an extension stemming from an amino acid residue between the C-terminal and N-terminal of the ISVD. Preferably, the extension is linked to the ISVD as a C-terminal extension thereof or a N-terminal extension thereof. Even more preferably, the extension is linked to the ISVD according to the first aspect of the invention as a C-terminal extension thereof.

It is further understood that the extension may be provided via any suitable means. For instance, the extension may be recombinantly expressed with the ISVD or conjugated to the ISVD by any suitable means, such as by chemical conjugation or click-chemistry for instance.

In preferred embodiments, the extension comprises one or more amino acid residues capable of reacting with a substituent having half-life extending properties. In further preferred embodiments, the extension comprises two amino acid residues, each residue capable of reacting with a substituent having half-life extending properties. Non-limiting examples of such amino acid residues are lysine and cysteine. If the extension comprises two or more amino acid residue which are each capable of reacting with a substituent having half-life extending properties, then each amino acid residue can be the same or different. For instance, the extension may comprise a lysine and a cysteine for instance, or a lysine and a lysine for instance, or a cysteine and a cysteine for instance. Conveniently, in some embodiments, the extension comprises two cysteine amino acid residues, wherein each of the cysteine amino acid residues individually is capable or reacting with a substituent having half-life extending properties. Non-limiting examples of substituents having half-life extending properties are disclosed herein.

In some embodiments, the extension comprises or consists of GGGGSCPC (SEQ ID NO: 90), which may be referred to as E3. In some embodiments, the extension comprises or consists of GGGGSC (SEQ ID NO: 91), which may be referred to as E4. In some embodiments, the extension comprises or consists of GGGGSKPK (SEQ ID NO: 92), which may be referred to as E5. In some embodiments, the extension comprises or consists of GGGGSKP (SEQ ID NO: 93), which may be referred to as E6.

In particularly preferred embodiments, the extension comprises or consists of GQACPC (SEQ ID NO: 72), which may be referred to as E2. A list of non-limiting examples of polypeptides comprising an extension of SEQ ID NO: 72 is shown in Table 6.

In some embodiments, the extension comprises or consists of GGGGSHHHHHH (SEQ ID NO: 71), which may be referred to as E1. A list of non-limiting examples of polypeptides comprising an extension of SEQ ID NO: 71 is shown in Table 5.

In preferred embodiments, the polypeptide is selected from the list consisting of SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, and SEQ ID NO: 102. In an even more preferred embodiment, the polypeptide comprises a sequence as set out in SEQ ID No. 78.

Non limiting examples of polypeptides of the disclosure are shown in Table 6 and Table 5. In these tables, the entries are identified by a polypeptide ID. The components forming part of the polypeptide (such as the ISVD and Extension) may be understood from the brief description of the polypeptide column.

TABLE 5

List of polypeptides comprising the extension E1 of SEQ ID NO: 71.

| Polypeptide ID | Brief Description of polypeptide | Amino acid sequence | Polypeptide SEQ ID No. |
|---|---|---|---|
| 1 | [VHH_2.1]-E1 | QVQLVESGGDLVQPGGSLRLSCTTSGRTFSSYAMGWFRQAPGKEREFVADIGENADNRWYAHSVKGRFTISRDNAKNTVYLQMNSLKPEDTAVYYCAADRYGVGGGAQGYYDSWGQGTQVTVSSGGGGSHHHHHH | 39 |
| 2 | [VHH_2.2]-E1 | EVQLVESGGGLVQPGGSLRLSCAASGFTFSNYWMYWVRQAPGKGLEWVSGINTGGSTPDYADSVKDRFTISRDNAKNTLYLQMNSLRPADTAVYYCAADTPRSFRLNHYAPLGQGTQVTVSSGGGGSHHHHHH | 40 |
| 3 | [VHH_2.3]-E1 | QVQLQESGGGLVQAGGSLRLSCTTSGRTFSSYAMGWFRQAPGKEREFVADIGENADNRWYAHSVKGRFTISRDNAKNTVYLQMNSLKPEDTAVYYCAADRYGVGGGAQGYYDSWGQGTQVTVSSGGGGSHHHHHH | 41 |
| 4 | [VHH_2.4]-E1 | QVQLQESGGGLVQAGGSLRLSCTVSGRTFSTYAMGWFRQAPGKEREFVADINWNSDNLWYADSVKGRFTISRDNAKNTMYLQMNSLKPEDTAVYYCAVDSYGVGGGKPEYYDSWGQGTQVTVSSGGGGSHHHHHH | 42 |
| 5 | [VHH_2.5]-E1 | QLQLVESGGGLVQPGGSLRLSCAASGFTFSNYWMYWVRQAPGKGLEWVSGINTGGSTPDYADSVKGRFTISRDNAKNTLYLQMNSLRPEDTAVYYCAADTPRVFRLDHYSPLGQGTQVTVSSGGGGSHHHHHH | 43 |
| 6 | [VHH_2.6]-E1 | QVQLQESGGGLVQAGGSLRLSCTTSGRTFSDYAMAWFRQAPGKDREFVADIGTNSENTWYAESVKGRFTISRDNTKNTIYLQMNSLKPEDTAVYYCAADSYGVGGGKQEYYDSWGQGAQVTVSSGGGGSHHHHHH | 44 |
| 7 | [VHH_2.7]-E1 | EVQLVESGGRWVQPGASLRLSCTTSGRTFSSYAMGWFRQAPGKEREFVADIGENADNRWYAHSVKGRFTISRDNAKNTVYLQMNSLKPEDTAVYYCAADRYGVGGGAQGYYDSWGQGTQVTVSSGGGGSHHHHHH | 45 |
| 8 | [VHH_2.8]-E1 | QVQLVESGGGLVQPGGSLRLSCAASGFTFSSYWMYWVRQAPGKGLEWVSGINTGGSTPDYADSVKGRFTISRDNAKNTLYLQMNSLRPEDTAVYYCAADTPRSFRLNHYSPLGQGTQVTVSSGGGGSHHHHHH | 46 |
| 9 | [VHH_2.9]-E1 | QVQLVESGGGLVQPGGSLRLSCAASGFTFSNYMMYWVRQAPGKGLEWVSGIDTRGSTPDYADSVKGRFTISRDNAKSTFYLQMNSLRPEDTAVYYCATDTPRSFRLYHYVPLGQGTQVTVSSGGGGSHHHHHH | 47 |
| 10 | [VHH_2.10]-E1 | QVQLQESGGGLVQAGGSLRLSCTVSGRTFSTYAMGWFRQAPGKEREFVADINWNSDNIWYADSVKGRFTISRDNAKNVMYLQMNSLKPEDTAVYYCAADSYGVGGGKEEYYDSWGQGTQVTVSSGGGGSHHHHHH | 48 |
| 11 | [VHH_2.11]-E1 | EVQLVESGGGLVQAGGSLRLSCTASGRSFSSYAMGWFRQAPGKEREFVADIGVNPDNTWYADSAKGRFTISRDNAKNTMYLQMNSLKPEDTAVYYCAADSYGVGGGAERYYDSWGQGTQVTVSSGGGGSHHHHHH | 49 |
| 12 | [VHH_2.12]-E1 | QVQLVESGGGLVQAGGSLRLSCTTSGRTFSSYAMAWFRQAPGKDREFVADIGENSDNIWYADSVKGRFTISRDNAKNTILLQMNSLKPEDTAVYYCAADSYGVGGGKPEYYDSWGQGAQVTVSSGGGGSHHHHHH | 50 |

TABLE 5-continued

List of polypeptides comprising the extension E1 of SEQ ID NO: 71.

| Polypeptide ID | Brief Description of polypeptide | Amino acid sequence | Polypeptide SEQ ID No. |
|---|---|---|---|
| 13 | [VHH_2.13]-E1 | EVQLVESGGGLVQAGGPLRLSCTVSGRTF STYAMGWFRQAPGKEREFVADINWNSDNI WYADSVKGRFTISRDNAKNVMYLQMNSLK PEDTAVYYCAADSYGVGGGKEEYYDSWG QGTQVTVSSGGGGSHHHHHH | 51 |
| 14 | [VHH_2.14]-E1 | QLQLVESGGGSVQVGDSLRLSCTFSGRSF SSYAMGWFRQAPGKEREFVADIGENADNT WYAHSVKGRFTISRDNAKNTVYLQMNSLK PEDTAVYYCAADSYGVGGGAQGYYDSWG QGTQVTVSSGGGGSHHHHHH | 52 |
| 15 | [VHH_2.15]-E1 | QVQLQESGGGLVQAGGSLRLSCTASGGTF SEYAMAWFRQAPGKEREFVTDIGESGGT WYADSVKGRFTISRDNAKNTVYLQMNSLR PEDTAVYYCAADSYGVGGGAERYYDSWG QGTQVTVSSGGGGSHHHHHH | 53 |
| 16 | [VHH_2.16]-E1 | EVQLVESGGGLVQPGGSLSLSCTASGRTF SSYAMGWFRQAPGKEREFVADIGENADNR WYAHSVKGRFTISRDNAKNTVYLQMNSLK PEDTAVYYCAADRYGVGGGAQGYYDSWG QGTQVTVSSGGGGSHHHHHH | 54 |
| 17 | [VHH_2.17]-E1 | QVQLVESGGGLVQAGGSLRLSCTVSGRTF STYAMGWFRQAPGKEREFVADINWNSDNI WYADSVKGRFTISRDNAKNVMYLQMNSLK PEDTAVYYCAADSYGVGGGKEEYYDSWG QGTQVTVSSGGGGSHHHHHH | 55 |
| 18 | [VHH_1.16]-E1 | EVQLVESGGGLVQPGGSLRLSCAASGFTF SNYWMYWVRQAPGKGLEWVSGINTGGST PDYADSVKGRFAISRDNAKNTLYLQMNSLR PEDTAVYYCAADTPRVFRLDHYSPLGQGT QVTVSSGGGGSHHHHHH | 56 |
| 19 | [VHH_1.11]-E1 | QLQLVESGGGWVQPGGSLKLSCTTSGRTF SSYAVGWFRQAPGKEREFVADIGENADNT WYAHSVKGRFTISRDNAKNTVYLQMNSLK PEDTAVYYCAADSYGVGGGAQGYYDSWG QGTQVTVSSGGGGSHHHHHH | 57 |
| 20 | [VHH_2.18]-E1 | EVQLVESGGGLVQPGGSLQLSCTTSGRHF DEYAVGWFRQAPGKEREFVADIGENADNT WYAHSVKGRFTISRDDAKNTVYLEMDGLK PEDTAVYYCAADKYGVGGNAQGYYDSWG QGTQVTVSSGGGGSHHHHHH | 58 |
| 21 | [VHH_2.19]-E1 | EVQLVESGGGLVQPGGSLQLSCTTSGRHF DEYAVGWFRQGPGKEREFVADIGENADNT WYAHSVKGRFTISRDDAKNTVYLEMDGLK PEDTAVYYCAADKYGVGGNAQGYYDSWG QGTQVTVSSGGGGSHHHHHH | 59 |
| 22 | [VHH_1.2]-E1 | EVQLVESGGGLVQPGGSLKLSCTTSGRRF SEYAVGWFRQGPGKEREFVADIGEQAENT WYAESVLGRFTISRDDAKNTVYLQMDSLKP EDTAVYYCAADKYGVGGNAQGYYDSWGQ GTQVTVSSGGGGSHHHHHH | 60 |
| 23 | [VHH_2.20]-E1 | EVQLVESGGGLVQPGGSLQLSCTTSGRRF SEYAVGWFRQAPGKEREFVADIGEQAENT WYAHSVLGRFTISRDDAKNTVYLQMDSLK PEDTAVYYCAADKYGVGGNAQGYYDSWG QGTQVTVSSGGGGSHHHHHH | 61 |
| 24 | [VHH_1.3]-E1 | EVQLVESGGGLVQPGGSLQLSCTTSGRRF SEYAVGWFRQGPGKEREFVADIGEQAENT WYAHSVLGRFTISRDDAKNTVYLQMDSLK PEDTAVYYCAADKYGVGGNAQGYYDSWG QGTQVTVSSGGGGSHHHHHH | 62 |

TABLE 5-continued

List of polypeptides comprising the extension E1 of SEQ ID NO: 71.

| Polypeptide ID | Brief Description of polypeptide | Amino acid sequence | Polypeptide SEQ ID No. |
|---|---|---|---|
| 25 | [VHH_2.21]-E1 | EVQLVESGGGLVQPGGSLQLSCTTSGRRF SEYAVGWFRQGPGKEREFVADIGEQAENT WYAESVLGRFTISRDDAKNTVYLQMDSLKP EDTAVYYCAADKYGVGGNAQGYYDSWGQ GTQVTVSSGGGGSHHHHHH | 63 |
| 26 | [VHH_2.22]-E1 | EVQLVESGGGLVQPGGSLKLSCTTSGRKF DEYAVGWFRQAPGKEREFVADIGENAENT WYAHSVLGRFTISRDDAKNTVYLQMDSLK PEDTAVYYCAADKYGVGGNAQGYYDSWG QGTQVTVSSGGGGSHHHHHH | 64 |
| 27 | [VHH_1.4]-E1 | EVQLVESGGGLVQPGGSLQLSCTTSGRKF DEYAVGWFRQAPGKEREFVADIGENAENT WYAHSVLGRFTISRDDAKNTVYLQMDSLK PEDTAVYYCAADKYGVGGNAQGYYDSWG QGTQVTVSSGGGGSHHHHHH | 65 |
| 28 | [VHH_1.5]-E1 | EVQLVESGGGLVQPGGSLQLSCTTSGRKF DEYAVGWFRQGPGKEREFVADIGENAENT WYAESVLGRFTISRDDAKNTVYLQMDSLKP EDTAVYYCAADKYGVGGNAQGYYDSWGQ GTQVTVSSGGGGSHHHHHH | 66 |
| 29 | [VHH_1.6]-E1 | EVQLVESGGGLVQPGGSLKLSCTTSGRRF SEYAVGWFRQGPGKEREFVADIGEQAENT WYAESVLGRFTISRDDAKNTVYLEMDGLKP EDTAVYYCAADKYGVGGNAQGYYDSWGQ GTQVTVSSGGGGSHHHHHH | 67 |
| 30 | [VHH_2.23]-E1 | EVQLVESGGGLVQPGGSLKLSCTTSGRRF SEYAVGWFRQGPGKEREFVADIGEQAENT WYAHSVLGRFTISRDDAKNTVYLEMDGLK PEDTAVYYCAADKYGVGGNAQGYYDSWG QGTQVTVSSGGGGSHHHHHH | 68 |
| 31 | [VHH_1.7]-E1 | EVQLVESGGGLVQPGGSLQLSCTTSGRKF DEYAVGWFRQGPGQEREFVADIGENAENT WYAESVLGRFTISRDDAKNTVYLEMDGLKP EDTAVYYCAADKYGVGGNAQGYYDSWGQ GTQVTVSSGGGGSHHHHHH | 69 |
| 32 | [VHH_2.24]-E1 | EVQLVESGGGWVQPGGSLKLSCTTSGRR FSEYAVGWFRQAPGKEREFVADIGEQAEN TWYAHSVLGRFTISRDDAKNTVYLQMDSLK PEDTAVYYCAADKYGVGGNAQGYYDSWG QGTQVTVSSGGGGSHHHHHH | 70 |
| 33 | [VHH_1.9]-E1 | EVQLVESGGGLVQPGGSLRLSCTTSGRTF SSYAVGWFRQAPGKEREFVADIGENADNT WYAHSVKGRFTISRDNAKNTVYLQMNSLK PEDTAVYYCAADSYGVGGGAQGYYDSWG QGTQVTVSSGGGGSHHHHHH | 84 |
| 34 | [VHH_1.8]-E1 | EVQLVESGGGLVQAGGSLRLSCTASGGTF SEYAMAWFRQAPGKEREFVTDIGESGGT WYADSVKGRFTISRDNAKNTVYLQMNSLR PEDTAVYYCAADSYGVGGGAERYYDSWG QGTQVTVSSGGGGSHHHHHH | 85 |
| 35 | [VHH_1.10]-E1 | QVQLVESGGGLVQAGGSLRLSCTASGGTF GEYAMAWFRQAPGKEREFVTDIGESGGT WYADSVKGRFTISRDNAKNTVYLQMNSLR PEDTAVYYCAADSYGVGGGAERYYDSWG QGTQVTVSSGGGGSHHHHHH | 86 |
| 47 | [VHH_1.15]-E1 | QLQLVESGGGWVQPGGSLKLSCTTSGRR FSEYAVGWFRQAPGKEREFVADIGEQAEN TWYAHSVLGRFTISRDEAKNTVYLQMNSLK PEDTAVYYCAADKYGVGGNAQGYYDSWG QGTQVTVSSGGGGSHHHHHH | 99 |

TABLE 6

List of polypeptides comprising the extension E2 of SEQ ID NO: 72.

| Polypeptide ID | Brief Description of polypeptide | Amino acid sequence | Polypeptide SEQ ID No. |
|---|---|---|---|
| 36 | [VHH_1.1]-E2 | EVQLVESGGGWVQPGGSLQLSCTTSG RRFSEYAVGWFRQAPGQEREFVADIGE QAENTWYAHSVLGRFTISRDEAKNTVYL QMDSLKPEDTAVYYCAADKYGVGGNAQ GYYDSWGQGTQVTVSSGQACPC | 73 |
| 37 | [VHH_1.2]-E2 | EVQLVESGGGLVQPGGSLKLSCTTSGR RFSEYAVGWFRQGPGKEREFVADIGEQ AENTWYAESVLGRFTISRDDAKNTVYLQ MDSLKPEDTAVYYCAADKYGVGGNAQG YYDSWGQGTQVTVSSGQACPC | 74 |
| 38 | [VHH_1.3]-E2 | EVQLVESGGGLVQPGGSLQLSCTTSGR RFSEYAVGWFRQGPGKEREFVADIGEQ AENTWYAHSVLGRFTISRDDAKNTVYLQ MDSLKPEDTAVYYCAADKYGVGGNAQG YYDSWGQGTQVTVSSGQACPC | 75 |
| 39 | [VHH_1.4]-E2 | EVQLVESGGGLVQPGGSLQLSCTTSGR KFDEYAVGWFRQAPGKEREFVADIGEN AENTWYAHSVLGRFTISRDDAKNTVYLQ MDSLKPEDTAVYYCAADKYGVGGNAQG YYDSWGQGTQVTVSSGQACPC | 76 |
| 40 | [VHH_1.5]-E2 | EVQLVESGGGLVQPGGSLQLSCTTSGR KFDEYAVGWFRQGPGKEREFVADIGEN AENTWYAESVLGRFTISRDDAKNTVYLQ MDSLKPEDTAVYYCAADKYGVGGNAQG YYDSWGQGTQVTVSSGQACPC | 77 |
| 41 | [VHH_1.6]-E2 | EVQLVESGGGLVQPGGSLKLSCTTSGR RFSEYAVGWFRQAPGKEREFVADIGEQ AENTWYAESVLGRFTISRDDAKNTVYLE MDGLKPEDTAVYYCAADKYGVGGNAQ GYYDSWGQGTQVTVSSGQACPC | 78 |
| 42 | [VHH_1.7]-E2 | EVQLVESGGGLVQPGGSLQLSCTTSGR KFDEYAVGWFRQGPGQEREFVADIGEN AENTWYAESVLGRFTISRDDAKNTVYLE MDGLKPEDTAVYYCAADKYGVGGNAQ GYYDSWGQGTQVTVSSGQACPC | 79 |
| 43 | [VHH_1.16]-E2 | EVQLVESGGGLVQPGGSLRLSCAASGF TFSNYWMYWVRQAPGKGLEWVSGINT GGSTPDYADSVKGRFAISRDNAKNTLYL QMNSLRPEDTAVYYCAADTPRVFRLDH YSPLGQGTQVTVSSGQACPC | 80 |
| 44 | [VHH_1.12]-E2 | QLQLVESGGGWVQPGGSLQLSCTTSG RTFSSYAVGWFRQAPGQEREFVADIGE NADNTWYAHSVKGRFTISRDNAKNTVYL QMDSLKPEDTAVYYCAADSYGVGGGA QGYYDSWGQGTQVTVSSGQACPC | 81 |
| 45 | [VHH_1.13]-E2 | EVQLVESGGGLVQAGGSLQLSCTASGG TFSEYAMAWFRQAPGQEREFVTDIGES GGTWYADSVKGRFTISRDNAKNTVYLQ MDSLRPEDTAVYYCAADSYGVGGGAER YYDSWGQGTQVTVSSGQACPC | 94 |
| 46 | [VHH_1.14]-E2 | QLQLVESGGGWVQPGGSLQLSCTTSG RRFSEYAVGWFRQAPGQEREFVADIGE QAENTWYAHSVLGRFTISRDEAKNTVYL QMDSLKPEDTAVYYCAADKYGVGGNAQ GYYDSWGQGTQVTVSSGQACPC | 95 |
| 48 | [VHH_1.17]-E2 | EVQLVESGGGLVQPGGSLQLSCAASGF TFSNYWMYWVRQAPGQGLEWVSGINT GGSTPDYADSVKGRFAISRDNAKNTLYL QMDSLRPEDTAVYYCAADTPRVFRLDH YSPLGQGTQVTVSSGQACPC | 102 |

It is understood that the above extensions, as well as the exemplified polypeptides (comprising an $V_HH$ and an extension), are examples only and not limitative in any way. Various alternatives are clear to one of skill in the art. For example, it is understood that extension E2 (SEQ ID No. 72) may be provided at the N-terminal of the ISVD. For instance, should this be the case with $V_HH\_1.6$, this may create a polypeptide that may be briefly described as E2-[VHH_1.6].

One of skill further understands that a portion of any one of the extensions E1-E6 may be used as an extension. In certain embodiments, it may be desirable to shorten the extension, such as for instance shorten extension E2 (SEQ ID No. 72). For instance, in one embodiment, the extension may have 4 or 5 contiguous amino acid residues of the sequence of extension E2 (SEQ ID No. 72), such that the extension comprises the sequence GQAC (E7; SEQ ID No. 128) or GQACP (E8; SEQ ID No. 129), for instance. In one embodiment, the extension may comprise at least 5 contiguous nucleotides of SEQ ID No. 72. In another embodiment, the extension may comprise or consist of an amino acid sequence of GQACP (E8; SEQ ID No. 129). In another embodiment, the extension may comprise at least 4 contiguous nucleotides of SEQ ID No. 72. In another embodiment, the extension may comprise or consist of an amino acid sequence of GQAC (E7; SEQ ID No. 128). These are examples only and are not to be construed as limitative in any way.

Polypeptide Derivatives

In a third aspect, the disclosure relates to a polypeptide derivative comprising an ISVD according to the first aspect of the invention or a polypeptide according to the second aspect of the invention, and a substituent. As is understood by one of skill in the art, the term polypeptide derivative in this context refers to the resultant of a construct comprised of a polypeptide (ie. the polypeptide of an ISVD in accordance with the first aspect of the invention, or a polypeptide comprising an ISVD in accordance with the second aspect of the invention) which further carries a at least one substituent, as will be discussed in detail below.

As will be described in detail below, the substituent may comprise a series of individually defined moieties; these moieties may be referred to as "substituent elements". Non-limiting examples of "substituent elements" are a "protractor"/"protraction moiety" (P) and a "linker" ($L_p$). Such linker ($L_p$) may be composed of one or various "linker elements". For ease of understanding, a non-limiting figurative description of an exemplary compound (compound 9) in accordance with this disclosure may be referred to in FIGS. 3A and 3B. An preferred polypeptide derivative is also provided as Chem. 31 below.

Conveniently, the substituent is capable of extending the half-life of the polypeptide derivative. For instance, the polypeptide derivative has a longer half-life than the corresponding polypeptide.

The substituent may be capable of forming non-covalent binding interactions with albumin, thereby promoting the circulation of the compound in the blood stream, and thus having the effect of protracting the time of which the compound is present in the blood stream, since the aggregate of the substituent-carrying compound and albumin is only slowly disintegrated to release the free form of the compound; thus, the substituent, as a whole, may also be referred to as an "albumin-binding moiety", and the substituent may be said to have a "protracting effect". Alternatively, it can be said that the substituent is a half-life extending moiety.

A substituent may comprise a portion which is particularly relevant for the albumin binding and thereby the protraction, which portion may be referred to as a "protractor" or a "protracting moiety". The protraction or protraction moiety is optionally attached to the ISVD or polypeptide via a "linker" ($L_p$). Such linker ($L_p$) may be composed of one or various "linker elements". The protractor/protraction moiety (P) and linker ($L_p$) may be provided in series such as to form P-$L_p$ or $L_p$-P, or more explicitly P-$L_p$-Rn or Rn-$L_p$-P, wherein Rn refers to an attachment point of an ISVD or polypeptide, and n is an integer such that each attachment point can be labeled R1, R2, R3, and so forth where R1≠R2≠R3 and so forth.

Figure 1D:
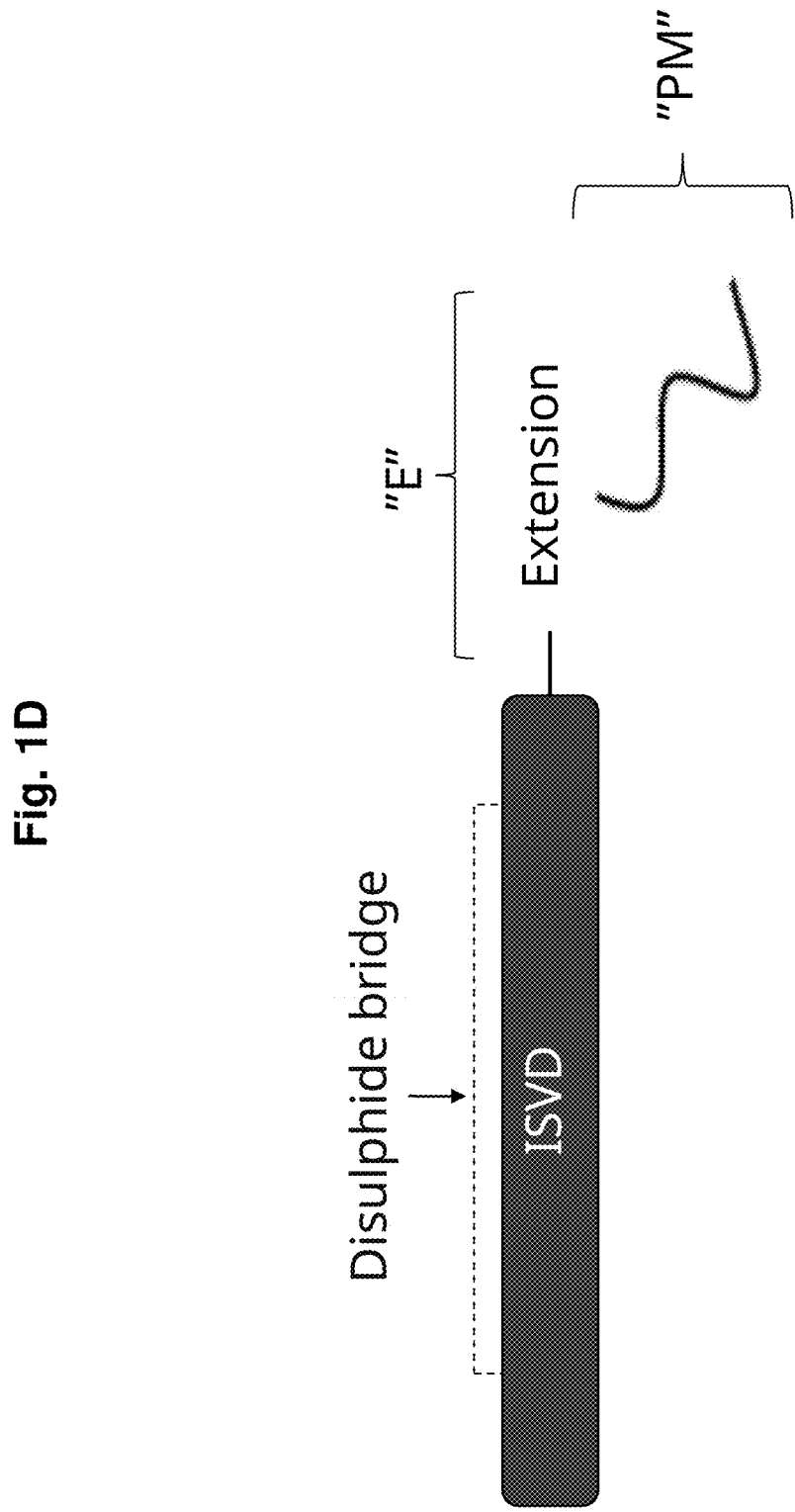
Figure 1E:
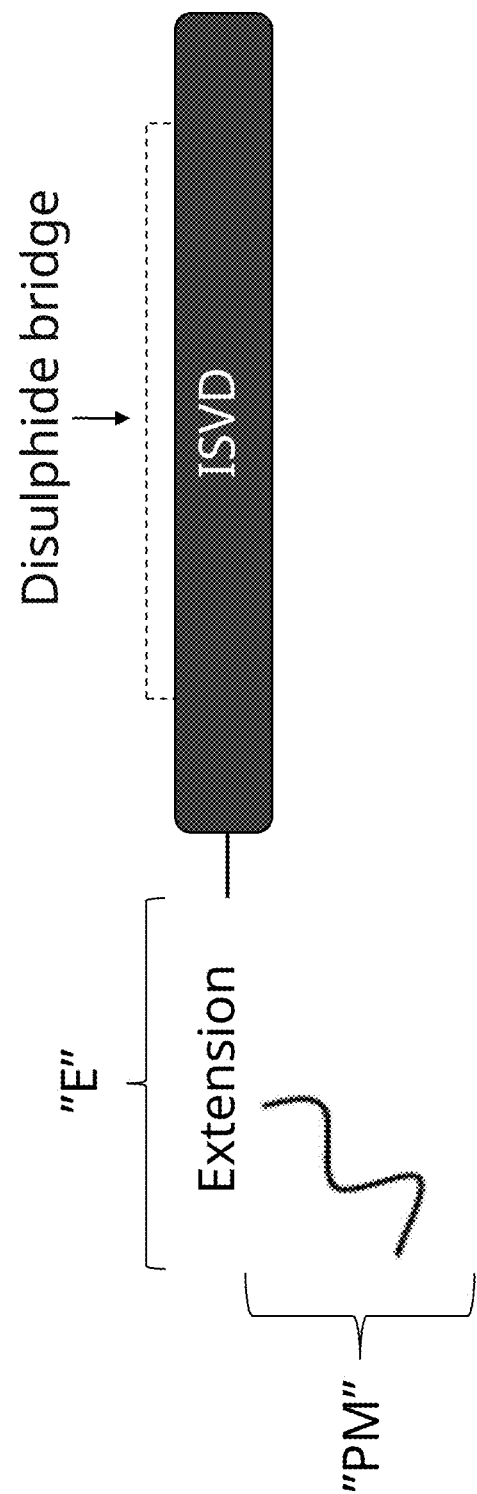
Figure 2:
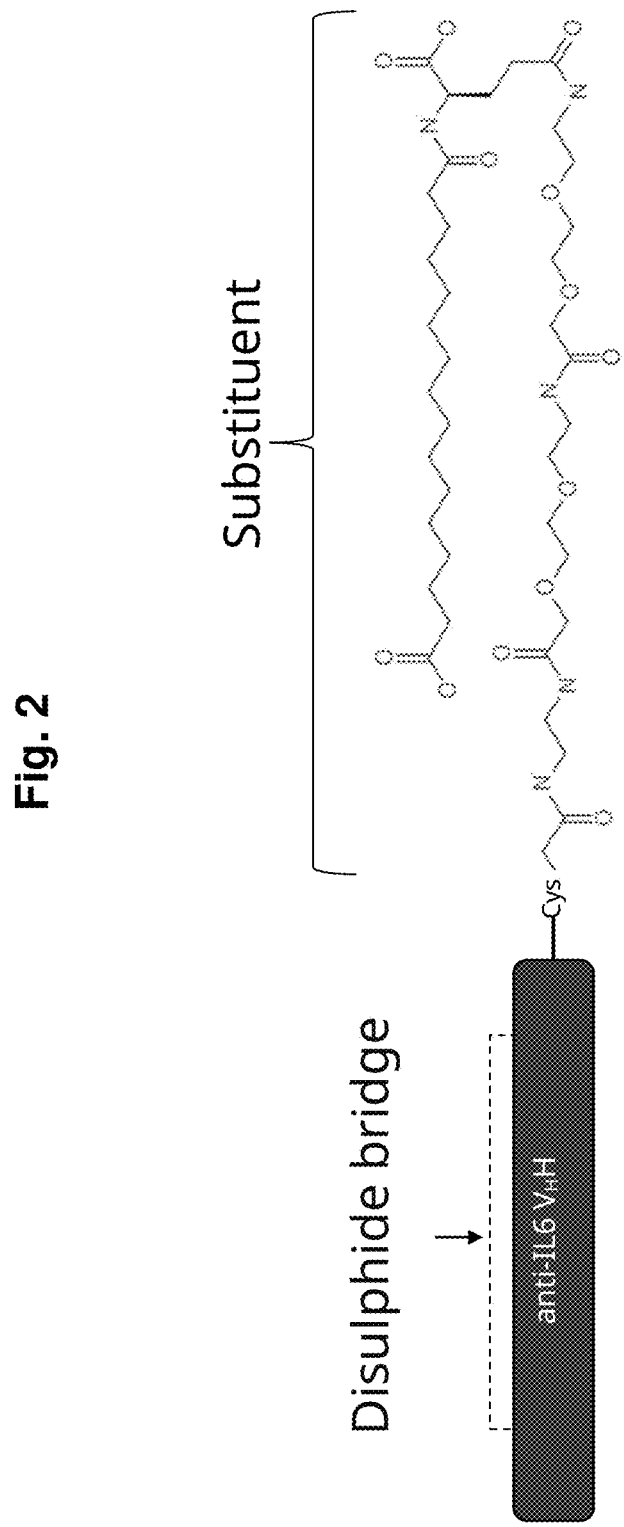
FIG. 2 shows a non-limiting example of an anti-IL-6 polypeptide derivative comprising a single substituent. The dashed line indicates a disulphide bond. Hydrogen atoms have been omitted for clarity.

Written otherwise, in some embodiments, the polypeptide derivative may have a structure such as [ISVD]-E-$L_p$-P (see FIG. 1A or 1D for instance) or P-$L_p$-E-[ISVD] (see FIG. 1B or 1E for instance), wherein "[ISVD]" refers to the ISVD in accordance with the first aspect of the invention, "E" refers to an extension (such as E1, E2, E3, etc.) as discussed above (such that the result of "[ISVD]-E" or "E-[ISVD]" corresponds to a polypeptide in accordance with the second aspect of the invention), "$L_p$" refers to the linker and "P" refers to a protraction moiety. It is understood that, while in these examples only one substituent is described as attached to the extension E, one or more substituent(s) may be provided and said one or more substituents may be attached different residues of the same extension E.

Further, one of skill understands that the above examples of polypeptide derivatives are examples only and should not be construed as limitative in any way. For instance, in some embodiments, the substituent may be attached to a residue between the N-terminal and C-terminal of an ISVD or polypeptide comprising an ISVD, such as is illustratively shown in FIG. 1C (or FIG. 1F should the substituent consist of a protraction moiety).

The polypeptide derivatives disclosed herein conveniently have at least one, preferably two substituent(s). In some embodiments, each of the substituent(s) is attached to a corresponding cysteine or lysine amino acid residue of the extension.

In some embodiments, the one or more substituents are attached to a polypeptide of the disclosure, such as a polypeptide comprising an ISVD in accordance with the second aspect of the invention. In some embodiments, a substituent is attached to an ISVD of the disclosure, such as an ISVD according to the first aspect of the invention.

Protractor/Protraction Moiety

The substituent may comprise a portion which is particularly relevant for the albumin binding and thereby the protraction, which portion may be referred to as a "protractor" or a "protracting moiety". The term "protractor" and "protracting moiety" are used interchangeably herein. The "protractor" may be a lipophilic moiety (e.g. a fatty acid). The "protractor" may be a fatty acid (e.g. a $C_{16}$-$C_{22}$ carboxylic acid). In preferred embodiments, the protractor is a $C_{16}$ or a $C_{18}$ carboxylic acid. A non-limiting example of a "protractor" is shown in Table 7. In the chemical structure identified as Chem. 1,

is used to describe an attachment point to the linker or the polypeptide via a covalent bond.

The protractor/protraction moiety ("P") may comprise a tetrazole group. The protractor/protraction moiety may comprise an aryl group. The protractor/protraction moiety may comprise a sulfonic acid group. The protractor/protraction moiety may comprise a phenoxy group. The protractor/protraction moiety may comprise a benzoic acid group.

TABLE 7

Non-limiting example of a "protractor"/"protraction moiety".

| Chem. ID | Structure |
|---|---|
| Chem. 1 | HO-C(=O)-(CH2)n-C(=O)- wherein n = 12, 14, 16, 18 or 20 |

Linker ($L_p$)

The substituent may comprise a portion between the protracting moiety and the point of attachment to the amino acid residue of the polypeptide, which portion may be referred to as a "linker ($L_p$)". The linker may comprise several "linker elements". The linker elements may be selected so that they improve the overall properties of the molecule, e.g., so that they improve the oral bioavailability, the conversion half-life, and/or the protracting effect, thus improving the overall exposure profile upon oral administration of the compound.

Non-limiting examples of linker elements are listed in Table 8. In the chemical structures identified as Chem. 2-6,

is used to describe an attachment point to the protractor or to the polypeptide.

TABLE 8

Non-limiting examples of linker elements.

| Chem. ID | Structure | Abbreviation |
|---|---|---|
| Chem. 2 | (structure with N-H, COOH side chain) | γGlu |
| Chem. 3 | (structure with N-H, ethylene glycol linker) | Ado |
| Chem. 4 | (structure with N-H, glycine) | Gly |
| Chem. 5 | (structure with N-H, lysine with NH2) | εLys |
| Chem. 6 | (structure with N-H, ethylenediamine carbonyl) | — |

Substituent

In some embodiments, the substituent is represented by "$L_p$-P", wherein P comprises or consists of a lipophilic moiety with a distal carboxylic acid and P has protracting properties.

In some embodiments, P is Chem. 1. The term "distal carboxylic acid" as used herein in context of the lipophilic moiety, refers to a carboxylic acid attached to the most remote (terminal) point of the lipophilic moiety relative to the lipophilic moiety's point of attachment to adjacent moieties, e.g. in the compounds as described herein, the lipophilic moiety with distal carboxylic acid (e.g. Chem. 1) is a protracting moiety, and the carboxylic acid is attached to the most remote (terminal) point of the lipophilic moiety relative to the lipophilic moiety's point of attachment to the adjacent linker elements (e.g. Chem. 2, Chem. 3, Chem. 4, Chem. 5, or Chem. 6) or, in the absence of linker elements, relative to the lipophilic moiety's point of attachment to the adjacent polypeptide. A non-limiting example of a lipophilic moiety with distal carboxylic acid is Chem. 1.

In some embodiments, P is Chem. 1 and $L_p$ is a linker comprising linker element(s), wherein each linker element is selected from a group consisting of Chem. 2, Chem. 3, Chem. 4, Chem. 5, and Chem. 6. Non-limiting examples of substituents comprising a lipophilic moiety are listed in Table 9. In some embodiments, the substituent is selected from Table 9.

TABLE 9
Non-limiting examples of substituents.
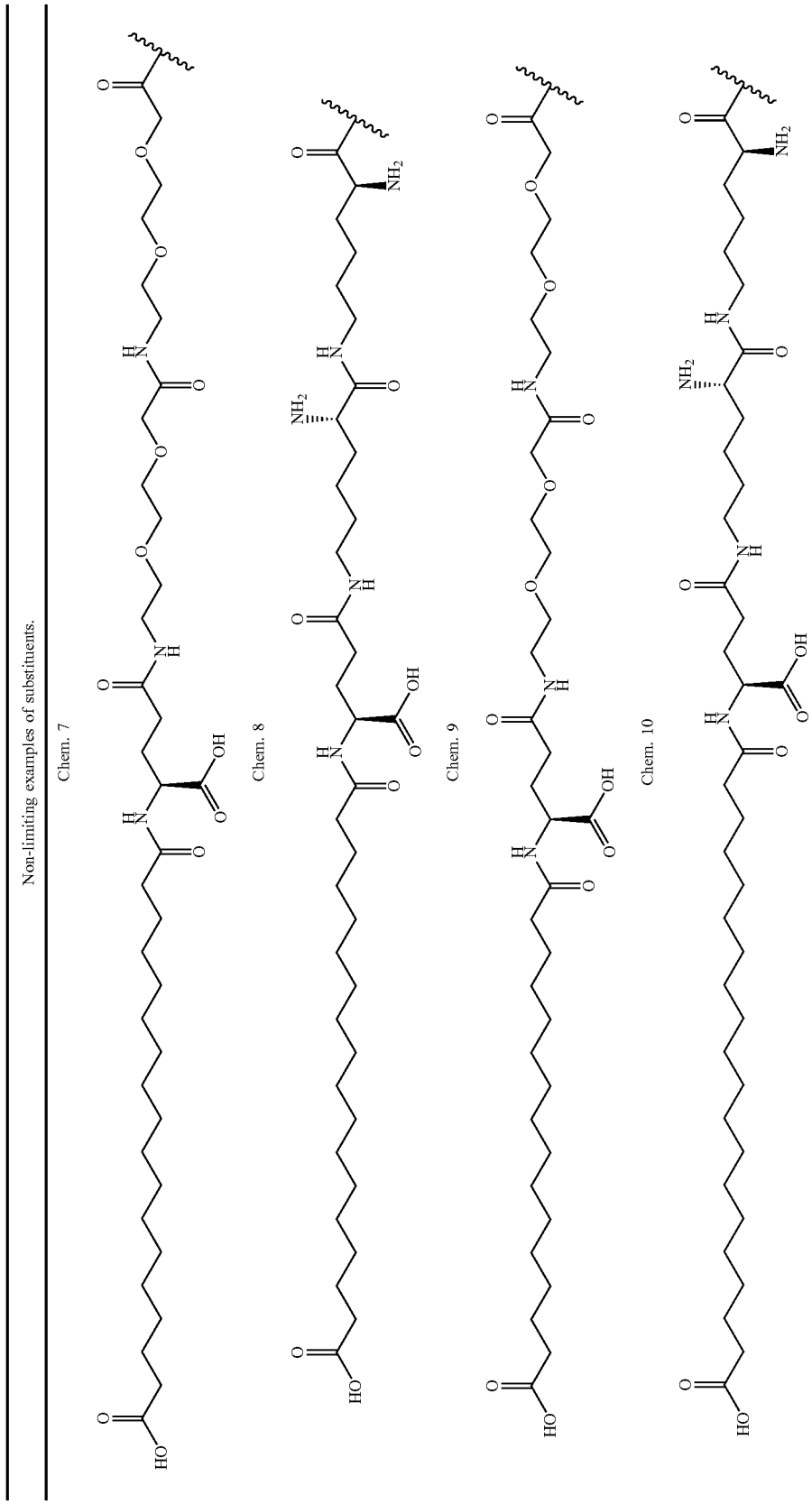

TABLE 9-continued
Non-limiting examples of substituents.
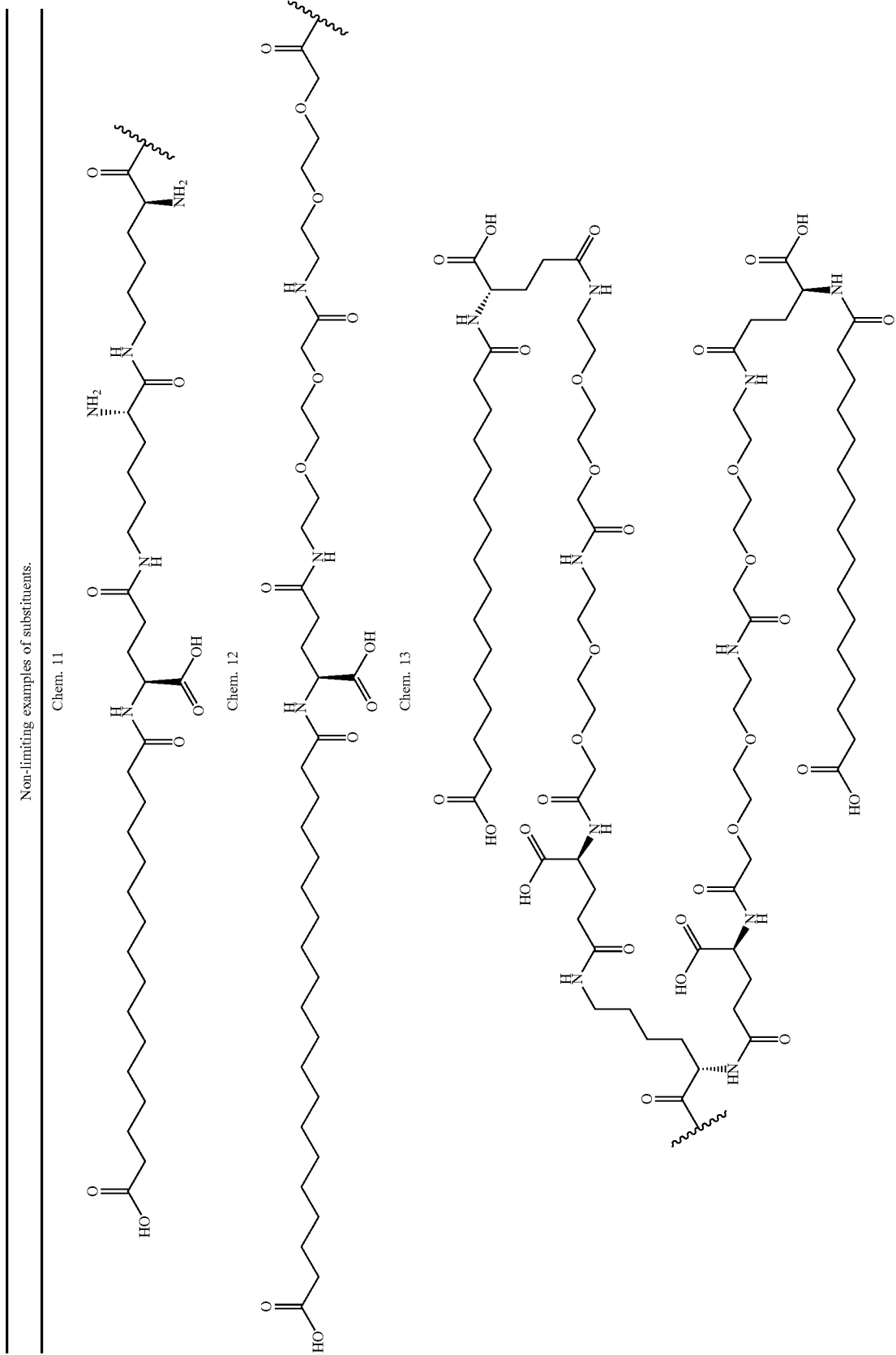
Chem. 11
Chem. 12
Chem. 13

TABLE 9-continued
Non-limiting examples of substituents.
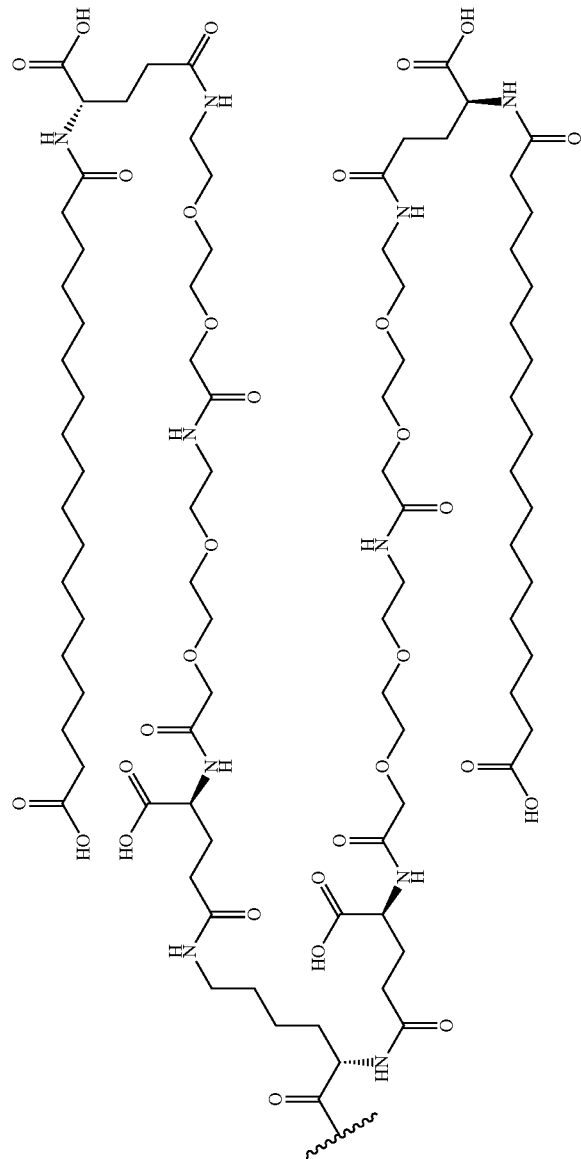
Chem. 14
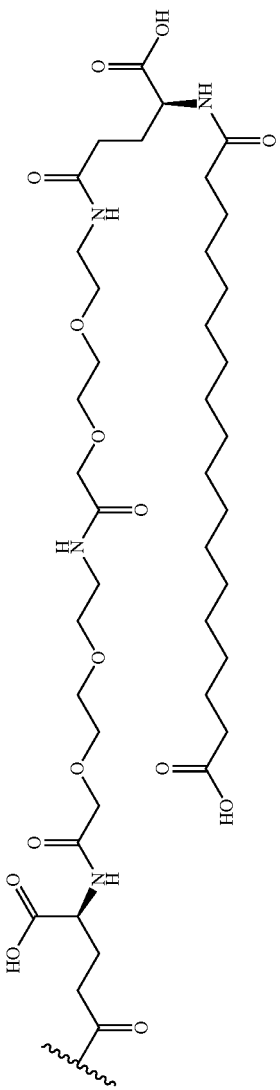
Chem. 15

TABLE 9-continued
Non-limiting examples of substituents.
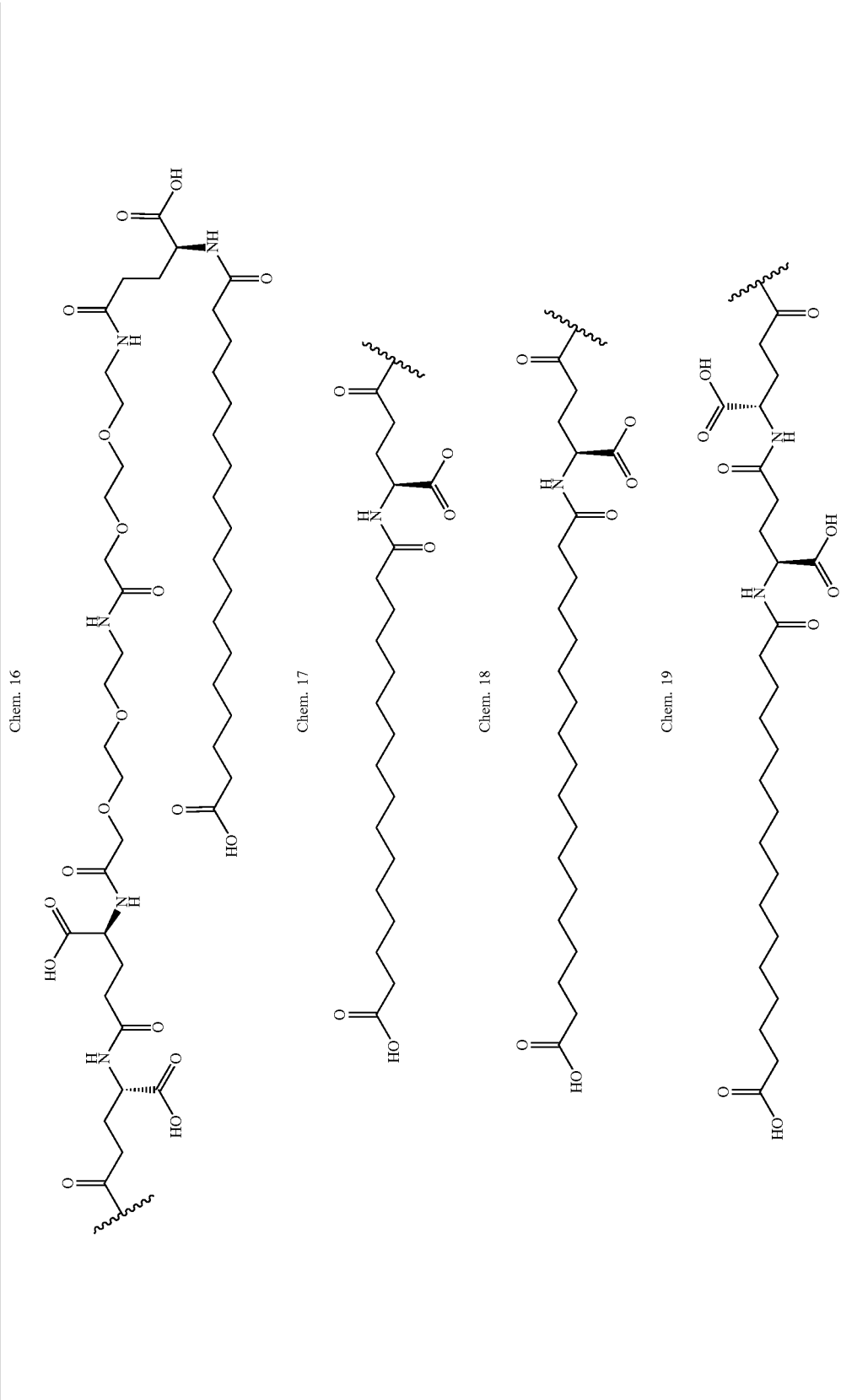
Chem. 16
Chem. 17
Chem. 18
Chem. 19

TABLE 9-continued
Non-limiting examples of substituents.
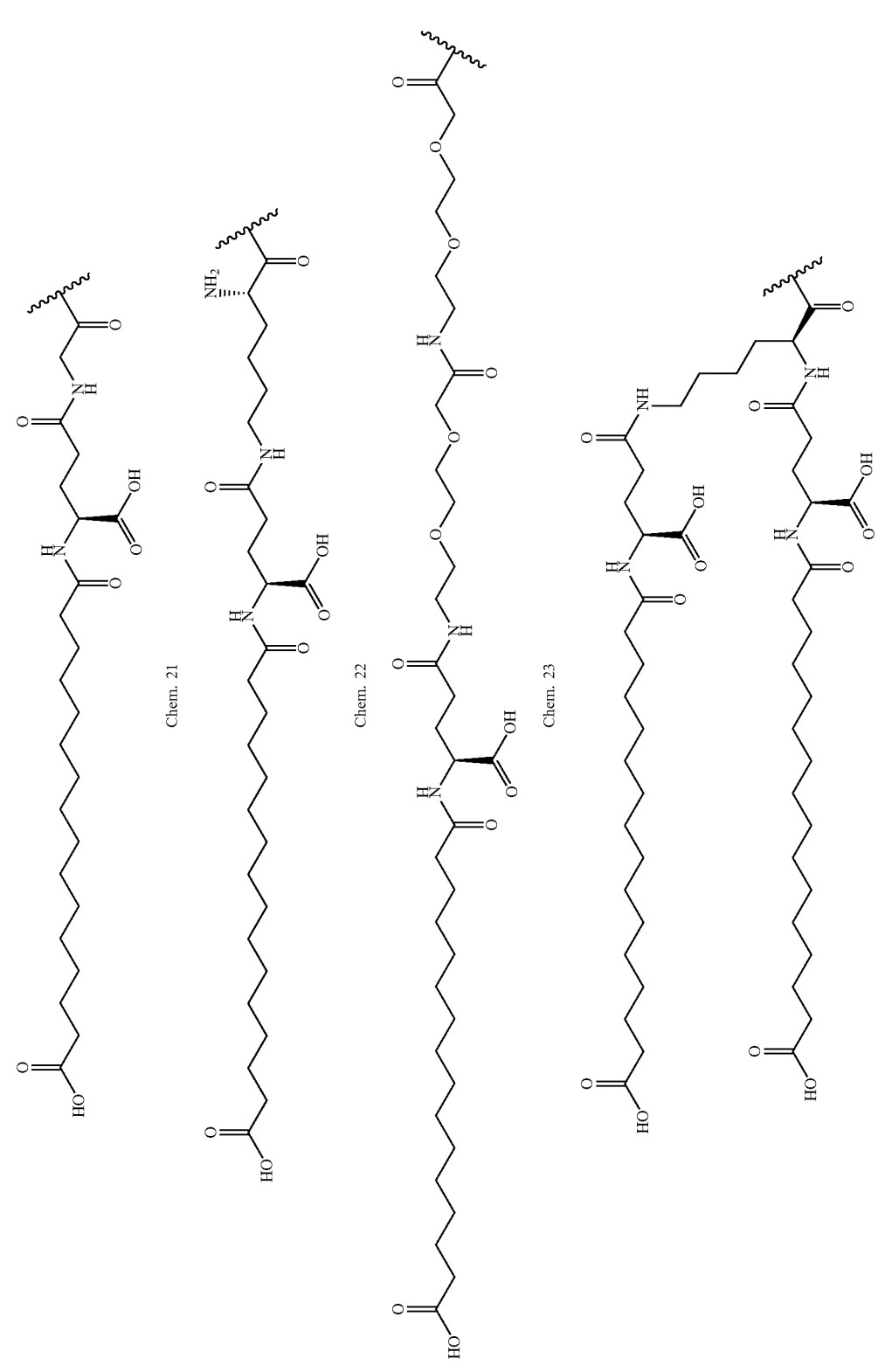

TABLE 9-continued
Non-limiting examples of substituents.
Chem. 24
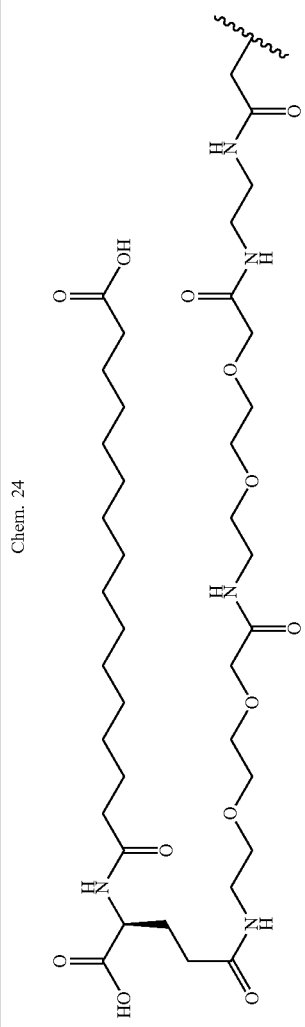
Chem. 25
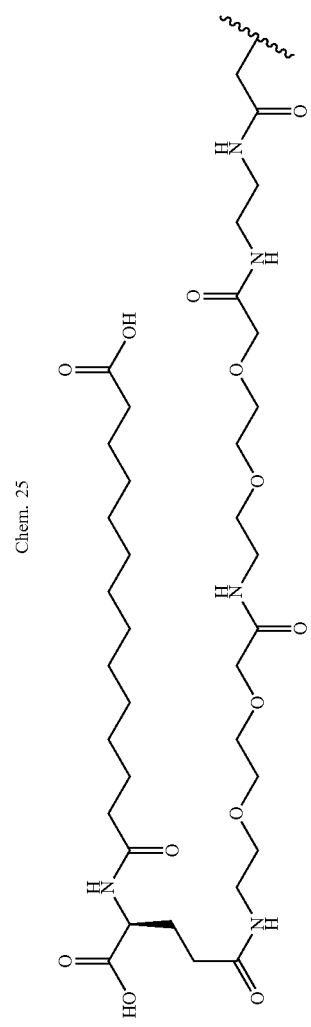
Chem. 26
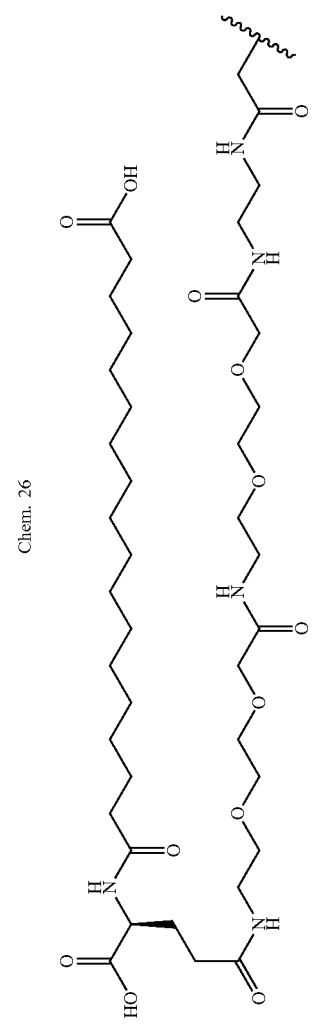

TABLE 9-continued
Non-limiting examples of substituents.
Chem. 27
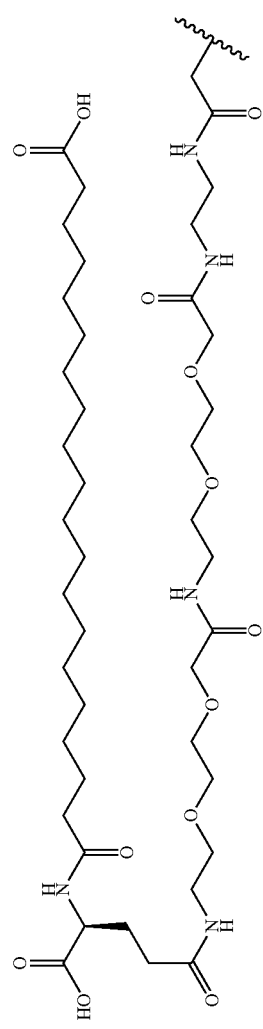

In some embodiments, the substituent comprises a protractor/protraction moiety according to Chem. 1, wherein n is 14, 16 or 18; and optionally a linker, wherein the linker comprises one or more γGlu (Chem. 2), and/or one or more Ado (Chem. 3) and/or one or more Gly (Chem. 4) and/or one or more εLys (Chem. 5) and/or Chem. 6. In some embodiments, the substituent is selected from Table 9. In preferred embodiments, each substituent is Chem. 24.

In preferred embodiments, the polypeptide derivative comprises two or more substituents. The two or more substituents may be the same or different. In further preferred embodiments, the polypeptide derivative comprises two substituents, wherein each substituent is represented by Chem. 24.

In some embodiments, the polypeptide derivative is selected from the list consisting of compound 1, compound 2, compound 3, compound 4, compound 5, compound 6, compound 7, compound 8, compound 9, and compound 10. In a preferred embodiment, the polypeptide derivative is compound 9.

Non-limiting examples of polypeptide derivatives are described in Examples section and Table 10.

TABLE 10

List of non-limiting examples of polypeptide derivatives.

| Compound ID | Substituent[1] | Polypeptide[2] $V_HH$ | extension |
|---|---|---|---|
| 1 | 2xChem. 24 | $V_HH$_1.12; SEQ ID NO: 34 | E2; SEQ ID NO: 72 |
| 2 | 2xChem. 24 | $V_HH$_1.13; SEQ ID NO: 35 | E2; SEQ ID NO: 72 |
| 3 | 2xChem. 24 | $V_HH$_1.14; SEQ ID NO: 36 | E2; SEQ ID NO: 72 |
| 4 | 2xChem. 24 | $V_HH$_1.1; SEQ ID NO: 23 | E2; SEQ ID NO: 72 |
| 5 | 2xChem. 24 | $V_HH$_1.2; SEQ ID NO: 24 | E2; SEQ ID NO: 72 |
| 6 | 2xChem. 24 | $V_HH$_1.3; SEQ ID NO: 25 | E2; SEQ ID NO: 72 |
| 7 | 2xChem. 24 | $V_HH$_1.4; SEQ ID NO: 26 | E2; SEQ ID NO: 72 |
| 8 | 2xChem. 24 | $V_HH$_1.5; SEQ ID NO: 27 | E2; SEQ ID NO: 72 |
| 9 | 2xChem. 24 | $V_HH$_1.6; SEQ ID NO: 28 | E2; SEQ ID NO: 72 |
| 10 | 2xChem. 24 | $V_HH$_1.7; SEQ ID NO: 29 | E2; SEQ ID NO: 72 |
| 12 | 2xChem. 24 | VhH_1.17; SEQ ID NO: 103 | E2; SEQ ID NO: 72 |

[1] Substituent attachment sites are Cys4 and Cys6 of E2 (SEQ ID NO: 72).
[2] Polypeptide consists of a $V_HH$ that has an extension at its C-terminal end. An exemplary structure can be seen in FIG. 3A/3B, which shows Compound 9.

In a preferred embodiment, the polypeptide derivative has a structure as follows:

(Chem. 31, SEQ ID NO: 78)

EVQLVESGGG LVQPGGSLKL SCTTSGRRFS EYAVGWFRQA PGKEREFVAD IGEQAENTWY
AESVLGRFTI SRDDAKVTVY LEMDGLKPED TAVYYCAADK YGVGGNAQGY YDSWGQGTQV

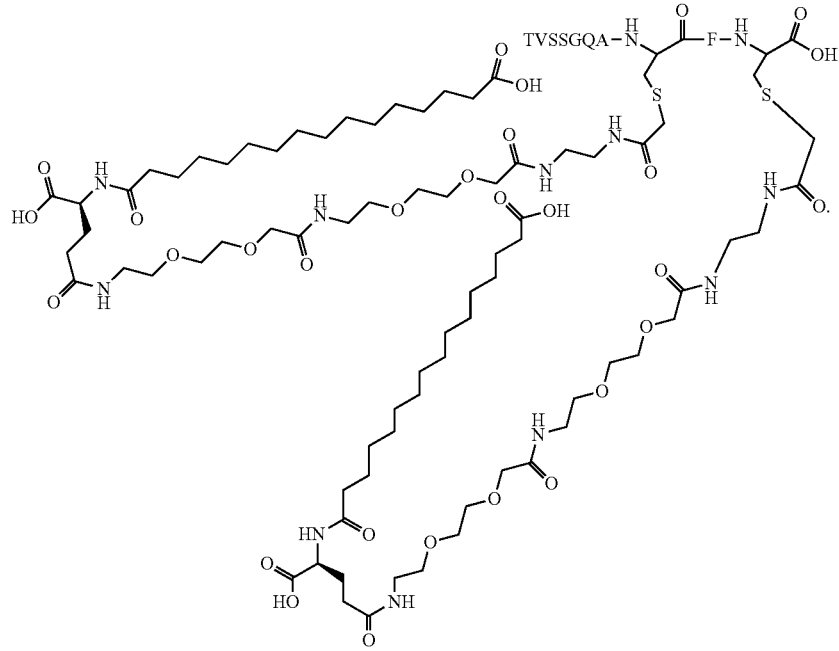

In some embodiments, the polypeptide derivative has a small molecular weight. In some embodiments, the molecular weight of the polypeptide derivative is between 10 kDa and 20 kDa. In some embodiments, the molecular weight of the polypeptide derivative is about 10 kDa, about 11 kDa, about 12 kDa, about 13 kDa, about 14 kDa, about 15 kDa, about 15.5 kDa, about 16 kDa, about 17 kDa, about 18 kDa, about 19 kDa or about 20 kDa. In some embodiments, the molecular weight of the polypeptide derivative is between 12-18 kDa, between 13-17 kDa or 14-16 kDa. In preferred embodiments, the molecular weight of the polypeptide derivative is between 12-18 kDa. In an even preferable embodiment, the molecular weight of the polypeptide derivative is between 14-16 kDa. In an even more preferable embodiment, the molecular weight of the polypeptide derivative is about 15.5 kDa. In some embodiments, the molecular weight of the polypeptide derivative is about 15 kDa.

One of skill in the art understands that the polypeptide derivative of the present disclosure may be capable of binding to IL-6 and providing therapeutic effect while further providing a construct of small size, such as a molecular weight of between 12-18 kDa for instance.

Antibodies or Fragments Thereof

In a fourth aspect, the disclosure relates to an antibody or antibody fragment or an antibody derivative or a polypeptide derivative, wherein the antibody or the antibody fragment or the antibody derivative or polypeptide derivative is capable of binding IL-6 at an epitope comprising at least the amino acid residues 26, 30, 33, 34, 73, 74, 75, 78, 171, 175, 178, 179, 182, and 183, as set forth in SEQ ID NO: 89.

In preferred embodiments, the antibody or the antibody fragment or the antibody derivative comprises tryptophan in a position that allows the antibody or the antibody fragment or the antibody derivative to form cation-pi interaction with Arg179 and/or hydrophobic interaction with Phe78, as set forth in SEQ ID NO: 89.

In preferred embodiments, the antibody or the antibody fragment or the antibody derivative is a polypeptide or polypeptide derivative comprising an ISVD, wherein the ISVD comprises a tryptophan in position 58 or 59.

In further preferred embodiments, the antibody or the antibody fragment or the antibody derivative is a polypeptide or polypeptide derivative comprising an ISVD, wherein the ISVD comprises a tryptophan capable of forming cation-pi interaction with Arg179 and/or hydrophobic interaction with Phe78, as set forth in SEQ ID NO: 89.

In a further aspect, the disclosure relates to an antibody or antibody fragment or an antibody derivative or a polypeptide derivative, wherein the antibody or the antibody fragment or the antibody derivative or polypeptide derivative is capable of binding IL-6 at an epitope comprising at least the amino acid residues 24, 27, 28, 31, 88, 92, 95, 99, 114, 116, 117, 118, 120, 121, 123, 124, 125, 127, 128, 138, and 139 as set forth in SEQ ID NO: 89.

Methods and Uses of the ISVD/Polypeptide/Polypeptide Derivative

In fifth aspect, the disclosure relates to a nucleic acid molecule, preferably in isolated form, encoding an ISVD according to first aspect of the disclosure or a polypeptide according the second aspect of the disclosure. The nucleic acid molecules may be DNA and/or RNA. Genomic DNA, cDNA, mRNA, or other RNA; of synthetic origin, or any combination thereof can encode an ISVD or polypeptide according to the disclosure.

In sixth aspect, the disclosure relates to an expression vector comprising a nucleic acid molecule according to the fifth aspect of the disclosure.

In seventh aspect, the invention relates to a host cell carrying an expression vector according to the sixth aspect of the disclosure.

In an eighth aspect, the invention relates to a method of manufacturing an ISVD according to first aspect of the disclosure or a polypeptide according the second aspect of the disclosure or a polypeptide derivative according to the third aspect of the disclosure, comprising the steps of e. Culturing a host cell according to the seventh aspect of the disclosure under conditions that allow expression of an ISVD according to the first aspect of the disclosure or a polypeptide according to the second aspect of the disclosure;

f. Recovering the ISVD or the polypeptide obtainable in step a; and/or optionally g. Attaching one or more substituent(s) capable of extending the half-life of the polypeptide, optionally wherein each substituent is Chem. 24; and/or optionally h. purifying the so-obtained ISVD or polypeptide or polypeptide derivative.

In some embodiments, the ISVDs according to the first aspect of the disclosure or the polypeptides according to the second aspect of the disclosure are expressed at a yield of at least 0.5 g/L in the cell supernatant after initial fermentation, preferably at a yield of >1 g/L. In some embodiments, the ISVDs according to the first aspect of the disclosure or the polypeptides according to the second aspect of the disclosure are expressed at a yield of about 0.5-5 g/L in the cell supernatant after initial fermentation. Solubility should be >5 mg/ml, preferably, >20 mg/mL, without significant aggregation or degradation of the ISVDs or polypeptides.

Pharmaceutical Compositions

In a ninth aspect, the disclosure relates to a pharmaceutical composition comprising an ISVD according to the first aspect of the invention or a polypeptide according to the second aspect of the disclosure or a polypeptide derivative according to the third aspect of the disclosure. Preferably, the pharmaceutical composition is for oral administration.

In preferred embodiments, the pharmaceutical composition is a solid oral dosage form, such as a tablet.

In some embodiments, the pharmaceutical composition comprises an adsorption enhancer. In preferred embodiments, the enhancer is a salt of N-(8-2-hydroxybenzoyl) amino) caprylic acid. In particularly preferred embodiments, the enhancer is sodium N-(8-(2-hydroxybenzoyl)amino) caprylate (SNAC).

In some embodiments, the pharmaceutical composition comprises a hydrotrope. In preferred embodiments, the hydrotrope is nicotinamide.

In some embodiments, the composition comprises a lubricant. In preferred embodiments, the lubricant is magnesium stearate or sodium fumarate.

In some embodiments, the pharmaceutical composition comprises an ISVD according to the first aspect of the disclosure or a polypeptide according to the second aspect of the disclosure or a polypeptide derivative according to the third aspect of the disclosure, SNAC, nicotinamide, and optionally a lubricant such as magnesium stearate or sodium fumarate. In a preferred embodiment, the pharmaceutical composition comprises compound 9 (Table 10) and SNAC, and optionally also comprises nicotinamide and a lubricant such as e.g. magnesium stearate; sodium fumarate.

Medical Use

In a tenth aspect, the disclosure relates to an ISVD according to the first aspect of the disclosure or a polypeptide according to the second aspect of the disclosure or a polypeptide derivative according to the third aspect of the disclosure or a pharmaceutical composition according to the ninth aspect of the disclosure for use in medicine. In some embodiments, the disclosure relates to an ISVD according to the first aspect of the disclosure or a polypeptide according to the second aspect of the disclosure or a polypeptide derivative according to the third aspect of the disclosure or a pharmaceutical composition according to the ninth aspect of the disclosure for use in the treatment of inflammatory disease.

In some embodiments, the disclosure relates to an ISVD according to the first aspect of the disclosure or a polypeptide according to the second aspect of the disclosure or a polypeptide derivative according to the third aspect of the disclosure or a pharmaceutical composition according to the ninth aspect of the disclosure for use in the treatment of inflammatory disease wherein the human subject has or is at risk of having a High-Sensitivity C-reactive Protein (Hs-CRP) above a value of 1 mg/L, preferably above a value of 1.5 mg/L, most preferably above or equal to a value of 2 mg/L. In some embodiments, the human subject has or is at risk of having a Hs-CRP above or equal to a value of 3 mg/L.

In some embodiments, the disclosure relates to an ISVD according to the first aspect of the disclosure or a polypeptide according to the second aspect of the disclosure or a polypeptide derivative according to the third aspect of the disclosure or a pharmaceutical composition according to the ninth aspect of the disclosure for use in the treatment of inflammatory disease wherein the human subject has or is at risk of having a High-Sensitivity C-reactive Protein (hsCRP) value above or equal to 2 mg/L (hsCRP≥2 mg/L). In some embodiments, the human subject has or is at risk of having a High-Sensitivity C-reactive Protein (hsCRP) value above or equal to 3 mg/L (hsCRP≥3 mg/L).

In some embodiments, the disclosure relates to an ISVD according to the first aspect of the disclosure or a polypeptide according to the second aspect of the disclosure or a polypeptide derivative according to the third aspect of the disclosure or a pharmaceutical composition according to the ninth aspect of the disclosure for use in the treatment of cardiovascular disease.

In some embodiments, the disclosure relates to an ISVD according to the first aspect of the disclosure or a polypeptide according to the second aspect of the disclosure or a polypeptide derivative according to the third aspect of the disclosure or a pharmaceutical composition according to the ninth aspect of the disclosure for use in the treatment of atherosclerotic cardiovascular disease (ASCVD).

In some embodiments, the disclosure relates to an ISVD according to the first aspect of the disclosure or a polypeptide according to the second aspect of the disclosure or a polypeptide derivative according to the third aspect of the disclosure or a pharmaceutical composition according to the ninth aspect of the disclosure for use in the treatment of atherosclerotic cardiovascular disease (ASCVD) defined as stroke and/or myocardial infarction (MI) and/or peripheral arterial disease (PAD).

In some embodiments, the disclosure relates to an ISVD according to the first aspect of the disclosure or a polypeptide according to the second aspect of the disclosure or a polypeptide derivative according to the third aspect of the disclosure or a pharmaceutical composition according to the ninth aspect of the disclosure for use in the treatment of stroke and/or myocardial infarction (MI) and/or peripheral arterial disease (PAD).

In some embodiments, the invention relates to the use of an ISVD according to the first aspect of the disclosure or a polypeptide according to the second aspect of the disclosure or a polypeptide derivative according to the third aspect of the disclosure or a pharmaceutical composition according to the ninth aspect of the disclosure in the manufacture of a medicament for the treatment of atherosclerotic cardiovascular disease (ASCVD).

In some embodiments, the invention relates to a method of treating inflammatory disease the method comprising administering to a subject an effective amount of an ISVD according to the first aspect of the disclosure or a polypeptide according to the second aspect of the disclosure or a polypeptide derivative according to the third aspect of the disclosure or a pharmaceutical composition according to the ninth aspect of the disclosure.

In some embodiments, the invention relates to a method of treating cardiovascular disease the method comprising administering to a subject an effective amount of an ISVD according to the first aspect of the disclosure or a polypeptide according to the second aspect of the disclosure or a polypeptide derivative according to the third aspect of the disclosure or a pharmaceutical composition according to the ninth aspect of the disclosure.

In some embodiments, the invention relates to a method of treating cardiovascular disease the method comprising administering to a subject suffering from chronic kidney disease (CKD) an effective amount of an ISVD according to the first aspect of the disclosure or a polypeptide according to the second aspect of the disclosure or a polypeptide derivative according to the third aspect of the disclosure or a pharmaceutical composition according to the ninth aspect of the disclosure.

In some embodiments, the invention relates to a method of treating cardiovascular disease, the method comprising administering to a subject suffering from stroke and/or myocardial infarction (MI) and/or peripheral arterial disease (PAD) an effective amount of an ISVD according to the first aspect of the disclosure or a polypeptide according to the second aspect of the disclosure or a polypeptide derivative according to the third aspect of the disclosure or a pharmaceutical composition according to the ninth aspect of the disclosure.

In some embodiments, the invention relates to a method of treating Atherosclerotic cardiovascular disease (ASCVD) the method comprising administering to a subject suffering from stroke and/or myocardial infarction (MI) and/or peripheral arterial disease (PAD) an effective amount of an ISVD according to the first aspect of the disclosure or a polypeptide according to the second aspect of the disclosure or a polypeptide derivative according to the third aspect of the disclosure or a pharmaceutical composition according to the ninth aspect of the disclosure.

The term "treatment", as used herein, refers to the medical treatment of any human subject in need thereof. The treatment may be preventive, prophylactic, palliative, symptomatic and/or curative. The timing and purpose of said treatment may vary from one individual to another, according to the status of the subject's health.

List of Embodiments

The invention is further described by the following non-limiting embodiments.

Immunoglobulin Single Variable Domain (ISVD)

1. An immunoglobulin single variable domain (ISVD) having the following complementarity-determining region (CDR) sequences:
    CDR1: EYAVG (SEQ ID NO: 3), or an amino acid sequence with 1 or 2 amino acid difference(s) with SEQ ID NO: 3;
    CDR2: DIGEQAENTWYAESVLG (SEQ ID NO: 7), or an amino sequence with 1, 2, 3, or 4 amino acid difference(s) with SEQ ID NO: 7;
    CDR3: DKYGVGGNAQGYYDS (SEQ ID NO: 17), or an amino acid sequence with 1 or 2 amino acid difference(s) with SEQ ID NO: 17. (Kabat definition)

2. An immunoglobulin single variable domain (ISVD) comprising
    a CDR1 selected from the list consisting of SEQ ID NO: 3, SEQ ID NO: 4, SEQ ID NO: 5, or SEQ ID NO: 6;
    a CDR2 selected from the list consisting of SEQ ID NO: 7, SEQ ID NO: 8, SEQ ID NO: 9, SEQ ID NO: 12, SEQ ID NO: 13, SEQ ID NO: 14, SEQ ID NO: 15, and SEQ ID NO: 16; and
    a CDR3 selected from the list consisting of SEQ ID NO: 17, SEQ ID NO: 18, SEQ ID NO: 19, and SEQ ID NO: 20. (Kabat definition)

3. An ISVD comprising or consisting of a sequence of $X_1X_2QLVESGGGX_{11}VQPGGSLX_{19}LSCTTSGRX_{28}FX_{30}X_{31}YAVGWFRQX_{40}PGX_{43}EREFVAX_{50}IGEX_{54}AX_{56}NTWYAX_{62}SVX_{65}GRFTISRDX_{74}AKNTVYLX_{82}MX_{84}X_{85}LKPEDTAVYYCAADX_{100}YGVGGX_{106}AQGYYDSWGQGTQVTVSS$ (SEQ ID NO: 21),
    wherein $X_1$ is Q or E; $X_2$ is L or V; $X_{11}$ is L or W, $X_{19}$ is K or Q; $X_{28}$ is R, T, E, H, or K; $X_{30}$ is S, Q, or D; $X_{31}$ is S or E; $X_{40}$ is A or G; $X_{43}$ is K or Q; $X_{50}$ is D or E; $X_{54}$ is Q, N, T, or E; $X_{56}$ is E or D; $X_{62}$ is H or E; $X_{65}$ is K or L; $X_{74}$ is E, N or D; $X_{82}$ is E or Q; $X_{84}$ is D or N; $X_{85}$ is G or S; $X_{100}$ is K or S; and $X_{106}$ is N or G. (consecutive numbering)

4. The ISVD according to embodiment 3, wherein $X_1$ is Q.

5. The ISVD according to embodiment 3, wherein $X_1$ is E.

6. The ISVD according to any one of embodiments 3 to 5, wherein $X_{11}$ is L.

7. The ISVD according to any one of embodiments 3 to 5, wherein $X_{11}$ is W.

8. The ISVD according to any one of embodiments 3 to 7, wherein $X_{19}$ is K.

9. The ISVD according to any one of embodiments 3 to 7, wherein $X_{19}$ is Q.

10. The ISVD according to any one of embodiments 3 to 9, wherein $X_{28}$ is R.

11. The ISVD according to any one of embodiments 3 to 9, wherein $X_{28}$ is T.

12. The ISVD according to any one of embodiments 3 to 9, wherein $X_{28}$ is E.

13. The ISVD according to any one of embodiments 3 to 9, wherein $X_{28}$ is H.

14. The ISVD according to any one of embodiments 3 to 9, wherein $X_{28}$ is K.

15. The ISVD according to any one of embodiments 3 to 14, wherein $X_{30}$ is S.

16. The ISVD according to any one of embodiments 3 to 14, wherein $X_{30}$ is Q.

17. The ISVD according to any one of embodiments 3 to 14, wherein $X_{30}$ is D.

18. The ISVD according to any one of embodiments 3 to 17, wherein $X_{31}$ is S.

19. The ISVD according to any one of embodiments 3 to 17, wherein $X_{31}$ is E.

20. The ISVD according to any one of embodiments 3 to 17, wherein $X_{40}$ is A.

21. The ISVD according to any one of embodiments 3 to 17, wherein $X_{40}$ is G.

22. The ISVD according to any one of embodiments 3 to 21, wherein $X_{43}$ is K.

23. The ISVD according to any one of embodiments 3 to 21, wherein $X_{43}$ is Q.

24. The ISVD according to any one of embodiments 3 to 23, wherein $X_{50}$ is D.

25. The ISVD according to any one of embodiments 3 to 23, wherein $X_{50}$ is E.

26. The ISVD according to any one of embodiments 3 to 25, wherein $X_{54}$ is Q.

27. The ISVD according to any one of embodiments 3 to 25, wherein $X_{54}$ is N.

28. The ISVD according to any one of embodiments 3 to 25, wherein $X_{54}$ is T.

29. The ISVD according to any one of embodiments 3 to 25, wherein $X_{54}$ is E.

30. The ISVD according to any one of embodiments 3 to 29, wherein $X_{56}$ is E.

31. The ISVD according to any one of embodiments 3 to 29, wherein $X_{56}$ is D.

32. The ISVD according to any one of embodiments 3 to 31, wherein $X_{62}$ is H.

33. The ISVD according to any one of embodiments 3 to 31, wherein $X_{62}$ is E.

34. The ISVD according to any one of embodiments 3 to 33, wherein $X_{65}$ is K.

35. The ISVD according to any one of embodiments 3 to 33, wherein $X_{65}$ is L.

36. The ISVD according to any one of embodiments 3 to 35, wherein $X_{74}$ is E.

37. The ISVD according to any one of embodiments 3 to 35, wherein $X_{74}$ is N.

38. The ISVD according to any one of embodiments 3 to 35, wherein $X_{74}$ is D.

39. The ISVD according to any one of embodiments 3 to 38, wherein $X_{82}$ is E.

40. The ISVD according to any one of embodiments 3 to 38, wherein $X_{82}$ is Q.

41. The ISVD according to any one of embodiments 3 to 40, wherein $X_{84}$ is D.

42. The ISVD according to any one of embodiments 3 to 40, wherein $X_{84}$ is N.

43. The ISVD according to any one of embodiments 3 to 42, wherein $X_{85}$ is G.

44. The ISVD according to any one of embodiments 3 to 42, wherein $X_{85}$ is S.

45. The ISVD according to any one of embodiments 3 to 44, wherein $X_{100}$ is K.

46. The ISVD according to any one of embodiments 3 to 44, wherein $X_{100}$ is S.

47. The ISVD according to any one of embodiments 3 to 46, wherein $X_{106}$ is N.

48. The ISVD according to any one of embodiments 3 to 46, wherein $X_{106}$ is G.

49. An ISVD comprising or consisting of SEQ ID NO: 23, SEQ ID NO: 24, SEQ ID NO: 25, SEQ ID NO: 26, SEQ ID NO: 27, SEQ ID NO: 28, SEQ ID NO: 29, or SEQ ID NO:

30, SEQ ID NO: 31, SEQ ID NO: 32, SEQ ID NO: 33, SEQ ID NO: 34, SEQ ID NO: 35, SEQ ID NO: 36, SEQ ID NO: 37, or SEQ ID NO: 103.

50. An ISVD comprising or consisting of SEQ ID NO: 38.

51. An ISVD comprising or consisting of

```
                                        (SEQ ID NO: 28)
EVQLVESGGGLVQPGGSLKLSCTTSGRRFSEYAVGWFRQAP
GKEREFVADIGEQAENTWYAESVLGRFTISRDDAKNTVYLE
MDGLKPEDTAVYYCAADKYGVGGNAQGYYDSWGQGTQVTVS
S.
```

52. An immunoglobulin single variable domain (ISVD) comprising the amino acid sequence:

```
                                        (SEQ ID NO: 28)
EVQLVESGGGLVQPGGSLKLSCTTSGRRFSEYAVGWFRQAP
GKEREFVADIGEQAENTWYAESVLGRFTISRDDAKNTVYLE
MDGLKPEDTAVYYCAADKYGVGGNAQGYYDSWGQGTQVTVS
S.
```

53. An immunoglobulin single variable domain (ISVD) consisting of the amino acid sequence:

```
                                        (SEQ ID NO: 28)
EVQLVESGGGLVQPGGSLKLSCTTSGRRFSEYAVGWFRQAP
GKEREFVADIGEQAENTWYAESVLGRFTISRDDAKNTVYLE
MDGLKPEDTAVYYCAADKYGVGGNAQGYYDSWGQGTQVTVS
S.
```

54. An ISVD comprises or consists of a sequence having at least 80, 81, 82, 83, 84, 85, 86, 87, 88, 90, 91, 92, 93, 94, 95, 96, 97, 98, or 99% sequence identity with SEQ ID NO: 38 or SEQ ID NO: 28.

55. The ISVD according to embodiment 2, wherein the ISVD has the following complementarity-determining region (CDR) sequences:

```
CDR1:
                                         (SEQ ID NO: 3)
EYAVG;

CDR2:
                                         (SEQ ID NO: 7)
DIGEQAENTWYAESVLG;
and/or CDR3:
                                        (SEQ ID NO: 17)
DKYGVGGNAQGYYDS. (Kabat definition)
```

56. The ISVD according to embodiment 2, wherein the ISVD has the following complementarity-determining region (CDR) sequences:

```
CDR1:
                                         (SEQ ID NO: 3)
EYAVG;

CDR2:
                                         (SEQ ID NO: 7)
DIGEQAENTWYAESVLG;
and/or CDR3:
                                        (SEQ ID NO: 17)
DKYGVGGNAQGYYDS. (Kabat definition)
```

57. The ISVD according to embodiment 2, wherein the ISVD has the following complementarity-determining region (CDR) sequences:

```
CDR1:
                                         (SEQ ID NO: 3)
EYAVG;

CDR2:
                                         (SEQ ID NO: 8)
DIGENAENTWYAESVLG;
and/or CDR3:
                                        (SEQ ID NO: 17)
DKYGVGGNAQGYYDS.
(Kabat definition)
```

58. The ISVD according to embodiment 2, wherein the ISVD has the following complementarity-determining region (CDR) sequences:

```
CDR1:
                                         (SEQ ID NO: 3)
EYAVG;

CDR2:
                                         (SEQ ID NO: 9)
DIGENAENTWYAHSVLG;
and/or CDR3:
                                        (SEQ ID NO: 17)
DKYGVGGNAQGYYDS.
(Kabat definition)
```

59. The ISVD according to embodiment 2, wherein the ISVD has the following complementarity-determining region (CDR) sequences:

```
CDR1:
                                         (SEQ ID NO: 3)
EYAVG;

CDR2:
                                        (SEQ ID NO: 12)
DIGEQAENTWYAHSVLG;
and/or CDR3:
                                        (SEQ ID NO: 17)
DKYGVGGNAQGYYDS.
(Kabat definition)
```

60. The ISVD according to embodiment 2, wherein the ISVD has the following complementarity-determining region (CDR) sequences:

```
CDR1:
                                         (SEQ ID NO: 3)
EYAVG;

CDR2:
                                         (SEQ ID NO: 7)
DIGEQAENTWYAESVLG;
and/or CDR3:
                                        (SEQ ID NO: 17)
DKYGVGGNAQGYYDS.
(Kabat definition)
```

61. The ISVD according to embodiment 2, wherein the ISVD has the following complementarity-determining region (CDR) sequences:

```
CDR1:
                       (SEQ ID NO: 3)
EYAVG;

CDR2:
                       (SEQ ID NO: 12)
DIGEQAENTWYAHSVLG;
and/or

CDR3:
                       (SEQ ID NO: 17)
DKYGVGGNAQGYYDS.
(Kabat definition)
```

62. The ISVD according to embodiment 2, wherein the ISVD has the following complementarity-determining region (CDR) sequences:

```
CDR1:
                       (SEQ ID NO: 3)
EYAVG;

CDR2:
                       (SEQ ID NO: 8)
DIGENAENTWYAESVLG;
and/or

CDR3:
                       (SEQ ID NO: 17)
DKYGVGGNAQGYYDS.
(Kabat definition)
```

63. The ISVD according to embodiment 2, wherein the ISVD has the following complementarity-determining region (CDR) sequences:

```
CDR1:
                       (SEQ ID NO: 5)
EYAMA;

CDR2:
                       (SEQ ID NO: 14)
DIGESGGTWYADSVKG;
and/or

CDR3:
                       (SEQ ID NO: 19)
DSYGVGGGAERYYDS.
(Kabat definition)
```

64. The ISVD according to embodiment 2, wherein the ISVD has the following complementarity-determining region (CDR) sequences:

```
CDR1:
                       (SEQ ID NO: 4)
SYAVG;

CDR2:
                       (SEQ ID NO: 15)
DIGENADNTWYAHSVKG;
and/or

CDR3:
                       (SEQ ID NO: 18)
DSYGVGGGAQGYYDS.
(Kabat definition)
```

65. The ISVD according to embodiment 2, wherein the ISVD has the following complementarity-determining region (CDR) sequences:

```
CDR1:
                       (SEQ ID NO: 6)
NYWMY;

CDR2:
                       (SEQ ID NO: 16)
GINTGGSTPDYADSVKG;
and/or

CDR3:
                       (SEQ ID NO: 20)
DTPRVFRLDHYSP.
(Kabat definition)
```

66. The ISVD according to any one of embodiments 1 to 65, wherein the ISVD comprises one or more substitution(s).

67. The ISVD according to embodiment 66, wherein the substitution(s) is/are conservative substitutions.

68. The ISVD according to any one of embodiments 1-67, wherein the ISVD is an isolated ISVD.

69. The ISVD according to any one of embodiments 1-68, wherein the ISVD is a $V_HH$, such as humanised $V_HH$.

70. The ISVD according to any one of embodiments 1-69, wherein the ISVD is capable of binding IL-6, preferably hIL-6 (SEQ ID NO: 89).

71. The ISVD according to any one of embodiments 1-70, wherein the ISVD has a paratope comprising amino acid residues D50, E53, N54, N57, T58, W59, Y60, K65, D99, Y101, G102, V103, G104, G105, G106, and Y110 (consecutive numbering) or wherein the ISVD has a paratope comprising amino acid residues D50, E53, Q54, N57, T58, W59, Y60, L65, D99, Y101, G102, V103, G104, G105, N106, and Y110 (consecutive numbering).

72. The ISVD according to any one of the embodiments 1-71, wherein the ISVD has a pI in the range of 3-6.

73. The ISVD according to any one of the embodiments 1-71, wherein the ISVD has a pI in the range of 3.5-5.5.

74. The ISVD according to any one of the embodiments 1-71, wherein the ISVD has a pI in the range of 4.0-5.0.

75. The ISVD according to any one of the embodiments 1-71, wherein the ISVD has a pI in the range of 4.5-5.0.

76. The ISVD according to any one of the embodiments 1-71, wherein the ISVD has a pI of about 3.5, about 3.6, about 3.7, about 3.8, 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, or about 5.5.

Polypeptide

77. A polypeptide comprising an ISVD according to any one of the embodiments 1 to 76 and an extension.

78. The polypeptide according to embodiment 77, wherein the extension is a C-terminal extension.

79. The polypeptide according to embodiment 77, wherein the extension is a N-terminal extension.

80. The polypeptide according to embodiment 77, wherein the extension is provided between the C-terminal and N-terminal of the ISVD.

81. The polypeptide according to any one of the embodiments 77-80, wherein the extension is 1 to 6 amino acid residues in length.

82. The polypeptide according to any one of the embodiments 77-80, wherein the extension is 1 to 10 amino acid residues in length.

83. The polypeptide according to any one of the embodiments 77-80, wherein the extension is 1 to 20 amino acid residues in length.

84. The polypeptide according to any one of the embodiments 77-80, wherein the extension is 1 to 13 amino acid residues in length.

85. The polypeptide according to any one of the embodiments 77-84, wherein the extension is 4 to 6 amino acid residues in length.

86. The polypeptide according to any one of the embodiments 77-85, wherein the extension is 4 amino acid residues in length.

87. The polypeptide according to any one of the embodiments 77-85, wherein the extension is 5 amino acid residues in length.

88. The polypeptide according to any one of the embodiments 77-85, wherein the extension is 6 amino acid residues in length.

89. The polypeptide according to any one of embodiments 77-88, wherein the extension comprises a cysteine amino acid residue.

90. The polypeptide according to any one of embodiments 77-88, wherein the extension comprises two cysteine amino acid residues.

91. The polypeptide according to any one of embodiments 77-88, wherein the extension comprises two or more amino acid residues.

92. The polypeptide according to any one of embodiments 77-88, wherein the extension comprises an amino acid residue capable of reacting with a half-life extending moiety.

93. The polypeptide according to any one of embodiments 77-88, wherein the extension comprises two amino acid residues capable of reacting with a half-life extending moiety.

94. The polypeptide according to embodiment 93, wherein the each of the two amino acid residues is selected from Lys or Cys.

95. The polypeptide according to embodiment 93, wherein the each of the two amino acid residues is a Cys.

96. The polypeptide according to any one of the embodiments 77-91, wherein the extension comprises an at least one amino acid residue capable of reacting with a substituent.

97. The polypeptide according to the embodiment 96, wherein the at least one amino acid residue capable of reacting with a substituent is at least 2 amino acid residues capable of reacting with a substituent.

98. The polypeptide according to any one of the embodiments 96-97, wherein each one of the at least one amino acid residue is selected from Lys and Cys.

99. The polypeptide according to embodiments 96-97, wherein the each one of the at least one amino acid residue is a Cys.

100. The polypeptides according to any one of the embodiments 77-84 and 91-94, wherein the extension comprises or consists of an amino acid sequence as set out in any one of SEQ ID Nos. 72, 71, 90, 91, 92, 93.

101. The polypeptides according to the embodiment 100, wherein the extension comprises or consists of an amino acid sequence as set out in any one of SEQ ID Nos. 72, 90, 91, 92, 93.

102. The polypeptides according to the embodiment 100, wherein the extension comprises an amino acid sequence as set out in SEQ ID No. 72.

103. The polypeptides according to the embodiment 100, wherein the extension consists of an amino acid sequence as set out in SEQ ID No. 72.

104. The polypeptides according to any one of the embodiments 77-84 and 91-94, wherein the extension comprises 4 contiguous amino acid residues of the sequence set out in SEQ ID No. 72.

105. The polypeptide according to the embodiment 104, wherein the extension comprises or consist of the amino acid sequence as set out in SEQ ID No. 128.

106. The polypeptides according to any one of the embodiments 77-84 and 91-94, wherein the extension comprises 5 contiguous amino acid residues of the sequence set out in SEQ ID No. 72.

107. The polypeptide according to the embodiment 106, wherein the extension comprises or consist of the amino acid sequence as set out in SEQ ID No. 129.

108. The polypeptide according to embodiments 69 or 70, wherein the extension comprises or consists of the amino acid residues GQACPC (SEQ ID NO: 72).

109. The polypeptide according to any one of embodiments 69 to 83, wherein the polypeptide is capable of binding IL-6, preferably hIL-6 (SEQ ID NO: 89).

Polypeptide Derivative

110. A polypeptide derivative comprising a polypeptide according to any one of the embodiments 77 to 109, wherein the polypeptide derivative comprises a substituent.

111. The polypeptide derivative according to embodiment 110, wherein the substituent is capable of extending the half-life and/or binding albumin.

112. A polypeptide derivative comprising an ISVD according to any one of the embodiments 1 to 76 or a polypeptide according to any one of the embodiments 77 to 109, wherein the polypeptide derivative comprises two substituents.

113. The polypeptide derivative according to the embodiment 112, wherein at least one of the two substituents is capable of extending the half-life and/or binding albumin.

114. The polypeptide derivative according to the embodiment 112, wherein each of the two substituents is capable of extending the half-life and/or binding albumin.

115. The polypeptide derivative according to embodiment 112, wherein each one of the two substituents is capable of extending the half-life in comparison ISVD or polypeptide without the substituent.

116. The polypeptide derivative according to embodiment 112, wherein each one of the two substituents is capable of binding albumin.

117. The polypeptide derivative according to any one of embodiments 112, wherein each/the substituent is a half-life extending moiety.

118. The polypeptide derivative according to any one of the embodiments 110 to 117, wherein each/the substituent comprises Chem. 1.

119. The polypeptide derivative according to any one of the embodiments 110 to 117, wherein the substituent comprises (Chem. 1)

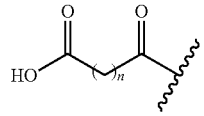

wherein n=12, 14, 16, 18 or 20.

120. The polypeptide derivative according to any one of the embodiments 112 to 117, wherein each one of the two substituents comprises

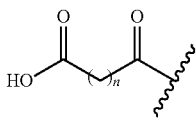

(Chem. 1)

wherein n=12, 14, 16, 18 or 20.

121. The polypeptide derivative according to any one of the embodiments 110 to 120, wherein each/the substituent further comprises one or more of Chem. 2, Chem. 3, Chem. 4, Chem. 5, or Chem. 6.

122. The polypeptide derivative according to any one of the embodiments 110 to 120, wherein each/the substituent further comprises one or more of

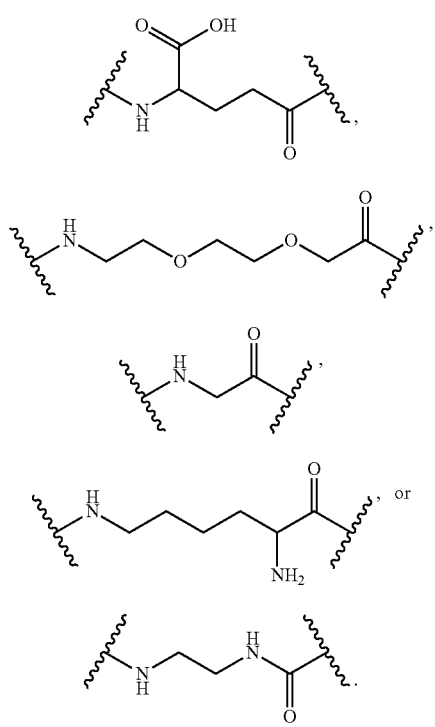

(Chem. 2)

(Chem. 3)

(Chem. 4)

(Chem. 5)

(Chem. 6)

123. The polypeptide derivative according to any one of the embodiments 110 to 122, wherein each/the substituent comprises or essentially consists of a protracting moiety and at least one linker.

124. The polypeptide derivative according to any one of the embodiments 110 to 122, wherein each/the substituent comprises a protracting moiety and at least one linker.

125. The polypeptide derivative according to any one of the embodiments 110 to 122, wherein each/the substituent comprises a protracting moiety and a linker.

126. The polypeptide derivative according to any one of the embodiments 123-125, wherein the protracting moiety is
   Chem. 1; HOOC-benzene-O—$(CH_2)_x$—CO—*; or HO—$S(=O)_2$—$(CH_2)_x$—CO—*; and wherein x is an integer in the range of 8-18.

127. The polypeptide derivative according to any one of the embodiments 123-125, wherein the protracting moiety comprises

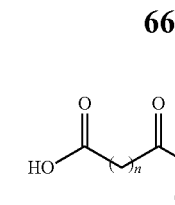

(Chem. 1)

wherein n=12, 14, 16, 18 or 20;
   HOOC-benzene-O—$(CH_2)_x$—CO—*, wherein x is an integer in the range of 8-18; or
   HO—$S(=O)_2$—$(CH_2)_x$—CO—*, wherein x is an integer in the range of 8-18.

128. The polypeptide derivative according to any one of the embodiments 123-127, wherein the protracting moiety comprises (Chem. 1)

wherein n=12, 14, 16, 18 or 20.

129. The polypeptide derivative according to any one of the embodiments 123-127, wherein the protracting moiety comprises (Chem. 1)

wherein n=14.

130. The polypeptide derivative according to the embodiments 121 or the embodiment 123, wherein the linker comprises one or more of Chem. 2, Chem. 3, Chem. 4, Chem. 5, or Chem. 6.

131. The polypeptide derivative according to any one of the embodiments 123-129, wherein the linker comprises one or more of

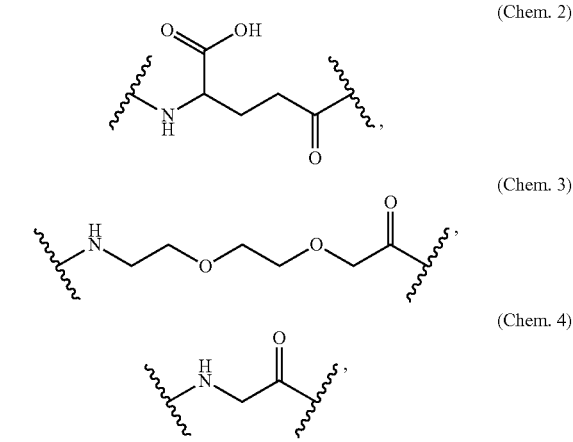

(Chem. 2)

(Chem. 3)

(Chem. 4)

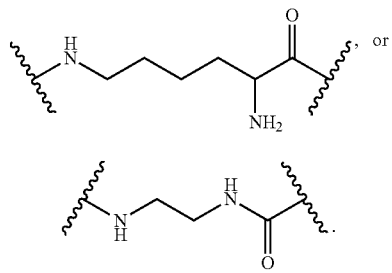

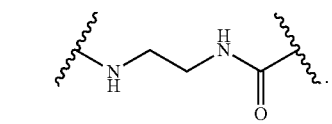

132. The polypeptide derivative according to any one of the embodiments 123-131, wherein the at least one linker is composed of one or more linker elements.

133. The polypeptide derivative according to the embodiment 132, wherein the linker elements are selected from

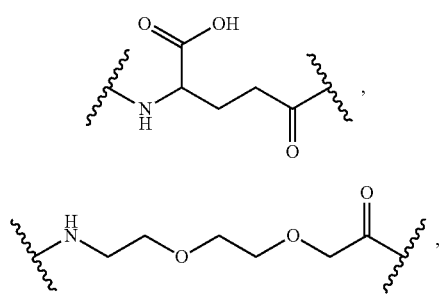

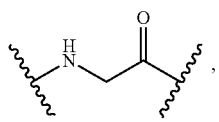

(Chem. 4)

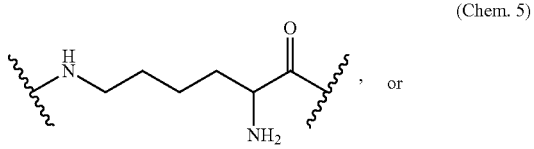

(Chem. 5)

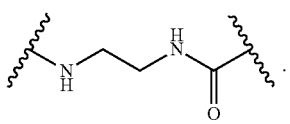

(Chem. 6)

134. The polypeptide derivative according to any one of the embodiments 110 to 133, wherein each/the substituent is selected from Chem. 7, Chem. 8, Chem. 9, Chem. 10, Chem. 11, Chem. 12, Chem. 13, Chem. 14, Chem. 15, Chem. 16, Chem. 17, Chem. 18, Chem. 19, Chem. 20, Chem. 21, Chem. 22, Chem. 23, and Chem. 24.

135. The polypeptide derivative according to any one of the embodiments 110 to 133, wherein each/the substituent is selected from

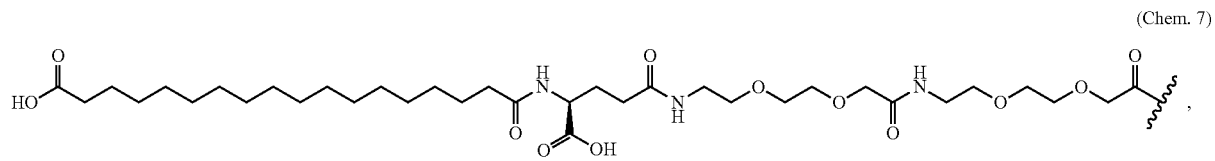

(Chem. 7)

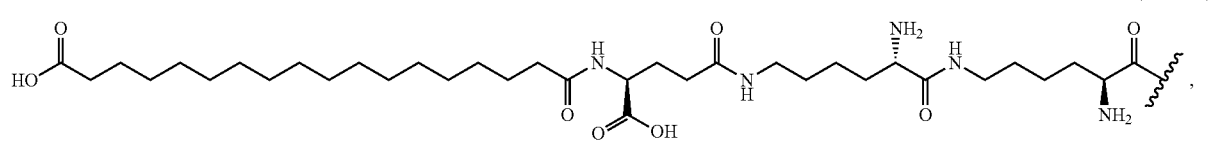

(Chem. 8)

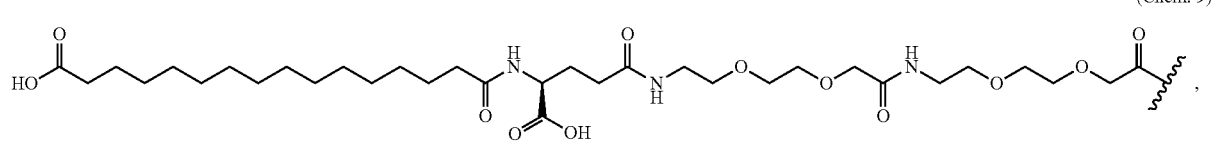

(Chem. 9)

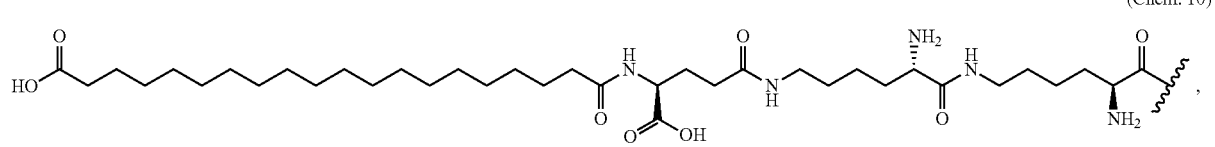

(Chem. 10)

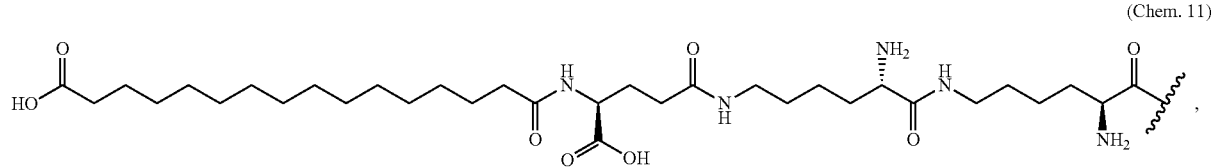

(Chem. 11)

(Chem. 12)
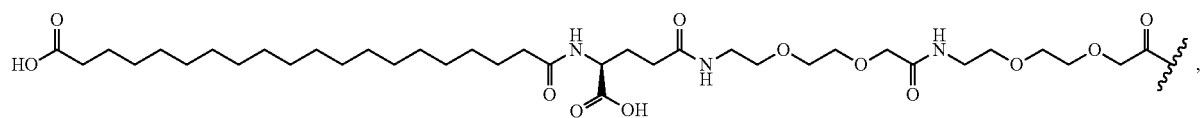
(Chem. 13)
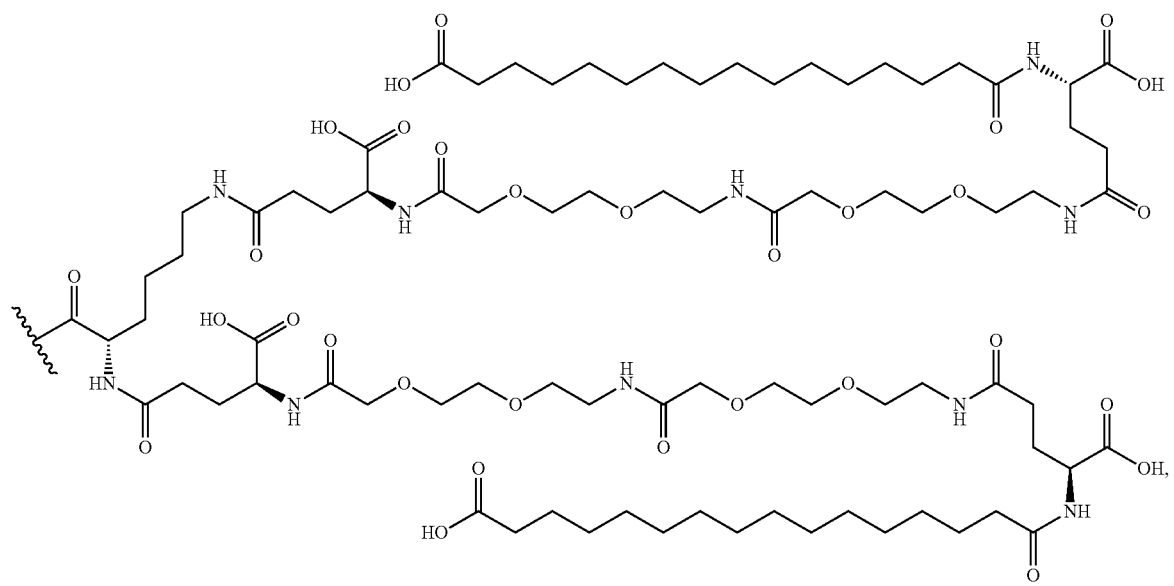 [SMILES: *C(=O)[C@H](CCCCNC(=O)CC[C@H](NC(=O)COCCOCCNC(=O)COCCOCCNC(=O)CC[C@H](NC(=O)CCCCCCCCCCCCCCC(=O)O)C(=O)O)C(=O)O)NC(=O)CC[C@H](NC(=O)COCCOCCNC(=O)COCCOCCNC(=O)CC[C@H](NC(=O)CCCCCCCCCCCCCCC(=O)O)C(=O)O)C(=O)O]
(Chem. 14)
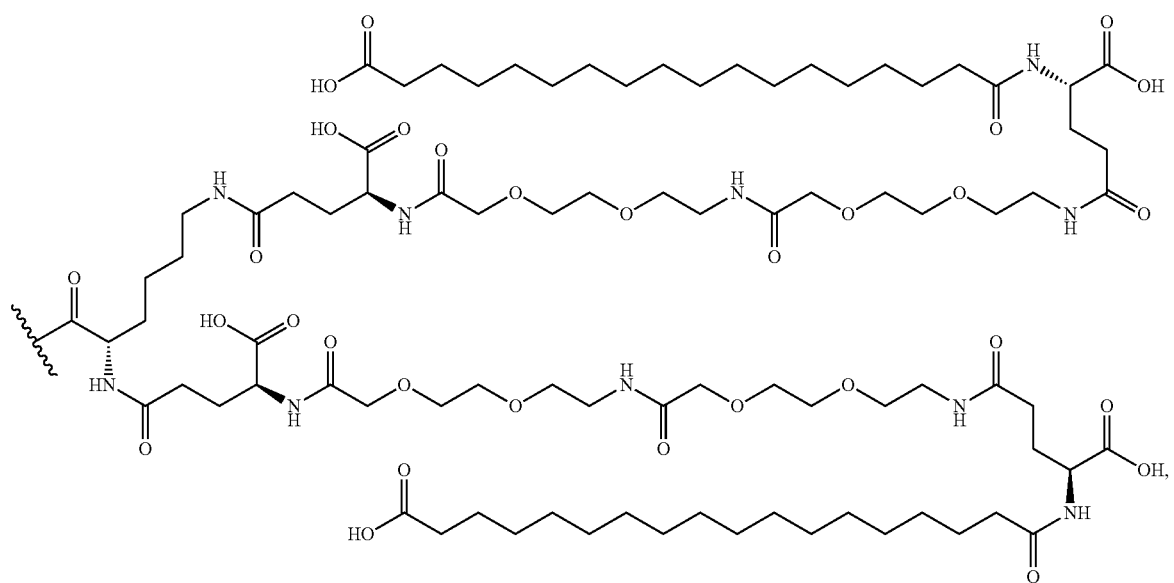 [SMILES: *C(=O)[C@H](CCCCNC(=O)CC[C@H](NC(=O)COCCOCCNC(=O)COCCOCCNC(=O)CC[C@H](NC(=O)CCCCCCCCCCCCCCCCC(=O)O)C(=O)O)C(=O)O)NC(=O)CC[C@H](NC(=O)COCCOCCNC(=O)COCCOCCNC(=O)CC[C@H](NC(=O)CCCCCCCCCCCCCCCCC(=O)O)C(=O)O)C(=O)O]
(Chem. 15)
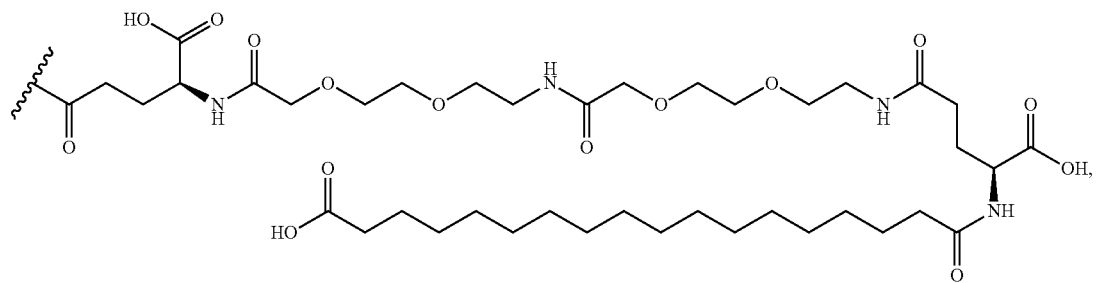 [SMILES: *C(=O)CC[C@H](NC(=O)COCCOCCNC(=O)COCCOCCNC(=O)CC[C@H](NC(=O)CCCCCCCCCCCCCCCCC(=O)O)C(=O)O)C(=O)O]

-continued
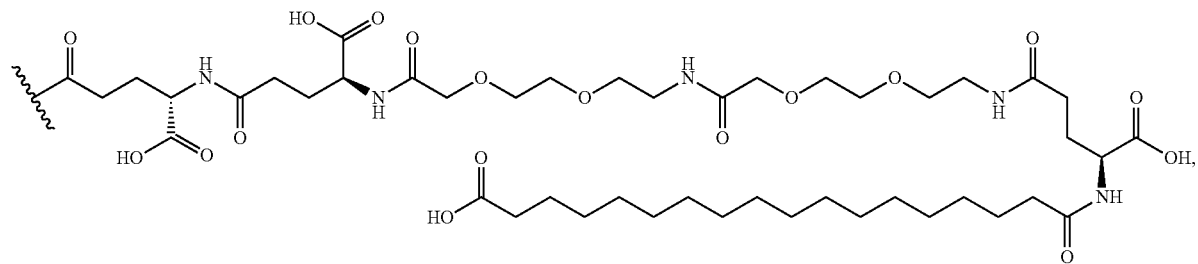 [SMILES: *C(=O)CC[C@H](NC(=O)CC[C@H](NC(=O)COCCOCCNC(=O)COCCOCCNC(=O)CC[C@H](NC(=O)CCCCCCCCCCCCCCCCC(=O)O)C(=O)O)C(=O)O)C(=O)O]
(Chem. 16)
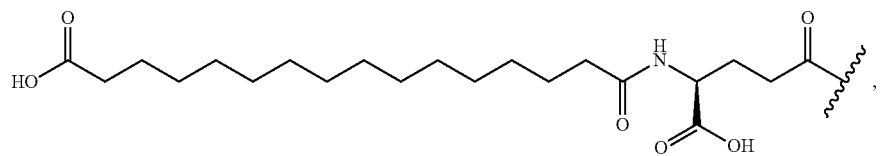
(Chem. 17)
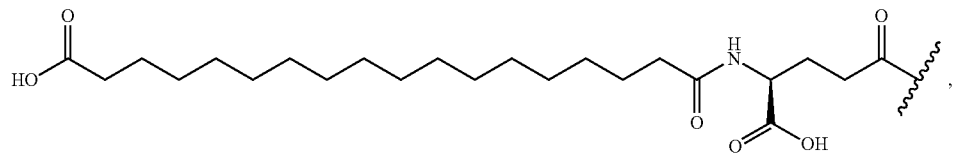
(Chem. 18)
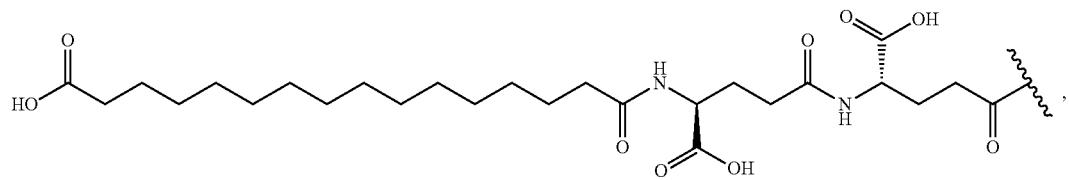
(Chem. 19)
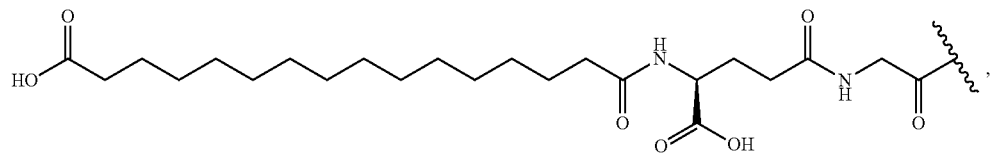
(Chem. 20)
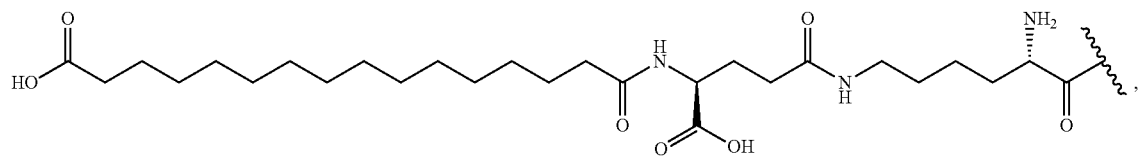
(Chem. 21)
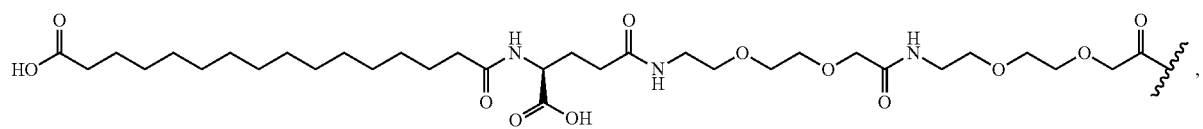
(Chem. 22)

(Chem. 23)
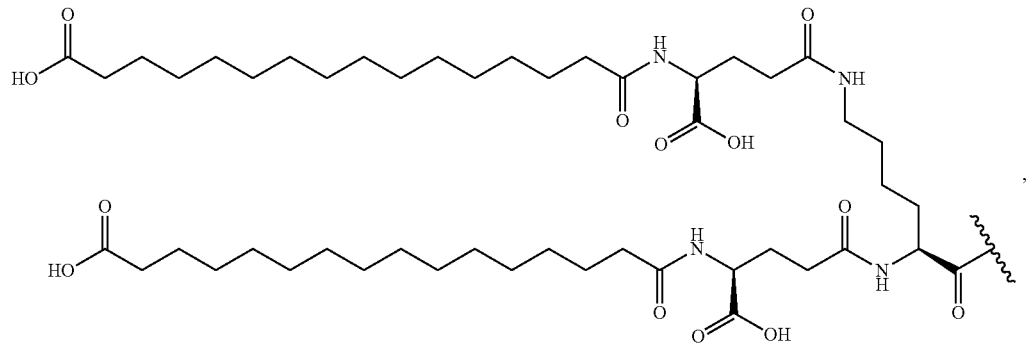
(Chem. 24)
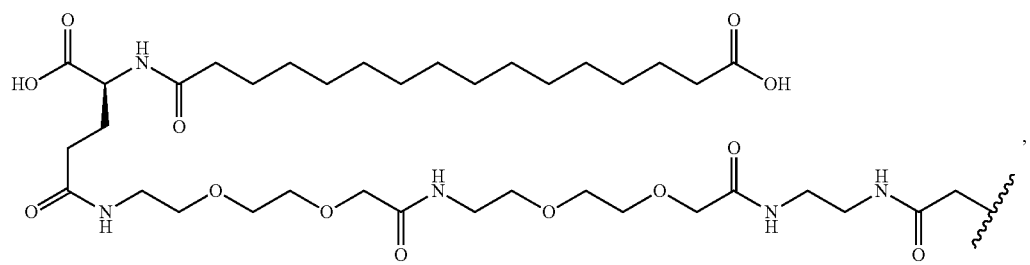
(Chem. 25)
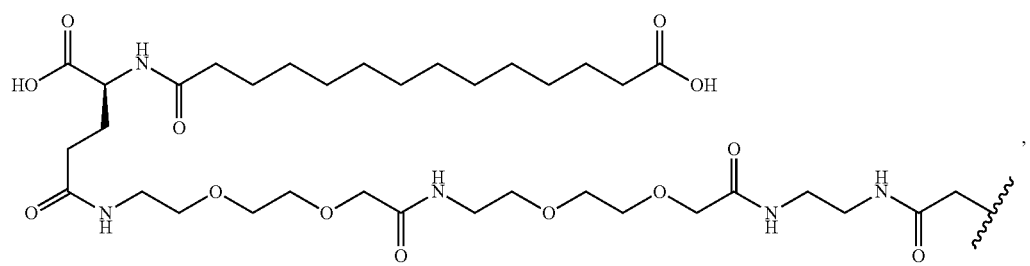
(Chem. 26)
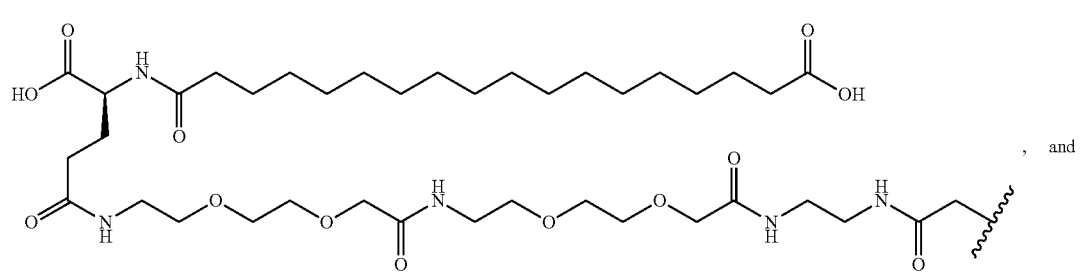
, and
(Chem. 27)
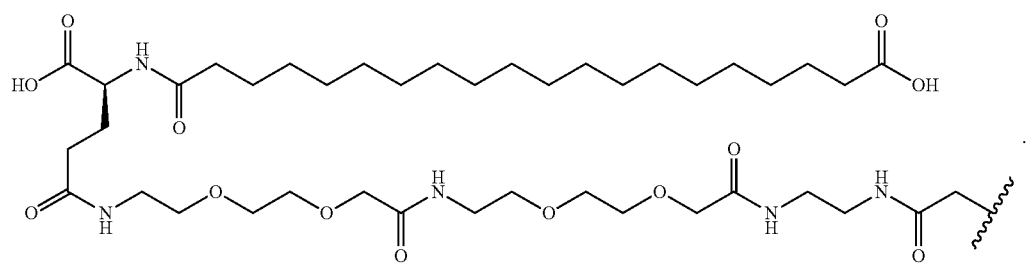
.

136. The polypeptide derivative according to the embodiment 135, wherein each/the substituent is selected from
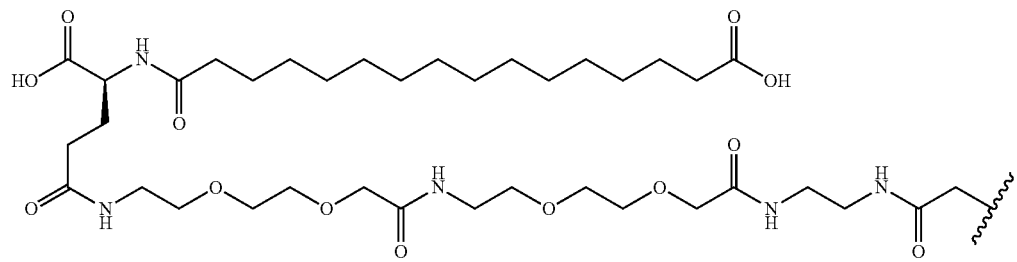 [SMILES: *CC(=O)NCCNC(=O)COCCOCCNC(=O)COCCOCCNC(=O)CC[C@H](NC(=O)CCCCCCCCCCCCCCC(=O)O)C(=O)O]
(Chem. 24)
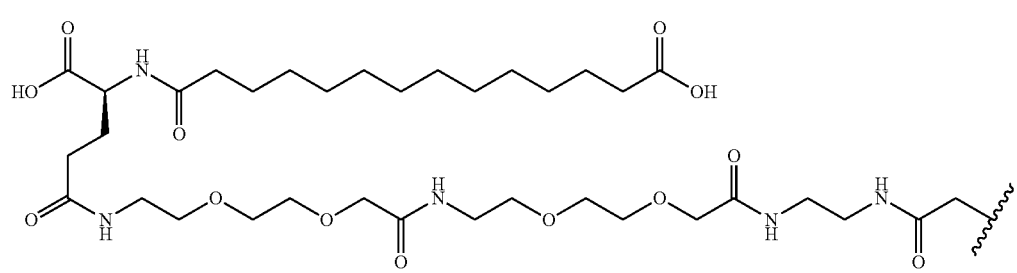 [SMILES: *CC(=O)NCCNC(=O)COCCOCCNC(=O)COCCOCCNC(=O)CC[C@H](NC(=O)CCCCCCCCCCCCC(=O)O)C(=O)O]
(Chem. 25)
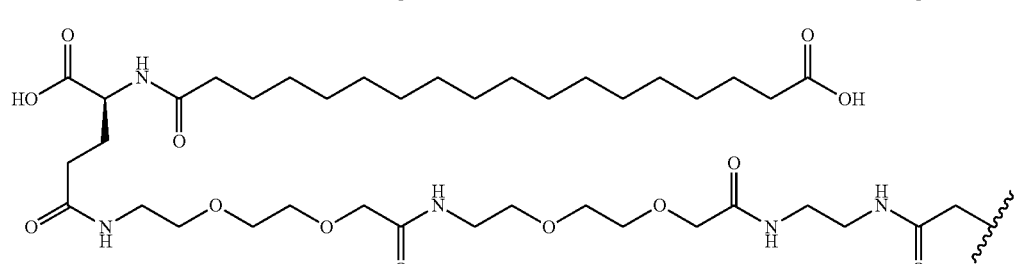
(Chem. 26)
, and
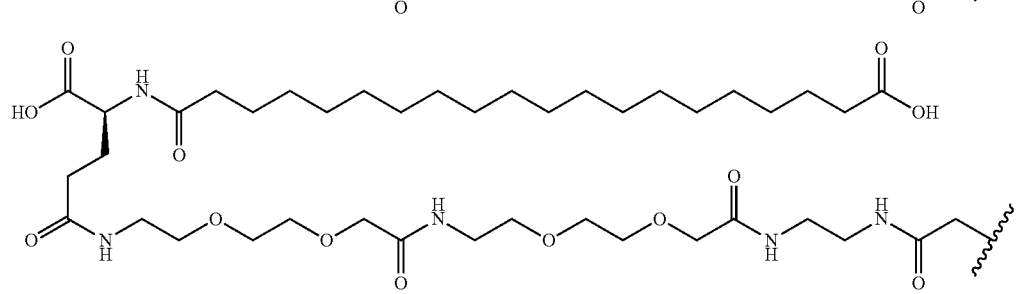
(Chem. 27)
137. The polypeptide derivative according to the embodiment 135, wherein each/the substituent is
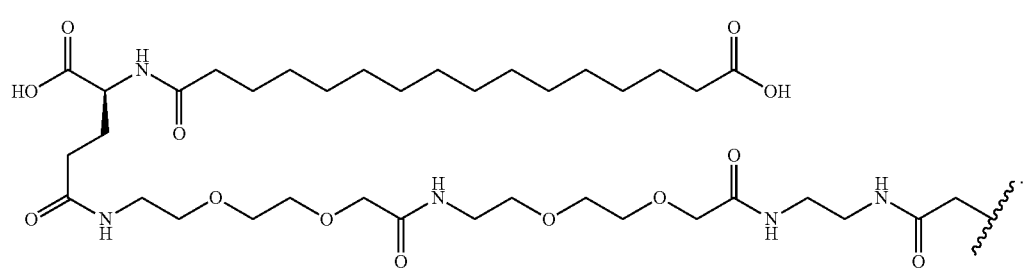
(Chem. 24)

138. The polypeptide derivative according to any one of embodiments 110 to 137 having the structure of Chem. 31:

(SEQ ID NO: 78)

EVQLVESGGG LVQPGGSLKL SCTTSGRRFS EYAVGWFRQA PGKEREFVAD IGEQAENTWY
AESVLGRFTI SRDDAKVTVY LEMDGLKPED TAVYYCAADK YGVGGNAQGY YDSWGQGTQV

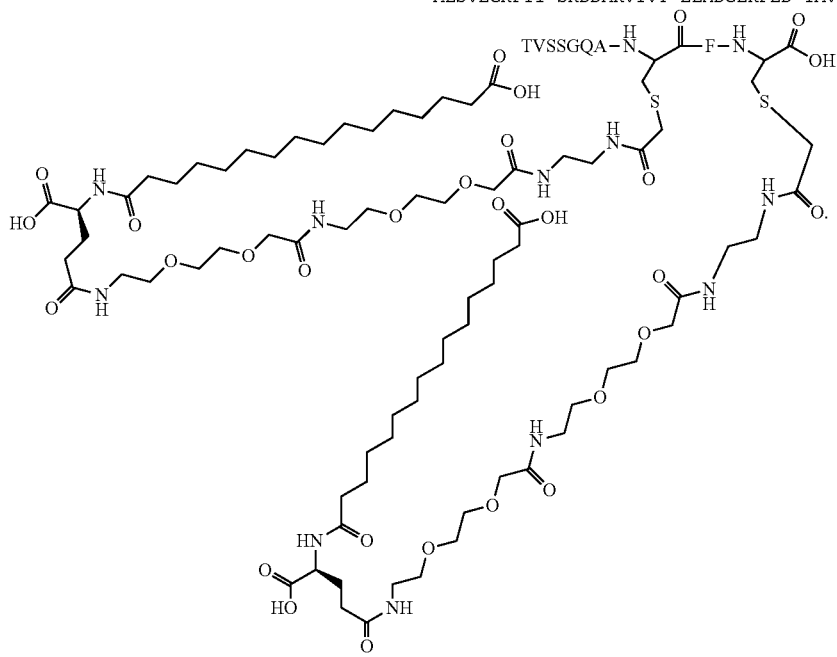

139. A polypeptide derivative comprising an ISVD of SEQ ID NO: 28, wherein the ISVD is fused to a C-terminal extension consisting of SEQ ID NO: 78, and wherein each cysteine of the C-terminal extension carries a substituent of Chem. 24.

140. A polypeptide derivative comprising an immunoglobulin single variable domain (ISVD) of SEQ ID NO: 28, wherein the ISVD is fused to a C-terminal extension consisting of SEQ ID NO: 72, and wherein each cysteine of the C-terminal extension carries a substituent comprising the structure

CDR1:
(SEQ ID NO: 3)
EYAVG;

CDR2:
(SEQ ID NO: 7)
DIGEQAENTWYAESVLG; and

CDR3:
(SEQ ID NO: 17)
DKYGVGGNAQGYYDS (Kabat definition), (Chem. 24)

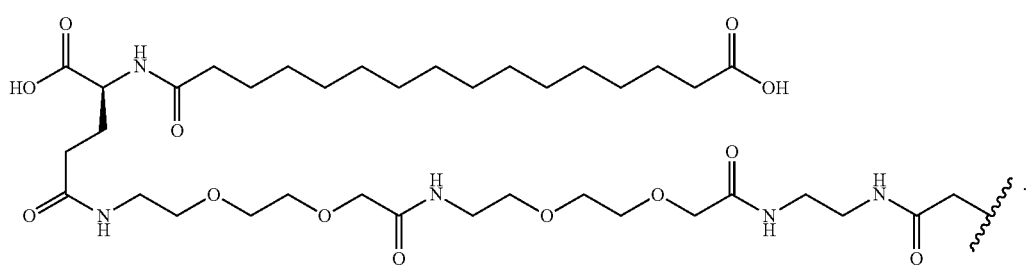

141. A polypeptide derivative capable of binding IL-6 comprising an immunoglobulin single variable domain (ISVD), an extension and two substituents, wherein the ISVD comprises the complementarity-determining regions (CDR)

wherein the extension is attached to the C-terminal of the ISVD and comprises an amino acid sequence as set out in SEQ ID No. 72, and
wherein each one of the substituents is attached to a cysteine of the extension and each one of the substituents comprises the structure

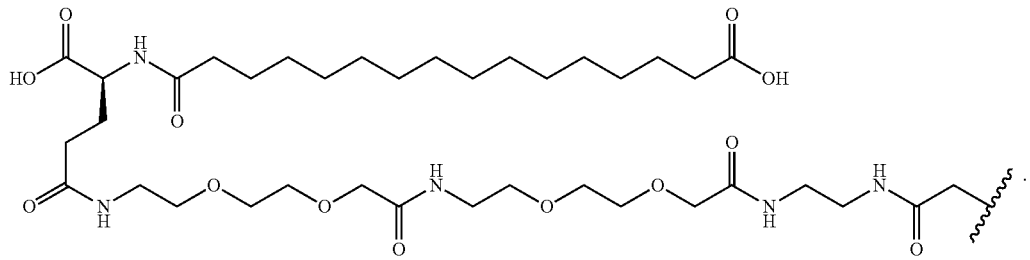
(Chem. 24)

142. A polypeptide derivative capable of binding IL-6 comprising an immunoglobulin single variable domain (ISVD), an extension and two substituents, wherein the ISVD comprises the complementarity-determining regions (CDR)

CDR1:
    (SEQ ID NO: 3)
EYAVG;

CDR2:
    (SEQ ID NO: 7)
DIGEQAENTWYAESVLG; and

CDR3:
    (SEQ ID NO: 17)
DKYGVGGNAQGYYDS (Kabat definition), wherein the extension is attached to the C-terminal of the ISVD and comprises an amino acid sequence as set out in SEQ ID No. 72, and
wherein a first substituent is attached to the cysteine at position 4 of the extension, a second substituent is attached to the cysteine at position 6 of the extension, and each one of the substituents comprises the structure

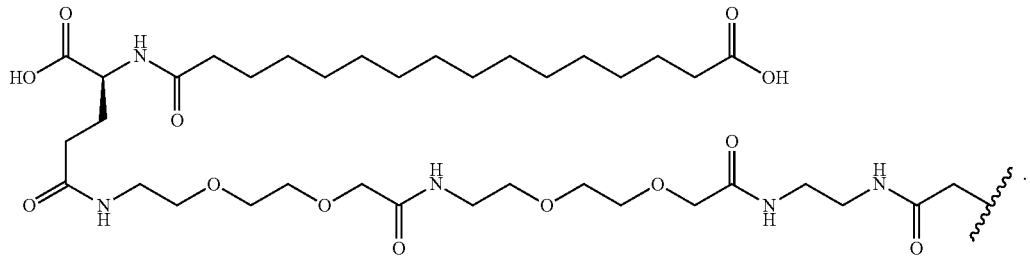
(Chem. 24)

substituent, wherein the ISVD comprises the complementarity-determining regions (CDR)

CDR1:
    (SEQ ID NO: 3)
EYAVG;

CDR2:
    (SEQ ID NO: 7)
DIGEQAENTWYAESVLG; and

CDR3:
    (SEQ ID NO: 17)
DKYGVGGNAQGYYDS (Kabat definition), wherein the extension comprises an amino acid sequence as set out in SEQ ID No. 72 with a cysteine in position 4 and position 6, and the extension is attached to the C-terminal of the ISVD,
wherein the first substituent is attached to the cysteine in position 4 of the extension and the second substituent is attached to the cysteine in position 6 of the extension, and wherein each one of the first substituent and second substituent comprises the structure (Chem. 24)

143. A polypeptide derivative capable of binding IL-6 comprising an immunoglobulin single variable domain (ISVD), an extension, a first substituent and a second

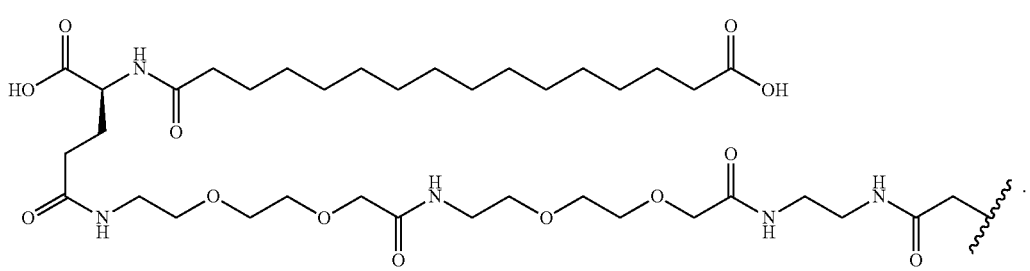
(Chem. 24)

144. A polypeptide derivative capable of binding IL-6 comprising an immunoglobulin single variable domain (ISVD), an extension, a first substituent and a second substituent, wherein the ISVD comprises the complementarity-determining regions (CDR)

CDR1:
(SEQ ID NO: 3)
EYAVG;

CDR2:
(SEQ ID NO: 7)
DIGEQAENTWYAESVLG; and

CDR3:
(SEQ ID NO: 17)
DKYGVGGNAQGYYDS (Kabat definition), wherein the extension comprises an amino acid sequence as set out in SEQ ID No. 72 with a cysteine in position 4 and position 6 of SEQ ID No. 72, and the extension is attached to the C-terminal of the ISVD, wherein the first substituent is attached to the cysteine in position 4 of SEQ ID No. 72 and the second substituent is attached to the cysteine in position 6 of SEQ ID No. 72, and wherein each one of the first substituent and second substituent comprises the structure

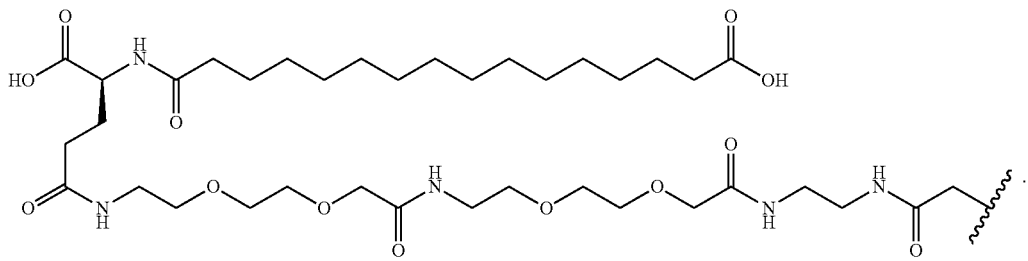

(Chem. 24)

145. A polypeptide derivative capable of binding IL-6 comprising a $V_HH$, an extension, a first substituent and a second substituent, wherein the $V_HH$ comprises the complementarity-determining regions (CDR)

CDR1:
(SEQ ID NO: 3)
EYAVG;

CDR2:
(SEQ ID NO: 7)
DIGEQAENTWYAESVLG; and

CDR3:
(SEQ ID NO: 17)
DKYGVGGNAQGYYDS (Kabat definition), wherein the extension is attached to the C-terminal of the $V_HH$ and comprises an amino acid sequence as set out in SEQ ID No. 72, wherein the first substituent is attached to a cysteine in position 4 of SEQ ID No. 72 and the second substituent is attached to a cysteine in position 6 of SEQ ID No. 72, and wherein each one of the first substituent and second substituent comprises the structure

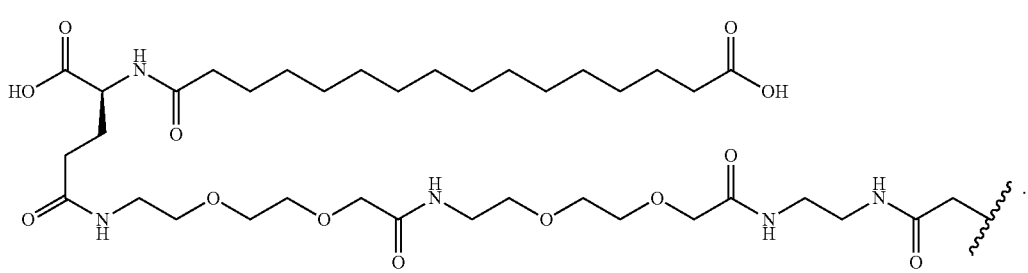

(Chem. 24)

146. A polypeptide derivative capable of binding IL-6 comprising an immunoglobulin single variable domain (ISVD), an extension and two substituents, wherein the ISVD comprises the complementarity-determining regions (CDR)

```
CDR1:
                                        (SEQ ID NO: 3)
EYAVG;

CDR2:
                                        (SEQ ID NO: 7)
DIGEQAENTWYAESVLG; and CDR3:
                                        (SEQ ID NO: 17)
DKYGVGGNAQGYYDS (Kabat definition),
``` wherein the extension is attached to the C-terminal of the ISVD and consists of an amino acid sequence as set out in SEQ ID No. 72, and wherein each one of the substituents is attached to a cysteine and comprises the structure

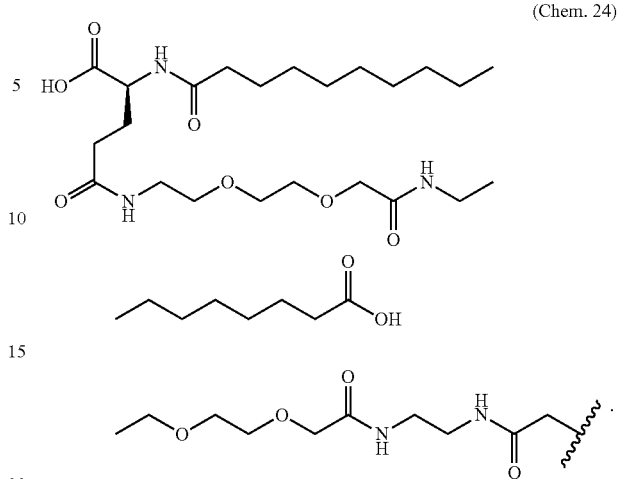

(Chem. 24)

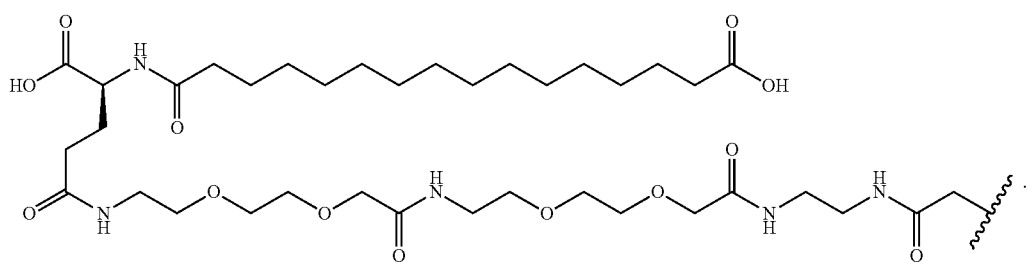

(Chem. 24)

147. A polypeptide derivative capable of binding IL-6 comprising an immunoglobulin single variable domain (ISVD), an extension and two substituents, wherein the ISVD comprises an amino acid sequence as set out in SEQ ID No. 28, wherein the extension is attached to the C-terminal of the ISVD and comprises an amino acid sequence as set out in SEQ ID No. 72, and wherein each one of the substituents is attached to a cysteine of the extension and comprises the structure 148. A polypeptide derivative capable of binding IL-6 comprising an immunoglobulin single variable domain (ISVD), an extension and two substituents, wherein the ISVD comprises an amino acid sequence as set out in SEQ ID No. 28, wherein the extension is attached to the C-terminal of the ISVD and comprises an amino acid sequence as set out in SEQ ID No. 72, and wherein a first substituent is attached to the cysteine at position 4 of the extension, a second substituent is attached to the cysteine at position 6 of the extension, and each one of the substituents comprises the structure (Chem. 24)

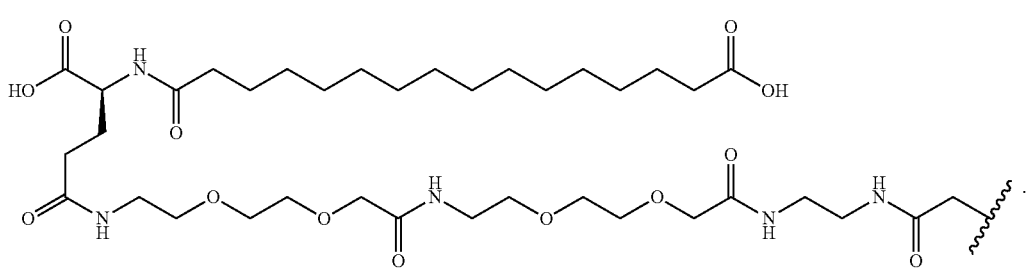

149. A polypeptide derivative capable of binding IL-6 having the structure of Chem. 31:

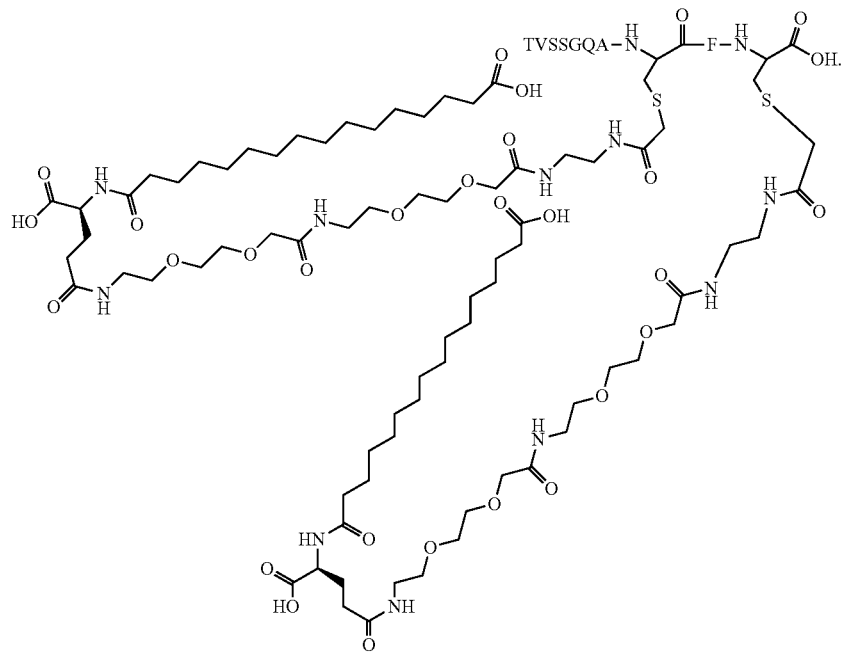

(SEQ ID NO: 78)

150. The polypeptide derivative according to any one of the embodiments 110 to 149, wherein the ISVD is a $V_HH$, preferably a humanised $V_HH$.

151. The polypeptide derivatives according to any one of the embodiments 110 to 150, wherein the polypeptide derivative has an in vitro potency of about 1-50 pM.

152. The polypeptide derivative according to any one of the embodiments 110 to 150, wherein the polypeptide derivative has an in vitro potency of about 5-35 pM.

153. The polypeptide derivative according to any one of the embodiments 110 to 150, wherein the polypeptide derivative has an in vitro potency of about 10-20 pM.

154. The polypeptide derivative according to any one of the embodiments 110 to 150, wherein the polypeptide derivative has an in vitro potency of about 12-19 pM.

155. The polypeptide derivative according to any one of the embodiments 151-154, wherein the in vitro potency is measured as described in Example 8.1: In vitro activity of anti-IL-6 VHH in stat-3-luc reporter gene assay.

156. The polypeptide derivative according to any one of the embodiments 151-154, wherein the in vitro potency is measured via stat-3-luc reporter gene assay.

157. A polypeptide derivative as shown in FIG. 3A.

Figure 3B:
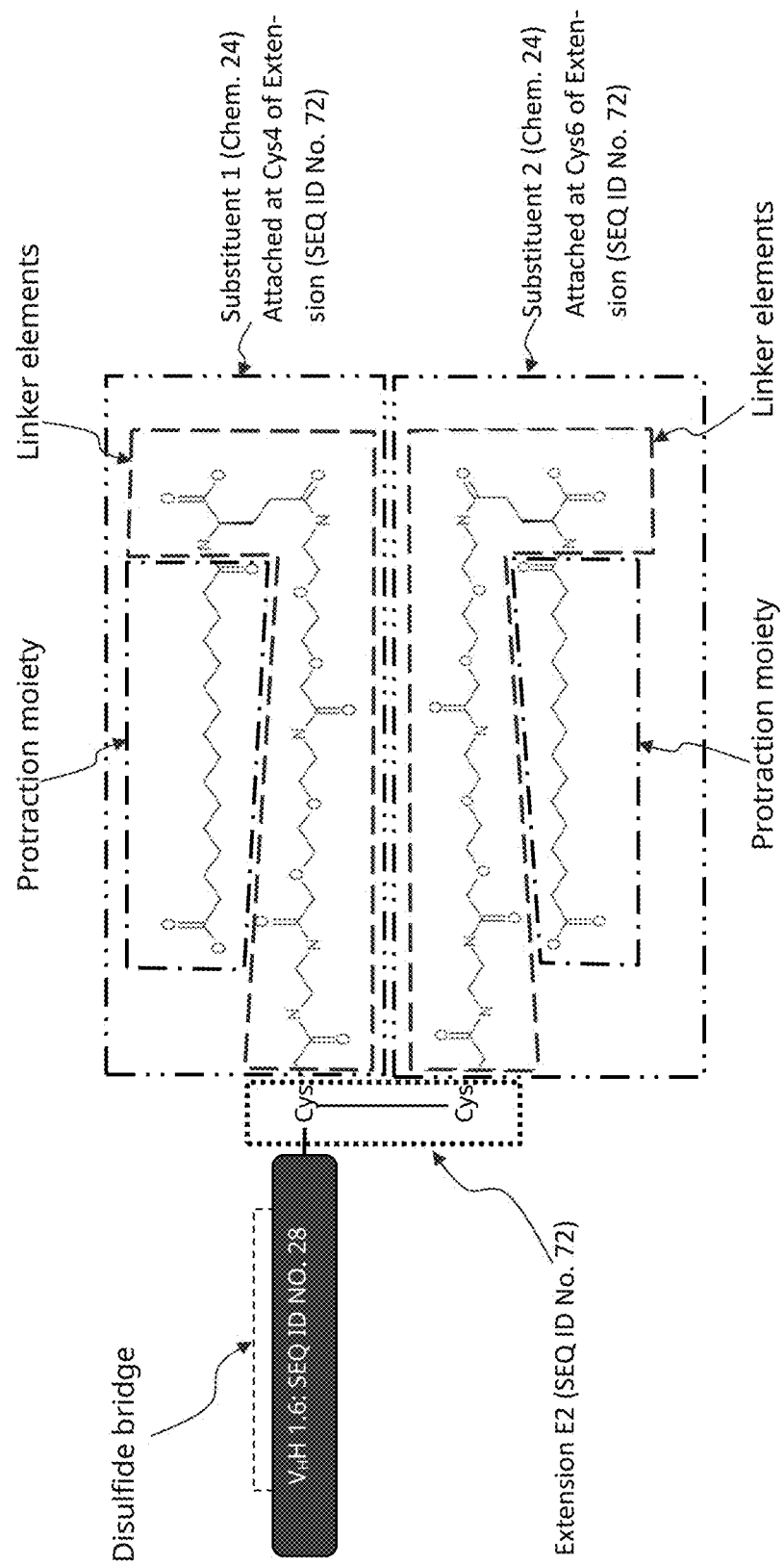
FIG. 3B shows the same non-limitative figurative description of compound 9 as identified in FIG. 3A, wherein details of the construct are provided. In this embodiment, the extension is provided at the C-terminus of the $V_HH$, comprises the amino acid residues of SEQ ID No. 72 and is identified by a box with the ･････････ dashed pattern. Each one of the two substituents (Chem. 24), labeled substituent 1 and substituent 2 respectively, are identified by a box with the ▬ ▪ ▪ ▬ dashed pattern. The protraction moieties are identified by boxes with the ▬ ▪ ▬ dashed pattern. The linker elements are identified by boxes with the ▬ ▬ dashed pattern. The ----- dashed line indicates a disulphide bond. Hydrogen atoms have been omitted for clarity.

158. A polypeptide derivative as shown in FIG. 3A or 3B.

159. A polypeptide derivative as shown in FIG. 3B.

160. A polypeptide derivative as shown in Chem. 31:

(SEQ ID NO: 78)

EVQLVESGGG LVQPGGSLKL SCTTSGRRFS EYAVGWFRQA PGKEREFVAD IGEQAENTWY
AESVLGRFTI SRDDAKVTVY LEMDGLKPED TAVYYCAADK YGVGGNAQGY YDSWGQGTQV

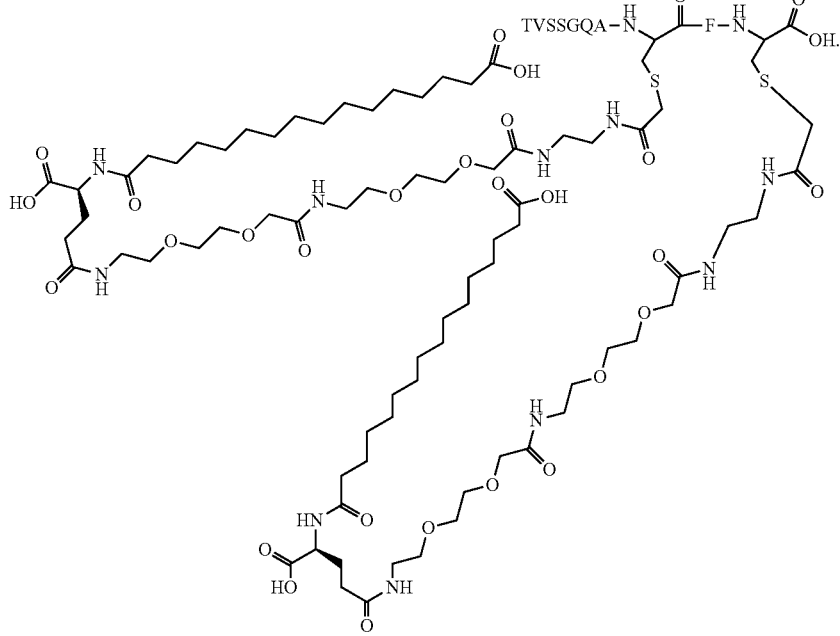

161. A polypeptide derivative comprising a polypeptide according to any one of the embodiments 77 to 109 and further comprising a half-life extending moiety.

162. The polypeptide derivative according to the embodiment 161, wherein the half-life extending moiety is an albumin binder, a fatty acid, a Fc domain, a FcRn binder, or an Fc-binder peptide.

163. The polypeptide derivative according to any one of the embodiments 110 to 162, wherein the polypeptide derivative is capable of binding IL-6, preferably hIL-6 (SEQ ID NO: 89)

164. The polypeptide derivative according to any one of the embodiments 110 to 163, wherein the molecular weight of said polypeptide derivative is between 10-20 kDa, such as between 10-20 kDa, between 12-18 kDa, between 13-17 kDa, and between 14-16 kDa.

165. The polypeptide derivative according to any one of the embodiments 110 to 163, wherein the molecular weight of said polypeptide derivative is between 12-18 kDa.

166. The polypeptide derivative according to any one of the embodiments 110 to 163, wherein the molecular weight of said polypeptide derivative is between 14-16 kDa.

167. The polypeptide derivative according to any one of the embodiments 110 to 163, wherein the molecular weight of said polypeptide derivative is about 10 kDa, about 11 kDa, about 12 kDa, about 13 kDa, about 14 kDa, about 15 kDa, about 16 kDa, about 17 kDa, about 18 kDa, about 19 kDa or about 20 kDa.

168. The polypeptide derivative according to any one of the embodiments 110 to 163, wherein the molecular weight of said polypeptide derivative is 14 kDa.

169. The polypeptide derivative according to any one of the embodiments 110 to 163, wherein the molecular weight of said polypeptide derivative is about 15 kDa.

170. The polypeptide derivative according to any one of the embodiments 110 to 163, wherein the molecular weight of said polypeptide derivative is about 15.5 kDa.

171. The polypeptide derivative according to any one of the embodiments 110 to 163, wherein the molecular weight of said polypeptide derivative is 16 kDa.

172. The polypeptide derivative according to any one of the embodiments 110 to 171, wherein the polypeptide derivative has a pI in the range of 3.5-5.5, such as 4.0-5.0.

173. The polypeptide derivative according to any one of the embodiments 110 to 171, wherein the polypeptide derivative has a pI of about 3.5, about 3.6, about 3.7, about 3.8, 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, or about 5.5.

Further Embodiments

174. A nucleic acid molecule, preferably in isolated form, encoding an ISVD according to any one of embodiments 1 to 76 or a polypeptide according to any one of embodiments 77 to 109.

175. An expression vector comprising a nucleic acid molecule according to the embodiment 174.

176. A host cell carrying an expression vector according to the embodiment 175.

177. A method of manufacturing an ISVD according to any one of embodiments 1 to 76 or a polypeptide according to any one of embodiments 77 to 109 or a polypeptide derivative according to any one of embodiments 110-173, comprising the steps of
 i. Culturing a host cell according to embodiment 176 under conditions that allow expression of an ISVD according to any one of embodiments 1 to 76 or a polypeptide according to any one of embodiments 77 to 109;
 j. Recovering the ISVD or the polypeptide;
 k. Optionally attaching one or more substituent(s) capable of extending the half-life of the polypeptide, optionally wherein each substituent is Chem. 24; and l. Optionally purifying the so-obtained ISVD or polypeptide or polypeptide derivative.

178. An isolated ISVD for use as an intermediate in the manufacture of an anti-IL6 polypeptide derivative comprising the following complementarity-determining region (CDR) sequences:
CDR1: EYAVG (SEQ ID NO: 3), or an amino acid sequence with 1 or 2 amino acid difference(s) with SEQ ID NO: 3;
CDR2: DIGEQAENTWYAESVLG (SEQ ID NO: 7), or an amino sequence with 1, 2, or 3 amino acid difference(s) with SEQ ID NO: 7
CDR3: DKYGVGGNAQGYYDS (SEQ ID NO: 17), or an amino acid sequence with 1 or 2 amino acid difference(s) with SEQ ID NO: 17. (Kabat definition).

179. An isolated immunoglobulin single variable domain (ISVD) for use as an intermediate in the manufacture of an anti-IL6 polypeptide derivative comprising the following complementarity-determining region (CDR) sequences:

```
CDR1:
                              (SEQ ID NO: 3)
EYAVG;

CDR2:
                              (SEQ ID NO: 7)
DIGEQAENTWYAESVLG;
and

CDR3:
                              (SEQ ID NO: 17)
DKYGVGGNAQGYYDS.
  (Kabat definition).
```

Pharmaceutical Composition

180. A pharmaceutical composition comprising an ISVD according to any one of the embodiments 1 to 76 or a polypeptide according to any one of the embodiments 77 to 109 or a polypeptide derivative according to any one of the embodiments 110-173.

181. An oral pharmaceutical composition comprising an ISVD according to any one of the embodiments 1 to 76 or a polypeptide according to any one of the embodiments 77 to 109 or a polypeptide derivative according to any one of the embodiments 110-173.

182. The pharmaceutical composition according to the embodiment 181, wherein the composition comprises an adsorption enhancer.

183. The pharmaceutical composition according to the embodiment 181 or the embodiment 182, wherein the composition comprises a salt of N-(8-2-hydroxybenzoyl)amino) caprylic acid.

184. The pharmaceutical composition according to the embodiment 181 or the embodiment 182, comprising sodium N-(8-(2-hydroxybenzoyl)amino)caprylate (SNAC).

185. The pharmaceutical composition according to any one of the embodiments 181 to 184, further comprising nicotinamide.

186. The pharmaceutical composition according to any one of the embodiments 181 to 185, wherein said composition is a solid composition.

Medical Use

187. An ISVD according to any one of embodiments 1 to 76 or a polypeptide according to any one of embodiments 77 to 109 or a polypeptide derivative according to any one of embodiments 110 to 173 for use in medicine.

188. A polypeptide derivative according to any one of embodiments 110-173 for use in medicine.

189. An ISVD according to any one of embodiments 1 to 76 or a polypeptide according to any one of embodiments 77 to 109 or a polypeptide derivative according to any one of embodiments 110 to 173 for use in the treatment of inflammatory diseases.

190. An ISVD according to any one of embodiments 1 to 76 or a polypeptide according to any one of embodiments 77 to 109 or a polypeptide derivative according to any one of embodiments 110 to 173 for use in the treatment of inflammatory diseases, wherein the human subject has or is at risk of having a High-Sensitivity C-reactive Protein (Hs-CRP) above a value of 1 mg/L, preferably above a value of 1.5 mg/L.

191. An ISVD according to any one of embodiments 1 to 76 or a polypeptide according to any one of embodiments 77 to 109 or a polypeptide derivative according to any one of embodiments 110 to 173 for use in the treatment of inflammatory diseases, wherein the human subject has or is at risk of having a High-Sensitivity C-reactive Protein (Hs-CRP) value above or equal to 2 mg/L (hsCRP≥2 mg/L).

192. An ISVD according to any one of embodiments 1 to 76 or a polypeptide according to any one of embodiments 77 to 109 or a polypeptide derivative according to any one of embodiments 110 to 173 for use in the treatment of cardiovascular disease.

193. An ISVD according to any one of embodiments 1 to 76 or a polypeptide according to any one of embodiments 77 to 109 or a polypeptide derivative according to any one of embodiments 110 to 173 for use in the treatment of atherosclerotic cardiovascular disease.

194. An ISVD according to any one of embodiments 1 to 76 or a polypeptide according to any one of embodiments 77 to 109 or a polypeptide derivative according to any one of embodiments 110 to 173 for use in the treatment of atherosclerotic cardiovascular disease (ASCVD) defined as stroke and/or myocardial infarction (MI) and/or peripheral arterial disease (PAD).

195. An ISVD according to any one of embodiments 1 to 76 or a polypeptide according to any one of embodiments 77 to 109 or a polypeptide derivative according to any one of embodiments 110 to 173 for use in the treatment of stroke and/or myocardial infarction (MI) and/or peripheral arterial disease (PAD).

196. Use of an ISVD according to any one of embodiments 1 to 76 or a polypeptide according to any one of embodiments 77 to 109 or a polypeptide derivative according to any one of embodiments 110 to 173 in the manufacture of a medicament for the treatment of cardiovascular disease, such as, e.g., atherosclerotic cardiovascular disease.

197. Use of an ISVD according to any one of embodiments 1 to 76 or a polypeptide according to any one of embodiments 77 to 109 or a polypeptide derivative according to any one of embodiments 110 to 173 in the manufacture of a medicament for the treatment of cardiovascular disease, such as for the treatment of stroke and/or myocardial infarction (MI) and/or peripheral arterial disease (PAD).

198. Use of an ISVD according to any one of embodiments 1 to 76 or a polypeptide according to any one of embodiments 77 to 109 or a polypeptide derivative according to any one of embodiments 110 to 173 in the manufacture of a medicament for the treatment of inflammatory disease.

199. A method of treating inflammatory disease, the method comprising administering to a subject an effective amount of an ISVD according to any one of embodiments 1 to 76 or a polypeptide according to any one of embodiments 77 to 109 or a polypeptide derivative according to any one of embodiments 110 to 173.

200. A method of treating inflammatory disease, the method comprising administering to a subject having a High-Sensitivity C-reactive Protein (Hs-CRP) above a value of 1 mg/L, preferably above a value of 1.5 mg/L, an effective amount of an ISVD according to any one of embodiments 1 to 76 or a polypeptide according to any one of embodiments 77 to 109 or a polypeptide derivative according to any one of embodiments 110 to 173.

201. A method of treating inflammatory disease, the method comprising administering to a subject having a High-Sensitivity C-reactive Protein (Hs-CRP) value above or equal to 2 mg/L an effective amount of an ISVD according to any one of embodiments 1 to 76 or a polypeptide according to any one of embodiments 77 to 109 or a polypeptide derivative according to any one of embodiments 110 to 173.

202. A method of treating cardiovascular disease, the method comprising administering to a subject an effective amount of an ISVD according to any one of embodiments 1 to 76 or a polypeptide according to any one of embodiments 77 to 109 or a polypeptide derivative according to any one of embodiments 110 to 173.

203. A method of treating cardiovascular disease, the method comprising administering to a subject suffering from stroke and/or myocardial infarction (MI) and/or peripheral arterial disease (PAD) an effective amount of an ISVD according to any one of embodiments 1 to 76 or a polypeptide according to any one of embodiments 77 to 109 or a polypeptide derivative according to any one of embodiments 110 to 173.

204. A method of treating cardiovascular disease, the method comprising administering to a subject suffering from chronic kidney disease an effective amount of an ISVD according to any one of embodiments 1 to 76 or a polypeptide according to any one of embodiments 77 to 109 or a polypeptide derivative according to any one of embodiments 110 to 173.

205. A method of treating atherosclerotic cardiovascular disease, the method comprising administering to a subject an effective amount of an ISVD according to any one of embodiments 1 to 76 or a polypeptide according to any one of embodiments 77 to 109 or a polypeptide derivative according to any one of embodiments 110 to 173.

206. A method of treating atherosclerotic cardiovascular disease, the method comprising administering to a subject suffering from stroke and/or myocardial infarction (MI) and/or peripheral arterial disease (PAD) an effective amount of an ISVD according to any one of embodiments 1 to 76 or a polypeptide according to any one of embodiments 77 to 109 or a polypeptide derivative according to any one of embodiments 110 to 173.

Epitope

207. An ISVD, polypeptide, or polypeptide derivative capable of binding IL-6 at an epitope comprising at least the amino acid residues 26, 30, 33, 34, 74, 75, 78, 171, 175, 178, 179, 182, and 183, as set forth is SEQ ID NO: 89. (Consecutive numbering)

208. An ISVD, polypeptide, or polypeptide derivative capable of binding IL-6 at an epitope comprising at least the amino acid residues 26, 30, 33, 34, 73, 74, 75, 78, 171, 175, 178, 179, 182, and 183, as set forth is SEQ ID NO: 89. (Consecutive numbering)

209. The ISVD, polypeptide, or polypeptide derivative according to any one of the embodiments 1 to 173, comprising a tryptophan residue capable of forming cation-pi interaction with Arg179 and/or hydrophobic interaction with Phe78, as set forth in SEQ ID NO: 89. (Consecutive numbering)

210. An ISVD, polypeptide, or polypeptide derivative capable of binding IL-6 at an epitope comprising at least the amino acid residues 24, 27, 28, 31, 88, 92, 95, 99, 114, 116, 117, 118, 120, 121, 132, 124, 125, 127, 128, and 139 as set forth is SEQ ID NO: 89. (Consecutive numbering)

211. An ISVD, polypeptide, or polypeptide derivative capable of binding IL-6 at an epitope comprising at least the amino acid residues 24, 27, 28, 31, 88, 92, 95, 99, 114, 116, 117, 118, 120, 121, 132, 124, 125, 127, 128, 138, and 139 as set forth is SEQ ID NO: 89. (Consecutive numbering)

212. An ISVD, polypeptide, or polypeptide derivative which binds hIL-6 (SEQ ID NO: 89) with a $K_D$ of 10-60 pM, such as 11-40 pM, such as 12-30 pM.

213. The ISVD, polypeptide, or polypeptide derivative according to any one of the embodiments 1 to 173, capable of binding hIL-6 (SEQ ID NO: 89) with a $K_D$ of 10-60 pM, such as 11-40 pM, such as 12-30 pM.

Equivalents: Those skilled in the art will recognise, or be able to ascertain using no more than routine experimentation, many equivalents to the specific embodiments of the invention described herein. Such equivalents are intended to be within the scope of protection of the appended claims.

EXAMPLES

List of Abbreviations

CDR: Complementarity Determining Region
$EC_{50}$ Half maximal effective concentration
$ED_{50}$ Half maximal effective dose
FACS: Fluorescence-Activated Cell Sorting
FBS/FCS: Fetal bovine/calf serum
FR: Framework Region
HSA: Hepes buffered saline
HSA: Human serum albumin
$IC_{50}$ Half maximal inhibitory concentration
ISVD: Immunoglobulin Single Variable Domain
IV: Intravenous
MSX: L-Methionine sulfoximine
NAM: Nicotinamide
MRTHL: Mean residence time terminal half-life
OEG: 8-amino-3,6-dioxa-octanoic acid
PBMC: Peripheral Blood Mononuclear Cells
PBS: Phosphate buffered saline
PCR: Polymerase Chain Reaction
PK: Pharmacokinetic
PO: Perorally
RGA: Reporter gene assay
RT-PCR: Reverse Transcriptase Polymerase Chain Reaction
SAA1: Serum amyloid A1
SIA: Sequence Identical Analogue
SC: Subcutaneous
SNAC: Sodium N-(8-[2-hydroxybenzoyl] Amino) Caprylate
SPR: Surface Plasmon Resonance
STAT: Signal transducer and activator of transcription
T½: Half-life
TMB: 3,3',5,5'-Tetramethylbenzidine Materials and Methods
Preparation of Reference anti-IL6 Mab & Reference anti-IL6 Fab Reference Anti-IL6 Mab (SEQ ID No. 130, with heavy chain: SEQ ID NO: 97 & light chain: SEQ ID NO: 101) (Table 35. Entry 1) and a Fab-derivative thereof, which may be referred to as Reference Anti-IL6 Fab (VH-CH1 of heavy chain: SEQ ID NO: 100; light chain: SEQ ID NO: 101), can be prepared following the procedure described in WO 2008/065378.

Generic Expression of V$_H$H
Generic Expression of V$_H$Hs in HEK293 Cells

Expression plasmids for transient expression in HEK293 cells were purchased from either Twist Biosciences or ThermoFisher Scientific. Plasmids from Twist Biosciences were based on the pTT vector described in Durocher, Y. et al., (2002) Nucleic Acid Res, 30: E9 while plasmids from ThermoFisher Scientific were based on the pcDNA34-Topo vector (Thermo Fisher Scientific). Plasmids were used for transient transfection of HEK293 suspension cells (293Expi,

| Amino Acid Sequence | SEQ ID No. |
|---|---|
| EVQLVESGGGLVQPGGSLRLSCAASGFTISSNYMIWVRQAPGKGLEWVSDLY YYAGDTYYADSVKGRFTMSRDISKNTVYLQMNSLRAEDTAVYYCARWADDHP PWIDLWGRGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHK PSNTKVDKRVEPKSCDKTHTCPPCPAPELLGGPSVFLFPPKPKDTLYITREP EVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSREEMTKN QVSLTCLVKGFYPSDIAVEWESNGQPENNYKTTPPVLDSDGSFFLYSKLTVD KSRWQQGNVFSCSVMHEALHNHYTQKSLSLSPGKDIQMTQSPSTLSASVGDR VTITCRASQGISSWLAWYQQKPGKAPKVLIYKASTLESGVPSRFSGSGSGTE FTLTISSLQPDDFATYYCQQSWLGGSFGQGTKLEIKRTVAAPSVFIFPPSDE QLKSGTASVVCLLNNFYPREAKVQWKVDNALQSGNSQESVTEQDSKDSTYSL SSTLTLSKADYEKHKVYACEVTHQGLSSPVTKSFNRGECEVQLVESGGGLVQ PGGSLRLSCAASGFTISSNYMIWVRQAPGKGLEWVSDLYYYAGDTYYADSVK GRFTMSRDISKNTVYLQMNSLRAEDTAVYYCARWADDHPPWIDLWGRGTLVT VSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKRVEPK SCDKTHTCPPCPAPELLGGPSVFLFPPKPKDTLYITREPEVTCVVVDVSHED PEVKFNWYVDGVEVHNAKTKPREEQYNSTYRVVSVLTVLHQDWLNGKEYKCK VSNKALPAPIEKTISKAKGQPREPQVYTLPPSREE | 130 |
| EVQLVESGGGLVQPGGSLRLSCAASGFTISSNYMIWVRQAPGKGLEWVSDLY YYAGDTYYADSVKGRFTMSRDISKNTVYLQMNSLRAEDTAVYYCARWADDHP PWIDLWGRGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHK PSNTKVDKRVEPKSCDKTHTCPPCPAPELLGGPSVFLFPPKPKDTLYITREP EVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSREEMTKN QVSLTCLVKGFYPSDIAVEWESNGQPENNYKTTPPVLDSDGSFFLYSKLTVD KSRWQQGNVFSCSVMHEALHNHYTQKSLSLSPGK | 97 |
| DIQMTQSPSTLSASVGDRVTITCRASQGISSWLAWYQQKPGKAPKVLIYKAS TLESGVPSRFSGSGSGTEFTLTISSLQPDDFATYYCQQSWLGGSFGQGTKLE IKRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSF NRGECEVQLVESGGGLVQPGGSLRLSCAASGFTISSNYMIWVRQAPGKGLEW VSDLYYYAGDTYYADSVKGRFTMSRDISKNTVYLQMNSLRAEDTAVYYCARW ADDHPPWIDLWGRGTLVTVSSASTKGPSVFPLAPSSKSTSGGTAALGCLVKD YFPEPVTVSWNSGALTSGVHTFPAVLQSSGLYSLSSVVTVPSSSLGTQTYIC NVNHKPSNTKVDKRVEPKSCDKTHTCPPCPAPELLGGPSVFLFPPKPKDTLY ITREPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSRE EMTKNQVSLTCLVKGFYPSDIAVEWESNGQPENNYKTTPPVLDSDGSFFLYS KLTVDKSRWQQGNVFSCSVMHEALHNHYTQKSLSLSPGKDIQMTQSPSTLSA SVGDRVTITCRASQGISSWLAWYQQKPGKAPKVLIYKASTLESGVPSRFSGS GSGTEFTLTISSLQPDDFATYYCQQSWLGGSFGQGTKLEIKRTVAAPSVFIF PPSDEQLKSGTASVVCLLNNFYPREAKVQWKVDNALQSGNSQESVTEQDSKD STYSLSSTLTLSKADYEKHKVYACEVTHQGLSSPVTKSFNRGEC | 101 |
| EVQLVESGGGLVQPGGSLRLSCAASGFTISSNYMIWVRQAPGKGLEWVSDLY YYAGDTYYADSVKGRFTMSRDISKNTVYLQMNSLRAEDTAVYYCARWADDHP PWIDLWGRGTLVTVSSASTKGPSVFPLAPCSRSTSESTAALGCLVKDYFPEP VTVSWNSGALTSGVHTFPAVLQSSGLYSLSSVVTVPSSSLGTKTYTCNVDHK PSNTKVDKRVESKY | 100 |

General Molecular Biology

For general molecular biology techniques, see Molecular Cloning: A Laboratory Manual (4$^{th}$ Edition, 2014, Sambrook, Fritsch and Maniatis eds., CSHL Press, Cold Spring Harbor, NY USA).

Invitrogen) essentially following manufacturer's instructions. 293Expi cells were typically subcultivated every 3-4 days in Expi293F expression medium (Invitrogen, catalogue number A1435104) supplemented with 1% P/S (GIBCO catalogue number 15140-122). Expi293F cells were transfected at a cell density of 2.5-3 mill/mL using Expifectamine. For each litre of Expi293F cells, the transfection was performed by diluting a total of 1 mg of plasmid DNA into 50 mL Optimem (GIBCO, cat. No. 51985-026, dilution A) and by diluting 2.7 mL Expifectamine into 50 mL Optimem (dilution B). For co-transfections (i.e., Fab and mAb), plasmids were used in a 1:1 ratio. Dilution A and B were mixed and incubated at room temperature for 10-20 minutes. The transfection mix was hereafter added to the Expi293F cells and cells were incubated at 37° C. in a humidified incubator with orbital rotation (85-140 rpm). One day post-transfection, transfected cells were supplemented with 5 ml of ExpiFectamine 293 Transfection Enhancer 1 and 50 ml of ExpiFectamine 293 Transfection Enhancer 2. Cell culture supernatants were typically harvested 4-5 days post-transfection by centrifugation followed by filtration.

Generic Expression of $V_H$Hs in S. cerevisiae

Plasmids for expression of $V_H$H polypeptides in S. cerevisiae were constructed by subcloning synthetic DNA fragments encoding the $V_H$H polypeptides obtained from Geneart AG (Regensburg, Germany) into a yeast multicopy vector derived from cPOT-type expression plasmids previously described in EP0171142. The resulting plasmids were transformed into yFI3104, a proprietary S. cerevisiae strain, using Frozen-EZ yeast transformation II Kit (Zymo Research, CA) according to manufacturer's instructions or other standard yeast transformation methods. Yeast transformants were selected by glucose utilization as carbon source on agar plates containing 1% yeast extract, 2% peptone, and 2% glucose. Yeast strains containing plasmids encoding $V_H$H polypeptides were cultivated in minimal media as described by Verduyn et al (Verduyn, C., Postma, E., Scheffers, W. A., Van Dijken, J. P. (1992) Yeast 8, 501-517) with the addition of 7 g/L yeast extract and 210 g/L glucose. Yeast supernatants were harvested by centrifugation.

Generic Purification and Analysis of $V_H$H

Hexa-histidine-tagged or non-tagged $V_H$Hs were purified by immobilized metal affinity chromatography (IMAC) on either Ni-Excel (Cytiva) resin with Imidazole or acidic elution followed by a desalting step (PD columns with Sephadex G25 resin, Cytiva) and if necessary, gel filtration chromatography (Superdex200 or Superdex75 columns, Cytiva) in PBS or HBS. Non-His6-tagged $V_H$H polypeptides were purified by multimodal resins (Cytiva) with acidic elution followed by a desalting step (e.g., PD columns with Sephadex G25 resin, Cytiva) and if necessary, gel filtration chromatography (e.g. Superdex200 or Superdex75 columns, Cytiva) in PBS or HBS. Protein integrity was analysed using a Size-Exclusion High-Performance Liquid Chromatographic (SE-HPLC) method setup on an Agilent LC 1100/1200 system and using a BIOSEP (column for separation biomolecules)-SEC-3000 300×7.8 mm column (Phenomenex, cat. no. OOH-2146-K0) and a running buffer composed of 200 mM NaPhosphate pH 6.9, 300 mM NaCl and 10% isopropanol. The molecular masses of the purified $V_H$H polypeptide batches were analysed using ElectroSpray Ionization Time of Flight Mass Spectrometry (ESI-TOF-MS) on a 6280 Agilent system (Agilent Technologies) with a MassPREP Desalt (Waters) column run at 0.4 ml/min in A-buffer composed of $MQ-H_2O$/0.1% formic acid and B-buffer composed of acetonitrile/0.1% formic acid for step elution. To measure the final protein concentration, a Nano-Drop™ spectrophotometer (Thermo Scientific) was used with theoretical calculated extinction coefficients.

Differential Scanning Fluorimetry (Nano DSF) Analysis of Anti-IL-6 $V_H$H

Thermal unfolding was measured using Prometheus NT.48 instrument from Nanotemper Technologies. A linear thermal ramp (1-1.5° C./min, from 20° C. to 95° C.) was used and fluorescence at 350 and 330 nm was measured, and the midpoints of the thermal unfolding reaction (Tm) were determined from the first derivative of the fluorescence ratio (F350/F330).

The thermal stability of various variants of $V_H$H polypeptides were addressed by Nano DSF. The final compound concentration was approx. 1 mg/ml and the buffer concentration 20 mM HEPES, pH 7.4 including 150 mM NaCl.

Reporter Gene Assay (RGA)

In detail, the reporter gene assay (RGA) tested the anti-IL-6 VHHs ability to inhibit IL-6-induced phosphorylation of STAT3 and thus transcription of the luciferase reporter gene in reporter cells expressing the IL-6R and gp130.

For this purpose, an IL-6 reporter cell line was developed by stable transfection of HEK293 cells (ATCC CRL-1573) with a reporter plasmid encoding a STAT3 response element coupled to luciferase. A single cell clone was isolated and propagated to the reporter cell line. On exposure to IL-6, transcription factor STAT3 becomes phosphorylated and activates transcription of the luciferase gene downstream of the response element. IL-6 activity can be directly measured by detection of bioluminescence on conversion of luciferase substrate luciferin to oxyluciferin.

To perform the assay, HEK293-STAT3-Luc cells were cultured in growth medium DMEM GlutaMAX (Gibco 31966-021), 10% fetal bovine serum (FBS, Gibco 10091-148), 1% penicillin/streptomycin (P/S, Lonza DE17-602E) and 1 µg/ml puromycin (Gibco #A11138-03). On the day of experiment, cells were resuspended in assay medium (DMEM w/o Phenol red (Gibco #31053), 10% FBS 1% P/S, and 12.500 cells/well were seeded in 22.5 µl/well in a 384-well plate (Greiner #781086).

The anti-IL-6 $V_H$Hs were serial diluted and pre-incubated for 30 min in assay medium containing 1 nM hIL-6 (in house). 2.5 µl/well were added to the seeded cells in duplicates or triplicates, resulting in a final concentration of 100 pM IL-6. After overnight incubation at 37° C., 5% $CO_2$, 25 µl/well detection reagent (Steady-GLO, Promega E2510) was added and the plate was incubated for 15 min at room temperature. Subsequently, luminescence was detected by an EnVision Multimode Plate Reader (PerkinELmer). To determine the $IC_{50}$ of each entry, a 4-parameter fit was performed on the raw data using GraphPad Prism software (GraphPad Prism version 9.0.1 for Windows, GraphPad Software, San Diego, California USA).

ISVDs, Polypeptides & Polypeptide Derivatives/Constructs Thereof

The below lists of ISVDs, polypeptides, and/or polypeptide derivatives are non-exhaustive lists of example structures which may be discussed in the example section and is understood to be presented for ease reference. These below lists and tables are examples only and are not to be construed as limitative in any way.

Immunoglobulin Single Variable Domains (ISVDs)

The below are examples of Immunoglobulin Single Variable Domains (ISVDs) comprising a $V_H$H. The non-limitative $V_H$H examples provided in Table 11 further identify their amino acid sequence and SEQ ID Nos in their respective columns. The below are examples only and are not to be construed as limitative in any way.

TABLE 11

| VHH ID | Amino acid sequence | SEQ ID NO |
|---|---|---|
| VHH_1.1 | EVQLVESGGGWVQPGGSLQLSCTTSGRRFSEYAVGWFRQAPGQEREFV<br>ADIGEQAENTWYAHSVLGRFTISRDEAKNTVYLQMDSLKPEDTAVYYC<br>AADKYGVGGNAQGYYDSWGQGTQVTVSS | 23 |
| VHH_1.2 | EVQLVESGGGLVQPGGSLKLSCTTSGRRFSEYAVGWFRQGPGKEREFV<br>ADIGEQAENTWYAESVLGRFTISRDDAKNTVYLQMDSLKPEDTAVYYC<br>AADKYGVGGNAQGYYDSWGQGTQVTVSS | 24 |
| VHH_1.3 | EVQLVESGGGLVQPGGSLQLSCTTSGRRFSEYAVGWFRQGPGKEREFV<br>ADIGEQAENTWYAHSVLGRFTISRDDAKNTVYLQMDSLKPEDTAVYYC<br>AADKYGVGGNAQGYYDSWGQGTQVTVSS | 25 |
| VHH_1.4 | EVQLVESGGGLVQPGGSLQLSCTTSGRKFDEYAVGWFRQAPGKEREFV<br>ADIGENAENTWYAHSVLGRFTISRDDAKNTVYLQMDSLKPEDTAVYYC<br>AADKYGVGGNAQGYYDSWGQGTQVTVSS | 26 |
| VHH_1.5 | EVQLVESGGGLVQPGGSLQLSCTTSGRKFDEYAVGWFRQGPGKEREFV<br>ADIGENAENTWYAESVLGRFTISRDDAKNTVYLQMDSLKPEDTAVYYC<br>AADKYGVGGNAQGYYDSWGQGTQVTVSS | 27 |
| VHH_1.6 | EVQLVESGGGLVQPGGSLKLSCTTSGRRFSEYAVGWFRQAPGKEREFV<br>ADIGEQAENTWYAESVLGRFTISRDDAKNTVYLEMDGLKPEDTAVYYC<br>AADKYGVGGNAQGYYDSWGQGTQVTVSS | 28 |
| VHH_1.7 | EVQLVESGGGLVQPGGSLQLSCTTSGRKFDEYAVGWFRQGPGQEREFV<br>ADIGENAENTWYAESVLGRFTISRDDAKNTVYLEMDGLKPEDTAVYYC<br>AADKYGVGGNAQGYYDSWGQGTQVTVSS | 29 |
| VHH_1.8 | EVQLVESGGGLVQAGGSLRLSCTASGGTFSEYAMAWFRQAPGKEREFV<br>TDIGESGGTWYADSVKGRFTISRDNAKNTVYLQMNSLRPEDTAVYYCA<br>ADSYGVGGGAERYYDSWGQGTQVTVSS | 30 |
| VHH_1.9 | EVQLVESGGGLVQPGGSLRLSCTTSGRTFSSYAVGWFRQAPGKEREFV<br>ADIGENADNTWYAHSVKGRFTISRDNAKNTVYLQMNSLKPEDTAVYYC<br>AADSYGVGGGAQGYYDSWGQGTQVTVSS | 31 |
| VHH_1.10 | QVQLVESGGGLVQAGGSLRLSCTASGGTFGEYAMAWFRQAPGKEREFV<br>TDIGESGGTWYADSVKGRFTISRDNAKNTVYLQMNSLRPEDTAVYYCA<br>ADSYGVGGGAERYYDSWGQGTQVTVSS | 32 |
| VHH_1.11 | QLQLVESGGGWVQPGGSLKLSCTTSGRTFSSYAVGWFRQAPGKEREFV<br>ADIGENADNTWYAHSVKGRFTISRDNAKNTVYLQMNSLKPEDTAVYYC<br>AADSYGVGGGAQGYYDSWGQGTQVTVSS | 33 |
| VHH_1.12 | QLQLVESGGGWVQPGGSLQLSCTTSGRTFSSYAVGWFRQAPGQEREFV<br>ADIGENADNTWYAHSVKGRFTISRDNAKNTVYLQMDSLKPEDTAVYYC<br>AADSYGVGGGAQGYYDSWGQGTQVTVSS | 34 |
| VHH_1.13 | EVQLVESGGGLVQAGGSLQLSCTASGGTFSEYAMAWFRQAPGQEREFV<br>TDIGESGGTWYADSVKGRFTISRDNAKNTVYLQMDSLRPEDTAVYYCA<br>ADSYGVGGGAERYYDSWGQGTQVTVSS | 35 |
| VHH_1.14 | QLQLVESGGGWVQPGGSLQLSCTTSGRRFSEYAVGWFRQAPGQEREFV<br>ADIGEQAENTWYAHSVLGRFTISRDEAKNTVYLQMDSLKPEDTAVYYC<br>AADKYGVGGNAQGYYDSWGQGTQVTVSS | 36 |
| VHH_1.15 | QLQLVESGGGWVQPGGSLKLSCTTSGRRFSEYAVGWFRQAPGKEREFV<br>ADIGEQAENTWYAHSVLGRFTISRDEAKNTVYLQMNSLKPEDTAVYYC<br>AADKYGVGGNAQGYYDSWGQGTQVTVSS | 37 |
| VHH_1.16 | EVQLVESGGGLVQPGGSLRLSCAASGFTFSNYWMYWVRQAPGKGLEWV<br>SGINTGGSTPDYADSVKGRFAISRDNAKNTLYLQMNSLRPEDTAVYYC<br>AADTPRVFRLDHYSPLGQGTQVTVSS | 38 |
| VHH_1.17 | EVQLVESGGGLVQPGGSLQLSCAASGFTFSNYWMYWVRQAPGQGLEWV<br>SGINTGGSTPDYADSVKGRFAISRDNAKNTLYLQMDSLRPEDTAVYYC<br>AADTPRVFRLDHYSPLGQGTQVTVSS | 103 |
| VHH_2.1 | QVQLVESGGDLVQPGGSLRLSCTTSGRTFSSYAMGWFRQAPGKEREFV<br>ADIGENADNRWYAHSVKGRFTISRDNAKNTVYLQMNSLKPEDTAVYYC<br>AADRYGVGGGAQGYYDSWGQGTQVTVSS | 104 |
| VHH_2.2 | EVQLVESGGGLVQPGGSLRLSCAASGFTFSNYWMYWVRQAPGKGLEWV<br>SGINTGGSTPDYADSVKDRFTISRDNAKNTLYLQMNSLRPADTAVYYC<br>AADTPRSFRLNHYAPLGQGTQVTVSS | 105 |

TABLE 11-continued

Non-limiting examples of ISVDs comprising a V$_H$H

| V$_H$H ID | Amino acid sequence | SEQ ID NO |
|---|---|---|
| VHH_2.3 | QVQLQESGGGLVQAGGSLRLSCTTSGRTFSSYAMGWFRQAPGKEREFV ADIGENADNRWYAHSVKGRFTISRDNAKNTVYLQMNSLKPEDTAVYYC AADRYGVGGGAQGYYDSWGQGTQVTVSS | 106 |
| VHH_2.4 | QVQLQESGGGLVQAGGSLRLSCTVSGRTFSTYAMGWFRQAPGKEREFV ADINWNSDNLWYADSVKGRFTISRDNAKNTMYLQMNSLKPEDTAVYYC AVDSYGVGGGKPEYYDSWGQGTQVTVSS | 107 |
| VHH_2.5 | QLQLVESGGGLVQPGGSLRLSCAASGFTFSNYWMYWVRQAPGKGLEWV SGINTGGSTPDYADSVKGRFTISRDNAKNTLYLQMNSLRPEDTAVYYC AADTPRVFRLDHYSPLGQGTQVTVSS | 108 |
| VHH_2.6 | QVQLQESGGGLVQAGGSLRLSCTTSGRTFSDYAMAWFRQAPGKDREFV ADIGTNSENTWYAESVKGRFTISRDNTKNTIYLQMNSLKPEDTAVYYC AADSYGVGGGKQEYYDSWGQGAQVTVSS | 109 |
| VHH_2.7 | EVQLVESGGRWVQPGASLRLSCTTSGRTFSSYAMGWFRQAPGKEREFV ADIGENADNRWYAHSVKGRFTISRDNAKNTVYLQMNSLKPEDTAVYYC AADRYGVGGGAQGYYDSWGQGTQVTVSS | 110 |
| VHH_2.8 | QVQLVESGGGLVQPGGSLRLSCAASGFTFSSYWMYWVRQAPGKGLEWV SGINTGGSTPDYADSVKGRFTISRDNAKNTLYLQMNSLRPEDTAVYYC AADTPRSFRLNHYSPLGQGTQVTVSS | 111 |
| VHH_2.9 | QVQLVESGGGLVQPGGSLRLSCAASGFTFSNYWMYWVRQAPGKGLEWV SGIDTRGSTPDYADSVKGRFTISRDNAKSTFYLQMNSLRPEDTAVYYC ATDTPRSFRLYHYVPLGQGTQVTVSS | 112 |
| VHH_2.10 | QVQLQESGGGLVQAGGSLRLSCTVSGRTFSTYAMGWFRQAPGKEREFV ADINWNSDNIWYADSVKGRFTISRDNAKNVMYLQMNSLKPEDTAVYYC AADSYGVGGGKEEYYDSWGQGTQVTVSS | 113 |
| VHH_2.11 | EVQLVESGGGLVQAGGSLRLSCTASGRSFSSYAMGWFRQAPGKEREFV ADIGVNPDNTWYADSAKGRFTISRDNAKNTMYLQMNSLKPEDTAVYYC AADSYGVGGGAERYYDSWGQGTQVTVSS | 114 |
| VHH_2.12 | QVQLVESGGGLVQAGGSLRLSCTTSGRTFSSYAMAWFRQAPGKDREFV ADIGENSDNIWYADSVKGRFTISRDNAKNTILLQMNSLKPEDTAVYYC AADSYGVGGGKPEYYDSWGQGAQVTVSS | 115 |
| VHH_2.13 | EVQLVESGGGLVQAGGPLRLSCTVSGRTFSTYAMGWFRQAPGKEREFV ADINWNSDNIWYADSVKGRFTISRDNAKNVMYLQMNSLKPEDTAVYYC AADSYGVGGGKEEYYDSWGQGTQVTVSS | 116 |
| VHH_2.14 | QLQLVESGGGSVQVGDSLRLSCTFSGRSFSSYAMGWFRQAPGKEREFV ADIGENADNTWYAHSVKGRFTISRDNAKNTVYLQMNSLKPEDTAVYYC AADSYGVGGGAQGYYDSWGQGTQVTVSS | 117 |
| VHH_2.15 | QVQLQESGGGLVQAGGSLRLSCTASGGTFSEYAMAWFRQAPGKEREFV TDIGESGGTWYADSVKGRFTISRDNAKNTVYLQMNSLRPEDTAVYYCA ADSYGVGGGAERYYDSWGQGTQVTVSS | 118 |
| VHH_2.16 | EVQLVESGGGLVQPGGSLSLSCTASGRTFSSYAMGWFRQAPGKEREFV ADIGENADNRWYAHSVKGRFTISRDNAKNTVYLQMNSLKPEDTAVYYC AADRYGVGGGAQGYYDSWGQGTQVTVSS | 119 |
| VHH_2.17 | QVQLVESGGGLVQAGGSLRLSCTVSGRTFSTYAMGWFRQAPGKEREFV ADINWNSDNIWYADSVKGRFTISRDNAKNVMYLQMNSLKPEDTAVYYC AADSYGVGGGKEEYYDSWGQGTQVTVSS | 120 |
| VHH_2.18 | EVQLVESGGGLVQPGGSLQLSCTTSGRHFDEYAVGWFRQAPGKEREFV ADIGENADNTWYAHSVKGRFTISRDDAKNTVYLEMDGLKPEDTAVYYC AADKYGVGGNAQGYYDSWGQGTQVTVSS | 121 |
| VHH_2.19 | EVQLVESGGGLVQPGGSLQLSCTTSGRHFDEYAVGWFRQGPGKEREFV ADIGENADNTWYAHSVKGRFTISRDDAKNTVYLEMDGLKPEDTAVYYC AADKYGVGGNAQGYYDSWGQGTQVTVSS | 122 |
| VHH_2.20 | EVQLVESGGGLVQPGGSLQLSCTTSGRRFSEYAVGWFRQAPGKEREFV ADIGEQAENTWYAHSVLGRFTISRDDAKNTVYLQMDSLKPEDTAVYYC AADKYGVGGNAQGYYDSWGQGTQVTVSS | 123 |

TABLE 11-continued

Non-limiting examples of ISVDs comprising a V$_H$H

| V$_H$H ID | Amino acid sequence | SEQ ID NO |
|---|---|---|
| VHH_2.21 | EVQLVESGGGLVQPGGSLQLSCTTSGRRFSEYAVGWFRQGPGKEREFV ADIGEQAENTWYAESVLGRFTISRDDAKNTVYLQMDSLKPEDTAVYYC AADKYGVGGNAQGYYDSWGQGTQVTVSS | 124 |
| VHH_2.22 | EVQLVESGGGLVQPGGSLKLSCTTSGRKFDEYAVGWFRQAPGKEREFV ADIGENAENTWYAHSVLGRFTISRDDAKNTVYLQMDSLKPEDTAVYYC AADKYGVGGNAQGYYDSWGQGTQVTVSS | 125 |
| VHH_2.23 | EVQLVESGGGLVQPGGSLKLSCTTSGRRFSEYAVGWFRQGPGKEREFV ADIGEQAENTWYAHSVLGRFTISRDDAKNTVYLEMDGLKPEDTAVYYC AADKYGVGGNAQGYYDSWGQGTQVTVSS | 126 |
| VHH_2.24 | EVQLVESGGGWVQPGGSLKLSCTTSGRRFSEYAVGWFRQAPGKEREFV ADIGEQAENTWYAHSVLGRFTISRDDAKNTVYLQMDSLKPEDTAVYYC AADKYGVGGNAQGYYDSWGQGTQVTVSS | 127 |
| VHH_3.1 | QVQLVESGGGLVQPGGSLKLSCTTSGRRFSEYAVGWFRQAPGKEREFV ADIGEQAENTWYAESVLGRFTISRDDAKNTVYLEMDGLKPEDTAVYYC AADKYGVGGNAQGYYDSWGQGTQVTVSS | 145 |
| VHH_3.2 | ELQLVESGGGLVQPGGSLKLSCTTSGRRFSEYAVGWFRQAPGKEREFV ADIGEQAENTWYAESVLGRFTISRDDAKNTVYLEMDGLKPEDTAVYYC AADKYGVGGNAQGYYDSWGQGTQVTVSS | 146 |
| VHH_3.3 | EVQLVESGGGWVQPGGSLKLSCTTSGRRFSEYAVGWFRQAPGKEREFV ADIGEQAENTWYAESVLGRFTISRDDAKNTVYLEMDGLKPEDTAVYYC AADKYGVGGNAQGYYDSWGQGTQVTVSS | 147 |
| VHH_3.4 | EVQLVESGGGLVQPGGSLKLSCTTSGRTFSEYAVGWFRQAPGKEREFV ADIGEQAENTWYAESVLGRFTISRDDAKNTVYLEMDGLKPEDTAVYYC AADKYGVGGNAQGYYDSWGQGTQVTVSS | 148 |
| VHH_3.5 | EVQLVESGGGLVQPGGSLKLSCTTSGRRFSSYAVGWFRQAPGKEREFV ADIGEQAENTWYAESVLGRFTISRDDAKNTVYLEMDGLKPEDTAVYYC AADKYGVGGNAQGYYDSWGQGTQVTVSS | 149 |
| VHH_3.6 | EVQLVESGGGLVQPGGSLKLSCTTSGRRFSEYAVGWFRQAPGKEREFV ADIGENAENTWYAESVLGRFTISRDDAKNTVYLEMDGLKPEDTAVYYC AADKYGVGGNAQGYYDSWGQGTQVTVSS | 150 |
| VHH_3.7 | EVQLVESGGGLVQPGGSLKLSCTTSGRRFSEYAVGWFRQAPGKEREFV ADIGEQADNTWYAESVLGRFTISRDDAKNTVYLEMDGLKPEDTAVYYC AADKYGVGGNAQGYYDSWGQGTQVTVSS | 151 |
| VHH_3.8 | EVQLVESGGGLVQPGGSLKLSCTTSGRRFSEYAVGWFRQAPGKEREFV ADIGEQAENTWYAHSVLGRFTISRDDAKNTVYLEMDGLKPEDTAVYYC AADKYGVGGNAQGYYDSWGQGTQVTVSS | 152 |
| VHH_3.9 | EVQLVESGGGLVQPGGSLKLSCTTSGRRFSEYAVGWFRQAPGKEREFV ADIGEQAENTWYAESVKGRFTISRDDAKNTVYLEMDGLKPEDTAVYYC AADKYGVGGNAQGYYDSWGQGTQVTVSS | 153 |
| VHH_3.10 | EVQLVESGGGLVQPGGSLKLSCTTSGRRFSEYAVGWFRQAPGKEREFV ADIGEQAENTWYAESVLGRFTISRDNAKNTVYLEMDGLKPEDTAVYYC AADKYGVGGNAQGYYDSWGQGTQVTVSS | 154 |
| VHH_3.11 | EVQLVESGGGLVQPGGSLKLSCTTSGRRFSEYAVGWFRQAPGKEREFV ADIGEQAENTWYAESVLGRFTISRDDAKNTVYLEMNGLKPEDTAVYYC AADKYGVGGNAQGYYDSWGQGTQVTVSS | 155 |
| VHH_3.12 | EVQLVESGGGLVQPGGSLKLSCTTSGRRFSEYAVGWFRQAPGKEREFV ADIGEQAENTWYAESVLGRFTISRDDAKNTVYLEMDSLKPEDTAVYYC AADKYGVGGNAQGYYDSWGQGTQVTVSS | 156 |
| VHH_3.13 | EVQLVESGGGLVQPGGSLKLSCTTSGRRFSEYAVGWFRQAPGKEREFV ADIGEQAENTWYAESVLGRFTISRDDAKNTVYLEMDGLKPEDTAVYYC AADSYGVGGNAQGYYDSWGQGTQVTVSS | 157 |
| VHH_3.14 | EVQLVESGGGLVQPGGSLKLSCTTSGRRFSEYAVGWFRQAPGKEREFV ADIGEQAENTWYAESVLGRFTISRDDAKNTVYLEMDGLKPEDTAVYYC AADKYGVGGGAQGYYDSWGQGTQVTVSS | 158 |

TABLE 11-continued

Non-limiting examples of ISVDs comprising a V$_H$H

| V$_H$H ID | Amino acid sequence | SEQ ID NO |
|---|---|---|
| VHH_3.15 | QLQLVESGGGWVQPGGSLKLSCTTSGRHFQEYAVGWFRQAPGKEREFV ADIGETAEVTWYAHSVKGRFTISRDNAKNTVYLEMNGLKPEDTAVYYC AADKYGVGGGAQGYYDSWGQGTQVTVSS | 160 |

Polypeptides & Polypeptide Derivatives/Compounds

The below are examples of polypeptides and/or polypeptide derivatives. The polypeptides will be given an identifier of the type "Polypeptide_n", where n is to an integer for identification (eg. Polypeptide_1, Polypeptide_2, Polypeptide_3, and so forth). Similarly, polypeptide derivatives will be given an identifier with the prefix "Compound", such that the resulting identifier (ID) is of the type "Compound n", where n is an integer for identification (eg. Compound 1, Compound 2, Compound 3, and so forth). In the below table, it is understood that any reference to a given position of a substituent in an extension refers to the relative position in the full length of the amino acid sequence of said extension, from N-terminus to C-terminus of the Extension. For instance, should one refer to the position of a substituent as being at "Cys in position 4 of Extension", then it is understood to refer to the cysteine residue found in position 4 in accordance with the full length of the sequence of the extension as defined by the SEQ ID No. provided in the respective extension column for the given polypeptide derivative, starting with residue number 1 which is closest to the N-terminus. Further, it is understood that the position column when referring to the extension refers to the positioning of the extension with reference to the V$_H$H. For instance, should the entry state "C-term" in the position column of the extension, it is understood that it refers to the fact that said extension is found at the C-terminus of the V$_H$H for that Polypeptide, which May likewise be the polypeptide found in a Polypeptide derivative.

Chem. 24 refers to the substituent identified as such in Table 9. The extension/tag is identified by its SEQ ID No. In the case of an extension that is a combination of subelements (such as an extension with a his-tag for instance), the ID will identify the name of the subelements and the SEQ ID No. refers to the full sequence of the extension.

The below are examples only and are not to be construed as limitative in any way. Polypeptide derivative ID "Compound 13" is purposefully omitted.

TABLE 12

Non-limiting examples of polypeptides and polypeptide derivatives

| Polypeptide ID | SEQ ID No. | Polypeptide Derivative ID | V$_H$H ID | SEQ ID No. | Position relative to V$_H$H | Tag/Extension SEQ ID | SEQ ID No. | ID | Substituent Position |
|---|---|---|---|---|---|---|---|---|---|
| Poly-peptide_1 | 39 | — | VHH_2.1 | 104 | C-term | GGGGSH HHHHH E1 | 71 | — | — |
| Poly-peptide_2 | 40 | — | VHH_2.2 | 105 | C-term | GGGGSH HHHHH E1 | 71 | — | — |
| Poly-peptide_3 | 41 | — | VHH_2.3 | 106 | C-term | GGGGSH HHHHH E1 | 71 | — | — |
| Poly-peptide_4 | 42 | — | VHH_2.4 | 107 | C-term | GGGGSH HHHHH E1 | 71 | — | — |
| Poly-peptide_5 | 43 | — | VHH_2.5 | 108 | C-term | GGGGSH HHHHH E1 | 71 | — | — |
| Poly-peptide_6 | 44 | — | VHH_2.6 | 109 | C-term | GGGGSH HHHHH E1 | 71 | — | — |
| Poly-peptide_7 | 45 | — | VHH_2.7 | 110 | C-term | GGGGSH HHHHH E1 | 71 | — | — |
| Poly-peptide_8 | 46 | — | VHH_2.8 | 111 | C-term | GGGGSH HHHHH E1 | 71 | — | — |
| Poly-peptide_9 | 47 | — | VHH_2.9 | 112 | C-term | GGGGSH HHHHH E1 | 71 | — | — |
| Poly-peptide_10 | 48 | — | VHH_2.10 | 113 | C-term | GGGGSH HHHHH E1 | 71 | — | — |

TABLE 12-continued

Non-limiting examples of polypeptides and polypeptide derivatives

| Polypeptide | | V<sub>H</sub>H | | Tag/Extension SEQ ID No. | | | Substituent | |
|---|---|---|---|---|---|---|---|---|
| SEQ ID | Polypeptide Derivative No. ID | ID | SEQ ID No. | Position relative to V<sub>H</sub>H | SEQ ID | SEQ ID No. ID | Substituent | Position |
| Poly-peptide_11 | 49 — | VHH_2.11 | 114 | C-term | GGGGSH HHHHH | E1 | 71 — | — |
| Poly-peptide_12 | 50 — | VHH_2.12 | 115 | C-term | GGGGSH HHHHH | E1 | 71 — | — |
| Poly-peptide_13 | 51 — | VHH_2.13 | 116 | C-term | GGGGSH HHHHH | E1 | 71 — | — |
| Poly-peptide_14 | 52 — | VHH_2.14 | 117 | C-term | GGGGSH HHHHH | E1 | 71 — | — |
| Poly-peptide_15 | 53 — | VHH_2.15 | 118 | C-term | GGGGSH HHHHH | E1 | 71 — | — |
| Poly-peptide_16 | 54 — | VHH_2.16 | 119 | C-term | GGGGSH HHHHH | E1 | 71 — | — |
| Poly-peptide_17 | 55 — | VHH_2.17 | 120 | C-term | GGGGSH HHHHH | E1 | 71 — | — |
| Poly-peptide_18 | 56 — | VHH_1.16 | 38 | C-term | GGGGSH HHHHH | E1 | 71 — | — |
| Poly-peptide_19 | 57 — | VHH_1.11 | 33 | C-term | GGGGSH HHHHH | E1 | 71 — | — |
| Poly-peptide_20 | 58 — | VHH_2.18 | 121 | C-term | GGGGSH HHHHH | E1 | 71 — | — |
| Poly-peptide_21 | 59 — | VHH_2.19 | 122 | C-term | GGGGSH HHHHH | E1 | 71 — | — |
| Poly-peptide_22 | 60 — | VHH_1.2 | 24 | C-term | GGGGSH HHHHH | E1 | 71 — | — |
| Poly-peptide_23 | 61 — | VHH_2.20 | 123 | C-term | GGGGSH HHHHH | E1 | 71 — | — |
| Poly-peptide_24 | 62 — | VHH_1.3 | 25 | C-term | GGGGSH HHHHH | E1 | 71 — | — |
| Poly-peptide_25 | 63 — | VHH_2.21 | 124 | C-term | GGGGSH HHHHH | E1 | 71 — | — |
| Poly-peptide_26 | 64 — | VHH_2.22 | 125 | C-term | GGGGSH HHHHH | E1 | 71 — | — |
| Poly-peptide_27 | 65 — | VHH_1.4 | 26 | C-term | GGGGSH HHHHH | E1 | 71 — | — |
| Poly-peptide_28 | 66 — | VHH_1.5 | 27 | C-term | GGGGSH HHHHH | E1 | 71 — | — |
| Poly-peptide_29 | 67 — | VHH_1.6 | 28 | C-term | GGGGSH HHHHH | E1 | 71 — | — |
| Poly-peptide_30 | 68 — | VHH_2.23 | 126 | C-term | GGGGSH HHHHH | E1 | 71 — | — |
| Poly-peptide_31 | 69 — | VHH_1.7 | 29 | C-term | GGGGSH HHHHH | E1 | 71 — | — |
| Poly-peptide_32 | 70 — | VHH_2.24 | 127 | C-term | GGGGSH HHHHH | E1 | 71 — | — |
| Poly-peptide_33 | 84 — | VHH_1.9 | 31 | C-term | GGGGSH HHHHH | E1 | 71 — | — |

TABLE 12-continued

Non-limiting examples of polypeptides and polypeptide derivatives

| Polypeptide | | V<sub>H</sub>H | | Tag/Extension SEQ ID No. | | | Substituent | |
|---|---|---|---|---|---|---|---|---|
| ID | SEQ ID No. | Polypeptide Derivative ID | ID | SEQ ID No. | Position relative to V<sub>H</sub>H | SEQ | SEQ ID No. | ID Position |
| Polypeptide_34 | 85 | — | VHH_1.8 | 30 | C-term | GGGGSH HHHHH | E1 | 71 — — |
| Polypeptide_35 | 86 | — | VHH_1.10 | 32 | C-term | GGGGSH HHHHH | E1 | 71 — — |
| Polypeptide_36 | 73 | — | VHH_1.1 | 23 | C-term | GQACPC | E2 | 72 — — |
| Polypeptide_37 | 74 | — | VHH_1.2 | 24 | C-term | GQACPC | E2 | 72 — — |
| Polypeptide_38 | 75 | — | VHH_1.3 | 25 | C-term | GQACPC | E2 | 72 — — |
| Polypeptide_39 | 76 | — | VHH_1.4 | 26 | C-term | GQACPC | E2 | 72 — — |
| Polypeptide_40 | 77 | — | VHH_1.5 | 27 | C-term | GQACPC | E2 | 72 — — |
| Polypeptide_41 | 78 | — | VHH_1.6 | 28 | C-term | GQACPC | E2 | 72 — — |
| Polypeptide_42 | 79 | — | VHH_1.7 | 29 | C-term | GQACPC | E2 | 72 — — |
| Polypeptide_43 | 80 | — | VHH_1.16 | 38 | C-term | GQACPC | E2 | 72 — — |
| Polypeptide_44 | 81 | — | VHH_1.12 | 34 | C-term | GQACPC | E2 | 72 — — |
| Polypeptide_45 | 94 | — | VHH_1.13 | 35 | C-term | GQACPC | E2 | 72 — — |
| Polypeptide_46 | 95 | — | VHH_1.14 | 36 | C-term | GQACPC | E2 | 72 — — |
| Polypeptide_47 | 99 | — | VHH_1.15 | 37 | C-term | GGGGSH HHHHH | E1 | 71 — — |
| Polypeptide_48 | 102 | — | VHH_1.17 | 103 | C-term | GQACPC | E2 | 72 — — |
| Polypeptide_49 | 131 | — | VHH_3.1 | 145 | C-term | GGGGSH HHHHH | E1 | 71 — — |
| Polypeptide_50 | 132 | — | VHH_3.2 | 146 | C-term | GGGGSH HHHHH | E1 | 71 — — |
| Polypeptide_51 | 133 | — | VHH_3.3 | 147 | C-term | GGGGSH HHHHH | E1 | 71 — — |
| Polypeptide_52 | 134 | — | VHH_3.4 | 148 | C-term | GGGGSH HHHHH | E1 | 71 — — |
| Polypeptide_53 | 135 | — | VHH_3.5 | 149 | C-term | GGGGSH HHHHH | E1 | 71 — — |
| Polypeptide_54 | 136 | — | VHH_3.6 | 150 | C-term | GGGGSH HHHHH | E1 | 71 — — |
| Polypeptide_55 | 137 | — | VHH_3.7 | 151 | C-term | GGGGSH HHHHH | E1 | 71 — — |
| Polypeptide_56 | 138 | — | VHH_3.8 | 152 | C-term | GGGGSH HHHHH | E1 | 71 — — |

TABLE 12-continued

Non-limiting examples of polypeptides and polypeptide derivatives

| Polypeptide ID | SEQ ID No. | Polypeptide Derivative ID | V$_H$H ID | SEQ ID No. | Tag/Extension Position relative to V$_H$H | SEQ ID | SEQ ID No. | Substituent Position |
|---|---|---|---|---|---|---|---|---|
| Poly-peptide_57 | 139 | — | VHH_3.9 | 153 | C-term | GGGGSH HHHHH | E1 71 | — — |
| Poly-peptide_58 | 140 | — | VHH_3.10 | 154 | C-term | GGGGSH HHHHH | E1 71 | — — |
| Poly-peptide_59 | 141 | — | VHH_3.11 | 155 | C-term | GGGGSH HHHHH | E1 71 | — — |
| Poly-peptide_60 | 142 | — | VHH_3.12 | 156 | C-term | GGGGSH HHHHH | E1 71 | — — |
| Poly-peptide_61 | 143 | — | VHH_3.13 | 157 | C-term | GGGGSH HHHHH | E1 71 | — — |
| Poly-peptide_62 | 144 | — | VHH_3.14 | 158 | C-term | GGGGSH HHHHH | E1 71 | — — |
| Poly-peptide_63 | 159 | — | VHH_3.15 | 160 | C-term | GGGGSH HHHHH | E1 71 | — — |
| — | — | Compound 1 | VHH_1.12 | 34 | C-term | GQACPC | E2 72 | Chem. 24 Cys in position 4 of Extension<br>Chem. 24 Cys in position 6 of Extension |
| — | — | Compound 2 | VHH_1.13 | 35 | C-term | GQACPC | E2 72 | Chem. 24 Cys in position 4 of Extension<br>Chem. 24 Cys in position 6 of Extension |
| — | — | Compound 3 | VHH_1.14 | 36 | C-term | GQACPC | E2 72 | Chem. 24 Cys in position 4 of Extension<br>Chem. 24 Cys in position 6 of Extension |
| — | — | Compound 4 | VHH_1.1 | 23 | C-term | GQACPC | E2 72 | Chem. 24 Cys in position 4 of Extension<br>Chem. 24 Cys in position 6 of Extension |
| — | — | Compound 5 | VHH_1.2 | 24 | C-term | GQACPC | E2 72 | Chem. 24 Cys in position 4 of Extension<br>Chem. 24 Cys in position 6 of Extension |
| — | — | Compound 6 | VHH_1.3 | 25 | C-term | GQACPC | E2 72 | Chem. 24 Cys in position 4 of Extension<br>Chem. 24 Cys in position 6 of Extension |
| — | — | Compound 7 | VHH_1.4 | 26 | C-term | GQACPC | E2 72 | Chem. 24 Cys in position 4 of Extension<br>Chem. 24 Cys in position 6 of Extension |
| — | — | Compound 8 | VHH_1.5 | 27 | C-term | GQACPC | E2 72 | Chem. 24 Cys in position 4 of Extension<br>Chem. 24 Cys in position 6 of Extension |
| — | — | Compound 9 | VHH_1.6 | 28 | C-term | GQACPC | E2 72 | Chem. 24 Cys in position 4 of Extension<br>Chem. 24 Cys in position 6 of Extension |
| — | — | Compound 10 | VHH_1.7 | 29 | C-term | GQACPC | E2 72 | Chem. 24 Cys in position 4 of Extension<br>Chem. 24 Cys in position 6 of Extension |
| — | — | Compound 12 | VHH_1.17 | 103 | C-term | GQACPC | E2 72 | Chem. 24 Cys in position 4 of Extension<br>Chem. 24 Cys in position 6 of Extension |
| — | — | Compound 14 | VHH_1.6 | 28 | C-term | GQACPH HHHHH [6xHis tag] | E8- 161 | Chem. 24 Cys in position 4 of Extension |
| — | — | Compound 15 | VHH_1.6 | 28 | C-term | GQACPH HHHHH [6xHis tag] | E8- 161 | Chem. 26 Cys in position 4 of Extension |
| — | — | Compound 16 | VHH_1.6 | 28 | C-term | GQACPH HHHHH [6xHis tag] | E8- 161 | Chem. 27 Cys in position 4 of Extension |
| — | — | Compound 17 | VHH_1.6 | 28 | C-term | GQACPC HHHHHH [6xHis tag] | E2- 162 | Chem. 24 Cys in position 4 of Extension<br>Chem. 24 Cys in position 6 of Extension |

TABLE 12-continued

Non-limiting examples of polypeptides and polypeptide derivatives

| Polypeptide | | | V$_H$H | | Tag/Extension SEQ ID No. | | | | |
|---|---|---|---|---|---|---|---|---|---|
| ID | SEQ ID No. | Polypeptide Derivative ID | ID | SEQ ID No. | Position relative to V$_H$H | SEQ ID | SEQ ID No. | Substituent ID | Position |
| — | — | Compound 18 | VHH_1.6 | 28 | C-term | GQACPC HHHHHH [6xHis tag] | E2-162 | Chem. 26 Chem. 26 | Cys in position 4 of Extension Cys in position 6 of Extension |
| — | — | Compound 19 | VHH_1.6 | 28 | C-term | GQACPC HHHHHH [6xHis tag] | E2-162 | Chem. 27 Chem. 27 | Cys in position 4 of Extension Cys in position 6 of Extension |

Example 1: Immunization and Construction of V$_H$H Library

The purpose of this example is to construct an anti-IL-6 V$_H$H library for developing suitable anti-IL6 V$_H$H polypeptides for further development into drug candidates for oral and/or subcutaneous delivery.

At the outset an anti-IL-6 V$_H$H library was generated. The most promising set of V$_H$H in terms of, e.g., appropriate binding K$_D$ affinities, IC$_{50}$ values and biophysical stabilities, were selected for further optimization, which, for example, included reducing pI, humanization, and adding protractors for development of, for example, an optimized anti-IL-6 oral drug candidate.

1.1 Immunisation

Single domain antibodies were obtained from llamas immunized with the human IL-6 with N-term His tag (SEQ ID NO: 82; hIL-6-His) protein antigen. Animals were immunized with six subcutaneous injections at weekly intervals (100 μg of antigen on the first two injections and 50 μg of antigen on the remaining injections). One week after the last boost, sera were collected to define antibody titres against biotinylated hIL-6-His (SEQ ID NO: 82; bio-hIL-6-His) and biotinylated cynomolgus IL-6 with N-term His tag (SEQ ID NO: 83; bio-cyIL-6-His) by ELISA. In this ELISA, 96-well plates (Maxisorp; Nunc) were coated with neutravidin (Thermo Scientific) at 5 μg/ml, diluted in PBS (pH 7.4), overnight at 4° C. The next day, plates were washed with PBS-Tween 0.05% (pH 7.4) and blocked at room temperature for 2 h with 1% casein (Sigma). After blocking, bio-hIL-6-His and bio-cyIL-6-His antigens at 1 nM, diluted in 0.1% casein/PBS (pH 7.4), were captured and the sequentially diluted sera samples in 0.1% casein/PBS (pH 7.4) were then added. The presence of anti-hIL-6 antibodies was demonstrated by using a mouse anti-llama IgG antibody followed by donkey anti-mouse immunoglobulin peroxidase conjugate antibody (Jackson ImmunoResearch). Incubations were performed for 1 h at room temperature. Between incubation steps, plates were washed with PBS Tween 0.05% (pH 7.4) and a final wash with PBS (pH 7.4) prior to development was performed. ELISA signal development was performed by adding the substrate solution (TMB solution) to the plates, followed by H$_2$SO$_4$. ELISA signals were obtained by using a plate reader at 450 nm.

TABLE 13

Reagents used for immunisation screening and isolation of V$_H$Hs.

| Brief description | Amino acid sequence | SEQ ID # |
|---|---|---|
| human IL-6 with N-term His tag | HHHHHHGGGGSVPPGEDSKDVAAPHRQPLTSSERIDKQIRYIL DGISALRKETCNKSNMCESSKEALAENNLNLPKMAEKDGCFQS GFNEETCLVKIITGLLEFEVYLEYLQNRFESSEEQARAVQMST KVLIQFLQKKAKNLDAITTPDPTTNASLLTKLQAQNQWLQDMT THLILRSFKEFLQSSLRALRQM | 82 |
| cynomolgus IL-6 with N-term His tag | HHHHHHGGGGSAPVLPGEDSKDVAAPHSQPLTSSERIDKHIRY ILDGISALRKETCNRSNMCESSKEALAENNLNLPKMAEKDGCF QSGFNEDTCLVKIITGLLEFEVYLEYLQNRFESSEEQARAVQM STKVLIQFLQKKAKNLDAITTPEPTTNASLLTKLQAQNQWLQD MTTHLILRSFKEFLQSSLRALRQM | 83 |
| human IL-6 Avi tagged with N-term His tag | HHHHHHGGGGSGLNDIFEAQKIEWHEGGGGSVPPGEDSKDVAA PHRQPLTSSERIDKQIRYILDGISALRKETCNKSNMCESSKEA LAENNLNLPKMAEKDGCFQSGFNEETCLVKIITGLLEFEVYLE YLQNRFESSEEQARAVQMSTKVLIQFLQKKAKNLDAITTPDPT TNASLLTKLQAQNQWLQDMTTHLILRSFKEFLQSSLRALRQM | 96 |

1.2 Library Construction

RNA was extracted from PBMC of two immunized llamas. Extracted RNA was used for cDNA synthesis using random primers. The cDNA was used in a primary PCR amplification using non-tagged primers annealing at the Leader sequence and Hinge CH1 regions, followed by a secondary PCR amplification introducing restriction endonuclease sites for cloning of $V_HH$ genes in the phagemid vector. The libraries were electroporated into TG1 E. coli cells and bacterial glycerol stocks of the immune libraries were stored at −80° C.

1.3 Isolation of VHHs

Phage production from the llama $V_HH$ library pool were used in three consecutive rounds of phage display selections using biotinylated human IL-6 Avi tagged with N-term His tag (bio-hIL-6-Avi-His, SEQ ID NO: 96) and bio-cyIL-6-His proteins (SEQ ID NO: 83) at decreasing concentrations at pH 7.4 (PBS buffer) (bio-hIL-6-Avi-His and bio-cyIL-6-His at 50 nM, 5 nM and 0.5 nM (pre-captured on beads) on the first round, bio-hIL-6-Avi-His at 50 nM, 5 nM and 0.5 nM on the second round and bio-hIL-6-Avi-His and bio-cyIL-6-His at 50 nM, 5 nM, 0.5 nM and 0.05 nM on the last round) with washing of non-specific phage, followed by phage elution with trypsin (total elution) and inhibition of trypsin protease activity with 4-(2-aminoethyl)-benzene-sulfonyl fluoride and specific elution using an anti-IL-6 monoclonal antibody ("Reference anti-IL6 Mab"; SEQ ID No. 130, with heavy chain: SEQ ID NO: 97 & light chain: SEQ ID NO: 101). Serial dilutions of the eluted phage were performed and used to infect exponentially growing TG1. Infected TG1 was plated on LB+Carb$^{100}$+Glu$^{2\%}$ plates and enrichment values calculated over the background (without antigen for selection).

Individual clones from the second and third rounds of selection conditions outputs were picked into 96-well Master Plates and tested as periplasmic extract (P.E.) for binding to bio-hIL-6-Avi-His (SEQ ID NO: 96) and bio-cyIL-6-His (SEQ ID NO: 83) proteins captured via neutravidin by binding ELISA. For P.E. binding ELISA, MaxiSorp™ high protein-binding capacity 96 well ELISA plates, were coated with neutravidin (Thermo Scientific) at 5 μg/ml, diluted in PBS (pH 7.4), overnight at 4° C. The next day, plates were washed with PBS-Tween 0.05% (pH 7.4) and blocked at room temperature for 2 h with 1% casein (Sigma). After blocking, bio-hIL-6-Avi-His (SEQ ID NO: 96) and bio-cyIL-6-His (SEQ ID NO: 83) antigens at 1 nM, diluted in 0.1% casein/PBS (pH 7.4), were captured. Periplasmic extracts containing soluble $V_HH$ were then added to the plates and incubated at 1:5 dilution in 0.1% casein/PBS (pH 7.4). Detection of P.E. sample binding was performed using the mouse anti-c-Myc antibody (Roche) followed by the secondary antibody anti-mouse immunoglobulin peroxidase conjugate (Jackson ImmunoResearch). Incubations were performed for 1 h at room temperature and between incubation steps plates were washed with PBS-Tween 0.05% (pH 7.4) and a final wash with PBS (pH 7.4) prior to development. ELISA signal development was performed by adding the substrate solution (TMB solution) to the plates, followed by $H_2SO_4$. ELISA signals were obtained by using a plate reader at 450 nm.

The $V_HH$ genes of positive binders were sequenced. Clones were classified by variants according to the different HCDR3 sequences. The $V_HH$ genes of positive binders were sequenced. Clones were classified by variants according to the different HCDR3 sequences. 182 $V_HH$ sequences were selected for further characterizations based on sequence similarities and on/off rate kinetics using a Fortebio instrument as described by the vendor (instrument Octet Fortebio Red384 from Sartorius).

In particular, 22 sequences were selected for thorough characterizations including affinity measurements, in vitro assaying and biophysical assaying. An overview of the selected $V_HH$ sequences is given in Table 14, with the properties of the $V_HH$ polypeptides further presented in Table 15. As can be understood by one of skill in the art, the described $V_HH$ polypeptide sequences identified below comprise the $V_HH$ sequence itself as well as a C-terminal His tag GGGGSHHHHHH (Extension E1, SEQ ID NO. 71), which may alternatively be referred to as a C-terminal extension of the $V_HH$.

TABLE 14

Overview of the composition of 22 selected $V_HH$ sequences

| Polypeptide | | $V_HH$ | | C-term. Tag/Extension | |
|---|---|---|---|---|---|
| ID | SEQ ID No. | ID | SEQ ID No. | ID | SEQ ID No. |
| Polypeptide_1 | 39 | VHH_2.1 | 104 | E1 | 71 |
| Polypeptide_2 | 40 | VHH_2.2 | 105 | E1 | 71 |
| Polypeptide_3 | 41 | VHH_2.3 | 106 | E1 | 71 |
| Polypeptide_4 | 42 | VHH_2.4 | 107 | E1 | 71 |
| Polypeptide_5 | 43 | VHH_2.5 | 108 | E1 | 71 |
| Polypeptide_6 | 44 | VHH_2.6 | 109 | E1 | 71 |
| Polypeptide_7 | 45 | VHH_2.7 | 110 | E1 | 71 |
| Polypeptide_8 | 46 | VHH_2.8 | 111 | E1 | 71 |
| Polypeptide_9 | 47 | VHH_2.9 | 112 | E1 | 71 |
| Polypeptide_10 | 48 | VHH_2.10 | 113 | E1 | 71 |
| Polypeptide_11 | 49 | VHH_2.11 | 114 | E1 | 71 |
| Polypeptide_12 | 50 | VHH_2.12 | 115 | E1 | 71 |
| Polypeptide_13 | 51 | VHH_2.13 | 116 | E1 | 71 |
| Polypeptide_14 | 52 | VHH_2.14 | 117 | E1 | 71 |
| Polypeptide_15 | 53 | VHH_2.15 | 118 | E1 | 71 |
| Polypeptide_16 | 54 | VHH_2.16 | 119 | E1 | 71 |
| Polypeptide_17 | 55 | VHH_2.17 | 120 | E1 | 71 |
| Polypeptide_18 | 56 | VHH_1.16 | 38 | E1 | 71 |
| Polypeptide_19 | 57 | VHH_1.11 | 33 | E1 | 71 |
| Polypeptide_33 | 84 | VHH_1.9 | 31 | E1 | 71 |
| Polypeptide_34 | 85 | VHH_1.8 | 30 | E1 | 71 |
| Polypeptide_35 | 86 | VHH_1.10 | 32 | E1 | 71 |

TABLE 15

Overview of the 22 selected $V_HH$ sequences properties.

| Polypeptide | | | Harvest yield, expressed in Expi293F [mg/l] | nDSF Tm [° C.] | SPR Kd [M] | Reporter gene-assay [pM] |
|---|---|---|---|---|---|---|
| ID | SEQ ID No. | pI | | | | |
| Polypeptide_1 | 39 | 7.53 | 174 | 54.5 | 6.27E−10 | 47.4 |
| Polypeptide_2 | 40 | 8.41 | 37 | 51.6 | 1.31E−09 | 20.7 |
| Polypeptide_3 | 41 | 8.09 | 188 | 56.7 | 8.72E−10 | 39.8 |
| Polypeptide_18 | 56 | 7.88 | 214 | 54.9 | 7.05E−10 | 18.5 |
| Polypeptide_4 | 42 | 7.12 | 216 | 75.5 | 1.46E−09 | 198.0 |
| Polypeptide_5 | 43 | 8.11 | 181 | 55.1 | 6.96E−10 | 23.2 |

TABLE 15-continued

Overview of the 22 selected V$_H$H sequences properties.

| Polypeptide | | | Harvest yield, expressed in | nDSF | | Reporter gene- |
|---|---|---|---|---|---|---|
| ID | SEQ ID No. | pI | Expi293F [mg/l] | Tm [° C.] | SPR Kd [M] | assay [pM] |
| Polypeptide_6 | 44 | 6.85 | 68 | 66.3 | 1.52E−09 | 73.4 |
| Polypeptide_7 | 45 | 8.39 | 80 | 56.1 | 6.31E−10 | 42.1 |
| Polypeptide_8 | 46 | 8.70 | 68 | 59.9 | 8.16E−10 | 36.8 |
| Polypeptide_9 | 47 | 8.67 | 49 | 56.2 | 9.03E−10 | 33.7 |
| Polypeptide_10 | 48 | 6.85 | 42 | 71.3 | 1.03E−09 | 113.5 |
| Polypeptide_11 | 49 | 6.98 | 111 | 55.3 | 7.01E−11 | 98.2 |
| Polypeptide_34 | 85 | 6.42 | 283 | 63.9 | 1.00E−12 | 43.6 |
| Polypeptide_12 | 50 | 6.85 | 239 | 61.5 | 1.00E−12 | 77.4 |
| Polypeptide_13 | 51 | 6.70 | 273 | 66.4 | 1.00E−12 | 80.9 |
| Polypeptide_33 | 84 | 7.07 | 197 | 64.2 | 3.58E−10 | 62.1 |
| Polypeptide_14 | 52 | 6.94 | 220 | 63.3 | 3.96E−10 | 72.9 |
| Polypeptide_35 | 86 | 6.61 | 308 | 62.4 | 1.00E−12 | 24.6 |
| Polypeptide_15 | 53 | 6.61 | 293 | 52.8 | 1.00E−12 | 16.8 |
| Polypeptide_19 | 57 | 7.19 | 265 | 65.5 | 1.00E−12 | 40.6 |
| Polypeptide_16 | 54 | 7.40 | 317 | 57.9 | 1.00E−12 | 52.4 |
| Polypeptide_17 | 55 | 6.85 | 265 | 70.6 | 2.57E−10 | 84.1 |

As can be derived from Table 15, entries Polypeptide_19 (SEQ ID No. 57), Polypeptide_35 (SEQ ID No. 86), Polypeptide_33 (SEQ ID No. 84), and Polypeptide_34 (SEQ ID No. 85) showed not only sequence diversity, but each V$_H$H sequence also showed optimal stability, expressibility, binding affinity, and potency. Hence, these four polypeptides were chosen to further optimize and move forward in the development.

Example 2: Epitope Mapping

The purpose of this example was to solve the protein crystal structures of selected anti-IL-6 V$_H$H polypeptides (SEQ ID Nos: 84, 86, and 57), in complex with human IL-6, to determine the paratope and epitope interaction between the selected anti-IL-6 V$_H$H's and human IL-6. The anti-IL-6 V$_H$H polypeptides selected were Polypeptide_33 (SEQ ID No. 84), Polypeptide_35 (SEQ ID No. 86) and Polypeptide_19 (SEQ ID No. 57), identified in detail in Table 14.

The results led to an improved understanding of the detailed molecular mode-of-action and guided further optimization of the V$_H$H polypeptides, in particular, with respect to further optimizing potency via introducing mutations in CDR loops and other paratope residues.

2.1 Preparation of Crystal Structures

A mixture of IL-6 (1 equiv.) and V$_H$H polypeptide (1.2 equiv.) dissolved in HBS buffer was incubated for 60 min at 4° C. and purified by size exclusion chromatography on a Superdex75 16/60 column running in 10 mM Tris pH 7.5, 150 mM NaCl. SEC elution peak fractions of the purified complexes were collected, pooled, and concentrated to 5-20 mg/ml and used for crystallization trials in 96 well sitting drops using commercial crystallization screens.

2.1.1 Crystallization and Structure Determination of SEQ ID NO: 84 (Polypeptide 33) in Complex with IL-6.

Crystals were obtained with the following reservoir condition: 2M Ammonium sulfate, 0.1M Bis-Tris pH 6.5. The crystals were cryo protected in glycerol and frozen in liquid nitrogen. X-ray diffraction data was collected on a Rigaku FR-X rotating anode with a Rigaku Dectris Pilatus3R 1M detector, processed in XDS/XSCALE to a resolution of 2.4 Å in spacegroup 5 (C2). The structure was determined by molecular replacement running in Phenix using the following PDB entries as search models; IL-6 (PDBid: 1alu) and V$_H$H template (PDBid: 5ivo). The solution from molecular replacement was in space group 5 (C2) and had two IL-6/SEQ ID NO: 84 complexes in the asymmetric unit. The structure was refined in Phenix.refine to 2.4 Å resolution. The two complexes in the asymmetric unit showed high structural similarity with RMSD of 0.286 Å calculated in PyMOL using "Align". Both IL-6 molecules in the asymmetric unit showed high structural similarity with the IL-6 PDB entry 1alu: RMSD below 0.48 Å for both IL-6 molecules calculated in PyMOL using "Align".

2.1.2 Crystallization and Structure Determination of SEQ ID NO: 86 (Polypeptide 35) in Complex with IL-6.

Crystals were obtained with the following reservoir condition: 0.2M Magnesium chloride hexahydrate, 0.1M Sodium HEPES pH 7.5, 25% w/v PEG 3350. The crystals were cryo protected in glycerol and frozen in liquid nitrogen. Synchrotron X-ray diffraction data were collected at the Swiss Light Source, processed in XDS/XSCALE to a resolution of 3.0 Å in spacegroup 90 (P4212). The structure was determined by molecular replacement running in Phenix using the following PDB entries as search models; IL-6 (PDBid: 1alu) and V$_H$H template (PDBid: 5ivo). The solution from molecular replacement was in space group 90 (P4212) and had two IL-6/SEQ ID NO: 86 complexes in the asymmetric unit. The structure was refined in Phenix.refine to 3.0 resolution. The two complexes in the asymmetric unit showed high structural similarity with RMSD of 0.337 Å calculated in PyMOL using "Align". Both IL-6 molecules in the asymmetric unit showed high structural similarity with the IL-6 PDB entry 1alu: RMSD below 0.58 Å for both IL-6 molecules calculated in PyMOL using "Align".

2.1.3 Crystallization and Structure Determination of SEQ ID NO: 57 (Polypeptide 19) in Complex with IL-6.

Crystals were obtained with the following reservoir condition: 2.0 M Ammonium sulfate, 0.1 M Sodium acetate 4.6. The crystals were cryo protected in glycerol and frozen in liquid nitrogen. Synchrotron X-ray diffraction data were collected at the Swiss Light Source, processed in XDS/XSCALE to a resolution of 2.4 Å in spacegroup 20 (C2221). The structure was determined by molecular replacement running in Phenix using the IL-6/SEQ ID NO: 33 complex as search model. The solution from molecular replacement was in space group 20 (C2221) and had one IL-6/SEQ ID NO: 57 complex in the asymmetric unit. The structure was refined in Phenix.refine to 2.4 resolution. The IL-6 molecule in the asymmetric unit showed high structural similarity with the IL-6 pdb entry 1alu: RMSD=0.554 Å calculated in PyMOL using "Align".

2.2 Epitope and Paratope Mapping

The epitopes of IL-6 and the paratopes of the VHHs are described by two different methods.

Method 1

PyMOL InterfaceResidues with cutoff of 1.0 was used to calculate the difference in surface accessible area between complex and free components and thereby defining interface residues.

Method 2

Method 2 is based on the distance between amino acid residues of IL-6 and amino acid residues of the VHHs using a distance cut off <4.5 Å, by manual inspection.

The crystal structures of SEQ ID NO: 84 and SEQ ID NO: 86 in complex with IL-6 each contain two complexes (cfr. Table 16 & Table 17. Indicated by "Comp1", "Comp2" for SEQ ID NO: 84 and SEQ ID NO: 86) in the asymmetric unit.

The crystal structure of SEQ ID NO: 57 in complex with IL-6 contains only one complex in the asymmetric unit referred to as SEQ ID NO: 57 complex 1.

The epitope and paratope residues of the IL-6/polypeptide complexes are listed in Table 16 and Table 17, respectively.

TABLE 16

IL-6 epitope residues.

| SEQ ID NO: 84 | | | | SEQ ID NO: 86 | | | | SEQ ID NO: 57 | |
|---|---|---|---|---|---|---|---|---|---|
| Method 1 | | Method 2 | | Method 1 | | Method 2 | | Method 1 | Method 2 |
| Comp1 | Comp2 | Comp1 | Comp2 | Comp1 | Comp2 | Comp1 | Comp2 | Comp1 | Comp1 |
| S22 | | | | | | | | | |
| | | | | E23 | | | | | |
| D26 | D26 | D26 | D26 | D26 | D26 | D26 | D26 | D26 | D26 |
| | | | | I29 | | | | | |
| R30 | R30 | R30 | R30 | R30 | R30 | R30 | R30 | R30 | R30 |
| L33 | L33 | L33 | L33 | L33 | L33 | L33 | L33 | L33 | L33 |
| D34 | D34 | D34 | D34 | D34 | D34 | D34 | D34 | D34 | D34 |
| | | | | R40 | R40 | R40 | R40 | | |
| | | | | K41 | | | | | |
| | | | | | | | | K66 | |
| C73 | C73 | C73 | C73 | C73 | C73 | C73 | C73 | C73 | C73 |
| F74 | F74 | F74 | F74 | F74 | F74 | F74 | F74 | F74 | F74 |
| Q75 | Q75 | Q75 | Q75 | Q75 | Q75 | Q75 | Q75 | Q75 | Q75 |
| S76 | S76 | | | S76 | | | | S76 | |
| F78 | F78 | F78 | F78 | F78 | F78 | F78 | F78 | F78 | F78 |
| K171 | K171 | K171 | K171 | K171 | K171 | K171 | K171 | K171 | K171 |
| E172 | E172 | | | E172 | E172 | | | E172 | E172 |
| Q175 | Q175 | Q175 | Q175 | Q175 | Q175 | Q175 | Q175 | Q175 | Q175 |
| S176 | S176 | S176 | S176 | S176 | S176 | | | S176 | S176 |
| L178 | L178 | L178 | L178 | L178 | L178 | L178 | L178 | L178 | L178 |
| R179 | R179 | R179 | R179 | R179 | R179 | R179 | R179 | R179 | R179 |
| | | | | | A180 | | A180 | | |
| R182 | R182 | R182 | R182 | R182 | R182 | R182 | R182 | R182 | R182 |
| Q183 | Q183 | Q183 | Q183 | Q183 | Q183 | Q183 | Q183 | Q183 | Q183 |

TABLE 17

$V_HH$ paratope residues.

| SEQ ID NO: 84 | | | | SEQ ID NO: 86 | | | | SEQ ID NO: 57 | |
|---|---|---|---|---|---|---|---|---|---|
| Method 1 | | Method 2 | | Method 1 | | Method 2 | | Method 1 | Method 2 |
| Comp1 | Comp2 | Comp1 | Comp2 | Comp1 | Comp2 | Comp1 | Comp2 | Comp1 | Comp1 |
| | | | | E31 | E31 | E31 | E31 | | |
| F47 | | F47 | F47 | F47 | F47 | | | | |
| D50 | D50 | D50 | D50 | D50 | D50 | D50 | D50 | D50 | D50 |
| E53 | E53 | E53 | E53 | E53 | E53 | E53 | E53 | E53 | E53 |
| N54 | N54 | | | S54 | S54 | | | N54 | N54 |
| N57 | N57 | N57 | N57 | T57 | T57 | T57 | T57 | N57 | N57 |
| T58 | T58 | T58 | T58 | W58 | W58 | W58 | W58 | T58 | T58 |
| W59 | W59 | W59 | W59 | Y59 | Y59 | Y59 | Y59 | W59 | W59 |
| Y60 | Y60 | Y60 | Y60 | | | | | Y60 | Y60 |
| | | | | K64 | K64 | K64 | K64 | | |
| K65 | K65 | K65 | K65 | | | | | K65 | K65 |
| | | | | D98 | D98 | D98 | D98 | | |
| D99 | D99 | D99 | D99 | | | | | D99 | D99 |
| | | | | Y100 | Y100 | Y100 | Y100 | | |
| Y101 | Y101 | Y101 | Y101 | G101 | G101 | G101 | G101 | Y101 | Y101 |
| G102 | G102 | G102 | G102 | V102 | V102 | V102 | V102 | G102 | G102 |
| V103 | V103 | V103 | V103 | G103 | G103 | G103 | G103 | V103 | V103 |

TABLE 17-continued

V$_H$H paratope residues.

| SEQ ID NO: 84 | | | | SEQ ID NO: 86 | | | | SEQ ID NO: 57 | |
|---|---|---|---|---|---|---|---|---|---|
| Method 1 | | Method 2 | | Method 1 | | Method 2 | | Method 1 | Method 2 |
| Comp1 | Comp2 | Comp1 | Comp2 | Comp1 | Comp2 | Comp1 | Comp2 | Comp1 | Comp1 |
| G104 | G104 | G104 | G104 | G104 | G104 | G104 | G104 | G104 | G104 |
| G105 | G105 | G105 | G105 | G105 | G105 | G105 | G105 | G105 | G105 |
| G106 | G106 | G106 | G106 | | | | | G106 | G106 |
| | | | | R108 | | | | | |
| | | | | Y109 | Y109 | Y109 | Y109 | | |
| Y110 | Y110 | Y110 | Y110 | | | | | Y110 | Y110 |

Figure 4A:
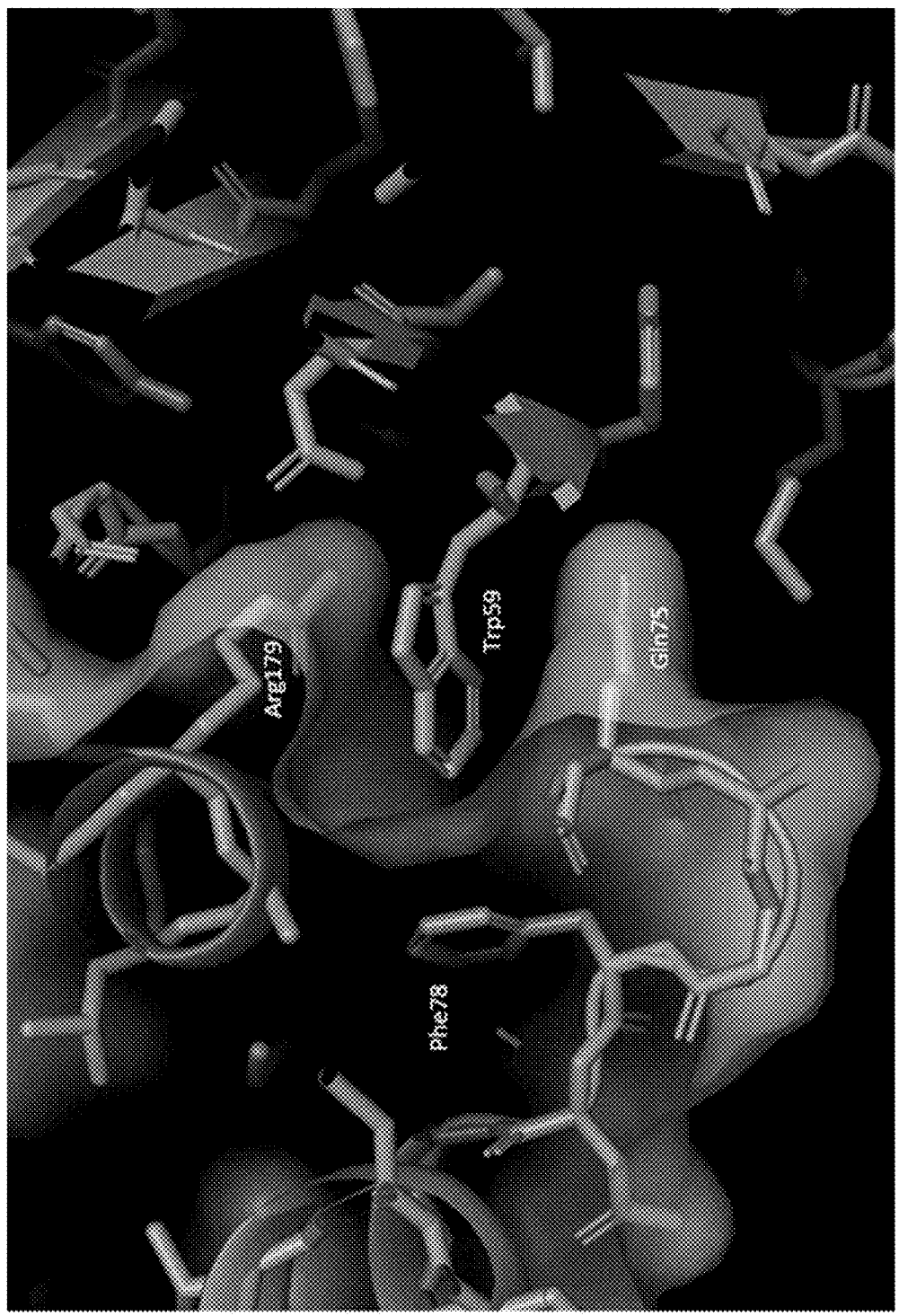
FIG. 4A shows the molecular structure of part of the paratope:epitope interaction between SEQ ID NO: 57 and human IL-6 (hIL-6), as obtained from X-ray crystallographic experiments described in Example 2.
Figure 4B:
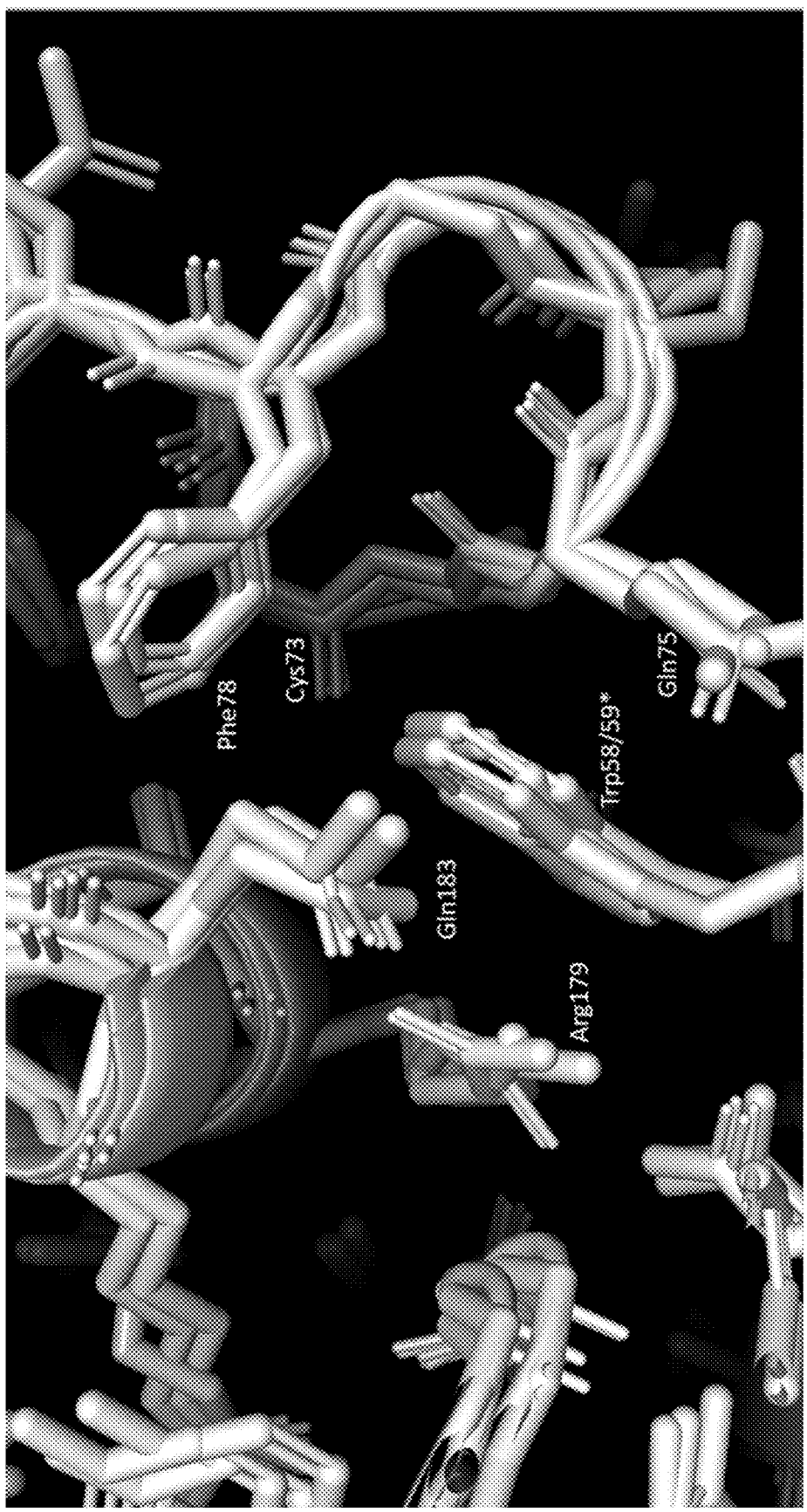
FIG. 4B shows the molecular structure of part of the paratope:epitope interaction between the overlayed structures of $V_HH$ polypeptides 19, 33, and 35 and human IL-6. Amino acid residues belonging to either one of the $V_HH$ polypeptides are indicated with an asterisk "*", e.g., Trp 58/59. The remaining numbered amino acid residues belong to hIL-6.

As can be seen in FIG. 4A, an aromatic pi-cation interaction between the aromatic side-chain of Trp59 (polypeptide_19; SEQ ID NO: 57) and the basic side chain of Arg179 (human IL-6) can be observed, which appear to be important for the very strong affinity and potencies observed in vitro and in vivo for the V$_H$H as well as for variants thereof.

Based on the crystallographic experiments, molecular structures were obtained at resolutions 2.4 and 3.0 Å showing the detailed epitope:paratope interactions between human IL-6 and the tested anti-IL-6 V$_H$H polypeptides. These data were used as input data for optimizing the V$_H$H polypeptides as described hereunder as part of design cycle optimizations.

2.3 Computational Modelling for Structure Prediction

AlphaFold-Multimer version 2.2.0 was used to generate the complex structure of V$_H$H and hIL-6 by using sequence-based approach. AlphaFold-Multimer version 2.2.0 generates several structures per model by default, and the top model was selected by the ranking_confidence score and rank 1 was selected. Ranking_confidence is a linear combination of the interface score ipTM (interface predicted Template Modeling score) and overall structural score pTM: 0.8 ipTM+0.2 pTM. The interface residue was analyzed in a same manner as Method 1.

TABLE 18

Comparison of the IL-6 epitope residues obtained by X-ray structure using for SEQ ID NO: 84 and by computational structure prediction using SEQ ID NO: 84.
SEQ ID NO: 84

| Method 1 | | Method 2 | | Computational |
|---|---|---|---|---|
| Comp1 | Comp2 | Comp1 | Comp2 | Method |
| S22 | | | | |
| D26 | D26 | D26 | D26 | D26 |
| R30 | R30 | R30 | R30 | R30 |
| L33 | L33 | L33 | L33 | L33 |
| D34 | D34 | D34 | D34 | D34 |
| C73 | | | | C73 |
| F74 | F74 | F74 | F74 | F74 |
| Q75 | Q75 | Q75 | Q75 | Q75 |
| S76 | S76 | | | S76 |
| F78 | F78 | F78 | F78 | F78 |
| K171 | K171 | K171 | K171 | K171 |
| E172 | E172 | | | E172 |
| Q175 | Q175 | Q175 | Q175 | Q175 |
| S176 | S176 | S176 | S176 | S176 |
| L178 | L178 | L178 | L178 | L178 |
| R179 | R179 | R179 | R179 | R179 |
| R182 | R182 | R182 | R182 | R182 |
| Q183 | Q183 | Q183 | Q183 | Q183 |

TABLE 19

Comparison of the V$_H$H paratope residues of SEQ ID NO: 84 obtained by X-ray structure and by computational prediction.
SEQ ID NO: 84

| Method 1 | | Method 2 | | Computational |
|---|---|---|---|---|
| Comp1 | Comp2 | Comp1 | Comp2 | Method |
| F47 | | F47 | F47 | F47 |
| D50 | D50 | D50 | D50 | D50 |
| | | | | G52 |
| E53 | E53 | E53 | E53 | E53 |
| N54 | N54 | | | N54 |
| | | | | D56 |
| N57 | N57 | N57 | N57 | N57 |
| T58 | T58 | T58 | T58 | T58 |
| W59 | W59 | W59 | W59 | W59 |
| Y60 | Y60 | Y60 | Y60 | Y60 |
| K65 | K65 | K65 | K65 | K65 |
| D99 | D99 | D99 | D99 | D99 |
| Y101 | Y101 | Y101 | Y101 | Y101 |
| G102 | G102 | G102 | G102 | G102 |
| V103 | V103 | V103 | V103 | V103 |
| G104 | G104 | G104 | G104 | G104 |
| G105 | G105 | G105 | G105 | G105 |
| G106 | G106 | G106 | G106 | G106 |
| Y110 | Y110 | Y110 | Y110 | Y110 |

Table 18 and Table 19 show a comparison between experimentally determined complex structure with computational structure prediction and resolving the paratope:epitope information at high resolution. We observed sub-angstrom structure difference in a protein backbone alignment between two methodologies, as well as high side-chain accuracy when the backbone prediction is accurate. As the result, the determination of paratope:epitope from two methods reaches a close agreement. To further rationalize the epitope/paratope prediction for the structurally unsolved complex.

TABLE 20

IL-6 epitope residues and V$_H$H paratope residues based on computational structure prediction of a SEQ ID NO: 56 and hIL-6 by using deep-learning approach with supplying sequence Information.

| Epitope | Paratope |
|---|---|
| R24 | V37 |
| K27 | Q39 |
| Q28 | G42 |
| Y31 | K43 |
| I88 | G44 |
| L92 | L45 |
| E95 | Y95 |
| E99 | R105 |
| A114 | L106 |

TABLE 20-continued

IL-6 epitope residues and V$_H$H paratope residues based on computational structure prediction of a SEQ ID NO: 56 and hIL-6 by using deep-learning approach with supplying sequence Information.

| Epitope | Paratope |
|---------|----------|
| Q116 | D107 |
| M117 | H108 |
| S118 | Y109 |
| K120 | L112 |
| V121 | Q114 |
| I123 | |
| Q124 | |
| F125 | |
| Q127 | |
| K128 | |
| T138 | |
| P139 | |

Example 3: Design Cycle and Generation of Polypeptides 3.1 Design Cycle

To optimize the anti-IL-6 polypeptides, a series of design cycles were conducted. These design cycles were conducted to optimize one or more of the following:

the paratope:epitope interactions by introducing mutations that enhanced the affinity and the functional potency effect, mutations that reduced the pI of the anti-IL-6 V$_H$H polypeptide thereby enhancing the oral bioavailability, mutations to humanize the llama derived V$_H$H sequence and thus de-risk immunogenicity by human exposure, introduction a fatty acid protractor moiety (substituent) by conjugating the protractor moiety to the cysteine residues of the C-terminal extension of the V$_H$H polypeptides, and fixing of liable residues, such as mutating the N-terminally positioned glutamine to glutamate to hinder pyroglutamate formation.

3.2 Generation of Polypeptides

Examples of V$_H$H Polypeptides Generated as Part of the Design Cycle.

As described above, as part of the design cycle optimization campaigns, Table 21 below showcases polypeptides that were optimized via mutations to increase potency/affinity, mutations to increase oral bioavailability, mutations to de-risk immunogenicity, and/or mutations to fix liable residues. This design cycle was based on polypeptide_19 (SEQ ID No. 57) as originally identified in EXAMPLE 1: IMMUNIZATION AND CONSTRUCTION OF VHH LIBRARY. For ease of reference, the underlying V$_H$H for each one of the polypeptides is provided in Table 21, one may also refer to Table 12 for the detailed composition of the example polypeptides.

For example, starting from polypeptide_19, SEQ ID No. 57 (or more specifically the V$_H$H composing polypeptide_19), polypeptide_29 was generated and comprises the below identified mutations:

mutations to increase potency/affinity: T28R, S31E, N54Q, D56E, H62E, K65L, N74D, S85G, S100K, G106N;

mutations to increase oral bioavailability: Q1E, S31E, H62E, K65L, N74D, Q82E, N84D;

mutations to de-risk immunogenicity: Q1E, L2V, W11L, H62E, Q82E, N84D; and mutations to fix liable residues: Q1E, W11L.

TABLE 21

Overview of the key V$_H$H polypeptides of the design cycle based on the polypeptide_19 of SEQ ID NO. 57.

| Polypeptide | | | V$_H$H | |
|---|---|---|---|---|
| ID | SEQ ID No. | Modifications to V$_H$H of Reference Polypeptide_19 | ID | SEQ ID No. |
| Polypeptide_19 (Reference) | 57 | — | VHH_1.11 | 33 |
| Polypeptide_20 | 58 | Q1E, L2V, W11L, K19Q, T28H, S30D, S31E, N74D, Q82E, N84D, S85G, S100K, G106N | VHH_2.18 | 121 |
| Polypeptide_21 | 59 | Q1E, L2V, W11L, K19Q, T28H, S30D, S31E, A40G, N74D, Q82E, N84D, S85G, S100K, G106N | VHH_2.19 | 122 |
| Polypeptide_22 | 60 | Q1E, L2V, W11L, T28R, S31E, A40G, N54Q, D56E, H62E, K65L, N74D, N84D, S100K, G106N | VHH_1.2 | 24 |
| Polypeptide_23 | 61 | Q1E, L2V, W11L, K19Q, T28R, S31E, N54Q, D56E, K65L, N74D, N84D, S100K, G106N | VHH_2.20 | 123 |
| Polypeptide_24 | 62 | Q1E, L2V, W11L, K19Q, T28R, S31E, A40G, N54Q, D56E, K65L, N74D, N84D, S100K, G106N | VHH_1.3 | 25 |
| Polypeptide_25 | 63 | Q1E, L2V, W11L, K19Q, T28R, S31E, A40G, N54Q, D56E, H62E, K65L, N74D, N84D, S100K, G106N | VHH_2.21 | 124 |
| Polypeptide_26 | 64 | Q1E, L2V, W11L, T28K, S30D, S31E, D56E, K65L, N74D, N84D, S100K, G106N | VHH_2.22 | 125 |
| Polypeptide_27 | 65 | Q1E, L2V, W11L, K19Q, T28K, S30D, S31E, D56E, K65L, N74D, N84D, S100K, G106N | VHH_1.4 | 26 |
| Polypeptide_28 | 66 | Q1E, L2V, W11L, K19Q, T28K, S30D, S31E, A40G, D56E, H62E, K65L, N74D, N84D, S100K, G106N | VHH_1.5 | 27 |
| Polypeptide_29 | 67 | Q1E, L2V, W11L, T28R, S31E, N54Q, D56E, H62E, K65L, N74D, Q82E, N84D, S85G, S100K, G106N | VHH_1.6 | 28 |

TABLE 21-continued

Overview of the key V$_H$H polypeptides of the design
cycle based on the polypeptide_19 of SEQ ID NO. 57.

| Polypeptide | | | V$_H$H | |
|---|---|---|---|---|
| ID | SEQ ID No. | Modifications to V$_H$H of Reference Polypeptide_19 | ID | SEQ ID No. |
| Polypeptide_30 | 68 | Q1E, L2V, W11L, T28R, S31E, A40G, N54Q, D56E, K65L, N74D, Q82E, N84D, S85G, S100K, G106N | VHH_2.23 | 126 |
| Polypeptide_31 | 69 | Q1E, L2V, W11L, K19Q, T28K, S30D, S31E, A40G, K43Q, D56E, H62E, K65L, N74D, Q82E, N84D, S85G, S100K, G106N | VHH_1.7 | 29 |
| Polypeptide_32 | 70 | Q1E, L2V, T28R, S31E, N54Q, D56E, K65L, N74D, N84D, S100K, G106N | VHH_2.24 | 127 |

TABLE 22

Overview of the properties of key V$_H$H polypeptides of the
design cycle based on the polypeptide_19 (SEQ ID NO. 57).

| Polypeptide | | | | Expression yield, |
|---|---|---|---|---|
| ID | SEQ ID No. | pI | Tm (° C., stability) | expressed in Expi293F [mg/l] |
| Polypeptide_19 (Reference) | 57 | 7.2 | 65 | ND |
| Polypeptide_20 | 58 | 6 | 50 | 69 |
| Polypeptide_21 | 59 | 6 | 48 | 73 |
| Polypeptide_22 | 60 | 6.1 | 59 | 74 |
| Polypeptide_23 | 61 | 6.3 | 59 | 93 |
| Polypeptide_24 | 62 | 6.3 | 55 | 116 |
| Polypeptide_25 | 63 | 5.8 | 57 | 128 |
| Polypeptide_26 | 64 | 6.3 | 59 | 76 |
| Polypeptide_27 | 65 | 6.1 | 57 | 98 |
| Polypeptide_28 | 66 | 5.4 | 57 | 105 |
| Polypeptide_29 | 67 | 5.8 | 59 | 88 |
| Polypeptide_30 | 68 | 6.3 | 54 | 74 |
| Polypeptide_31 | 69 | 5 | 52 | 143 |
| Polypeptide_32 | 70 | 6.6 | 60 | 53 |

As observed from Table 22, the indicated polypeptides are shown to have lowered pI values (pI calculations performed as described herein) obtained via mutations of specific surface-exposed residues as identified in Table 21. As can be observed, these polypeptides showed distinct lowering of the pI as compared to the reference polypeptide. Measured Tm values were also shown in the table for the indicated polypeptides, which were measured as described in the generic MATERIALS AND METHODS section: Differential Scanning Fluorimetry (Nano DSF) Analysis of anti-IL-6 V$_H$H. All the polypeptides above showed relatively high melting temperatures between 48-60° C., with most between 50-60° C., which were acceptable melting temperatures for a pharmaceutical compound suitable for human administration, wherein the normal physiological temperature is of 37° C.

Specifically, polypeptide 29 showed a reduced pI of 5.8 in comparison to the reference polypeptide_19 while maintaining a suitable melting temperature of 59° C. Such a polypeptide, or more specifically the underlying V$_H$H therein, thus provided a pharmaceutical profile, such as pI, melting temperature and potency (see further examples below), that are desirable. Further details will be provided in the examples below.

Example 4: In Vitro Activity of Anti-IL-6 VHH Variants in STAT-3-LUC Reporter Gene Assay, Deconvolution of Mutated IL-6 Interacting Residues in VHH_1.6

Purpose

The purpose of this example was to test the ability of deconvoluted CDR/FR residue variants of anti-IL-6 V$_H$H VHH_1.6 to inhibit IL-6-dependent STAT3 signaling and hence IL-6 activity in vitro. Thus, this provides understanding of the effect of individual CDR/FR residues for the interaction of anti-IL-6 VHH_1.6 to human IL-6. Data are presented in Table 23 and Table 24.

Methods

In-Silico Mutagenesis to Sampling Energetically Favorable Mutations for Binding Improvement The X-ray crystal structure of the V$_H$H-IL-6 protein complex was obtained. The structure was cleaned to remove any missing residues or atoms using PyMOL (Schrödinger, LLC). Hydrogen atoms were added, and the structures were minimized to relieve any steric clashes using the Rosetta-Suite. Residues within 5 Å of the IL-6 surface were identified as potential mutation sites. For each identified residue, in silico site-saturation mutagenesis (SSM) was performed by computationally mutating the residue to all 19 possible amino acid substitutions and evaluating the impact on binding energy using the Rosetta scoring function (i.e., Score function named ref2015). The substitutes from the reference polypeptide_29 (SEQ ID No. 67) comprising VHH_1.6 are summarized in Table 23. To better simulate the backbone movement upon the introduction of mutations, a 0.2 Å backbone perturbation was allowed.

For the top-ranked mutations from the SSM, molecular dynamics (MD) simulations were performed to further evaluate the binding affinity and recapitulate binding dynamics. The AMBER99SB force field was used for the protein, and simulations were carried out using the GROMACS software package. Each system was minimized, equilibrated, and then subjected to a 100 ns production run at 300 K and 1 atm pressure. Selected trajectories were extracted to calculate the binding energy using the Rosetta cartesian ddg application.

Reporter Gene Assay (RGA)

The Reporter Gene Assay was conducted as described in the MATERIALS AND METHODS section. The reported values are the means of two technical replicates (Table 24).

Results

As described above, Polypeptide_29 of the design cycle was identified as a starting point. Each one of the mutations explored as part of the design cycle in comparison to Polypeptide_19 (SEQ ID No. 57, originally identified in EXAMPLE 1: IMMUNIZATION AND CONSTRUCTION OF VHH LIBRARY) were deconvoluted in order to gain a better understanding of the individual role of the given residue modifications. Table 23 below provides an overview of the polypeptides of this example, where the Polypeptide column provides for the information of each entry, the modification column identifies the residue modification in comparison to Polypeptide_29 and the VHH column identifies the underlying $V_HH$ for each one of the polypeptides. One may also refer to Table 12 for the detailed composition of the example polypeptides. Table 24 shows the potency (IC50) of the Anti-IL6 $V_HH$ polypeptide entries and relative potency to reference Polypeptide_29. Table 23 and Table 24 further identify reference Polypeptide_19 for ease of understanding.

TABLE 23

Overview of the Anti-IL6 VHH variant polypeptides tested as part of the deconvolution of Polypeptide_29

| Polypeptide | | | $V_HH$ | |
|---|---|---|---|---|
| ID | SEQ ID No. | Modifications to $V_HH$ of Reference Polypeptide_29 | ID | SEQ ID No. |
| Polypeptide_19 | 57 | E1Q, V2L, L11W, R28T, E31S, Q54N, E56D, E62H, L65K, D74N, E82Q, D84N, G85S, K100S, N106G | VHH_1.11 | 33 |
| Polypeptide_29 (Reference) | 67 | — | VHH_1.6 | 28 |
| Polypeptide_49 | 131 | E1Q | VHH_3.1 | 145 |
| Polypeptide_50 | 132 | V2L | VHH_3.2 | 146 |
| Polypeptide_51 | 133 | L11W | VHH_3.3 | 147 |
| Polypeptide_52 | 134 | R28T | VHH_3.4 | 148 |
| Polypeptide_53 | 135 | E31S | VHH_3.5 | 149 |
| Polypeptide_54 | 136 | Q54N | VHH_3.6 | 150 |
| Polypeptide_55 | 137 | E56D | VHH_3.7 | 151 |
| Polypeptide_56 | 138 | E62H | VHH_3.8 | 152 |
| Polypeptide_57 | 139 | L65K | VHH_3.9 | 153 |
| Polypeptide_58 | 140 | D74N | VHH_3.10 | 154 |
| Polypeptide_59 | 141 | D84N | VHH_3.11 | 155 |
| Polypeptide_60 | 142 | G85S | VHH_3.12 | 156 |
| Polypeptide_61 | 143 | K100S | VHH_3.13 | 157 |
| Polypeptide_62 | 144 | N106G | VHH_3.14 | 158 |

TABLE 24

Potency (IC50) and relative potency of Anti-IL6 $V_HH$ variant polypeptides. Relative potency is in comparison to reference Polypeptide_29.

| Polypeptide | | | Relative IC50 to Reference |
|---|---|---|---|
| ID | SEQ ID No. | IC50 (nM) | Polypeptide_29 |
| Polypeptide_19 | 57 | 0.185 | 5.4 |
| Polypeptide_29 (Reference) | 67 | 0.034 | 1.0 |
| Polypeptide_49 | 131 | 0.051 | 1.5 |
| Polypeptide_50 | 132 | 0.049 | 1.4 |
| Polypeptide_51 | 133 | 0.053 | 1.5 |
| Polypeptide_52 | 134 | 0.055 | 1.6 |
| Polypeptide_53 | 135 | 0.050 | 1.5 |
| Polypeptide_54 | 136 | 0.150 | 4.4 |
| Polypeptide_55 | 137 | 0.278 | 8.1 |
| Polypeptide_56 | 138 | 0.168 | 4.9 |
| Polypeptide_57 | 139 | 0.080 | 2.3 |
| Polypeptide_58 | 140 | 0.047 | 1.4 |

TABLE 24-continued

Potency (IC50) and relative potency of Anti-IL6 $V_HH$ variant polypeptides. Relative potency is in comparison to reference Polypeptide_29.

| Polypeptide | | | Relative IC50 to Reference |
|---|---|---|---|
| ID | SEQ ID No. | IC50 (nM) | Polypeptide_29 |
| Polypeptide_59 | 141 | 0.043 | 1.2 |
| Polypeptide_60 | 142 | 0.057 | 1.7 |
| Polypeptide_61 | 143 | 0.054 | 1.6 |
| Polypeptide_62 | 144 | 0.130 | 3.8 |

As show in Table 24, Polypeptide_29 displayed a potency of 0.034 nM. The variants polypeptides generally resulted in lower potency. For instance, Polypeptide_54, Polypeptide_55 and Polypeptide_56 showed a 4.4-, 8.1- and 4.9-fold decrease in potency, respectively, in comparison to Polypeptide 29. These variant Polypeptides incorporated mutations at positions 54, 56 and 62, emphasizing the importance of these residues. Furthermore, a 2.3-fold decrease in potency was also observed in variant Polypeptide_57 mutated at position 65, while the mutation at position 106 shown on variant Polypeptide_62 resulted in a 3.8-fold decrease in potency.

Figure 5:
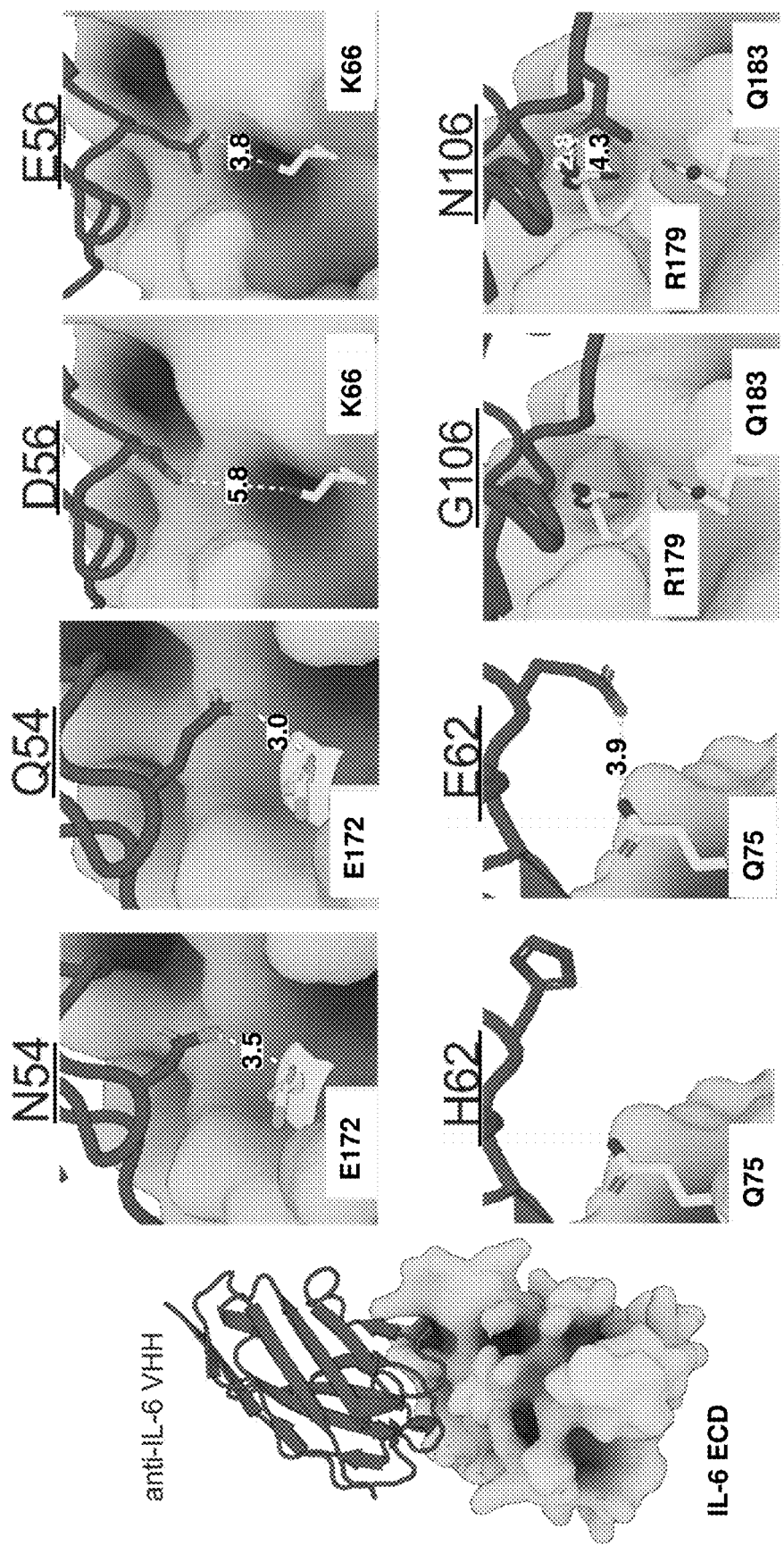
FIG. 5 an example polypeptide comprising an anti-IL6 $V_HH$ and a structural representation of the salt bridge stabilizations generated via mutations at positions 54, 56, 62 and 106. The description over each one of the chemical representations identifies the residue of the Anti-IL6 $V_HH$ being observed.

This data demonstrated that the mutations identified in the design cycle for Polypeptide_29 played a role in achieving the higher potency, which is desirable. In some cases, the deconvolution data showed that changing some of these residues results in loss of potency of 2- or more folds. The data showed that the 54Q, 56E, 62E, and 106N residues found in Polypeptide_29 (or more specifically found in the underlying VHH_1.6) played roles in either increasing the salt bridge (54Q & 56E) or generating a new salt bridge (62E & 106N) between the anti-IL6 $V_HH$ and the IL-6. A structural analysis of the salt bridge stabilizations at positions 54, 56, 62 and 106 ensuring better binding to IL-6 and thus increasing the potency of Polypeptide_29 are shown in FIG. 5.

Example 5: In Vitro Activity of Anti-IL-6 VHH_1.6 and Comparators in STAT-3-LUC Reporter Gene Assay Purpose The purpose of this example was to compare the potency of VHH_1.6 in inhibiting IL-6-dependent STAT3 signaling, and hence IL-6 activity in vitro, with that of other IL-6 inhibitor antibodies.

Methods

The Reporter Gene Assay was conducted as described in the MATERIALS AND METHODS section. The reported values are the means of two technical replicates.

Polypeptide_29 (comprising VHH_1.6) and Reference anti-IL6 Fab were prepared as described herein above.

Two comparator constructs were produced recombinantly as described generically above in Materials and Methods sections "Generic expression of $V_HH$" and "Generic purification and analysis of $V_HH$" and used for face-to-face comparison of IC50 measurements and for the calculation of relative potency. A sequence identical analogue (SIA) of anti-IL-6R domain (SEQ ID No. 163) of the bi-specific domain antibody Vobarilizumab (CAS registry no.: 1628814-88-9) was prepared as first comparator. Further, a sequence identical analogue (SIA) of the anti-IL-6 VHH building block 7G05 found in the multispecific ISVD constructs described in WO2022/129572 (SEQ ID No. 165) was prepared as the second comparator.

Results

TABLE 25

Potencies (IC50) and relative potencies to Polypeptide_29 and Reference anti-IL6 Fab

| Entry ID | IC50 (nM) | Relative IC50 to Polypeptide_29 | Relative IC50 to Reference Anti-IL6 Fab |
|---|---|---|---|
| Reference Anti-IL6 Fab | 0.039 | 0.9 | 1 |
| Polypeptide_29 | 0.044 | 1 | 1.1 |
| Vobarilizumab anti-IL-6R domain SIA comparator | 0.114 | 2.6 | 2.9 |
| anti-IL-6 VHH building block 7G05 SIA comparator | 0.115 | 2.6 | 2.9 |

As can be seen above, reference Anti-IL6 Fab and Polypeptide_29 had comparable potencies at 39 and 44 pM, respectively. Further, it was observed that the sequence identical analogue (SIA) of the anti-IL-6R domain of the bi-specific antibody Vobarilizumab and the sequence identical analogue (SIA) of anti-IL-6 VHH building block 7G05 had higher IC50 values, which were both approximately 2.6-fold higher than Polypeptide_29. Written otherwise, the data showed that the comparators have a potency which is 2.6 times lower than that of Polypeptide_29.

Conclusion

As is clear from the above, Polypeptide_29 was shown to have substantially higher potency in comparison to comparator anti-IL6 constructs. Polypeptide_29 or more specifically the underlying $V_HH\_1.6$ was shown to provide a potency that was similar to that demonstrated by the Reference Anti-IL6 Fab. It is understood that achieving high potency is a highly desirable trait.

Example 6: Generation and Characterization of Polypeptide Derivatives

To improve pharmacokinetic properties, polypeptides comprising two free cysteine residues in C-terminal extension were conjugated with two substituents, each comprising a fatty acid protraction moiety and linker elements. The resulting construct thus formed polypeptide derivatives, as described further below.

To attach the substituent to the polypeptides, an intermediate reagent in the form of a modified substituent was used (e.g. Chem. 28, see Table 26).

The intermediate reagent comprising the protraction moiety was prepared as described in WO 2016/102562 and non-limiting examples of intermediate reagents for further suitable substituents (e.g. for substituents shown in Table 9) is shown in Table 26 below:

TABLE 26

Example of an intermediate reagent comprising the protraction moiety.

| Intermediate reagent structure and IUPAC name (short name) | Chem # |
|---|---|
| 15-{(S)-1-carboxy-3-[2-(2-{[2-(2-{[2-(2-bromoacetyl-amino)ethylcarbamoyl]methoxy}ethoxy)ethylcarbamoyl]methoxy}ethoxy)ethylcarbamoyl]propylcarbamoyl}pentadecanoic acid (C16 diacid-linker reagent) | Chem. 28 |

TABLE 26-continued

Example of an intermediate reagent comprising the protraction moiety.

| Intermediate reagent structure and IUPAC name (short name) | Chem # |
|---|---|

Chem. 29

17-{(S)-1-carboxy-3-[2-(2-{[2-(2-{[2-(2-bromoacetyl-amino)ethylcarbamoyl]methoxy}ethoxy)ethylcarbamoyl]methoxy}ethoxy)ethyl-carbamoyl]propylcarbamoyl}heptadecanoic acid (C18 diacid linker reagent)

Chem. 30

19-{(S)-1-carboxy-3-[2-(2-{[2-(2-{[2-(2-bromoacetyl-amino)ethylcarbamoyl]methoxy}ethoxy)ethylcarbamoyl]methoxy}ethoxy)ethyl-carbamoyl]propylcarbamoyl}nonadecanoic acid (C20 diacid linker reagent)

Conjugation, Purification, and Analysis

To the water or PBS or HBS formulated solution containing the purified $V_HH$ polypeptide with introduced 5 eq. BSPP cysteine residues for conjugation, (Bis(p-sulfonatophenyl)phenylphosphine dihydrate dipotassium salt) or 1.1 eq TCEP (Tris(2-carboxyethyl)phosphine hydrochloride) per capped cysteine (i.e. cysteines that are blocked, from the recombinant expression in host cells, with small thiols such as cysteines, homocysteine, glutathione etc.) was added. After 1-2 h of stirring, pH was adjusted to 8.5 with aq. NaOH and 5 eq. of intermediate reagent Chem. 28 in 0.1 M NaHCO$_3$ (aq.) per free cysteine in the respective $V_HH$ polypeptide were added. The mixture was stirred gently in the dark for 1.5-16 hours. The reaction mixture was diluted with water before purification by anion exchange (AIEX) method using an Äkta system. The $V_HH$ polypeptide with the side-chain conjugation was purified using an AIEX chromatography separation method. Thus, the AIEX resin Source 30Q packed in a suitable column was used together with a sodium chloride or ammonium acetate gradient program setup on an Äkta Avant chromatography system. The buffer systems used were an equilibration buffer composed of 20 mM Tris, pH 8.5 and an elution buffer composed of 20 mM Tris, 1 M NaCl, pH 8.5; or 20 mM Tris, 1 M ammonium acetate, pH 8.5. The reaction mixture was adjusted to pH 8.5 and diluted to a conductivity below 4 mS/cm using MilliQ-H$_2$O or equilibration buffer. The sample was applied to the column and the column was washed after application with 5 to 10 column volumes of equilibration buffer. Separation chromatography was then performed using a shallow gradient of 30 to 50 column volumes. The gradient used was from 0% and up to 50% depending on pI of the $V_HH$ polypeptide derivative that was purified. Generally, the non-conjugated parental $V_HH$ polypeptides eluted early in the gradient, $V_HH$ polypeptides with single conjugation eluted in the middle of the gradient and $V_HH$ polypeptides with multi-conjugations, meaning more than one side-chain conjugation per $V_HH$ polypeptide molecule, eluted late in the gradient. Pooling of fractions over the main peak was conducted in a way, so high purities between 90 to 99% of $V_HH$ polypeptide with double conjugate preparations were obtained. The purity analysis was performed using a reverse-phase ultra-performance liquid chromatography (RP-UPLC) method based on HALO DiPhenyl column 1000 Å, 2.7 µm, 150×2.1 mm (Scantec Nordic USDPF001316) and running buffers composed of A) 0.1% v/v TFA in water and B) 0.09% v/v TFA in acetonitrile setup on a Waters Acquity UPLC system with UV and FLD detector. Column temperature was set to 60° C. The gradient program was 1) 0.0-8.0 min: 20-50% B, 2) 8.0-8.1 min: 50-80% B, 3) 8.1-9.0 min: 80% B, 4) 9.0-9.1 min: 80-20% B, and 5) 9.1-11.0 min: 20% B. The un-conjugated parental $V_HH$ polypeptide eluted between 4.6-4.8 min. The $V_HH$ polypeptide derivative with single conjugation eluted between 5.1-5.6 min. $V_HH$ polypeptide derivative with double conjugations eluted between 5.7-5.8 and later for offsite multi-conjugated VAH polypeptides. Integrity of $V_HH$ polypeptides with conjugation(s) were analysed using a SE-HPLC method setup on an Agilent LC 1100/1200 system and a BIOSEP-SEC-3000 300×7.8 mm column (Phenomenex, cat. no. OOH-2146-K0) and a running buffer composed of 200 mM NaPhosphate pH 6.9, 300 mM NaCl and 10% isopropanol. The molecular masses of $V_HH$ polypeptide with conjugation(s) were analysed using ESI-TOF-MS on a 6280 Agilent system (Agilent Technologies) with a MassPREP Desalt (Waters) column run at 0.4 ml/min in A-buffer composed of MilliQ-H$_2$O/0.1% formic acid and B-buffer composed of acetonitrile/0.1% formic acid for step elution. An ESI-TOF-MS method was also used to evaluate and with the outlined reverse phase UPLC purity method by analysing intact protein masses and peptide masses from tryptic-digested proteins collected in the indicated eluting peaks described above for the RP-UPLC run method. To measure protein concentration of batch preparations of V$_H$H polypeptide derivative with conjugation(s), a NanoDrop™ spectrophotometer (Thermo Scientific) was used with theoretical calculated extinction coefficients.

Examples of Polypeptide Derivatives

An overview of the synthesized polypeptide derivatives is shown in Table 27 for ease of reference. One may further refer to Table 12 for an overview of the polypeptide derivatives. Characterization data of the polypeptide derivatives is shown in Table 28. It is understood that these are examples only and are not to be construed as limitative in any way.

TABLE 27

Overview of polypeptide derivatives.

| Compound ID | V$_H$H SEQ ID # | C-terminal Extension ID | C-terminal Extension SEQ ID # | Substituent[1] Chem. # |
|---|---|---|---|---|
| Compound 1 | VHH_1.12 | 34 | E2 | 72 | 24 |
| Compound 2 | VHH_1.13 | 35 | E2 | 72 | 24 |
| Compound 3 | VHH_1.14 | 36 | E2 | 72 | 24 |
| Compound 4 | VHH_1.1 | 23 | E2 | 72 | 24 |
| Compound 5 | VHH_1.2 | 24 | E2 | 72 | 24 |
| Compound 6 | VHH_1.3 | 25 | E2 | 72 | 24 |
| Compound 7 | VHH_1.4 | 26 | E2 | 72 | 24 |
| Compound 8 | VHH_1.5 | 27 | E2 | 72 | 24 |
| Compound 9 | VHH_1.6 | 28 | E2 | 72 | 24 |
| Compound 10 | VHH_1.7 | 29 | E2 | 72 | 24 |
| Compound 12 | VHH_1.17 | 103 | E2 | 72 | 24 |

[1]Two substituents. One substituent attached to Cys in position 4 and one substituent attached to Cys in position 6 of SEQ ID NO: 72. For a schematic drawing, see FIG. 3A/3B showing Compound 9.

TABLE 28

Characterization data of the polypeptide derivatives.

| Compound ID | Calc. M$_W$ [Da] | Found M$_W$ [Da] | UPLC method[1] - purity [%] |
|---|---|---|---|
| Compound 1 | 15532 | 15532 | 99.4 |
| Compound 2 | 15302 | 15299 | 94.4 |
| Compound 3 | 15755 | 15736 [incl. pos1 Gln to pyroGlu formation] | 98.9 |
| Compound 4 | 15740 | 15740 | 95.3 |
| Compound 5 | 15631 | 15631 | 94.9 |
| Compound 6 | 15639 | 15639 | 88.7 |
| Compound 7 | 15639 | 15639 | 92.0 |
| Compound 8 | 15617 | 15616 | 96.1 |
| Compound 9 | 15616 | 15615 | 94.3 |
| Compound 10 | 15588 | 15587 | 95.8 |

[1]For method details, see RP-UPLC method using HALO DiPhenyl column provided in Conjugation, purification, and analysis section.

Properties of Select Polypeptide Derivatives

TABLE 29

Properties of select polypeptide derivatives

| Compound ID | pI | Tm (° C., stability) | Expression yield, expressed in Expi293F [mg/l] |
|---|---|---|---|
| Compound 4 | 4.65 | 53.0 | 130 |
| Compound 5 | 4.69 | 55.8 | 74 |

TABLE 29-continued

Properties of select polypeptide derivatives

| Compound ID | pI | Tm (° C., stability) | Expression yield, expressed in Expi293F [mg/l] |
|---|---|---|---|
| Compound 6 | 4.78 | 51.5 | 116 |
| Compound 7 | 4.67 | 54.7 | 143 |
| Compound 8 | 4.49 | 55.0 | 105 |
| Compound 9 | 4.61 | 56.1 | 88 |
| Compound 10 | 4.34 | 48.7 | 143 |

As observed from Table 27, Table 28 and Table 29, the indicated compound constructs have shown high purities and correct measured molecular weights as well as lowered pI values (pI calculations performed as described herein) obtained via mutations of specific surface-exposed residues (as previously indicated in Table 21) and via diacid substituent conjugates. Thus, these compounds showed, yet again, distinct lowering of the pI as compared to the reference Polypeptide_19 and/or a corresponding polypeptide construct without substituent(s) as was discussed above with reference to Table 21 and Table 22. Measured Tm values are also shown in Table 29 for the indicated compounds/polypeptide derivatives, which were measured as described in the MATERIALS AND METHODS section: Differential Scanning Fluorimetry (Nano DSF) Analysis of anti-IL-6 VHH. All compounds showed relatively high melting temperatures between 48.7-56.1° C., most above 51° C., which were acceptable melting temperatures for a pharmaceutical compound suitable for human administration, wherein the normal physiological temperature is of 37° C.

Expression levels of the precursor polypeptides leading to production of these polypeptide conjugates were in the range of 74 to 143 mg/L using the transient mammalian expression system Expi293F, which is an acceptable initial expression level for further scalable development and manufacturing work.

Specifically, Compound 9 showed a pI of 4.61 and a melting temperature of 56.1° C. which are desirable in a pharmaceutical construct. Further details will be provided in the examples below.

Conclusion

The generation of polypeptides and polypeptide derivatives as described above provided for the development of constructs which show desirable pharmaceutical profiles. The polypeptides and/or polypeptide derivatives demonstrated lower pI while maintaining suitable melting temperatures and suitable expressibility. For instance, Compound 9 showed a low pI, high melting temperature and good expressibility.

Example 7: In Vitro Activity of Anti-IL-6 VHH Variants in STAT-3-LUC Reporter Gene Assay, Effect of Fatty Acid Substituent Purpose The purpose of this example was to test the effect of fatty acid protractor length at C-terminus on the variants' potency to inhibit IL-6-dependent STAT3 signaling and hence IL-6 activity in vitro. This elucidates the effect of serum albumin binding on potency of anti-IL-6 V$_H$H Polypeptide derivatives to bind to human IL-6.

Methods

The Reporter Gene Assay was conducted as described in the MATERIALS AND METHODS section. The reported values are the means of two technical replicates or two experimental replicates (n=2).

Results

Table 30 identifies the polypeptide derivatives tested as part of this experiment, labelled as "Compound", and provides the detailed composition of each one of the polypeptide derivatives. One may also refer to Table 12 for the detailed composition of the polypeptide derivatives. As can be seen, Compound 14 to Compound 19 are polypeptide derivatives comprising VHH_1.6 therein, comprising a C-terminal extension with either 1 or 2 Cysteines. These cysteines were the cite of conjugation of 1 or more substituents with differing fatty acids.

Table 33 shows mean IC50 values and relative IC50 values to the non-protracted polypeptide (Polypeptide_29) comprising the same underlying VHH (VHH_1.6). The polypeptide derivatives, identified as compounds, had one or more substituent(s) attached to the polypeptide, which comprised a fatty acid protraction. The effect of conjugating 1 or 2 substituents, while further exploring the effect of different types of protraction moieties via the use C16, C18 and C20 fatty acids were observed. Polypeptide derivatives identified as Compound 14 and Compound 17 comprised 1× or 2× C16 fatty acid(s) (Chem. 24), respectively. Polypeptide derivatives identified as Compound 15 and Compound 18 comprised 1× or 2× C18 fatty acid(s) (Chem. 26), respectively. Polypeptide derivatives identified as Compound 16 and Compound 19 comprised 1× or 2× C20 fatty acid(s) (Chem. 27), respectively. The potency of Polypeptide_29 comprising the same underlying VHH (VHH_1.6) and an extension without any substituents is also provided in Table 33 for comparison purposes.

TABLE 31

Potency (IC50) and relative potency of polypeptide derivatives comprising VHH_1.6 conjugated to varying substituents. Relative potency is in comparison to Polypeptide_29, comprising the same VHH_1.6 and no substituent.

| Entry ID | Substituent Note | n | IC50 (nM) mean | Relative IC50 to Polypeptide_29 |
|---|---|---|---|---|
| Polypeptide_29 (Reference) | No substituent | 1 | 0.039 | 1 |
| Compound 14 | Chem. 24 (1x) | 2 | 0.041 | 1.1 |
| Compound 15 | Chem. 26 (1x) | 2 | 0.046 | 1.3 |
| Compound 16 | Chem. 27 (1x) | 2 | 0.054 | 1.6 |
| Compound 17 | Chem. 24 (2x) | 1 | 0.040 | 1.0 |
| Compound 18 | Chem. 26 (2x) | 2 | 0.043 | 1.2 |
| Compound 19 | Chem. 27 (2x) | 2 | 0.042 | 1.1 |

Conclusion

The polypeptide derivatives which comprised a fatty acids substituent displayed IC50 values which were comparable to that of the non-protracted reference Polypeptide_29. The data demonstrated that the potency remained generally stable irrespective whether there was a single substituent or a double substituent attached to the polypeptide or whether the substituent comprised Chem. 24, Chem 25 or Chem. 26. Compound 17, with two substituents (one attached to the Cysteine residue at position 4 of the C-terminal extension and the other attached to the Cysteine residue at position 6 of the C-terminal extension), resulted in the least amount of variation in the potency of the polypeptide derivative.

TABLE 30

List of Polypeptides derivatives tested as part of the experiment and detailed composition.

| Entry ID | VHH ID | SEQ ID no. | C-terminal Extension/tag ID | SEQ ID No. | Substituent ID | Position |
|---|---|---|---|---|---|---|
| Compound 14 | VHH_1.6 | 28 | E8-[6xHis tag] | 161 | Chem. 24 | Cys in position 4 of Extension |
| Compound 15 | VHH_1.6 | 28 | E8-[6xHis tag] | 161 | Chem. 26 | Cys in position 4 of Extension |
| Compound 16 | VHH_1.6 | 28 | E8-[6xHis tag] | 161 | Chem. 27 | Cys in position 4 of Extension |
| Compound 17 | VHH_1.6 | 28 | E2-[6xHis tag] | 162 | Chem. 24 | Cys in position 4 of Extension |
| | | | | | Chem. 24 | Cys in position 6 of Extension |
| Compound 18 | VHH_1.6 | 28 | E2-[6xHis tag] | 162 | Chem. 26 | Cys in position 4 of Extension |
| | | | | | Chem. 26 | Cys in position 6 of Extension |
| Compound 19 | VHH_1.6 | 28 | E2-[6xHis tag] | 162 | Chem. 27 | Cys in position 4 of Extension |
| | | | | | Chem. 27 | Cys in position 6 of Extension |

Example 8: Reporter Gene Assay and SPR Experiments

In vitro characterization was conducted as part of optimizations of the $V_HH$s in the form of polypeptides and polypeptide derivatives using reporter gene assay and direct binding SPR-based assay.

8.1: In Vitro Activity of Anti-IL-6 $V_HH$ in stat-3-luc Reporter Gene Assay

Purpose

The purpose of this example was to test the ability of anti-IL-6 VHHs to inhibit IL-6-dependent STAT3 signalling and hence IL-6 activity in vitro.

The assay was used to probe that additional modifications, such as the pI mutations, deimmunization mutations and fatty acid conjugations, did not result in unwanted reduction of the potency of the $V_HH$ polypeptide and/or polypeptide derivative, including in the presence of HSA.

Methods

The Reporter Gene Assay was conducted as described in the MATERIALS AND METHODS section. It is to be noted, however, that FBS was replaced by 1% human serum albumin (HSA, (Sigma #A9511)) for testing of acylated VHHs. The reported values were averaged across all experiments.

A sequence identical analogue (SIA) of bi-specific domain antibody Vobarilizumab (CAS registry no.: 1628814-88-9, SEQ ID No. 164), and the anti-IL-6R domain thereof (SEQ ID No. 163, previously discussed in Table 26) are shown for comparison purposes. The bi-specific domain antibody Vobarilizumab and the anti-IL-6R domain thereof were produced recombinantly as described generically above in Materials and Methods sections "Generic expression of $V_HH$" and "Generic purification and analysis of $V_HH$".

The Reference Anti-IL6 Fab described in detail above is also shown.

Results

Table 32 below shows the IC50 values of select anti-IL-6 VHHs polypeptides (identified with a polypeptide ID) or polypeptide derivatives (identified with a compound ID) in a medium with 1% human serum albumin (HSA) or without HSA. For ease of reference, the underlying $V_HH$ for each one of these polypeptides/polypeptide derivatives is shown. One may further refer to Table 12 for the detailed composition of the example polypeptides/polypeptide derivatives. $IC_{50}$s are determined performing a 4-parameter fit to a 12-step 1:3 serial dilution.

TABLE 32

$IC_{50}$ values of anti-IL-6 $V_HH$s polypeptides/polypeptide derivatives in medium with 1% or without HSA.

| Entry | Polypeptide ID/ Compound ID | $V_HH$ ID | HSA | n | IC 50 (nM) | STD (nM) | SEM (nM) |
|---|---|---|---|---|---|---|---|
| 1A | Polypeptide_18 | VHH_1.16 | 0% | 2 | 0.020 | 0.002 | 0.002 |
| 1B | Polypeptide_18 | VHH_1.16 | 1% | 1 | 0.020 | | |
| 2A | Polypeptide_34 | VHH_1.8 | 0% | 5 | 0.066 | 0.024 | 0.011 |
| 2B | Polypeptide_34 | VHH_1.8 | 1% | 2 | 0.046 | 0.010 | 0.007 |
| 3A | Polypeptide_19 | VHH_1.11 | 0% | 12 | 0.117 | 0.090 | 0.026 |
| 3B | Polypeptide_19 | VHH_1.11 | 1% | 2 | 0.064 | 0.006 | 0.005 |
| 4A | Polypeptide_47 | VHH_1.15 | 0% | 6 | 0.017 | 0.004 | 0.002 |
| 4B | Polypeptide_47 | VHH_1.15 | 1% | 1 | 0.010 | | |
| 5A | Compound 1 | VHH_1.12 | 0% | 1 | 0.029 | | |
| 5B | Compound 1 | VHH_1.12 | 1% | 3 | 0.060 | 0.005 | 0.003 |
| 6B | Compound 12 | VHH_1.17 | 1% | 2 | 0.021 | 0.001 | 0.001 |
| 7A | Compound 2 | VHH_1.13 | 0% | 2 | 0.065 | 0.001 | 0.001 |
| 7B | Compound 2 | VHH_1.13 | 1% | 2 | 0.041 | 0.003 | 0.002 |
| 8A | Polypeptide_46 | VHH_1.14 | 0% | 1 | 0.021 | | |
| 9A | Compound 3 | VHH_1.14 | 0% | 1 | 0.029 | | |
| 9B | Compound 3 | VHH_1.14 | 1% | 1 | 0.029 | | |
| 10A | Polypeptide_22 | VHH_1.2 | 0% | 1 | 0.029 | | |
| 11A | Polypeptide_24 | VHH_1.3 | 0% | 1 | 0.019 | | |
| 12A | Polypeptide_27 | VHH_1.4 | 0% | 1 | 0.026 | | |
| 13A | Polypeptide_28 | VHH_1.5 | 0% | 1 | 0.027 | | |
| 14A | Polypeptide_29 | VHH_1.6 | 0% | 8 | 0.035 | 0.014 | 0.005 |
| 15A | Polypeptide_31 | VHH_1.7 | 0% | 1 | 0.023 | | |
| 16A | Compound 4 | VHH_1.1 | 0% | 1 | 0.024 | | |
| 16B | Compound 4 | VHH_1.1 | 1% | 1 | 0.015 | | |
| 17A | Compound 5 | VHH_1.2 | 0% | 1 | 0.019 | | |
| 17B | Compound 5 | VHH_1.2 | 1% | 1 | 0.012 | | |
| 18A | Compound 6 | VHH_1.3 | 0% | 1 | 0.018 | | |
| 18B | Compound 6 | VHH_1.3 | 1% | 1 | 0.016 | | |
| 19A | Compound 7 | VHH_1.4 | 0% | 2 | 0.025 | 0.001 | 0.001 |
| 19B | Compound 7 | VHH_1.4 | 1% | 2 | 0.019 | 0.006 | 0.005 |
| 20A | Compound 8 | VHH_1.5 | 0% | 1 | 0.020 | | |
| 20B | Compound 8 | VHH_1.5 | 1% | 1 | 0.017 | | |
| 21A | Compound 9 | VHH_1.6 | 0% | 3 | 0.022 | 0.002 | 0.001 |
| 21B | Compound 9 | VHH_1.6 | 1% | 2 | 0.014 | 0.004 | 0.003 |
| 23A | Compound 10 | VHH_1.7 | 0% | 1 | 0.022 | | |
| 23B | Compound 10 | VHH_1.7 | 1% | 1 | 0.016 | | |
| 24A | Reference Anti-IL6 Fab | — | 0% | 21 | 0.026 | 0.010 | 0.002 |
| 24B | Reference Anti-IL6 Fab | — | 1% | 4 | 0.017 | 0.008 | 0.004 |

TABLE 32-continued

IC$_{50}$ values of anti-IL-6 V$_H$Hs polypeptides/polypeptide derivatives in medium with 1% or without HSA.

| Entry | Polypeptide ID/ Compound ID | V$_H$H ID | HSA | n | IC 50 (nM) | STD (nM) | SEM (nM) |
|---|---|---|---|---|---|---|---|
| 25A | Vobarilizumab anti-IL-6R domain SIA comparator | — | 0% | 1 | 0.114 | | |
| 25B | Vobarilizumab SIA comparator | — | 0% | 1 | No inhibition | | | n = number of experiments.

Conclusion

The anti-IL-6-VHHs polypeptide/polypeptide derivatives were shown to inhibit IL-6 signaling at IC$_{50}$ values between 10 and 117 pM (Table 32).

As can be seen, the selected initial V$_H$H Polypeptide_19 (SEQ ID NO: 57) showed an IC$_{50}$ potency of approx. 117 pM. The introduction of selected mutations and C-term conjugation of two C16 diacid fatty acids (Chem. 24) on the Cys4 and Cys6 in the C-terminal extension E2 of SEQ ID No. 72 further showed suitable IC50/potency in presence of HSA of approx. 60 pM or less. For instance, Compound 9 was an IC50/potency in the presence of HSA of 14 pM.

The data additionally shows that the potency of the Polypeptides (or more specifically the underlying VHH) were not affected by the fatty acid substituents attached thereon, as was discussed in EXAMPLE 7: IN VITRO ACTIVITY OF ANTI-IL-6 VHH VARIANTS IN STAT-3-LUC REPORTER GENE ASSAY, EFFECT OF FATTY ACID SUBSTITUENT. In contrast, the Vobarilizumab (CAS registry no.: 1628814-88-9, SEQ ID No. 164) sequence identical analogue comparator resulted in complete loss of potency when conjugated with its anti-HSA domain. As can be seen from the data, while the sequence identical analogue of the anti-IL-6R domain in entry 25A (SEQ ID No. 163) of Vobarilizumab demonstrated some IL-6 signaling inhibition of low potency (as was previously discussed with reference to Table 25), the inclusion of the anti-HSA domain of Vobarilizumab resulted in a loss of IL-6 inhibitory properties of the construct.

Further, the Anti-IL-6-V$_H$Hs with fatty acid conjugations, referred to as polypeptide derivatives herein (identified as Compounds 1-10 in Table 32) did not show decreased activity when in the presence of HSA in the assay medium (0% vs 1% HSA).

The introduction of potency boosting mutations, deimmunization mutations and liability fixing mutations (example mutations see Table 21) resulted in V$_H$H polypeptide derivatives with high IC$_{50}$ potencies of between 12 and 25 pM, respectively (Table 32, Entries 16A-23B). The results further demonstrated that the polypeptide derivatives as described herein provided an IC50 potency that was on par with, if not better than, the potency provided by the reference Anti-IL6 Fab. Such high potencies are desirable for developing an oral drug candidate, and in particular, oral drug candidates based on an antibody-scaffold, since oral bioavailability is generally lower compared to other administration routes.

These high potencies were provided in combination with the low pI, high melting temperature and good expressibility previously discussed. For instance, Compound 9 was shown in the previous examples to provide low pI of 4.61, and high melting temperature of 56.1° C., while Table 32 above further demonstrated that the same polypeptide derivate provided for high IC50 potency of 14-22 pM (Entries 21A, 21B) which was maintained, or even enhanced, with the presence of HSA. This combination of features is desirable and demonstrated the potential suitability of this polypeptide derivative for a therapeutic product.

8.2: SPR Analysis Using HPC4-Tagged IL-6 as Analyte

Purpose

The purpose of this example was to estimate the binding constants of selected anti-IL-6 V$_H$H with human IL-6. Paratope:epitope interaction could be deliberately optimized by introducing specific mutations aimed at e.g. decreasing pI, deimmunizing, improving functionality, by measuring the binding constants of the modified polypeptides to assure that those modifications would not negatively affect the binding affinity to human IL-6.

SPR Analysis of HPC4-Tagged IL-6

Binding of purified anti-IL-6 VHHs to recombinant human HPC4-tagged IL-6 (SEQ ID NO: 98) was probed by Surface Plasmon Resonance (SPR).

Briefly, an anti-HPC4 antibody (as previously described (Rezaie et al (1992) Expression and Purification of a Soluble Tissue Factor Fusion Protein with an Epitope for an Unusual Calcium-Dependent Antibody. Protein Expression and Purification 3:453-460; Stearns et al (1988) The Interaction of a Ca2+-dependent Monoclonal Antibody with the Protein C Activation Peptide Region. JBC 263:826-832)) was immobilised on a CM4 sensor chip (Cytiva) or a Xantec HLC200M (Xantec) using standard amine coupling chemistry at pH 5. Immobilisation levels of 5500-6500 RU are obtained after injection of the antibody @ 25 g/ml at 10 µl/min for 420 seconds. IL-6 was captured at a flow rate of 10 µL/min for 30 seconds.

```
                          Anti HPC4 antibody

Heavy chain (anti HPC4 HC)                                              SEQ ID
QVTLLESGPGILQPSQTLTLTCSLSGFSLRTSGMGVGWIRQPSGKGLEWLAHIWWDDDKRY NO.  1
NPVLKSRLIISKDTSRKQVFLKIASVDTADTATYYCVRMMDDYDAMDYWGQGTSVTVSSAS
TKGPSVFPLAPCSRSTSESTAALGCLVKDYFPEPVTVSWNSGALTSGVHTFPAVLQSSGLY
SLSSVVTVPSSSLGTKTYTCNVDHKPSNTKVDKRVESKYGPPCPPCPAPEFLGGPSVFLFP
PKPKDTLMISRTPEVTCVVVDVSQEDPEVQFNWYVDGVEVHNAKTKPREEQFNSTYRVVSV
LTVLHQDWLNGKEYKCKVSNKGLPSSIEKTISKAKGQPREPQVYTLPPSQEEMTKNQVSLT
```

```
                    Anti HPC4 antibody

CLVKGFYPSDIAVEWESNGQPENNYKTTPPVLDSDGSFFLYSRLTVDKSRWQEGNVFSCSV
MHEALHNHYTQKSLSLSLGK

Light chain (anti HPC4 LC)                              SEQ ID
QIILTQSPAIMSASLGEEITLTCSATSSVTYVHWYQQKSGTSPKLLIYGTSNLASGVPSRF NO. 2
SGSGSGTFYSLTVSSVEAEDAADYYCHQWNSYPHTFGGGTKLEIKRTVAAPSVFIFPPSDE
QLKSGTASVVCLLNNFYPREAKVQWKVDNALQSGNSQESVTEQDSKDSTYSLSSTLTLSKA
DYEKHKVYACEVTHQGLSSPVTKSFNRGEC
```

Subsequently, concentration series of $V_HH$ polypeptides according to Table 33 were injected at a flow rate of 50 µL/min for 200 seconds to allow for binding to anti-IL-6 $V_HH$ polypeptide followed by 600 seconds running buffer (10 mM HEPES, 150 mM NaCl, 5 mM $CaCl_2$), 0.05% (v/v) Surfactant P20, 1 mg/mL bovine serum albumin, pH 7.4) injection allowing dissociation from IL-6. The running buffer was also used for dilution of anti-IL-6 VHHs and IL-6. Regeneration of the chip was achieved using a regeneration buffer consisting of 50 mM EDTA in running buffer without $CaCl_2$), 30 seconds contact time, and a 30 µL/min flow rate applied twice to the surface. The binding data were collected at 25° C. at either a Biacore instrument (Cytiva AB, Uppsala) or a Bruker SPR32 (Bruker Daltonics). Data were analysed according to a 1:1 model using either BiaEvaluation or Biacore Insight Evaluation (Cytiva AB, Uppsala) or Bruker Analyser (Bruker Daltonics).

Results

The below table identifies the calculated binding constants of the polypeptides and polypeptides derivatives based on kinetic data obtained on HPC4-human IL6. For ease of reference, the underlying $V_HH$ for each one of these polypeptides/polypeptide derivatives is shown. One may further refer to Table 12 for the detailed composition of the example polypeptides/polypeptide derivatives.

TABLE 33

Calculated binding constants of $V_HH$'s and derivatives based on kinetic data obtained on HPC4-human IL6.

| Entry | Polypeptide ID/ Compound ID | $V_HH$ ID | On rate ($k_{on}$) [$M^{-1}s^{-1}$] | Off rate ($k_{off}$) [$s^{-1}$] | Affinity ($K_D$) [M]$^a$ |
|---|---|---|---|---|---|
| 1 | Polypeptide_34 | VHH_1.8 | 2.88E+07 | | 1.36E-11 |
|   |                |         | 2.88E+07 | | 1.36E-11 |
| 2 | Polypeptide_47 | VHH_1.15 | 2.59E+07 | 1.40E-04 | 5.42E-12 |
|   |                |          | 1.05E+07 | 2.08E-04 | 1.82E-11 |
|   |                |          | 2.03E+07 | 1.37E-04 | 6.74E-12 |
| 3 | Polypeptide_22 | VHH_1.2 | 2.03E+07 | 1.47E-04 | 7.21E-12 |
| 4 | Polypeptide_24 | VHH_1.3 | 4.12E+07 | 1.32E-04 | 3.21E-12 |
| 5 | Polypeptide_27 | VHH_1.4 | 2.16E+07 | 1.63E-04 | 7.55E-12 |
| 6 | Polypeptide_28 | VHH_1.5 | 2.56E+07 | 1.30E-04 | 5.08E-12 |
| 7 | Polypeptide_29 | VHH_1.6 | 2.23E+07 | 8.69E-05 | 3.90E-12 |
| 8 | Polypeptide_31 | VHH_1.7 | 8.82E+06 | 1.54E-04 | 1.75E-11 |
| 9 | Compound 4 | VHH_1.1 | 4.90E+06 | 6.98E-05 | 1.42E-11 |
|   |            |         | 4.75E+06 | 9.08E-05 | 1.91E-11 |
| 10 | Compound 5 | VHH_1.2 | 4.94E+06 | 7.82E-05 | 1.59E-11 |
|    |            |         | 4.65E+06 | 9.95E-05 | 2.14E-11 |
| 11 | Compound 6 | VHH_1.3 | 4.94E+06 | 7.82E-05 | 1.61E-11 |
|    |            |         | 4.65E+06 | 9.95E-05 | 2.14E-11 |
| 12 | Compound 7 | VHH_1.4 | 5.05E+06 | 1.27E-04 | 2.52E-11 |
|    |            |         | 4.56E+06 | 1.54E-04 | 3.38E-11 |
| 13 | Compound 8 | VHH_1.5 | 4.58E+06 | 1.01E-04 | 2.21E-11 |
|    |            |         | 4.16E+06 | 1.23E-04 | 2.96E-11 |
| 14 | Compound 9 | VHH_1.6 | 4.66E+06 | 8.71E-05 | 1.87E-11 |
|    |            |         | 4.82E+06 | 1.05E-04 | 2.18E-11 |
|    |            |         | 4.53E+06 | 1.01E-04 | 2.23E-11 |
| 15 | Compound 10 | VHH_1.7 | 4.48E+06 | 9.33E-05 | 2.08E-11 |
|    |             |         | 5.68E+06 | 1.08E-04 | 1.91E-11 |
| 16 | Compound 1 | VHH_1.12 | 5.67E+06 | 3.64E-04 | 6.37E-11 |
|    |            |          | 8.18E+06 | 3.71E-04 | 4.54E-11 |
| 17 | Compound 12 | VHH_1.17 | 7.36E+06 | 2.16E-04 | 5.43E-11 |
| 18 | Compound 2 | VHH_1.13 | 6665000 | 3.48E-04 | 5.23E-11 |

$^a$Calculated as $K_D = k_{off}/k_{on}$.

Conclusion

It can be observed that low pM $K_D$ affinities were obtained across the design cycles and that only minor effects on binding affinities were observed across the design cycle optimizations. Written otherwise, it can be observed that suitable pM range affinity was achieved and maintained for the polypeptide derivatives. For example, the $V_HH$ polypeptide derivative Compound 1 showed an affinity of approx. 45-63 pM, while other polypeptide derivatives such as compounds 4-10, showed affinities between 14 and 34 pM.

Having a pM affinity in combination with the high potency, low pI and high melting temperature is a desirable combination. Among others, Compound 9 demonstrated a desirable $K_D$ of 18-22 pM on top of the high potency, low pI and high melting temperature properties.

In Vivo Experiments

Polypeptide derivatives identified as Compound 1, Compound 2, Compound 3, Compound 7 and Compound 9 were selected to proceed in a series of In vivo experiment.

EXAMPLE 9: IN VIVO INTRAVENOUS PHARMACOKINETIC STUDY IN RAT, EFFECT OF FATTY ACID SUBSTITUENT, EXAMPLE 10: DOSE-RESPONSE STUDIES IN ACUTE MOUSE HUMAN IL-6 MODEL, EXAMPLE 11: INTRAVENOUS PK IN MINIPIGS, and EXAMPLE 13: PERORAL AND INTRAVENOUS PHARMACOKINETIC STUDY IN DOG: VHH POLYPEPTIDE DERIVATIVES FORMULATED WITH SNAC AND NAM, described below, show in vivo data.

Example 9: In Vivo Intravenous Pharmacokinetic Study in Rat, Effect of Fatty Acid Substituent Purpose The purpose of this example was to test the effect of types and numbers (1 and 2) of fatty acid substituents of anti-IL-6 $V_HH$ compound on pharmacokinetic (PK) parameters in healthy Sprague Dawley rats after intravenous dosing.

Methods

Liquid formulations of anti-IL-6 $V_HH$ polypeptide derivatives, referred to in the example section as compounds, were dosed intravenously (IV) (IV formulation: 20 mM Hepes, 150 mM NaCl, pH 7.4). The formulated compounds were administered by IV to parallel groups of Sprague Dawley rats acclimated at least one week in-house prior to study and kept in group cages with ad libitum access to standard food and water. On the day of dosing, all rats were acclimated in the procedure room for 30 minutes.

Dosing solutions of the different anti-IL6 VHH variants were dosed at time 0 and blood samples were collected after 5 min and then at times 4, 24, 48, 96, 144, 168 and 240 hours post dosing. The blood samples were taken from the sublingual plexus of the tongue (150 μl) in EDTA coated vials, (Microvette 200K3E ref #20.1288.100, Sarstedt). The plasma was separated (4° C., 8000 RPM, 5 min) and transferred to tubes (Mirconic) for measurement of plasma exposure. Plasma concentrations of $V_HH$ conjugate compounds were measured using a His tag-based immunoassay, in which an anti-$V_HH$ antibody (Novo Nordisk, Denmark) and an anti-His-tag antibody towards the test compounds was used. Here, 96-well MaxiSorp plates (Nunc, 439454) were coated with 2 μg/ml His-Tag Antibody (R&D systems, MAB050), washed and blocked using PBS; 0.05% tween20; 1% BSA; pH 7.4. After a wash step, compound specific calibrator (0, 2.7, 8.2, 24.7, 74, 222, 667, 2000 pM) in 1% rat EDTA plasma and rat EDTA plasma samples in a minimal dilution of 100× were incubated on the plate, where the $V_HH$ conjugate compounds was captured via its His Tag. After an additional wash step, a biotinylated in-house $V_HH$ specific antibody was added to the plate (0.5 nM) to make up the sandwich ELISA. After a final wash step, horseradish peroxidase (HRP)-streptavidin was added to the plate as the detection reagent. The amount of biotin labelled antibody bound to the $V_HH$ polypeptide derivative was detected following addition of a chromogenic substrate (e.g., TMB (3,3′,5,5′-tetramethylbenzidine). Optical density was measured using a Spectrometer (e.g. a SpectraMax® M2 spectrometer (Molecular Devices)). The response was proportional to the concentration of peroxidase, which again was proportional to the concentration of the $V_HH$ polypeptide derivative compound.

Results

The polypeptide derivatives tested as part of this experiment, labelled as "Compound", correspond to those described in detail in EXAMPLE 7: IN VITRO ACTIVITY OF ANTI-IL-6 VHH VARIANTS IN STAT-3-LUC REPORTER GENE ASSAY, EFFECT OF FATTY ACID SUBSTITUENT. Table 30 identifies the polypeptide derivatives tested and provides the detailed composition of each one of the polypeptide derivatives. One may also refer to Table 12 for the detailed composition of the polypeptide derivatives.

As can be seen, Compound 14 to Compound 19 are polypeptide derivatives comprising VHH_1.6 therein, and comprising a C-terminal extension with either 1 or 2 Cysteines. These cysteines were the cite of conjugation of 1 or more substituents with differing fatty acids.

Results are provided in Table 34 below, identifying the terminal half-life ($T_{1/2}$) polypeptide derivatives, identified as compounds, as well as the substituent free (ie. non-protracted) polypeptide (Polypeptide_29) comprising the same underlying $V_HH$ (VHH_1.6) for reference. Results of another substituent free polypeptide (Polypeptide_63) is also provided. The polypeptide derivatives, identified as compounds, had one or more substituent(s) attached to the polypeptide, which comprised a fatty acid protraction. For ease of reference, these are identified in the Substituent note column.

TABLE 34

Terminal half-life (T½) of anti-IL-6 polypeptide derivatives with different substituents

| ID | Substituent Note | Dose nmol/kg | n | $T_{1/2}$ (hours) Mean ± SD |
|---|---|---|---|---|
| Polypeptide_29 (Reference) | No substituent | 10 | 1 | 0.6 ± n/a |
| Polypeptide_63 | No substituent | 217 | 3 | 0.6 ± 0.01 |
| Compound 14 | Chem. 24 (x1) | 10 | 3 | 5.1 ± 0.7 |
| Compound 15 | Chem. 26 (x1) | 10 | 1 | 25.6 ± n/a |
| Compound 16 | Chem. 27 (x1) | 10 | 3 | 37.7 ± 2.6 |
| Compound 17 | Chem. 24 (x2) | 10 | 3 | 29.6 ± 1.2 |
| Compound 18 | Chem. 26 (x2) | 10 | 2 | 28.2 ± 1.8 |
| Compound 19 | Chem. 27 (x2) | 10 | 3 | 26.0 ± 1.0 |

The data showed that non-protracted polypeptides (which may also be referred to as polypeptides having no substituents thereon), Polypeptide_29 and Polypeptide_63, are cleared rapidly in rat with a half-life of just above half an hour. All polypeptide derivatives, with a fatty diacid conjugate showed increased half-lives that were at least one order-of-magnitude higher. More specifically, it could be seen that Compound 15-Compound 19 showed half-lives which were approx. 40-60 folds higher in comparison to the substituent free $V_HH$ polypeptides (Polypeptide_29 and Polypeptide_63).

Conclusion

The provision a fatty diacid substituent showed increases in half-life.

Combined with the observation that such polypeptide derivates with a fatty diacid substituent showed conserved potency compared to the substituent-free polypeptide (Polypeptide_29) comprising the same VHH (see above), such improved pharmacokinetic results for these polypeptide derivatives are desirable, particularly when such a PK profile is combined with other desirable pharmaceutical properties. For instance, Compound 17, which aligns with the polypeptide derivative identified as Compound 9 herein (see Table 12, VHH_1.6 with a two Chem. 24 substituents) was shown to have a high half-life of 29.6 hrs, while also being shown in the other examples to have, among other things, high potency.

Example 10: Dose-Response Studies in Acute Mouse Human IL-6 Model

The purpose of this study was to investigate the ability of anti-IL-6 VHHs to inhibit the biomarker Serum Amyloid A1 (SAA1) response in an acute human IL-6 mouse model. The in vivo readout biomarker SAA1 was chosen, since it is a well-established proatherogenic effector molecule regulated by IL-6 levels, which have been used in atherosclerotic mice models (Thompson J C et al (2015)). A brief elevation of serum amyloid A is sufficient to increase atherosclerosis (J Lipid Res. 56(2):286-93). Levels of SAA1 have been associated with cardiovascular disease, with synergistic induction of levels of IL-6, as well as disease-promoting single-nucleotide polymorphisms (Hagihara K (2004) IL-6 plays a critical role in the synergistic induction of human serum amyloid A (SAA) gene when stimulated with proinflammatory cytokines as analyzed with an SAA isoform real-time quantitative RT-PCR assay system. Biochem Biophys Res Commun. 314(2):363-9; Carty C L et al (2009) Association of genetic variation in serum amyloid-A with cardiovascular disease and interactions with IL-6, IL1RN, IL1beta and TNF genes in the Cardiovascular Health Study. J Atheroscler Thromb. 16 (4): 419-30). Thus, SAA1 was chosen as primary readout based on its use in human clinical trials and its sensitivity in the acute mouse model.

In this in vivo mouse model, human IL-6 (hIL-6, SEQ ID NO: 82) was administered to healthy mice to elicit an acute phase reactant response, measured as SAA1, due to the limited cross-reactivity of the tested anti-IL-6 $V_HH$ polypeptide derivatives (see above) to murine IL-6.

Methods

Healthy male BALB/c mice (Charles River, Germany, n=7-8 per group) were injected with the IL-6 antagonist intravenously (i.v.) 30 minutes before injecting hIL-6 (in house produced (SEQ ID NO: 82) i.v. in the tail vein at a dose of 3.6 nmol/kg. Five (5) hours after the injection of hIL-6, a blood sample was collected to determine SAA1 levels using a commercially available ELISA kit (Mouse SAA ELISA kit, R&D Systems, Inc. a Bio-Techne Brand, MSAA00)). Compound concentration was determined via Luminescence Oxygen Channeling Immunoassay (LOCI).

Data were normalised in relation to the window between level in healthy control animals (set to 100%) and the level after upregulation of SAA1 by hIL-6 alone (set to 0%). The half maximal effective dose ($ED_{50}$) is provided as the dose of the antagonist giving a 50% lowering of SAA1 compared to the group upregulated with human IL-6. Based on plasma concentrations of the compound (exposure) if available, the half maximal effective concentration ($EC_{50}$) is reported as the plasma concentration of antagonist giving a 50% lowering of SAA1 compared to the group upregulated with hIL-6.

Results

The results are shown in Table 35. One may further refer to Table 12 for the detailed composition of the polypeptide derivatives.

TABLE 35

A summary of the dosing conditions as well as the study results ($ED_{50}$ & $EC_{50}$) based on the biomarker serum amyloid A 1 and modelling using the Hill equation.

| Entry | Compound. ID | Dose $V_HH$ (nmol/kg) | Dose hIL-6 (nmol/kg) | $ED_{50}$ (nmol/kg) | $EC_{50}$ (nM) |
|---|---|---|---|---|---|
| 1 | Reference anti-IL6 Mab | 0.8, 1.4, 2.4, 4.1 | 3.6 | 1.9 | — |
| 2 | Compound 1 | 1.7, 8.3, 41.4, 207.1 | 3.6 | 7.1 | 48 |
| 3 | Compound 2 | 5.0, 10.0, 25.0, 50.0 | 3.6 | 9.4 | 177 |
| 4 | Compound 3 | 1.5, 5.0, 15.0, 30.0 | 3.6 | 3.9 | 51 |
| 5 | Compound 7 | 1.0, 2.5, 5.0, 20.0 | 3.6 | 4.3 | 36 |
| 6 | Compound 9 | 1.0, 2.5, 5.0, 20.0 | 3.6 | 1.9 | 25 |

Conclusion

The data showed a dose-dependent reduction of SAA1 in mice treated with anti-IL-6 $V_HH$ polypeptide derivatives. The most potent polypeptide derivatives tested were Compound 7 and Compound 9 with $EC_{50}$ potencies of approx. 36 and 25 nM, respectively, which were comparable with observed potencies observed with in vitro reporter gene assay (see above).

Example 11: Intravenous PK in Minipigs

Aim

The aim of the study was to determine pharmacokinetic parameters following i.v. administration of anti-IL-6 $V_HH$ polypeptide derivatives. All the polypeptide derivatives tested comprised a C-terminal extended $V_HH$ with two substituents comprising a C16 diacid fatty acid protractor moiety for enhanced half-life. One may further refer to Table 12 for the detailed composition of the polypeptide derivatives detailed below. $V_HH$ polypeptides (ie. Non-protracted $V_HH$ constructs) were shown to have a short half-life (less than 15 hours in mini-pig, data not shown).

Methods

The studies were done in female Göttingen minipigs (Ellegaard Minipigs A/S, Dalmose, Denmark) with a body weight of approximately 25 kg and the dose given was 5 nmol/kg administered intravenously through a permanent catheter, n=3 per group. Vehicle for the single domain antibodies was 20 mM HEPES, 150 mM NaCl, pH 7.4, target concentration 100 nmol/ml.

Blood was sampled for up to 912 hours (39 days) through an indwelling permanent venous catheter and collected in EDTA tubes (Sarstedt, Germany). Plasma was separated and analysed for compound concentration using Luminescence Oxygen Channeling Immunoassay (LOCI).

Non-compartmental (NCA) pharmacokinetic analysis was done in Phoenix® WinNonlin® v. 8.1 (Certara L.P.

Princeton, NJ, USA). The AUC were calculated using the "Linear Up Log Down" method. The terminal elimination phase was fitted via linear regression with uniform weighting. Nominal sampling times and actual doses were used for NCA.

Results are shown in Table 36. One may further refer to Table 12 for the detailed composition of the polypeptide derivatives.

TABLE 36

Pharmacokinetic parameters of select polypeptide derivatives.

| Entry | Compound ID | Mean T½ [h] | Mean Clearance (CI) [L/h/kg] | Mean Volume of distribution (Vz) [L/kg] | Mean Residence time (MRT) [h] | Last sampling [day] |
|---|---|---|---|---|---|---|
| 1 | Compound 1[1] | 236 | ND | ND | ND | 22* |
| 2 | Compound 2 | 166 | 0.000094 | 0.0225 | 243 | 39 |
| 3 | Compound 3[1] | 226 | ND | ND | ND | 22* |
| 4 | Compound 7 | 204 | 0.000128 | 0.0373 | 290 | 39 |
| 5 | Compound 9 | 165 | 0.000138 | 0.0325 | 234 | 39 |

ND: not determined

[1]sampling time too short for accurate estimation of pharmacokinetic parameters. No clinical observations related to the test compounds was seen during the studies.

Conclusion

The observed half-life of the polypeptide derivatives (identified as Compounds in the table above) tested were between 165 and 236 hours, which is more than 10-fold higher compared to $V_HH$ polypeptides (ie. non-protracted constructs). Since the reported half-life of albumin in pig is approximately 197 hours, the observed polypeptide derivative compound half-lives observed approached a theoretical value. Written otherwise, the observed half-life approached the potential upper limit of how much an albumin-based protraction of a drug candidate molecule, such as a $V_HH$ polypeptide derivative, could theoretically gain (Dich J et al (1963) Metabolism and Distribution of I-labelled Albumin in the Pig. Can J Comp Med Vet Sci. 27(11):269-73).

Example 12: Formulation of Anti-IL-6 $V_HH$ Polypeptide Derivatives with SNAC and Niacinamde in Dosage Form Suitable for Peroral Administration To prepare for oral studies using tablets with sodium N-(8-[2-hydroxybenzoyl]amino) caprylate (SNAC), niacinamide (NAM) and either magnesium stearate (MgSt) or sodium stearyl fumarate (SSF) as excipients for oral administration, the following procedure was followed.

Method 1: Blending for Dry Granulation

Blending was carried out by manual geometric mixing of anti-IL-6 $V_HH$ with SNAC and niacinamide followed by blending on a turbula mixer for 7 min at 25 rpm. Lubricate (MgSt or SSF) was added in a secondary blending step by manual geometric mixing followed by blending on a turbula mixer for 2 min at 25 rpm. The blended product was used for further processing.

Method 2: Dry Granulation

Dry granulation was carried out by roller compaction simulation on a STYL'One Evo compaction simulator using flat face punches with dimension of 10 mm (width) and 20 mm (length). Settings were set to simulate Gerteis Mini-Pactor with a machine speed of 3 rpm.

Following dry granulation, hand sieving of ribblets into granules using an 800 μm conidur mesh screen was carried out on a Gerteis hand mill. The granulate was used for further processing by compression.

Method 3: Blending for Direct Compression

In cases where the dry granulation step is not included in the formulation, pre-made intermediate granules containing SNAC, niacinamide and SSF was used to blend with spray dried anti-IL-6 $V_HH$ conjugates. Blending was carried out by manual geometric mixing the intermediate granulates with anti-IL-6 $V_HH$ followed by blending on a turbula mixer for 7 min at 25 rpm. The product was used for further processing by compression.

Method 4: Compression of Tablets

Tablets were compressed on a STYL'One Evo compaction simulator using single set of punches with dimensions of 8 mm×14 mm or 8.1 mm×14.3 mm resulting in oval tablets. Settings were set to simulate rotary press Fette 102i with a machine speed of 20 rpm. Fill depth was adjusted to obtain tablets having target weights based on composition. Compression forces ranged from 10 kN to 20 kN to obtain tablets with an apparent density of around 1.18-1.22 g/m³.

Method 5: Analysis of Tablets

For content analysis of anti-IL-6 $V_HH$ conjugates, SNAC and NAM, the tablets are weighed before extraction of the components. Tablets were dissolved in a relevant amount of 50 mM phosphate buffer with 20% acetonitrile at pH 7.4 for two hours. Centrifuged samples were transferred to a suitable HPLC vial. Standards of relevant amount of anti-IL-6 $V_HH$ conjugates, SNAC and NAM were prepared using the same diluent as for the samples. UPLC system was used for determination of the content of anti-IL-6 $V_HH$ conjugates, SNAC and NAM.

Preparation of Oral Tablet Formulation

Formulations were prepared according to Table 37. The compositions of the formulations were prepared by using a combination of the methods defined above. Formulations 1-4 and 8 were produced using the methods blending for dry granulation, dry granulation, and compression of tablets (methods 1, 2 and 4). Formulations 5-7 were produced using the methods for blending for direct compression and compression of tablets (methods 3 and 4).

All tablet formulations were analyzed using method 5. One may further refer to Table 12 for the detailed composition of the polypeptide derivatives used (ie. Compound component identified in the table below).

TABLE 37

Composition of oral tablets formulations containing anti-IL-6 $V_HH$ polypeptide derivatives.

| Formulation # | Component | Amount |
|---|---|---|
| #1 | Compound 1 | 15 mg |
| | SNAC | 300 mg |
| | Niacinamide | 200 mg |
| | Magnesium stearate | 2.5 mg |
| #2 | Compound 1 | 15 mg |
| | SNAC | 300 mg |
| | Niacinamide | 200 mg |
| | Sodium stearyl fumarate | 11.4 mg |
| #3 | Compound 2 | 15 mg |
| | SNAC | 300 mg |
| | Niacinamide | 200 mg |
| | Sodium stearyl fumarate | 11.4 mg |
| #4 | Compound 3 | 15 mg |
| | SNAC | 300 mg |
| | Niacinamide | 200 mg |
| | Sodium stearyl fumarate | 11.4 mg |
| #5 | Compound 9 | 15 mg |
| | SNAC | 300 mg |
| | Niacinamide | 200 mg |
| | Sodium stearyl fumarate | 11.4 mg |
| #6 | Compound 7 | 15 mg |
| | SNAC | 300 mg |
| | Niacinamide | 200 mg |
| | Sodium stearyl fumarate | 11.4 mg |

Example 13: Peroral and Intravenous Pharmacokinetic Study in Dog: $V_HH$ Polypeptide Derivatives Formulated with SNAC and NAM Purpose The purpose of the present study was to evaluate the effect anti-IL-6 $V_HH$ polypeptide derivatives comprising a fatty acid protraction as part of the substituent to enhance half-life, and to evaluate if lowering of pI leads to enhanced oral bioavailability.

Methods

Appropriate formulations of anti-IL-6 $V_HH$ polypeptide derivatives were, respectively, dosed intravenously (formulation for i.v. was based on HBS buffer) or prepared as tablets as disclosed in EXAMPLE 12: FORMULATION OF ANTI-IL-6 $V_HH$ POLYPEPTIDE DERIVATIVES WITH SNAC AND NIACINAMDE IN DOSAGE FORM SUITABLE FOR PERORAL ADMINISTRATION, and dosed perorally to groups of Beagle dogs. The dogs were dosed in the morning after overnight fasting and kept fasting for 4 hours after a single dosing. In a subset (§) of oral studies the dogs were given a s.c. dosing of approximately 3 nmol/kg of glucagon 10 min prior to oral dosing. Blood samples were collected immediately prior to dosing and subsequently at different post-dose time points. Plasma concentrations of $V_HH$ polypeptides with fatty diacid substituents were measured using bead-based immunoassay named alphaLISA, in which recombinant human IL-6 receptor protein (Novo Nordisk, Denmark) binds to the $V_HH$ polypeptide together with an anti-gamma-Glu (Novo Nordisk, Denmark) towards the conjugate side-chain motif of the test molecule were used. First, compound specific calibrator (0, 6, 13, 25, 50, 100, 200, 400, 800, 1600, 3200, 6400 pM) in dog EDTA plasma and dog EDTA plasma samples in a minimal dilution of 30× were added into 384-well plates (Revivity AlphaPlate-384, 6005359), biotinylated human IL-6 receptor protein and alphaLISA acceptor bead conjugated anti-gamma-Glu linker antibody were added afterwards to capture the $V_HH$ polypeptide compound. After incubation overnight (16-24 hrs), alpha streptavidin-coated donor beads were added into the 384 well plate. When the analyte presented in the sample, the donor and acceptor beads were brought together. Upon excitation, a photosensitizer inside the donor bead converts ambient oxygen to an excited singlet state. Singlet oxygen diffuses up to 200 nm to produce a chemiluminescent reaction in the acceptor bead, leading to light emission. Luminescence readings were measured using a Spectrometer (e.g. Enspire (Perkin Elmer)). The response was proportional to the concentration of the $V_HH$ polypeptide compound.

In a separate and additional experiment, plasma concentrations after providing compounds 1-3, 7, and 9 as well as for an example $V_HH$ polypeptide (ie. without fatty diacid substituents) for reference were assayed by plasma sample preparation and analyzed by LC-MS. Calibrators were prepared by spiking blank dog plasma with analytes to achieve final concentrations typically ranging from 1 to 500 nM. Calibrators, plasma blanks, or study samples were mixed 1:1 with 8M guanidine hydrochloride to a final concentration of 4M and incubated at 37° C. for 30 minutes to dissociate non-covalent protein interactions. The supernatant was then diluted with 2 volumes of Milli-Q filtered water, hereinafter referred to as Milli-Q water, containing 1% formic acid before injection into the LC-MS system. The system used was a Transcend II TLX-2 System with Thermo Scientific Ultimate 3000 RSLC Pumps and a TriPlus RSI Autosampler, coupled to a Q-Exactive Plus mass spectrometer from Thermo Scientific. The LC was equipped with a Cyclone column (CH-953288, Thermo Scientific) as the first-dimensional trapping column at room temperature and used an XBridge Protein BEH C4 analytical column (2.1×50 mm from Waters) at 60° C. Mobile phase A consisted of Milli-Q water, 1% formic acid, and 5% methanol/acetonitrile (50/50), while mobile phase B consisted of methanol/acetonitrile (50/50), 1% formic acid, and 5% Milli-Q water. A gradient elution was performed with a ramping gradient from 0% mobile phase B to 30% mobile phase B in 0.25 minute, from 30% mobile phase B to 45% mobile phase B in 1.17 minutes, and from 45% mobile phase B to 100% mobile phase B in 1.17 minutes. The Q-Exactive Plus mass spectrometer (ThermoFisher Scientific) was used as the detector in single ion monitoring mode (m/z 1624.8-1628.8). Linear calibration curves (weighted $1/x^2$) were used for calculating the test compound concentrations in the plasma samples. Quality control samples for analytes were included. The deviation between nominal and calculated concentrations in the calibrators and quality control samples was below 15%, and the LLOQ sample deviation was below 20%

Based on these exposure data, non-compartmental pharmacokinetic parameters were calculated using either Phoenix WinNonlin or the open-source statistical analysis software R (package 'NonCompart').

Results

Results are given in Table 39 and Table 38 below for five $V_HH$ polypeptide derivatives (identified as compounds) and show a) the effect of fatty acid protraction on half-life, and
b) that lowering of pI leads to enhanced oral bioavailability.

One may further refer to Table 12 for the detailed composition of the polypeptide derivatives.

More specifically, Table 38 below shows a first set of results where the IV half-life of compounds 1-3, 7 & 9 were collected as well as that of a reference $V_HH$ polypeptide (without a substituent) Polypeptide_63. For each one of these entries, the n is of 2 and each animal was provided with a dosage of 0.05 mg/kg.

TABLE 38

IV PK data of polypeptide derivatives with engineered pI mutations and fatty diacid substituents tested in dog model.

| Compound ID | pI (theoretical) | n animals | Dosage (mg/kg) | Half-life (IV) (hours) |
|---|---|---|---|---|
| Polypeptide_63 (Reference) | 6.49 | 2 | 0.05 | 1.2 |
| Compound 1 | 4.79 | 2 | 0.05 | 227 |
| Compound 2 | 4.40 | 2 | 0.05 | 197 |
| Compound 3 | 4.74 | 2 | 0.05 | 152 |
| Compound 9 | 4.61 | 2 | 0.05 | 185 |
| Compound 7 | 4.67 | 2 | 0.05 | 183 |

As is seen above, the compounds 1-3, 7 and 9 all provided for a half-life which was various orders of magnitude higher than that which was provided by the reference $V_HH$ polypeptide, Polypeptide_63.

In Table 39 below, a second set of results where the oral bioavailability data is provided for compounds 1-3, 7 & 9. While the results below identify the compound ID, it is understood that the IV formulation was based on HBS buffer and the oral formulation were tablets as disclosed in EXAMPLE 12: FORMULATION OF ANTI-IL-6 $V_HH$ POLYPEPTIDE DERIVATIVES WITH SNAC AND NIACINAMDE IN DOSAGE FORM SUITABLE FOR PERORAL ADMINISTRATION. The use of the Compound ID is for ease of reference.

TABLE 39

Oral bioavailability data of polypeptide derivatives with engineered pI mutations tested in dog model.

| Compound ID | pI (theoretical) | n animals | Half-life (PO) (hours) | BA % PO vs. IV |
|---|---|---|---|---|
| Compound 1 | 4.79 | 6 | 178 | 1.76% |
| Compound 2 | 4.40 | 6 | 224 | 1.78% |
| Compound 3 | 4.74 | 6 | 156 | 0.91% |

TABLE 39-continued

Oral bioavailability data of polypeptide derivatives with engineered pI mutations tested in dog model.

| Compound ID | pI (theoretical) | n animals | Half-life (PO) (hours) | BA % PO vs. IV |
|---|---|---|---|---|
| Compound 9 | 4.61 | 8 | 203 | 0.77% |
| Compound 7 | 4.67 | 8 | 213 | 1.33% |

For the oral bioavailability observed in dog, the polypeptide derivatives formulated with NAM/SNAC, for instance, had a pronounced effect enabling the oral bioavailability to and above a level that is clinically relevant. The attained levels are particularly relevant given the other desirable pharmaceutical properties achieved for these same compounds such as potency, half-life, etc.

Conclusion

It was observed that excellent half-life and oral bioavailability was achieved. $V_HH$ polypeptide derivatives (ie. $V_HH$ polypeptides with fatty diacid substituents) were compared to a non-substituted reference $V_HH$ polypeptide, Polypeptide_63, and demonstrated two orders of magnitude increases in half-lives. Further, the bioavailability in comparison to the IV was shown to be in the range approximately 1-2%.

Overall considering the potency, the half-life and the oral bioavailability, the $V_HH$ polypeptide derivatives as disclosed herein would be expected to be a first-in-class anti-inflammatory orally administrated and antibody-like drug that targets IL-6.

For instance, Compound 9 has been shown to strike a desirable balance in the pharmaceutical features of high potency, long half-life and high bioavailability, highlighting its suitability as a therapeutic product.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

SEQUENCE LISTING

```
Sequence total quantity: 165
SEQ ID NO: 1              moltype = AA  length = 447
FEATURE                   Location/Qualifiers
source                    1..447
                          mol_type = protein
                          organism = synthetic construct
SEQUENCE: 1
QVTLLESGPG ILQPSQTLTL TCSLSGFSLR TSGMGVGWIR QPSGKGLEWL AHIWWDDDKR   60
YNPVLKSRLI ISKDTSRKQV FLKIASVDTA DTATYYCVRM MDDYDAMDYW GQGTSVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                     447

SEQ ID NO: 2              moltype = AA  length = 213
FEATURE                   Location/Qualifiers
source                    1..213
                          mol_type = protein
                          organism = synthetic construct
SEQUENCE: 2
QIILTQSPAI MSASLGEEIT LTCSATSSVT YVHWYQQKSG TSPKLLIYGT SNLASGVPSR   60
FSGSGSGTFY SLTVSSVEAE DAADYYCHQW NSYPHTFGGG TKLEIKRTVA APSVFIFPPS  120
```

```
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                213

SEQ ID NO: 3            moltype = AA  length = 5
FEATURE                 Location/Qualifiers
source                  1..5
                        mol_type = protein
                        organism = synthetic construct
SEQUENCE: 3
EYAVG                                                                 5

SEQ ID NO: 4            moltype = AA  length = 5
FEATURE                 Location/Qualifiers
source                  1..5
                        mol_type = protein
                        organism = synthetic construct
SEQUENCE: 4
SYAVG                                                                 5

SEQ ID NO: 5            moltype = AA  length = 5
FEATURE                 Location/Qualifiers
source                  1..5
                        mol_type = protein
                        organism = synthetic construct
SEQUENCE: 5
EYAMA                                                                 5

SEQ ID NO: 6            moltype = AA  length = 5
FEATURE                 Location/Qualifiers
source                  1..5
                        mol_type = protein
                        organism = synthetic construct
SEQUENCE: 6
NYWMY                                                                 5

SEQ ID NO: 7            moltype = AA  length = 17
FEATURE                 Location/Qualifiers
source                  1..17
                        mol_type = protein
                        organism = synthetic construct
SEQUENCE: 7
DIGEQAENTW YAESVLG                                                   17

SEQ ID NO: 8            moltype = AA  length = 17
FEATURE                 Location/Qualifiers
source                  1..17
                        mol_type = protein
                        organism = synthetic construct
SEQUENCE: 8
DIGENAENTW YAESVLG                                                   17

SEQ ID NO: 9            moltype = AA  length = 17
FEATURE                 Location/Qualifiers
source                  1..17
                        mol_type = protein
                        organism = synthetic construct
SEQUENCE: 9
DIGENAENTW YAHSVLG                                                   17

SEQ ID NO: 10           moltype =     length =
SEQUENCE: 10
000

SEQ ID NO: 11           moltype =     length =
SEQUENCE: 11
000

SEQ ID NO: 12           moltype = AA  length = 17
FEATURE                 Location/Qualifiers
source                  1..17
                        mol_type = protein
                        organism = synthetic construct
SEQUENCE: 12
DIGEQAENTW YAHSVLG                                                   17

SEQ ID NO: 13           moltype = AA  length = 17
FEATURE                 Location/Qualifiers
source                  1..17
                        mol_type = protein
```

```
                          organism = synthetic construct
SEQUENCE: 13
DIGENADNTW YAHSVLG                                                  17

SEQ ID NO: 14             moltype = AA   length = 16
FEATURE                   Location/Qualifiers
source                    1..16
                          mol_type = protein
                          organism = synthetic construct
SEQUENCE: 14
DIGESGGTWY ADSVKG                                                   16

SEQ ID NO: 15             moltype = AA   length = 17
FEATURE                   Location/Qualifiers
source                    1..17
                          mol_type = protein
                          organism = synthetic construct
SEQUENCE: 15
DIGENADNTW YAHSVKG                                                  17

SEQ ID NO: 16             moltype = AA   length = 17
FEATURE                   Location/Qualifiers
source                    1..17
                          mol_type = protein
                          organism = synthetic construct
SEQUENCE: 16
GINTGGSTPD YADSVKG                                                  17

SEQ ID NO: 17             moltype = AA   length = 15
FEATURE                   Location/Qualifiers
source                    1..15
                          mol_type = protein
                          organism = synthetic construct
SEQUENCE: 17
DKYGVGGNAQ GYYDS                                                    15

SEQ ID NO: 18             moltype = AA   length = 15
FEATURE                   Location/Qualifiers
source                    1..15
                          mol_type = protein
                          organism = synthetic construct
SEQUENCE: 18
DSYGVGGGAQ GYYDS                                                    15

SEQ ID NO: 19             moltype = AA   length = 15
FEATURE                   Location/Qualifiers
source                    1..15
                          mol_type = protein
                          organism = synthetic construct
SEQUENCE: 19
DSYGVGGGAE RYYDS                                                    15

SEQ ID NO: 20             moltype = AA   length = 13
FEATURE                   Location/Qualifiers
source                    1..13
                          mol_type = protein
                          organism = synthetic construct
SEQUENCE: 20
DTPRVFRLDH YSP                                                      13

SEQ ID NO: 21             moltype = AA   length = 124
FEATURE                   Location/Qualifiers
source                    1..124
                          mol_type = protein
                          organism = synthetic construct
VARIANT                   1
                          note = Q or E
VARIANT                   2
                          note = L or V
VARIANT                   11
                          note = L or W
VARIANT                   19
                          note = K or Q
VARIANT                   28
                          note = R, T, E, H, or K
VARIANT                   30
                          note = S, Q, or D
VARIANT                   31
                          note = S or E
```

```
VARIANT                 40
                        note = A or G
VARIANT                 43
                        note = K or Q
VARIANT                 50
                        note = Q, N, T, or E
VARIANT                 55
                        note = E or D
VARIANT                 56
                        note = E or D
VARIANT                 62
                        note = H or E
VARIANT                 65
                        note = K or L
VARIANT                 74
                        note = E, N, or D
VARIANT                 82
                        note = E or Q
VARIANT                 84
                        note = D or N
VARIANT                 85
                        note = G or S
VARIANT                 100
                        note = K or S
VARIANT                 106
                        note = N or G
SEQUENCE: 21
XXQLVESGGG XVQPGGSLXL SCTTSGRXFX XYAVGWFRQX PGXEREFVAX IGEXAXNTWY    60
AXSVXGRFTI SRDXAKNTVY LXMXXLKPED TAVYYCAADX YGVGGXAQGY YDSWGQGTQV   120
TVSS                                                                124

SEQ ID NO: 22           moltype = AA  length = 124
FEATURE                 Location/Qualifiers
source                  1..124
                        mol_type = protein
                        organism = synthetic construct
VARIANT                 11
                        note = L or W
VARIANT                 19
                        note = K or Q
VARIANT                 28
                        note = R or K
VARIANT                 30
                        note = S or D
VARIANT                 40
                        note = A or G
VARIANT                 43
                        note = K or Q
VARIANT                 54
                        note = Q or N
VARIANT                 62
                        note = H or E
VARIANT                 84
                        note = D or N
VARIANT                 85
                        note = G or S
SEQUENCE: 22
EVQLVESGGG XVQPGGSLXL SCTTSGRXFX EYAVGWFRQX PGXEREFVAD IGEXAENTWY    60
AXSVLGRFTI SRDXAKNTVY LXMXXLKPED TAVYYCAADK YGVGGNAQGY YDSWGQGTQV   120
TVSS                                                                124

SEQ ID NO: 23           moltype = AA  length = 124
FEATURE                 Location/Qualifiers
source                  1..124
                        mol_type = protein
                        organism = synthetic construct
SEQUENCE: 23
EVQLVESGGG WVQPGGSLQL SCTTSGRRFS EYAVGWFRQA PGQEREFVAD IGEQAENTWY    60
AHSVLGRFTI SRDEAKNTVY LQMDSLKPED TAVYYCAADK YGVGGNAQGY YDSWGQGTQV   120
TVSS                                                                124

SEQ ID NO: 24           moltype = AA  length = 124
FEATURE                 Location/Qualifiers
source                  1..124
                        mol_type = protein
                        organism = synthetic construct
SEQUENCE: 24
EVQLVESGGG LVQPGGSLKL SCTTSGRRFS EYAVGWFRQG PGKEREFVAD IGEQAENTWY    60
AESVLGRFTI SRDDAKNTVY LQMDSLKPED TAVYYCAADK YGVGGNAQGY YDSWGQGTQV   120
```

```
TVSS                                                                      124

SEQ ID NO: 25           moltype = AA   length = 124
FEATURE                 Location/Qualifiers
source                  1..124
                        mol_type = protein
                        organism = synthetic construct
SEQUENCE: 25
EVQLVESGGG LVQPGGSLQL SCTTSGRRFS EYAVGWFRQG PGKEREFVAD IGEQAENTWY          60
AHSVLGRFTI SRDDAKNTVY LQMDSLKPED TAVYYCAADK YGVGGNAQGY YDSWGQGTQV         120
TVSS                                                                      124

SEQ ID NO: 26           moltype = AA   length = 124
FEATURE                 Location/Qualifiers
source                  1..124
                        mol_type = protein
                        organism = synthetic construct
SEQUENCE: 26
EVQLVESGGG LVQPGGSLQL SCTTSGRKFD EYAVGWFRQA PGKEREFVAD IGENAENTWY          60
AHSVLGRFTI SRDDAKNTVY LQMDSLKPED TAVYYCAADK YGVGGNAQGY YDSWGQGTQV         120
TVSS                                                                      124

SEQ ID NO: 27           moltype = AA   length = 124
FEATURE                 Location/Qualifiers
source                  1..124
                        mol_type = protein
                        organism = synthetic construct
SEQUENCE: 27
EVQLVESGGG LVQPGGSLQL SCTTSGRKFD EYAVGWFRQG PGKEREFVAD IGENAENTWY          60
AESVLGRFTI SRDDAKNTVY LQMDSLKPED TAVYYCAADK YGVGGNAQGY YDSWGQGTQV         120
TVSS                                                                      124

SEQ ID NO: 28           moltype = AA   length = 124
FEATURE                 Location/Qualifiers
source                  1..124
                        mol_type = protein
                        organism = synthetic construct
SEQUENCE: 28
EVQLVESGGG LVQPGGSLKL SCTTSGRRFS EYAVGWFRQA PGKEREFVAD IGEQAENTWY          60
AESVLGRFTI SRDDAKNTVY LEMDGLKPED TAVYYCAADK YGVGGNAQGY YDSWGQGTQV         120
TVSS                                                                      124

SEQ ID NO: 29           moltype = AA   length = 124
FEATURE                 Location/Qualifiers
source                  1..124
                        mol_type = protein
                        organism = synthetic construct
SEQUENCE: 29
EVQLVESGGG LVQPGGSLQL SCTTSGRKFD EYAVGWFRQG PGQEREFVAD IGENAENTWY          60
AESVLGRFTI SRDDAKNTVY LEMDGLKPED TAVYYCAADK YGVGGNAQGY YDSWGQGTQV         120
TVSS                                                                      124

SEQ ID NO: 30           moltype = AA   length = 123
FEATURE                 Location/Qualifiers
source                  1..123
                        mol_type = protein
                        organism = synthetic construct
SEQUENCE: 30
EVQLVESGGG LVQAGGSLRL SCTASGGTFS EYAMAWFRQA PGKEREFVTD IGESGGTWYA          60
DSVKGRFTIS RDNAKNTVYL QMNSLRPEDT AVYYCAADSY GVGGGAERYY DSWGQGTQVT         120
VSS                                                                       123

SEQ ID NO: 31           moltype = AA   length = 124
FEATURE                 Location/Qualifiers
source                  1..124
                        mol_type = protein
                        organism = synthetic construct
SEQUENCE: 31
EVQLVESGGG LVQPGGSLRL SCTTSGRTFS SYAVGWFRQA PGKEREFVAD IGENADNTWY          60
AHSVKGRFTI SRDNAKNTVY LQMNSLKPED TAVYYCAADS YGVGGGAQGY YDSWGQGTQV         120
TVSS                                                                      124

SEQ ID NO: 32           moltype = AA   length = 123
FEATURE                 Location/Qualifiers
source                  1..123
                        mol_type = protein
                        organism = synthetic construct
SEQUENCE: 32
QVQLVESGGG LVQAGGSLRL SCTASGGTFG EYAMAWFRQA PGKEREFVTD IGESGGTWYA          60
```

```
DSVKGRFTIS RDNAKNTVYL QMNSLRPEDT AVYYCAADSY GVGGGAERYY DSWGQGTQVT    120
VSS                                                                 123

SEQ ID NO: 33           moltype = AA  length = 124
FEATURE                 Location/Qualifiers
source                  1..124
                        mol_type = protein
                        organism = synthetic construct
SEQUENCE: 33
QLQLVESGGG WVQPGGSLKL SCTTSGRTFS SYAVGWFRQA PGKEREFVAD IGENADNTWY    60
AHSVKGRFTI SRDNAKNTVY LQMNSLKPED TAVYYCAADS YGVGGGAQGY DSWGQGTQV     120
TVSS                                                                124

SEQ ID NO: 34           moltype = AA  length = 124
FEATURE                 Location/Qualifiers
source                  1..124
                        mol_type = protein
                        organism = synthetic construct
SEQUENCE: 34
QLQLVESGGG WVQPGGSLQL SCTTSGRTFS SYAVGWFRQA PGQEREFVAD IGENADNTWY    60
AHSVKGRFTI SRDNAKNTVY LQMDSLKPED TAVYYCAADS YGVGGGAQGY DSWGQGTQV     120
TVSS                                                                124

SEQ ID NO: 35           moltype = AA  length = 123
FEATURE                 Location/Qualifiers
source                  1..123
                        mol_type = protein
                        organism = synthetic construct
SEQUENCE: 35
EVQLVESGGG LVQAGGSLQL SCTASGGTFS EYAMAWFRQA PGQEREFVTD IGESGGTWYA    60
DSVKGRFTIS RDNAKNTVYL QMDSLRPEDT AVYYCAADSY GVGGGAERYY DSWGQGTQVT    120
VSS                                                                 123

SEQ ID NO: 36           moltype = AA  length = 124
FEATURE                 Location/Qualifiers
source                  1..124
                        mol_type = protein
                        organism = synthetic construct
SEQUENCE: 36
QLQLVESGGG WVQPGGSLQL SCTTSGRRFS EYAVGWFRQA PGQEREFVAD IGEQAENTWY    60
AHSVLGRFTI SRDEAKNTVY LQMDSLKPED TAVYYCAADK YGVGGNAQGY DSWGQGTQV     120
TVSS                                                                124

SEQ ID NO: 37           moltype = AA  length = 124
FEATURE                 Location/Qualifiers
source                  1..124
                        mol_type = protein
                        organism = synthetic construct
SEQUENCE: 37
QLQLVESGGG WVQPGGSLKL SCTTSGRRFS EYAVGWFRQA PGKEREFVAD IGEQAENTWY    60
AHSVLGRFTI SRDEAKNTVY LQMNSLKPED TAVYYCAADK YGVGGNAQGY DSWGQGTQV     120
TVSS                                                                124

SEQ ID NO: 38           moltype = AA  length = 122
FEATURE                 Location/Qualifiers
source                  1..122
                        mol_type = protein
                        organism = synthetic construct
SEQUENCE: 38
EVQLVESGGG LVQPGGSLRL SCAASGFTFS NYWMYWVRQA PGKGLEWVSG INTGGSTPDY    60
ADSVKGRFAI SRDNAKNTLY LQMNSLRPED TAVYYCAADT PRVFRLDHYS PLGQGTQVTV    120
SS                                                                  122

SEQ ID NO: 39           moltype = AA  length = 135
FEATURE                 Location/Qualifiers
source                  1..135
                        mol_type = protein
                        organism = synthetic construct
SEQUENCE: 39
QVQLVESGGD LVQPGGSLRL SCTTSGRTFS SYAMGWFRQA PGKEREFVAD IGENADNRWY    60
AHSVKGRFTI SRDNAKNTVY LQMNSLKPED TAVYYCAADR YGVGGGAQGY DSWGQGTQV     120
TVSSGGGGSH HHHH                                                     135

SEQ ID NO: 40           moltype = AA  length = 133
FEATURE                 Location/Qualifiers
source                  1..133
                        mol_type = protein
                        organism = synthetic construct
SEQUENCE: 40
```

```
EVQLVESGGG LVQPGGSLRL SCAASGFTFS NYWMYWVRQA PGKGLEWVSG INTGGSTPDY  60
ADSVKDRFTI SRDNAKNTLY LQMNSLRPAD TAVYYCAADT PRSFRLNHYA PLGQGTQVTV  120
SSGGGGSHHH HHH                                                   133

SEQ ID NO: 41           moltype = AA   length = 135
FEATURE                 Location/Qualifiers
source                  1..135
                        mol_type = protein
                        organism = synthetic construct
SEQUENCE: 41
QVQLQESGGG LVQAGGSLRL SCTTSGRTFS SYAMGWFRQA PGKEREFVAD IGENADNRWY  60
AHSVKGRFTI SRDNAKNTVY LQMNSLKPED TAVYYCAADR YGVGGGAQGY YDSWGQGTQV  120
TVSSGGGGSH HHHH                                                  135

SEQ ID NO: 42           moltype = AA   length = 135
FEATURE                 Location/Qualifiers
source                  1..135
                        mol_type = protein
                        organism = synthetic construct
SEQUENCE: 42
QVQLQESGGG LVQAGGSLRL SCTVSGRTFS TYAMGWFRQA PGKEREFVAD INWNSDNLWY  60
ADSVKGRFTI SRDNAKNTMY LQMNSLKPED TAVYYCAVDS YGVGGGKPEY YDSWGQGTQV  120
TVSSGGGGSH HHHH                                                  135

SEQ ID NO: 43           moltype = AA   length = 133
FEATURE                 Location/Qualifiers
source                  1..133
                        mol_type = protein
                        organism = synthetic construct
SEQUENCE: 43
QLQLVESGGG LVQPGGSLRL SCAASGFTFS NYWMYWVRQA PGKGLEWVSG INTGGSTPDY  60
ADSVKGRFTI SRDNAKNTLY LQMNSLRPED TAVYYCAADT PRVFRLDHYS PLGQGTQVTV  120
SSGGGGSHHH HHH                                                   133

SEQ ID NO: 44           moltype = AA   length = 135
FEATURE                 Location/Qualifiers
source                  1..135
                        mol_type = protein
                        organism = synthetic construct
SEQUENCE: 44
QVQLQESGGG LVQAGGSLRL SCTTSGRTFS DYAMAWFRQA PGKDREFVAD IGTNSENTWY  60
AESVKGRFTI SRDNTKNTIY LQMNSLKPED TAVYYCAADS YGVGGGKQEY YDSWGQGAQV  120
TVSSGGGGSH HHHH                                                  135

SEQ ID NO: 45           moltype = AA   length = 135
FEATURE                 Location/Qualifiers
source                  1..135
                        mol_type = protein
                        organism = synthetic construct
SEQUENCE: 45
EVQLVESGGR WVQPGASLRL SCTTSGRTFS SYAMGWFRQA PGKEREFVAD IGENADNRWY  60
AHSVKGRFTI SRDNAKNTVY LQMNSLKPED TAVYYCAADR YGVGGGAQGY YDSWGQGTQV  120
TVSSGGGGSH HHHH                                                  135

SEQ ID NO: 46           moltype = AA   length = 133
FEATURE                 Location/Qualifiers
source                  1..133
                        mol_type = protein
                        organism = synthetic construct
SEQUENCE: 46
QVQLVESGGG LVQPGGSLRL SCAASGFTFS SYWMYWVRQA PGKGLEWVSG INTGGSTPDY  60
ADSVKGRFTI SRDNAKNTLY LQMNSLRPED TAVYYCAADT PRSFRLNHYS PLGQGTQVTV  120
SSGGGGSHHH HHH                                                   133

SEQ ID NO: 47           moltype = AA   length = 133
FEATURE                 Location/Qualifiers
source                  1..133
                        mol_type = protein
                        organism = synthetic construct
SEQUENCE: 47
QVQLVESGGG LVQPGGSLRL SCAASGFTFS NYWMYWVRQA PGKGLEWVSG IDTRGSTPDY  60
ADSVKGRFTI SRDNAKSTFY LQMNSLRPED TAVYYCATDT PRSFRLYHYV PLGQGTQVTV  120
SSGGGGSHHH HHH                                                   133

SEQ ID NO: 48           moltype = AA   length = 135
FEATURE                 Location/Qualifiers
source                  1..135
                        mol_type = protein
                        organism = synthetic construct
```

```
SEQUENCE: 48
QVQLQESGGG LVQAGGSLRL SCTVSGRTFS TYAMGWFRQA PGKEREFVAD INWNSDNIWY    60
ADSVKGRFTI SRDNAKNVMY LQMNSLKPED TAVYYCAADS YGVGGGKEEY YDSWGQGTQV   120
TVSSGGGGSH HHHHH                                                    135

SEQ ID NO: 49           moltype = AA  length = 135
FEATURE                 Location/Qualifiers
source                  1..135
                        mol_type = protein
                        organism = synthetic construct
SEQUENCE: 49
EVQLVESGGG LVQAGGSLRL SCTASGRSFS SYAMGWFRQA PGKEREFVAD IGVNPDNTWY    60
ADSAKGRFTI SRDNAKNTMY LQMNSLKPED TAVYYCAADS YGVGGGAERY YDSWGQGTQV   120
TVSSGGGGSH HHHHH                                                    135

SEQ ID NO: 50           moltype = AA  length = 135
FEATURE                 Location/Qualifiers
source                  1..135
                        mol_type = protein
                        organism = synthetic construct
SEQUENCE: 50
QVQLVESGGG LVQAGGSLRL SCTTSGRTFS SYAMAWFRQA PGKDREFVAD IGENSDNIWY    60
ADSVKGRFTI SRDNAKNTIL LQMNSLKPED TAVYYCAADS YGVGGGKPEY YDSWGQGAQV   120
TVSSGGGGSH HHHHH                                                    135

SEQ ID NO: 51           moltype = AA  length = 135
FEATURE                 Location/Qualifiers
source                  1..135
                        mol_type = protein
                        organism = synthetic construct
SEQUENCE: 51
EVQLVESGGG LVQAGGPLRL SCTVSGRTFS TYAMGWFRQA PGKEREFVAD INWNSDNIWY    60
ADSVKGRFTI SRDNAKNVMY LQMNSLKPED TAVYYCAADS YGVGGGKEEY YDSWGQGTQV   120
TVSSGGGGSH HHHHH                                                    135

SEQ ID NO: 52           moltype = AA  length = 135
FEATURE                 Location/Qualifiers
source                  1..135
                        mol_type = protein
                        organism = synthetic construct
SEQUENCE: 52
QLQLVESGGG SVQVGDSLRL SCTFSGRSFS SYAMGWFRQA PGKEREFVAD IGENADNTWY    60
AHSVKGRFTI SRDNAKNTVY LQMNSLKPED TAVYYCAADS YGVGGGAQGY YDSWGQGTQV   120
TVSSGGGGSH HHHHH                                                    135

SEQ ID NO: 53           moltype = AA  length = 134
FEATURE                 Location/Qualifiers
source                  1..134
                        mol_type = protein
                        organism = synthetic construct
SEQUENCE: 53
QVQLQESGGG LVQAGGSLRL SCTASGGTFS EYAMAWFRQA PGKEREFVTD IGESGGTWYA    60
DSVKGRFTIS RDNAKNTVYL QMNSLRPEDT AVYYCAADSY GVGGGAERYY DSWGQGTQVT   120
VSSGGGGSHH HHHH                                                     134

SEQ ID NO: 54           moltype = AA  length = 135
FEATURE                 Location/Qualifiers
source                  1..135
                        mol_type = protein
                        organism = synthetic construct
SEQUENCE: 54
EVQLVESGGG LVQPGGSLSL SCTASGRTFS SYAMGWFRQA PGKEREFVAD IGENADNRWY    60
AHSVKGRFTI SRDNAKNTVY LQMNSLKPED TAVYYCAADR YGVGGGAQGY YDSWGQGTQV   120
TVSSGGGGSH HHHHH                                                    135

SEQ ID NO: 55           moltype = AA  length = 135
FEATURE                 Location/Qualifiers
source                  1..135
                        mol_type = protein
                        organism = synthetic construct
SEQUENCE: 55
QVQLVESGGG LVQAGGSLRL SCTVSGRTFS TYAMGWFRQA PGKEREFVAD INWNSDNIWY    60
ADSVKGRFTI SRDNAKNVMY LQMNSLKPED TAVYYCAADS YGVGGGKEEY YDSWGQGTQV   120
TVSSGGGGSH HHHHH                                                    135

SEQ ID NO: 56           moltype = AA  length = 133
FEATURE                 Location/Qualifiers
source                  1..133
                        mol_type = protein
```

-continued

```
                        organism = synthetic construct
SEQUENCE: 56
EVQLVESGGG LVQPGGSLRL SCAASGFTFS NYWMYWVRQA PGKGLEWVSG INTGGSTPDY    60
ADSVKGRFAI SRDNAKNTLY LQMNSLRPED TAVYYCAADT PRVFRLDHYS PLGQGTQVTV   120
SSGGGGSHHH HHH                                                     133

SEQ ID NO: 57           moltype = AA   length = 135
FEATURE                 Location/Qualifiers
source                  1..135
                        mol_type = protein
                        organism = synthetic construct
SEQUENCE: 57
QLQLVESGGG WVQPGGSLKL SCTTSGRTFS SYAVGWFRQA PGKEREFVAD IGENADNTWY    60
AHSVKGRFTI SRDNAKNTVY LQMNSLKPED TAVYYCAADS YGVGGGAQGY YDSWGQGTQV   120
TVSSGGGGSH HHHHH                                                   135

SEQ ID NO: 58           moltype = AA   length = 135
FEATURE                 Location/Qualifiers
source                  1..135
                        mol_type = protein
                        organism = synthetic construct
SEQUENCE: 58
EVQLVESGGG LVQPGGSLQL SCTTSGRHFD EYAVGWFRQA PGKEREFVAD IGENADNTWY    60
AHSVKGRFTI SRDDAKNTVY LEMDGLKPED TAVYYCAADK YGVGGNAQGY YDSWGQGTQV   120
TVSSGGGGSH HHHH                                                    135

SEQ ID NO: 59           moltype = AA   length = 135
FEATURE                 Location/Qualifiers
source                  1..135
                        mol_type = protein
                        organism = synthetic construct
SEQUENCE: 59
EVQLVESGGG LVQPGGSLQL SCTTSGRHFD EYAVGWFRQG PGKEREFVAD IGENADNTWY    60
AHSVKGRFTI SRDDAKNTVY LEMDGLKPED TAVYYCAADK YGVGGNAQGY YDSWGQGTQV   120
TVSSGGGGSH HHHH                                                    135

SEQ ID NO: 60           moltype = AA   length = 135
FEATURE                 Location/Qualifiers
source                  1..135
                        mol_type = protein
                        organism = synthetic construct
SEQUENCE: 60
EVQLVESGGG LVQPGGSLKL SCTTSGRRFS EYAVGWFRQG PGKEREFVAD IGEQAENTWY    60
AESVLGRFTI SRDDAKNTVY LQMDSLKPED TAVYYCAADK YGVGGNAQGY YDSWGQGTQV   120
TVSSGGGGSH HHHH                                                    135

SEQ ID NO: 61           moltype = AA   length = 135
FEATURE                 Location/Qualifiers
source                  1..135
                        mol_type = protein
                        organism = synthetic construct
SEQUENCE: 61
EVQLVESGGG LVQPGGSLQL SCTTSGRRFS EYAVGWFRQA PGKEREFVAD IGEQAENTWY    60
AHSVLGRFTI SRDDAKNTVY LQMDSLKPED TAVYYCAADK YGVGGNAQGY YDSWGQGTQV   120
TVSSGGGGSH HHHH                                                    135

SEQ ID NO: 62           moltype = AA   length = 135
FEATURE                 Location/Qualifiers
source                  1..135
                        mol_type = protein
                        organism = synthetic construct
SEQUENCE: 62
EVQLVESGGG LVQPGGSLQL SCTTSGRRFS EYAVGWFRQG PGKEREFVAD IGEQAENTWY    60
AHSVLGRFTI SRDDAKNTVY LQMDSLKPED TAVYYCAADK YGVGGNAQGY YDSWGQGTQV   120
TVSSGGGGSH HHHH                                                    135

SEQ ID NO: 63           moltype = AA   length = 135
FEATURE                 Location/Qualifiers
source                  1..135
                        mol_type = protein
                        organism = synthetic construct
SEQUENCE: 63
EVQLVESGGG LVQPGGSLQL SCTTSGRRFS EYAVGWFRQG PGKEREFVAD IGEQAENTWY    60
AESVLGRFTI SRDDAKNTVY LQMDSLKPED TAVYYCAADK YGVGGNAQGY YDSWGQGTQV   120
TVSSGGGGSH HHHH                                                    135

SEQ ID NO: 64           moltype = AA   length = 135
FEATURE                 Location/Qualifiers
source                  1..135
```

```
                            mol_type = protein
                            organism = synthetic construct
SEQUENCE: 64
EVQLVESGGG LVQPGGSLKL SCTTSGRKFD EYAVGWFRQA PGKEREFVAD IGENAENTWY      60
AHSVLGRFTI SRDDAKNTVY LQMDSLKPED TAVYYCAADK YGVGGNAQGY YDSWGQGTQV     120
TVSSGGGGSH HHHHH                                                     135

SEQ ID NO: 65              moltype = AA  length = 135
FEATURE                    Location/Qualifiers
source                     1..135
                            mol_type = protein
                            organism = synthetic construct
SEQUENCE: 65
EVQLVESGGG LVQPGGSLQL SCTTSGRKFD EYAVGWFRQA PGKEREFVAD IGENAENTWY      60
AHSVLGRFTI SRDDAKNTVY LQMDSLKPED TAVYYCAADK YGVGGNAQGY YDSWGQGTQV     120
TVSSGGGGSH HHHHH                                                     135

SEQ ID NO: 66              moltype = AA  length = 135
FEATURE                    Location/Qualifiers
source                     1..135
                            mol_type = protein
                            organism = synthetic construct
SEQUENCE: 66
EVQLVESGGG LVQPGGSLQL SCTTSGRKFD EYAVGWFRQG PGKEREFVAD IGENAENTWY      60
AESVLGRFTI SRDDAKNTVY LQMDSLKPED TAVYYCAADK YGVGGNAQGY YDSWGQGTQV     120
TVSSGGGGSH HHHHH                                                     135

SEQ ID NO: 67              moltype = AA  length = 135
FEATURE                    Location/Qualifiers
source                     1..135
                            mol_type = protein
                            organism = synthetic construct
SEQUENCE: 67
EVQLVESGGG LVQPGGSLKL SCTTSGRRFS EYAVGWFRQA PGKEREFVAD IGEQAENTWY      60
AESVLGRFTI SRDDAKNTVY LEMDGLKPED TAVYYCAADK YGVGGNAQGY YDSWGQGTQV     120
TVSSGGGGSH HHHHH                                                     135

SEQ ID NO: 68              moltype = AA  length = 135
FEATURE                    Location/Qualifiers
source                     1..135
                            mol_type = protein
                            organism = synthetic construct
SEQUENCE: 68
EVQLVESGGG LVQPGGSLKL SCTTSGRRFS EYAVGWFRQG PGKEREFVAD IGEQAENTWY      60
AHSVLGRFTI SRDDAKNTVY LEMDGLKPED TAVYYCAADK YGVGGNAQGY YDSWGQGTQV     120
TVSSGGGGSH HHHHH                                                     135

SEQ ID NO: 69              moltype = AA  length = 135
FEATURE                    Location/Qualifiers
source                     1..135
                            mol_type = protein
                            organism = synthetic construct
SEQUENCE: 69
EVQLVESGGG LVQPGGSLQL SCTTSGRKFD EYAVGWFRQG PGQEREFVAD IGENAENTWY      60
AESVLGRFTI SRDDAKNTVY LEMDGLKPED TAVYYCAADK YGVGGNAQGY YDSWGQGTQV     120
TVSSGGGGSH HHHHH                                                     135

SEQ ID NO: 70              moltype = AA  length = 135
FEATURE                    Location/Qualifiers
source                     1..135
                            mol_type = protein
                            organism = synthetic construct
SEQUENCE: 70
EVQLVESGGG WVQPGGSLKL SCTTSGRRFS EYAVGWFRQA PGKEREFVAD IGEQAENTWY      60
AHSVLGRFTI SRDDAKNTVY LQMDSLKPED TAVYYCAADK YGVGGNAQGY YDSWGQGTQV     120
TVSSGGGGSH HHHHH                                                     135

SEQ ID NO: 71              moltype = AA  length = 11
FEATURE                    Location/Qualifiers
source                     1..11
                            mol_type = protein
                            organism = synthetic construct
SEQUENCE: 71
GGGGSHHHHH H                                                          11

SEQ ID NO: 72              moltype = AA  length = 6
FEATURE                    Location/Qualifiers
source                     1..6
                            mol_type = protein
```

```
                        organism = synthetic construct
SEQUENCE: 72
GQACPC                                                                         6

SEQ ID NO: 73           moltype = AA   length = 130
FEATURE                 Location/Qualifiers
source                  1..130
                        mol_type = protein
                        organism = synthetic construct
SEQUENCE: 73
EVQLVESGGG WVQPGGSLQL SCTTSGRRFS EYAVGWFRQA PGQEREFVAD IGEQAENTWY              60
AHSVLGRFTI SRDEAKNTVY LQMDSLKPED TAVYYCAADK YGVGGNAQGY YDSWGQGTQV             120
TVSSGQACPC                                                                   130

SEQ ID NO: 74           moltype = AA   length = 130
FEATURE                 Location/Qualifiers
source                  1..130
                        mol_type = protein
                        organism = synthetic construct
SEQUENCE: 74
EVQLVESGGG LVQPGGSLKL SCTTSGRRFS EYAVGWFRQG PGKEREFVAD IGEQAENTWY              60
AESVLGRFTI SRDDAKNTVY LQMDSLKPED TAVYYCAADK YGVGGNAQGY YDSWGQGTQV             120
TVSSGQACPC                                                                   130

SEQ ID NO: 75           moltype = AA   length = 130
FEATURE                 Location/Qualifiers
source                  1..130
                        mol_type = protein
                        organism = synthetic construct
SEQUENCE: 75
EVQLVESGGG LVQPGGSLQL SCTTSGRRFS EYAVGWFRQG PGKEREFVAD IGEQAENTWY              60
AHSVLGRFTI SRDDAKNTVY LQMDSLKPED TAVYYCAADK YGVGGNAQGY YDSWGQGTQV             120
TVSSGQACPC                                                                   130

SEQ ID NO: 76           moltype = AA   length = 130
FEATURE                 Location/Qualifiers
source                  1..130
                        mol_type = protein
                        organism = synthetic construct
SEQUENCE: 76
EVQLVESGGG LVQPGGSLQL SCTTSGRKFD EYAVGWFRQA PGKEREFVAD IGENAENTWY              60
AHSVLGRFTI SRDDAKNTVY LQMDSLKPED TAVYYCAADK YGVGGNAQGY YDSWGQGTQV             120
TVSSGQACPC                                                                   130

SEQ ID NO: 77           moltype = AA   length = 130
FEATURE                 Location/Qualifiers
source                  1..130
                        mol_type = protein
                        organism = synthetic construct
SEQUENCE: 77
EVQLVESGGG LVQPGGSLQL SCTTSGRKFD EYAVGWFRQG PGKEREFVAD IGENAENTWY              60
AESVLGRFTI SRDDAKNTVY LQMDSLKPED TAVYYCAADK YGVGGNAQGY YDSWGQGTQV             120
TVSSGQACPC                                                                   130

SEQ ID NO: 78           moltype = AA   length = 130
FEATURE                 Location/Qualifiers
source                  1..130
                        mol_type = protein
                        organism = synthetic construct
SEQUENCE: 78
EVQLVESGGG LVQPGGSLKL SCTTSGRRFS EYAVGWFRQA PGKEREFVAD IGEQAENTWY              60
AESVLGRFTI SRDDAKNTVY LEMDGLKPED TAVYYCAADK YGVGGNAQGY YDSWGQGTQV             120
TVSSGQACPC                                                                   130

SEQ ID NO: 79           moltype = AA   length = 130
FEATURE                 Location/Qualifiers
source                  1..130
                        mol_type = protein
                        organism = synthetic construct
SEQUENCE: 79
EVQLVESGGG LVQPGGSLQL SCTTSGRKFD EYAVGWFRQG PGQEREFVAD IGENAENTWY              60
AESVLGRFTI SRDDAKNTVY LEMDGLKPED TAVYYCAADK YGVGGNAQGY YDSWGQGTQV             120
TVSSGQACPC                                                                   130

SEQ ID NO: 80           moltype = AA   length = 128
FEATURE                 Location/Qualifiers
source                  1..128
                        mol_type = protein
                        organism = synthetic construct
```

```
SEQUENCE: 80
EVQLVESGGG LVQPGGSLRL SCAASGFTFS NYWMYWVRQA PGKGLEWVSG INTGGSTPDY    60
ADSVKGRFAI SRDNAKNTLY LQMNSLRPED TAVYYCAADT PRVFRLDHYS PLGQGTQVTV   120
SSGQACPC                                                           128

SEQ ID NO: 81           moltype = AA  length = 130
FEATURE                 Location/Qualifiers
source                  1..130
                        mol_type = protein
                        organism = synthetic construct
SEQUENCE: 81
QLQLVESGGG WVQPGGSLQL SCTTSGRTFS SYAVGWFRQA PGQEREFVAD IGENADNTWY    60
AHSVKGRFTI SRDNAKNTVY LQMDSLKPED TAVYYCAADS YGVGGGAQGY YDSWGQGTQV   120
TVSSGQACPC                                                         130

SEQ ID NO: 82           moltype = AA  length = 194
FEATURE                 Location/Qualifiers
source                  1..194
                        mol_type = protein
                        organism = synthetic construct
SEQUENCE: 82
HHHHHHGGGG SVPPGEDSKD VAAPHRQPLT SSERIDKQIR YILDGISALR KETCNKSNMC    60
ESSKEALAEN NLNLPKMAEK DGCFQSGFNE ETCLVKIITG LLEFEVYLEY LQNRFESSEE   120
QARAVQMSTK VLIQFLQKKA KNLDAITTPD PTTNASLLTK LQAQNQWLQD MTTHLILRSF   180
KEFLQSSLRA LRQM                                                    194

SEQ ID NO: 83           moltype = AA  length = 196
FEATURE                 Location/Qualifiers
source                  1..196
                        mol_type = protein
                        organism = synthetic construct
SEQUENCE: 83
HHHHHHGGGG SAPVLPGEDS KDVAAPHSQP LTSSERIDKH IRYILDGISA LRKETCNRSN    60
MCESSKEALA ENNLNLPKMA EKDGCFQSGF NEDTCLVKII TGLLEFEVYL EYLQNRFESS   120
EEQARAVQMS TKVLIQFLQK KAKNLDAITT PEPTTNASLL TKLQAQNQWL QDMTTHLILR   180
SFKEFLQSSL RALRQM                                                  196

SEQ ID NO: 84           moltype = AA  length = 135
FEATURE                 Location/Qualifiers
source                  1..135
                        mol_type = protein
                        organism = synthetic construct
SEQUENCE: 84
EVQLVESGGG LVQPGGSLRL SCTTSGRTFS SYAVGWFRQA PGKEREFVAD IGENADNTWY    60
AHSVKGRFTI SRDNAKNTVY LQMNSLKPED TAVYYCAADS YGVGGGAQGY YDSWGQGTQV   120
TVSSGGGGSH HHHHH                                                   135

SEQ ID NO: 85           moltype = AA  length = 134
FEATURE                 Location/Qualifiers
source                  1..134
                        mol_type = protein
                        organism = synthetic construct
SEQUENCE: 85
EVQLVESGGG LVQAGGSLRL SCTASGGTFS EYAMAWFRQA PGKEREFVTD IGESGGTWYA    60
DSVKGRFTIS RDNAKNTVYL QMNSLRPEDT AVYYCAADSY GVGGGAERYY DSWGQGTQVT   120
VSSGGGGSHH HHHH                                                    134

SEQ ID NO: 86           moltype = AA  length = 134
FEATURE                 Location/Qualifiers
source                  1..134
                        mol_type = protein
                        organism = synthetic construct
SEQUENCE: 86
QVQLVESGGG LVQAGGSLRL SCTASGGTFG EYAMAWFRQA PGKEREFVTD IGESGGTWYA    60
DSVKGRFTIS RDNAKNTVYL QMNSLRPEDT AVYYCAADSY GVGGGAERYY DSWGQGTQVT   120
VSSGGGGSHH HHHH                                                    134

SEQ ID NO: 87           moltype = AA  length = 12
FEATURE                 Location/Qualifiers
source                  1..12
                        mol_type = protein
                        organism = synthetic construct
SEQUENCE: 87
EDQVDPRLID GK                                                       12

SEQ ID NO: 88           moltype = AA  length = 212
FEATURE                 Location/Qualifiers
source                  1..212
                        mol_type = protein
```

```
                            organism = Homo sapiens
SEQUENCE: 88
MNSFSTSAFG PVAFSLGLLL VLPAAFPAPV PPGEDSKDVA APHRQPLTSS ERIDKQIRYI    60
LDGISALRKE TCNKSNMCES SKEALAENNL NLPKMAEKDG CFQSGFNEET CLVKIITGLL   120
EFEVYLEYLQ NRFESSEEQA RAVQMSTKVL IQFLQKKAKN LDAITTPDPT TNASLLTKLQ   180
AQNQWLQDMT THLILRSFKE FLQSSLRALR QM                                 212

SEQ ID NO: 89               moltype = AA  length = 183
FEATURE                     Location/Qualifiers
source                      1..183
                            mol_type = protein
                            organism = Homo sapiens
SEQUENCE: 89
VPPGEDSKDV AAPHRQPLTS SERIDKQIRY ILDGISALRK ETCNKSNMCE SSKEALAENN    60
LNLPKMAEKD GCFQSGFNEE TCLVKIITGL LEFEVYLEYL QNRFESSEEQ ARAVQMSTKV   120
LIQFLQKKAK NLDAITTPDP TTNASLLTKL QAQNQWLQDM TTHLILRSFK EFLQSSLRAL   180
RQM                                                                 183

SEQ ID NO: 90               moltype = AA  length = 8
FEATURE                     Location/Qualifiers
source                      1..8
                            mol_type = protein
                            organism = synthetic construct
SEQUENCE: 90
GGGGSCPC                                                              8

SEQ ID NO: 91               moltype = AA  length = 6
FEATURE                     Location/Qualifiers
source                      1..6
                            mol_type = protein
                            organism = synthetic construct
SEQUENCE: 91
GGGGSC                                                                6

SEQ ID NO: 92               moltype = AA  length = 8
FEATURE                     Location/Qualifiers
source                      1..8
                            mol_type = protein
                            organism = synthetic construct
SEQUENCE: 92
GGGGSKPK                                                              8

SEQ ID NO: 93               moltype = AA  length = 7
FEATURE                     Location/Qualifiers
source                      1..7
                            mol_type = protein
                            organism = synthetic construct
SEQUENCE: 93
GGGGSKP                                                               7

SEQ ID NO: 94               moltype = AA  length = 129
FEATURE                     Location/Qualifiers
source                      1..129
                            mol_type = protein
                            organism = synthetic construct
SEQUENCE: 94
EVQLVESGGG LVQAGGSLQL SCTASGGTFS EYAMAWFRQA PGQEREFVTD IGESGGTWYA    60
DSVKGRFTIS RDNAKNTVYL QMDSLRPEDT AVYYCAADSY GVGGGAERYY DSWGQGTQVT   120
VSSGQACPC                                                           129

SEQ ID NO: 95               moltype = AA  length = 130
FEATURE                     Location/Qualifiers
source                      1..130
                            mol_type = protein
                            organism = synthetic construct
SEQUENCE: 95
QLQLVESGGG WVQPGGSLQL SCTTSGRRFS EYAVGWFRQA PGQEREFVAD IGEQAENTWY    60
AHSVLGRFTI SRDEAKNTVY LQMDSLKPED TAVYYCAADK YGVGGNAQGY DSWGQGTQV    120
TVSSGQACPC                                                          130

SEQ ID NO: 96               moltype = AA  length = 214
FEATURE                     Location/Qualifiers
source                      1..214
                            mol_type = protein
                            organism = synthetic construct
SEQUENCE: 96
HHHHHHGGGG SGLNDIFEAQ KIEWHEGGGG SVPPGEDSKD VAAPHRQPLT SSERIDKQIR    60
YILDGISALR KETCNKSNMC ESSKEALAEN NLNLPKMAEK DGCFQSGFNE ETCLVKIITG   120
LLEFEVYLEY LQNRFESSEE QARAVQMSTK VLIQFLQKKA KNLDAITTPD PTTNASLLTK   180
```

```
LQAQNQWLQD MTTHLILRSF KEFLQSSLRA LRQM                                   214

SEQ ID NO: 97             moltype = AA  length = 450
FEATURE                   Location/Qualifiers
source                    1..450
                          mol_type = protein
                          organism = synthetic construct
SEQUENCE: 97
EVQLVESGGG LVQPGGSLRL SCAASGFTIS SNYMIWVRQA PGKGLEWVSD LYYYAGDTYY        60
ADSVKGRFTM SRDISKNTVY LQMNSLRAED TAVYYCARWA DDHPPWIDLW GRGTLVTVSS       120
ASTKGPSVFP LAPSSKSTSG GTAALGCLVK DYFPEPVTVS WNSGALTSGV HTFPAVLQSS       180
GLYSLSSVVT VPSSSLGTQT YICNVNHKPS NTKVDKRVEP KSCDKTHTCP PCPAPELLGG       240
PSVFLFPPKP KDTLYITREP EVTCVVVDVS HEDPEVKFNW YVDGVEVHNA KTKPREEQYN       300
STYRVVSVLT VLHQDWLNGK EYKCKVSNKA LPAPIEKTIS KAKGQPREPQ VYTLPPSREE       360
MTKNQVSLTC LVKGFYPSDI AVEWESNGQP ENNYKTTPPV LDSDGSFFLY SKLTVDKSRW       420
QQGNVFSCSV MHEALHNHYT QKSLSLSPGK                                       450

SEQ ID NO: 98             moltype = AA  length = 200
FEATURE                   Location/Qualifiers
source                    1..200
                          mol_type = protein
                          organism = synthetic construct
SEQUENCE: 98
EDQVDPRLID GKGGGSVPP GEDSKDVAAP HRQPLTSSER IDKQIRYILD GISALRKETC         60
NKSNMCESSK EALAENNLNL PKMAEKDGCF QSGFNEETCL VKIITGLLEF EVYLEYLQNR       120
FESSEEQARA VQMSTKVLIQ FLQKKAKNLD AITTPDPTTN ASLLTKLQAQ NQWLQDMTTH       180
LILRSFKEFL QSSLRALRQM                                                  200

SEQ ID NO: 99             moltype = AA  length = 135
FEATURE                   Location/Qualifiers
source                    1..135
                          mol_type = protein
                          organism = synthetic construct
SEQUENCE: 99
QLQLVESGGG WVQPGGSLKL SCTTSGRRFS EYAVGWFRQA PGKEREFVAD IGEQAENTWY        60
AHSVLGRFTI SRDEAKNTVY LQMNSLKPED TAVYYCAADK YGVGGNAQGY YDSWGQGTQV       120
TVSSGGGGSH HHHHH                                                       135

SEQ ID NO: 100            moltype = AA  length = 222
FEATURE                   Location/Qualifiers
source                    1..222
                          mol_type = protein
                          organism = synthetic construct
SEQUENCE: 100
EVQLVESGGG LVQPGGSLRL SCAASGFTIS SNYMIWVRQA PGKGLEWVSD LYYYAGDTYY        60
ADSVKGRFTM SRDISKNTVY LQMNSLRAED TAVYYCARWA DDHPPWIDLW GRGTLVTVSS       120
ASTKGPSVFP LAPCSRSTSE STAALGCLVK DYFPEPVTVS WNSGALTSGV HTFPAVLQSS       180
GLYSLSSVVT VPSSSLGTKT YTCNVDHKPS NTKVDKRVES KY                          222

SEQ ID NO: 101            moltype = AA  length = 213
FEATURE                   Location/Qualifiers
source                    1..213
                          mol_type = protein
                          organism = synthetic construct
SEQUENCE: 101
DIQMTQSPST LSASVGDRVT ITCRASQGIS SWLAWYQQKP GKAPKVLIYK ASTLESGVPS        60
RFSGSGSGTE FTLTISSLQP DDFATYYCQQ SWLGGSFGQG TKLEIKRTVA APSVFIFPPS       120
DEQLKSGTAS VVCLLNNFYP REAKVQWKVD NALQSGNSQE SVTEQDSKDS TYSLSSTLTL       180
SKADYEKHKV YACEVTHQGL SSPVTKSFNR GEC                                   213

SEQ ID NO: 102            moltype = AA  length = 128
FEATURE                   Location/Qualifiers
source                    1..128
                          mol_type = protein
                          organism = synthetic construct
SEQUENCE: 102
EVQLVESGGG LVQPGGSLQL SCAASGFTFS NYWMYWVRQA PGQGLEWVSG INTGGSTPDY        60
ADSVKGRFAI SRDNAKNTLY LQMDSLRPED TAVYYCAADT PRVFRLDHYS PLGQGTQVTV       120
SSGQACPC                                                               128

SEQ ID NO: 103            moltype = AA  length = 122
FEATURE                   Location/Qualifiers
source                    1..122
                          mol_type = protein
                          organism = synthetic construct
SEQUENCE: 103
EVQLVESGGG LVQPGGSLQL SCAASGFTFS NYWMYWVRQA PGQGLEWVSG INTGGSTPDY        60
ADSVKGRFAI SRDNAKNTLY LQMDSLRPED TAVYYCAADT PRVFRLDHYS PLGQGTQVTV       120
SS                                                                     122
```

-continued

```
SEQ ID NO: 104         moltype = AA  length = 124
FEATURE                Location/Qualifiers
source                 1..124
                       mol_type = protein
                       organism = synthetic construct
SEQUENCE: 104
QVQLVESGGD LVQPGGSLRL SCTTSGRTFS SYAMGWFRQA PGKEREFVAD IGENADNRWY    60
AHSVKGRFTI SRDNAKNTVY LQMNSLKPED TAVYYCAADR YGVGGGAQGY YDSWGQGTQV   120
TVSS                                                                124

SEQ ID NO: 105         moltype = AA  length = 122
FEATURE                Location/Qualifiers
source                 1..122
                       mol_type = protein
                       organism = synthetic construct
SEQUENCE: 105
EVQLVESGGG LVQPGGSLRL SCAASGFTFS NYWMYWVRQA PGKGLEWVSG INTGGSTPDY    60
ADSVKDRFTI SRDNAKNTLY LQMNSLRPAD TAVYYCAADT PRSFRLNHYA PLGQGTQVTV   120
SS                                                                  122

SEQ ID NO: 106         moltype = AA  length = 124
FEATURE                Location/Qualifiers
source                 1..124
                       mol_type = protein
                       organism = synthetic construct
SEQUENCE: 106
QVQLQESGGG LVQAGGSLRL SCTTSGRTFS SYAMGWFRQA PGKEREFVAD IGENADNRWY    60
AHSVKGRFTI SRDNAKNTVY LQMNSLKPED TAVYYCAADR YGVGGGAQGY YDSWGQGTQV   120
TVSS                                                                124

SEQ ID NO: 107         moltype = AA  length = 124
FEATURE                Location/Qualifiers
source                 1..124
                       mol_type = protein
                       organism = synthetic construct
SEQUENCE: 107
QVQLQESGGG LVQAGGSLRL SCTVSGRTFS TYAMGWFRQA PGKEREFVAD INWNSDNLWY    60
ADSVKGRFTI SRDNAKNTMY LQMNSLKPED TAVYYCAVDS YGVGGGKPEY YDSWGQGTQV   120
TVSS                                                                124

SEQ ID NO: 108         moltype = AA  length = 122
FEATURE                Location/Qualifiers
source                 1..122
                       mol_type = protein
                       organism = synthetic construct
SEQUENCE: 108
QLQLVESGGG LVQPGGSLRL SCAASGFTFS NYWMYWVRQA PGKGLEWVSG INTGGSTPDY    60
ADSVKGRFTI SRDNAKNTLY LQMNSLRPED TAVYYCAADT PRVFRLDHYS PLGQGTQVTV   120
SS                                                                  122

SEQ ID NO: 109         moltype = AA  length = 124
FEATURE                Location/Qualifiers
source                 1..124
                       mol_type = protein
                       organism = synthetic construct
SEQUENCE: 109
QVQLQESGGG LVQAGGSLRL SCTTSGRTFS DYAMAWFRQA PGKDREFVAD IGTNSENTWY    60
AESVKGRFTI SRDNTKNTIY LQMNSLKPED TAVYYCAADS YGVGGGKQEY YDSWGQGAQV   120
TVSS                                                                124

SEQ ID NO: 110         moltype = AA  length = 124
FEATURE                Location/Qualifiers
source                 1..124
                       mol_type = protein
                       organism = synthetic construct
SEQUENCE: 110
EVQLVESGGR WVQPGASLRL SCTTSGRTFS SYAMGWFRQA PGKEREFVAD IGENADNRWY    60
AHSVKGRFTI SRDNAKNTVY LQMNSLKPED TAVYYCAADR YGVGGGAQGY YDSWGQGTQV   120
TVSS                                                                124

SEQ ID NO: 111         moltype = AA  length = 122
FEATURE                Location/Qualifiers
source                 1..122
                       mol_type = protein
                       organism = synthetic construct
SEQUENCE: 111
QVQLVESGGG LVQPGGSLRL SCAASGFTFS SYWMYWVRQA PGKGLEWVSG INTGGSTPDY    60
ADSVKGRFTI SRDNAKNTLY LQMNSLRPED TAVYYCAADT PRSFRLNHYS PLGQGTQVTV   120
```

```
SS                                                                            122

SEQ ID NO: 112          moltype = AA   length = 122
FEATURE                 Location/Qualifiers
source                  1..122
                        mol_type = protein
                        organism = synthetic construct
SEQUENCE: 112
QVQLVESGGG LVQPGGSLRL SCAASGFTFS NYWMYWVRQA PGKGLEWVSG IDTRGSTPDY   60
ADSVKGRFTI SRDNAKSTFY LQMNSLRPED TAVYYCATDT PRSFRLYHYV PLGQGTQVTV  120
SS                                                                122

SEQ ID NO: 113          moltype = AA   length = 124
FEATURE                 Location/Qualifiers
source                  1..124
                        mol_type = protein
                        organism = synthetic construct
SEQUENCE: 113
QVQLQESGGG LVQAGGSLRL SCTVSGRTFS TYAMGWFRQA PGEREFVAD INWNSDNIWY    60
ADSVKGRFTI SRDNAKNVMY LQMNSLKPED TAVYYCAADS YGVGGGKEEY YDSWGQGTQV  120
TVSS                                                              124

SEQ ID NO: 114          moltype = AA   length = 124
FEATURE                 Location/Qualifiers
source                  1..124
                        mol_type = protein
                        organism = synthetic construct
SEQUENCE: 114
EVQLVESGGG LVQAGGSLRL SCTASGRSFS SYAMGWFRQA PGEREFVAD IGVNPDNTWY    60
ADSAKGRFTI SRDNAKNTMY LQMNSLKPED TAVYYCAADS YGVGGGAERY YDSWGQGTQV  120
TVSS                                                              124

SEQ ID NO: 115          moltype = AA   length = 124
FEATURE                 Location/Qualifiers
source                  1..124
                        mol_type = protein
                        organism = synthetic construct
SEQUENCE: 115
QVQLVESGGG LVQAGGSLRL SCTTSGRTFS SYAMAWFRQA PGKDREFVAD IGENSDNIWY   60
ADSVKGRFTI SRDNAKNTIL LQMNSLKPED TAVYYCAADS YGVGGGKPEY YDSWGQGAQV  120
TVSS                                                              124

SEQ ID NO: 116          moltype = AA   length = 124
FEATURE                 Location/Qualifiers
source                  1..124
                        mol_type = protein
                        organism = synthetic construct
SEQUENCE: 116
EVQLVESGGG LVQAGGPLRL SCTVSGRTFS TYAMGWFRQA PGEREFVAD INWNSDNIWY    60
ADSVKGRFTI SRDNAKNVMY LQMNSLKPED TAVYYCAADS YGVGGGKEEY YDSWGQGTQV  120
TVSS                                                              124

SEQ ID NO: 117          moltype = AA   length = 124
FEATURE                 Location/Qualifiers
source                  1..124
                        mol_type = protein
                        organism = synthetic construct
SEQUENCE: 117
QLQLVESGGG SVQVGDSLRL SCTFSGRSFS SYAMGWFRQA PGEREFVAD IGENADNTWY    60
AHSVKGRFTI SRDNAKNTVY LQMNSLKPED TAVYYCAADS YGVGGGAQGY YDSWGQGTQV  120
TVSS                                                              124

SEQ ID NO: 118          moltype = AA   length = 123
FEATURE                 Location/Qualifiers
source                  1..123
                        mol_type = protein
                        organism = synthetic construct
SEQUENCE: 118
QVQLQESGGG LVQAGGSLRL SCTASGGTFS EYAMAWFRQA PGEREFVTD IGESGGTWYA    60
DSVKGRFTIS RDNAKNTVYL QMNSLRPEDT AVYYCAADSY GVGGGAERYY DSWGQGTQVT  120
VSS                                                               123

SEQ ID NO: 119          moltype = AA   length = 124
FEATURE                 Location/Qualifiers
source                  1..124
                        mol_type = protein
                        organism = synthetic construct
SEQUENCE: 119
EVQLVESGGG LVQPGGSLSL SCTASGRTFS SYAMGWFRQA PGEREFVAD IGENADNRWY    60
```

```
AHSVKGRFTI SRDNAKNTVY LQMNSLKPED TAVYYCAADR YGVGGGAQGY YDSWGQGTQV   120
TVSS                                                                124

SEQ ID NO: 120          moltype = AA  length = 124
FEATURE                 Location/Qualifiers
source                  1..124
                        mol_type = protein
                        organism = synthetic construct
SEQUENCE: 120
QVQLVESGGG LVQAGGSLRL SCTVSGRTFS TYAMGWFRQA PGKEREFVAD INWNSDNIWY   60
ADSVKGRFTI SRDNAKNVMY LQMNSLKPED TAVYYCAADS YGVGGGKEEY YDSWGQGTQV   120
TVSS                                                                124

SEQ ID NO: 121          moltype = AA  length = 124
FEATURE                 Location/Qualifiers
source                  1..124
                        mol_type = protein
                        organism = synthetic construct
SEQUENCE: 121
EVQLVESGGG LVQPGGSLQL SCTTSGRHFD EYAVGWFRQA PGKEREFVAD IGENADNTWY   60
AHSVKGRFTI SRDDAKNTVY LEMDGLKPED TAVYYCAADK YGVGGNAQGY YDSWGQGTQV   120
TVSS                                                                124

SEQ ID NO: 122          moltype = AA  length = 124
FEATURE                 Location/Qualifiers
source                  1..124
                        mol_type = protein
                        organism = synthetic construct
SEQUENCE: 122
EVQLVESGGG LVQPGGSLQL SCTTSGRHFD EYAVGWFRQG PGKEREFVAD IGENADNTWY   60
AHSVKGRFTI SRDDAKNTVY LEMDGLKPED TAVYYCAADK YGVGGNAQGY YDSWGQGTQV   120
TVSS                                                                124

SEQ ID NO: 123          moltype = AA  length = 124
FEATURE                 Location/Qualifiers
source                  1..124
                        mol_type = protein
                        organism = synthetic construct
SEQUENCE: 123
EVQLVESGGG LVQPGGSLQL SCTTSGRRFS EYAVGWFRQA PGKEREFVAD IGEQAENTWY   60
AHSVLGRFTI SRDDAKNTVY LQMDSLKPED TAVYYCAADK YGVGGNAQGY YDSWGQGTQV   120
TVSS                                                                124

SEQ ID NO: 124          moltype = AA  length = 124
FEATURE                 Location/Qualifiers
source                  1..124
                        mol_type = protein
                        organism = synthetic construct
SEQUENCE: 124
EVQLVESGGG LVQPGGSLQL SCTTSGRRFS EYAVGWFRQG PGKEREFVAD IGEQAENTWY   60
AESVLGRFTI SRDDAKNTVY LQMDSLKPED TAVYYCAADK YGVGGNAQGY YDSWGQGTQV   120
TVSS                                                                124

SEQ ID NO: 125          moltype = AA  length = 124
FEATURE                 Location/Qualifiers
source                  1..124
                        mol_type = protein
                        organism = synthetic construct
SEQUENCE: 125
EVQLVESGGG LVQPGGSLKL SCTTSGRKFD EYAVGWFRQA PGKEREFVAD IGENAENTWY   60
AHSVLGRFTI SRDDAKNTVY LQMDSLKPED TAVYYCAADK YGVGGNAQGY YDSWGQGTQV   120
TVSS                                                                124

SEQ ID NO: 126          moltype = AA  length = 124
FEATURE                 Location/Qualifiers
source                  1..124
                        mol_type = protein
                        organism = synthetic construct
SEQUENCE: 126
EVQLVESGGG LVQPGGSLKL SCTTSGRRFS EYAVGWFRQG PGKEREFVAD IGEQAENTWY   60
AHSVLGRFTI SRDDAKNTVY LEMDGLKPED TAVYYCAADK YGVGGNAQGY YDSWGQGTQV   120
TVSS                                                                124

SEQ ID NO: 127          moltype = AA  length = 124
FEATURE                 Location/Qualifiers
source                  1..124
                        mol_type = protein
                        organism = synthetic construct
SEQUENCE: 127
```

```
EVQLVESGGG WVQPGGSLKL SCTTSGRRFS EYAVGWFRQA PGKEREFVAD IGEQAENTWY    60
AHSVLGRFTI SRDDAKNTVY LQMDSLKPED TAVYYCAADK YGVGGNAQGY YDSWGQGTQV   120
TVSS                                                                124

SEQ ID NO: 128           moltype = AA  length = 4
FEATURE                  Location/Qualifiers
source                   1..4
                         mol_type = protein
                         organism = synthetic construct
SEQUENCE: 128
GQAC                                                                  4

SEQ ID NO: 129           moltype = AA  length = 5
FEATURE                  Location/Qualifiers
source                   1..5
                         mol_type = protein
                         organism = synthetic construct
SEQUENCE: 129
GQACP                                                                 5

SEQ ID NO: 130           moltype = AA  length = 1023
FEATURE                  Location/Qualifiers
source                   1..1023
                         mol_type = protein
                         organism = synthetic construct
SEQUENCE: 130
EVQLVESGGG LVQPGGSLRL SCAASGFTIS SNYMIWVRQA PGKGLEWVSD LYYYAGDTYY    60
ADSVKGRFTM SRDISKNTVY LQMNSLRAED TAVYYCARWA DDHPPWIDLW GRGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKRVEP KSCDKTHTCP PCPAPELLGG   240
PSVFLFPPKP KDTLYITREP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK DIQMTQSPST LSASVGDRVT ITCRASQGIS   480
SWLAWYQQKP GKAPKVLIYK ASTLESGVPS RFSGSGSGTE FTLTISSLQP DDFATYYCQQ   540
SWLGGSFGQG TKLEIKRTVA APSVFIFPPS DEQLKSGTAS VVCLLNNFYP REAKVQWKVD   600
NALQSGNSQE SVTEQDSKDS TYSLSSTLTL SKADYEKHKV YACEVTHQGL SSPVTKSFNR   660
GECEVQLVES GGGLVQPGGS LRLSCAASGF TISSNYMIWV RQAPGKGLEW VSDLYYYAGD   720
TYYADSVKGR FTMSRDISKN TVYLQMNSLR AEDTAVYYCA RWADDHPPWI DLWGRGTLVT   780
VSSASTKGPS VFPLAPSSKS TSGGTAALGC LVKDYFPEPV TVSWNSGALT SGVHTFPAVL   840
QSSGLYSLSS VVTVPSSSLG TQTYICNVNH KPSNTKVDKR VEPKSCDKTH TCPPCPAPEL   900
LGGPSVFLFP PKPKDTLYIT REPEVTCVVV DVSHEDPEVK FNWYVDGVEV HNAKTKPREE   960
QYNSTYRVVS VLTVLHQDWL NGKEYKCKVS NKALPAPIEK TISKAKGQPR EPQVYTLPPS  1020
REE                                                                1023

SEQ ID NO: 131           moltype = AA  length = 135
FEATURE                  Location/Qualifiers
source                   1..135
                         mol_type = protein
                         organism = synthetic construct
SEQUENCE: 131
QVQLVESGGG LVQPGGSLKL SCTTSGRRFS EYAVGWFRQA PGKEREFVAD IGEQAENTWY    60
AESVLGRFTI SRDDAKNTVY LEMDGLKPED TAVYYCAADK YGVGGNAQGY YDSWGQGTQV   120
TVSSGGGGSH HHHH                                                     135

SEQ ID NO: 132           moltype = AA  length = 135
FEATURE                  Location/Qualifiers
source                   1..135
                         mol_type = protein
                         organism = synthetic construct
SEQUENCE: 132
ELQLVESGGG LVQPGGSLKL SCTTSGRRFS EYAVGWFRQA PGKEREFVAD IGEQAENTWY    60
AESVLGRFTI SRDDAKNTVY LEMDGLKPED TAVYYCAADK YGVGGNAQGY YDSWGQGTQV   120
TVSSGGGGSH HHHH                                                     135

SEQ ID NO: 133           moltype = AA  length = 135
FEATURE                  Location/Qualifiers
source                   1..135
                         mol_type = protein
                         organism = synthetic construct
SEQUENCE: 133
EVQLVESGGG WVQPGGSLKL SCTTSGRRFS EYAVGWFRQA PGKEREFVAD IGEQAENTWY    60
AESVLGRFTI SRDDAKNTVY LEMDGLKPED TAVYYCAADK YGVGGNAQGY YDSWGQGTQV   120
TVSSGGGGSH HHHH                                                     135

SEQ ID NO: 134           moltype = AA  length = 135
FEATURE                  Location/Qualifiers
source                   1..135
                         mol_type = protein
```

```
                             organism = synthetic construct
SEQUENCE: 134
EVQLVESGGG LVQPGGSLKL SCTTSGRTFS EYAVGWFRQA PGKEREFVAD IGEQAENTWY    60
AESVLGRFTI SRDDAKNTVY LEMDGLKPED TAVYYCAADK YGVGGNAQGY YDSWGQGTQV   120
TVSSGGGGSH HHHHH                                                    135

SEQ ID NO: 135           moltype = AA  length = 135
FEATURE                  Location/Qualifiers
source                   1..135
                         mol_type = protein
                         organism = synthetic construct
SEQUENCE: 135
EVQLVESGGG LVQPGGSLKL SCTTSGRRFS SYAVGWFRQA PGKEREFVAD IGEQAENTWY    60
AESVLGRFTI SRDDAKNTVY LEMDGLKPED TAVYYCAADK YGVGGNAQGY YDSWGQGTQV   120
TVSSGGGGSH HHHHH                                                    135

SEQ ID NO: 136           moltype = AA  length = 135
FEATURE                  Location/Qualifiers
source                   1..135
                         mol_type = protein
                         organism = synthetic construct
SEQUENCE: 136
EVQLVESGGG LVQPGGSLKL SCTTSGRRFS EYAVGWFRQA PGKEREFVAD IGENAENTWY    60
AESVLGRFTI SRDDAKNTVY LEMDGLKPED TAVYYCAADK YGVGGNAQGY YDSWGQGTQV   120
TVSSGGGGSH HHHHH                                                    135

SEQ ID NO: 137           moltype = AA  length = 135
FEATURE                  Location/Qualifiers
source                   1..135
                         mol_type = protein
                         organism = synthetic construct
SEQUENCE: 137
EVQLVESGGG LVQPGGSLKL SCTTSGRRFS EYAVGWFRQA PGKEREFVAD IGEQADNTWY    60
AESVLGRFTI SRDDAKNTVY LEMDGLKPED TAVYYCAADK YGVGGNAQGY YDSWGQGTQV   120
TVSSGGGGSH HHHHH                                                    135

SEQ ID NO: 138           moltype = AA  length = 135
FEATURE                  Location/Qualifiers
source                   1..135
                         mol_type = protein
                         organism = synthetic construct
SEQUENCE: 138
EVQLVESGGG LVQPGGSLKL SCTTSGRRFS EYAVGWFRQA PGKEREFVAD IGEQAENTWY    60
AHSVLGRFTI SRDDAKNTVY LEMDGLKPED TAVYYCAADK YGVGGNAQGY YDSWGQGTQV   120
TVSSGGGGSH HHHHH                                                    135

SEQ ID NO: 139           moltype = AA  length = 135
FEATURE                  Location/Qualifiers
source                   1..135
                         mol_type = protein
                         organism = synthetic construct
SEQUENCE: 139
EVQLVESGGG LVQPGGSLKL SCTTSGRRFS EYAVGWFRQA PGKEREFVAD IGEQAENTWY    60
AESVKGRFTI SRDDAKNTVY LEMDGLKPED TAVYYCAADK YGVGGNAQGY YDSWGQGTQV   120
TVSSGGGGSH HHHHH                                                    135

SEQ ID NO: 140           moltype = AA  length = 135
FEATURE                  Location/Qualifiers
source                   1..135
                         mol_type = protein
                         organism = synthetic construct
SEQUENCE: 140
EVQLVESGGG LVQPGGSLKL SCTTSGRRFS EYAVGWFRQA PGKEREFVAD IGEQAENTWY    60
AESVLGRFTI SRDNAKNTVY LEMDGLKPED TAVYYCAADK YGVGGNAQGY YDSWGQGTQV   120
TVSSGGGGSH HHHHH                                                    135

SEQ ID NO: 141           moltype = AA  length = 135
FEATURE                  Location/Qualifiers
source                   1..135
                         mol_type = protein
                         organism = synthetic construct
SEQUENCE: 141
EVQLVESGGG LVQPGGSLKL SCTTSGRRFS EYAVGWFRQA PGKEREFVAD IGEQAENTWY    60
AESVLGRFTI SRDDAKNTVY LEMNGLKPED TAVYYCAADK YGVGGNAQGY YDSWGQGTQV   120
TVSSGGGGSH HHHHH                                                    135

SEQ ID NO: 142           moltype = AA  length = 135
FEATURE                  Location/Qualifiers
source                   1..135
```

```
                           mol_type = protein
                           organism = synthetic construct
SEQUENCE: 142
EVQLVESGGG LVQPGGSLKL SCTTSGRRFS EYAVGWFRQA PGKEREFVAD IGEQAENTWY      60
AESVLGRFTI SRDDAKNTVY LEMDSLKPED TAVYYCAADK YGVGGNAQGY YDSWGQGTQV     120
TVSSGGGGSH HHHHH                                                     135

SEQ ID NO: 143             moltype = AA   length = 135
FEATURE                    Location/Qualifiers
source                     1..135
                           mol_type = protein
                           organism = synthetic construct
SEQUENCE: 143
EVQLVESGGG LVQPGGSLKL SCTTSGRRFS EYAVGWFRQA PGKEREFVAD IGEQAENTWY      60
AESVLGRFTI SRDDAKNTVY LEMDGLKPED TAVYYCAADS YGVGGNAQGY YDSWGQGTQV     120
TVSSGGGGSH HHHHH                                                     135

SEQ ID NO: 144             moltype = AA   length = 135
FEATURE                    Location/Qualifiers
source                     1..135
                           mol_type = protein
                           organism = synthetic construct
SEQUENCE: 144
EVQLVESGGG LVQPGGSLKL SCTTSGRRFS EYAVGWFRQA PGKEREFVAD IGEQAENTWY      60
AESVLGRFTI SRDDAKNTVY LEMDGLKPED TAVYYCAADK YGVGGGAQGY YDSWGQGTQV     120
TVSSGGGGSH HHHHH                                                     135

SEQ ID NO: 145             moltype = AA   length = 124
FEATURE                    Location/Qualifiers
source                     1..124
                           mol_type = protein
                           organism = synthetic construct
SEQUENCE: 145
QVQLVESGGG LVQPGGSLKL SCTTSGRRFS EYAVGWFRQA PGKEREFVAD IGEQAENTWY      60
AESVLGRFTI SRDDAKNTVY LEMDGLKPED TAVYYCAADK YGVGGNAQGY YDSWGQGTQV     120
TVSS                                                                 124

SEQ ID NO: 146             moltype = AA   length = 124
FEATURE                    Location/Qualifiers
source                     1..124
                           mol_type = protein
                           organism = synthetic construct
SEQUENCE: 146
ELQLVESGGG LVQPGGSLKL SCTTSGRRFS EYAVGWFRQA PGKEREFVAD IGEQAENTWY      60
AESVLGRFTI SRDDAKNTVY LEMDGLKPED TAVYYCAADK YGVGGNAQGY YDSWGQGTQV     120
TVSS                                                                 124

SEQ ID NO: 147             moltype = AA   length = 124
FEATURE                    Location/Qualifiers
source                     1..124
                           mol_type = protein
                           organism = synthetic construct
SEQUENCE: 147
EVQLVESGGG WVQPGGSLKL SCTTSGRRFS EYAVGWFRQA PGKEREFVAD IGEQAENTWY      60
AESVLGRFTI SRDDAKNTVY LEMDGLKPED TAVYYCAADK YGVGGNAQGY YDSWGQGTQV     120
TVSS                                                                 124

SEQ ID NO: 148             moltype = AA   length = 124
FEATURE                    Location/Qualifiers
source                     1..124
                           mol_type = protein
                           organism = synthetic construct
SEQUENCE: 148
EVQLVESGGG LVQPGGSLKL SCTTSGRTFS EYAVGWFRQA PGKEREFVAD IGEQAENTWY      60
AESVLGRFTI SRDDAKNTVY LEMDGLKPED TAVYYCAADK YGVGGNAQGY YDSWGQGTQV     120
TVSS                                                                 124

SEQ ID NO: 149             moltype = AA   length = 124
FEATURE                    Location/Qualifiers
source                     1..124
                           mol_type = protein
                           organism = synthetic construct
SEQUENCE: 149
EVQLVESGGG LVQPGGSLKL SCTTSGRRFS SYAVGWFRQA PGKEREFVAD IGEQAENTWY      60
AESVLGRFTI SRDDAKNTVY LEMDGLKPED TAVYYCAADK YGVGGNAQGY YDSWGQGTQV     120
TVSS                                                                 124

SEQ ID NO: 150             moltype = AA   length = 124
FEATURE                    Location/Qualifiers
```

```
source                    1..124
                          mol_type = protein
                          organism = synthetic construct
SEQUENCE: 150
EVQLVESGGG LVQPGGSLKL SCTTSGRRFS EYAVGWFRQA PGKEREFVAD IGENAENTWY    60
AESVLGRFTI SRDDAKNTVY LEMDGLKPED TAVYYCAADK YGVGGNAQGY YDSWGQGTQV   120
TVSS                                                               124

SEQ ID NO: 151            moltype = AA  length = 124
FEATURE                   Location/Qualifiers
source                    1..124
                          mol_type = protein
                          organism = synthetic construct
SEQUENCE: 151
EVQLVESGGG LVQPGGSLKL SCTTSGRRFS EYAVGWFRQA PGKEREFVAD IGEQADNTWY    60
AESVLGRFTI SRDDAKNTVY LEMDGLKPED TAVYYCAADK YGVGGNAQGY YDSWGQGTQV   120
TVSS                                                               124

SEQ ID NO: 152            moltype = AA  length = 124
FEATURE                   Location/Qualifiers
source                    1..124
                          mol_type = protein
                          organism = synthetic construct
SEQUENCE: 152
EVQLVESGGG LVQPGGSLKL SCTTSGRRFS EYAVGWFRQA PGKEREFVAD IGEQAENTWY    60
AHSVLGRFTI SRDDAKNTVY LEMDGLKPED TAVYYCAADK YGVGGNAQGY YDSWGQGTQV   120
TVSS                                                               124

SEQ ID NO: 153            moltype = AA  length = 124
FEATURE                   Location/Qualifiers
source                    1..124
                          mol_type = protein
                          organism = synthetic construct
SEQUENCE: 153
EVQLVESGGG LVQPGGSLKL SCTTSGRRFS EYAVGWFRQA PGKEREFVAD IGEQAENTWY    60
AESVKGRFTI SRDDAKNTVY LEMDGLKPED TAVYYCAADK YGVGGNAQGY YDSWGQGTQV   120
TVSS                                                               124

SEQ ID NO: 154            moltype = AA  length = 124
FEATURE                   Location/Qualifiers
source                    1..124
                          mol_type = protein
                          organism = synthetic construct
SEQUENCE: 154
EVQLVESGGG LVQPGGSLKL SCTTSGRRFS EYAVGWFRQA PGKEREFVAD IGEQAENTWY    60
AESVLGRFTI SRDNAKNTVY LEMDGLKPED TAVYYCAADK YGVGGNAQGY YDSWGQGTQV   120
TVSS                                                               124

SEQ ID NO: 155            moltype = AA  length = 124
FEATURE                   Location/Qualifiers
source                    1..124
                          mol_type = protein
                          organism = synthetic construct
SEQUENCE: 155
EVQLVESGGG LVQPGGSLKL SCTTSGRRFS EYAVGWFRQA PGKEREFVAD IGEQAENTWY    60
AESVLGRFTI SRDDAKNTVY LEMNGLKPED TAVYYCAADK YGVGGNAQGY YDSWGQGTQV   120
TVSS                                                               124

SEQ ID NO: 156            moltype = AA  length = 124
FEATURE                   Location/Qualifiers
source                    1..124
                          mol_type = protein
                          organism = synthetic construct
SEQUENCE: 156
EVQLVESGGG LVQPGGSLKL SCTTSGRRFS EYAVGWFRQA PGKEREFVAD IGEQAENTWY    60
AESVLGRFTI SRDDAKNTVY LEMDSLKPED TAVYYCAADK YGVGGNAQGY YDSWGQGTQV   120
TVSS                                                               124

SEQ ID NO: 157            moltype = AA  length = 124
FEATURE                   Location/Qualifiers
source                    1..124
                          mol_type = protein
                          organism = synthetic construct
SEQUENCE: 157
EVQLVESGGG LVQPGGSLKL SCTTSGRRFS EYAVGWFRQA PGKEREFVAD IGEQAENTWY    60
AESVLGRFTI SRDDAKNTVY LEMDGLKPED TAVYYCAADS YGVGGNAQGY YDSWGQGTQV   120
TVSS                                                               124

SEQ ID NO: 158            moltype = AA  length = 124
```

```
FEATURE              Location/Qualifiers
source               1..124
                     mol_type = protein
                     organism = synthetic construct
SEQUENCE: 158
EVQLVESGGG LVQPGGSLKL SCTTSGRRFS EYAVGWFRQA PGKEREFVAD IGEQAENTWY    60
AESVLGRFTI SRDDAKNTVY LEMDGLKPED TAVYYCAADK YGVGGGAQGY YDSWGQGTQV   120
TVSS                                                                124

SEQ ID NO: 159       moltype = AA   length = 135
FEATURE              Location/Qualifiers
source               1..135
                     mol_type = protein
                     organism = synthetic construct
SEQUENCE: 159
QLQLVESGGG WVQPGGSLKL SCTTSGRHFQ EYAVGWFRQA PGKEREFVAD IGETAEVTWY    60
AHSVKGRFTI SRDNAKNTVY LEMNGLKPED TAVYYCAADK YGVGGGAQGY YDSWGQGTQV   120
TVSSGGGGSH HHHHH                                                    135

SEQ ID NO: 160       moltype = AA   length = 124
FEATURE              Location/Qualifiers
source               1..124
                     mol_type = protein
                     organism = synthetic construct
SEQUENCE: 160
QLQLVESGGG WVQPGGSLKL SCTTSGRHFQ EYAVGWFRQA PGKEREFVAD IGETAEVTWY    60
AHSVKGRFTI SRDNAKNTVY LEMNGLKPED TAVYYCAADK YGVGGGAQGY YDSWGQGTQV   120
TVSS                                                                124

SEQ ID NO: 161       moltype = AA   length = 11
FEATURE              Location/Qualifiers
source               1..11
                     mol_type = protein
                     organism = synthetic construct
SEQUENCE: 161
GQACPHHHHH H                                                         11

SEQ ID NO: 162       moltype = AA   length = 12
FEATURE              Location/Qualifiers
source               1..12
                     mol_type = protein
                     organism = synthetic construct
SEQUENCE: 162
GQACPCHHHH HH                                                        12

SEQ ID NO: 163       moltype = AA   length = 132
FEATURE              Location/Qualifiers
source               1..132
                     mol_type = protein
                     organism = synthetic construct
SEQUENCE: 163
EVQLVESGGG LVQPGGSLRL SCAASGSVFK INVMAWYRQA PGKGRELVAG IISGGSTSYA    60
DSVKGRFTIS RDNAKNTLYL QMNSLRPEDT AVYYCAFITT ESDYDLGRRY WGQGTLVTVS   120
SGGGGSHHHH HH                                                       132

SEQ ID NO: 164       moltype = AA   length = 256
FEATURE              Location/Qualifiers
source               1..256
                     mol_type = protein
                     organism = synthetic construct
SEQUENCE: 164
EVQLVESGGG LVQPGGSLRL SCAASGSVFK INVMAWYRQA PGKGRELVAG IISGGSTSYA    60
DSVKGRFTIS RDNAKNTLYL QMNSLRPEDT AVYYCAFITT ESDYDLGRRY WGQGTLVTVS   120
SGGGGSGGGS EVQLVESGGG LVQPGNSLRL SCAASGFTFS SFGMSWVRQA PGKGLEWVSS   180
ISGSGSDTLY ADSVKGRFTI SRDNAKTTLY LQMNSLRPED TAVYYCTIGG SLSRSSQGTL   240
VTVSSGGGGS HHHHHH                                                   256

SEQ ID NO: 165       moltype = AA   length = 128
FEATURE              Location/Qualifiers
source               1..128
                     mol_type = protein
                     organism = synthetic construct
SEQUENCE: 165
QVKLEESGGG LVQPGGSLRL SCAASGSISR FNIMGWYRQA PGKQRELVAD ITNGGTTMYA    60
DSVKGRFTIS RDNTKNTVYL QMNSLKPEDT AVYYCHTYYP TTGFDDWGQG AQVTVSSGGG   120
GSHHHHHH                                                            128
```

The invention claimed is:

1. A polypeptide derivative capable of binding IL-6 comprising a V$_H$H, an extension, a first substituent and a second substituent, wherein the V$_H$H comprises the complementarity-determining regions (CDR):

```
CDR1:
                                  (SEQ ID NO: 3)
EYAVG;

CDR2:
                                  (SEQ ID NO: 7)
DIGEQAENTWYAESVLG; and

CDR3:
                                  (SEQ ID NO: 17)
DKYGVGGNAQGYYDS (Kabat definition),
``` wherein the extension is attached to the C-terminal end of the V$_H$H and comprises an amino acid sequence as set out in SEQ ID NO: 72,
wherein the first substituent is attached to the cysteine in position 4 of SEQ ID NO: 72 and the second substituent is attached to the cysteine in position 6 of SEQ ID NO: 72, and
wherein each one of the first substituent and second substituent comprises the structure

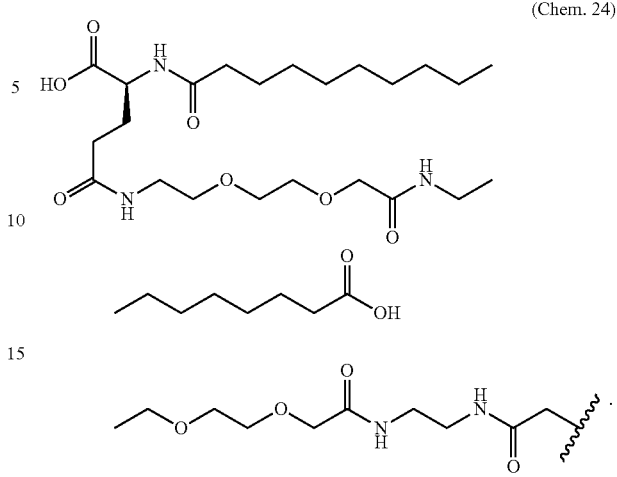

(Chem. 24)

2. The polypeptide derivative according to claim 1, wherein the molecular weight of said polypeptide derivative is between 12-18 kDa.

3. The polypeptide derivative of claim 1 that is:

(SEQ ID NO: 78)
```
EVQLVESGGG LVQPGGSLKL SCTTSGRRFS EYAVGWFRQA PGKEREFVAD IGEQAENTWY
AESVLGRFTI SRDDAKVTVY LEMDGLKPED TAVYYCAADK YGVGGNAQGY YDSWGQGTQV
```

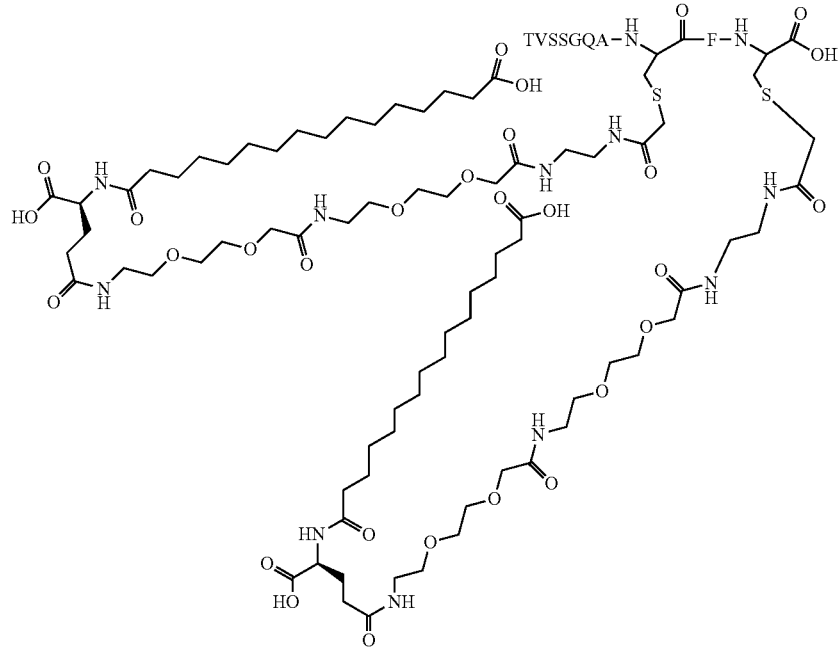

4. A pharmaceutical composition comprising a polypeptide derivative of claim 1 with a pharmaceutically acceptable carrier, diluent, or excipient.

5. The pharmaceutical composition of claim 4, wherein the composition further comprises sodium N-(8-(2-hydroxybenzoyl)amino)caprylate (SNAC).

6. The composition according to claim 5, wherein the composition further comprises nicotinamide.

7. A pharmaceutical composition comprising a polypeptide derivative of claim 3 with a pharmaceutically acceptable carrier, diluent, or excipient.

8. The pharmaceutical composition of claim 7, wherein the composition further comprises sodium N-(8-(2-hydroxybenzoyl)amino)caprylate (SNAC).

9. The composition according to claim 8, wherein the composition further comprises nicotinamide.

10. A method of treating inflammatory disease in a patient comprising administering to the patient an effective amount of a polypeptide derivative according to claim 1.

11. The method according to claim 10, wherein the inflammatory disease is cardiovascular disease.

12. The method according to claim 11, wherein the cardiovascular disease is atherosclerotic cardiovascular disease (ASCVD).

13. A method of treating inflammatory disease in a patient comprising administering to the patient an effective amount of a polypeptide derivative according to claim 3.

14. The method according to claim 13, wherein the inflammatory disease is cardiovascular disease.

15. The method according to claim 14, wherein the cardiovascular disease is atherosclerotic cardiovascular disease (ASCVD).

* * * * *